US007981898B2

(12) United States Patent
Johnson et al.

(10) Patent No.: US 7,981,898 B2
(45) Date of Patent: Jul. 19, 2011

(54) METHODS OF ENHANCING MUCOSAL HYDRATION AND MUCOSAL CLEARANCE BY TREATMENT WITH SODIUM CHANNEL BLOCKERS AND OSMOLYTES

(75) Inventors: Michael Ross Johnson, Chapel Hill, NC (US); Richard C. Boucher, Chapel Hill, NC (US); Andrew J. Hirsh, Durham, NC (US)

(73) Assignee: Parion Sciences, Inc., Durham, NC (US)

( * ) Notice: Subject to any disclaimer, the term of this patent is extended or adjusted under 35 U.S.C. 154(b) by 964 days.

(21) Appl. No.: 11/852,003

(22) Filed: Sep. 7, 2007

(65) Prior Publication Data

US 2009/0082287 A1    Mar. 26, 2009

Related U.S. Application Data

(60) Provisional application No. 60/842,963, filed on Sep. 8, 2006, provisional application No. 60/842,669, filed on Sep. 7, 2006.

(51) Int. Cl.
*A61K 31/4965* (2006.01)
(52) U.S. Cl. .............................. 514/255.06; 514/255.05
(58) Field of Classification Search ............. 514/255.05, 514/255.06
See application file for complete search history.

(56) References Cited

U.S. PATENT DOCUMENTS

| | | | |
|---|---|---|---|
| 4,501,729 A | 2/1985 | Boucher et al. |
| 5,656,256 A | 8/1997 | Boucher et al. |
| 5,725,842 A | 3/1998 | Boucher, Jr. et al. |
| 5,817,028 A | 10/1998 | Anderson |
| 5,876,700 A | 3/1999 | Boucher, Jr. et al. |
| 6,264,975 B1 | 7/2001 | Boucher, Jr. |
| 6,475,509 B1 | 11/2002 | Boucher, Jr. |
| 6,607,741 B2 | 8/2003 | Boucher, Jr. |
| 6,613,345 B2 | 9/2003 | Boucher, Jr. |
| 6,753,164 B2 | 6/2004 | Ni et al. |
| 6,858,614 B2 | 2/2005 | Johnson |
| 6,858,615 B2 | 2/2005 | Johnson |
| 6,903,105 B2 | 6/2005 | Johnson |
| 6,926,911 B1 | 8/2005 | Boucher, Jr. |
| 6,995,160 B2 | 2/2006 | Johnson |
| 7,026,325 B2 | 4/2006 | Johnson |
| 7,030,117 B2 | 4/2006 | Johnson |
| 7,056,524 B2 | 6/2006 | Boucher, Jr. |
| 7,064,129 B2 | 6/2006 | Johnson et al. |
| 7,186,833 B2 | 3/2007 | Johnson |
| 7,189,719 B2 | 3/2007 | Johnson |
| 7,192,958 B2 | 3/2007 | Johnson |
| 7,192,959 B2 | 3/2007 | Johnson |
| 7,192,960 B2 | 3/2007 | Johnson |
| 7,241,766 B2 | 7/2007 | Johnson |
| 7,247,636 B2 | 7/2007 | Johnson |
| 7,247,637 B2 | 7/2007 | Johnson et al. |
| 2004/0198747 A1 | 10/2004 | Johnson |
| 2004/0198749 A1 | 10/2004 | Johnson |
| 2005/0059676 A1 | 3/2005 | Johnson |
| 2005/0080092 A1 | 4/2005 | Johnson |
| 2005/0080093 A1 | 4/2005 | Johnson et al. |
| 2005/0090505 A1 | 4/2005 | Johnson et al. |
| 2005/0228182 A1 | 10/2005 | Johnson et al. |
| 2006/0040954 A1 | 2/2006 | Johnson |
| 2006/0052394 A1 | 3/2006 | Johnson et al. |
| 2006/0052395 A1 | 3/2006 | Johnson et al. |
| 2006/0063780 A1 | 3/2006 | Johnson |
| 2006/0142306 A1 | 6/2006 | Johnson |
| 2006/0142581 A1 | 6/2006 | Johnson |
| 2006/0205738 A1 | 9/2006 | Johnson et al. |
| 2007/0032509 A1 | 2/2007 | Johnson et al. |

FOREIGN PATENT DOCUMENTS

| | | |
|---|---|---|
| WO | WO-03/070182 A2 | 8/2003 |
| WO | WO-03070184 A2 | 8/2003 |
| WO | WO-2005/044180 A2 | 5/2005 |

OTHER PUBLICATIONS

U.S. Appl. No. 12/249,175, filed Oct. 10, 2008, Boucher, et al.
U.S. Appl. No. 12/304,006, filed Dec. 9, 2008, Johnson, et al.
U.S. Appl. No. 12/304,042, filed Dec. 9, 2008, Johnson.
U.S. Appl. No. 12/304,040, filed Dec. 9, 2008, Johnson.
U.S. Appl. No. 10/920,527, filed Aug. 18, 2004, Hopkins.
U.S. Appl. No. 11/573,693, filed Feb. 14, 2007, Johnson.
U.S. Appl. No. 11/573,413, filed Feb. 8, 2007, Johnson.
U.S. Appl. No. 11/573,421, filed Feb. 8, 2007, Johnson.
U.S. Appl. No. 11/695,936, filed Apr. 3, 2007, Johnson.
U.S. Appl. No. 11/696,003, filed Apr. 3, 2007, Johnson.
U.S. Appl. No. 11/851,803, filed Sep. 7, 2007, Johnson, et al.
U.S. Appl. No. 60/495,725, filed Aug. 18, 2003, Johnson.
U.S. Appl. No. 60/495,720, filed Aug. 18, 2003, Johnson.
U.S. Appl. No. 60/495,712, filed Aug. 18, 2003, Johnson.
U.S. Appl. No. 60/602,313, filed Aug. 18, 2004, Johnson.
U.S. Appl. No. 60/602,327, filed Aug. 18, 2004, Johnson.
U.S. Appl. No. 60/812,091, filed Jun. 9, 2006, Johnson.
U.S. Appl. No. 60/812,077, filed Jun. 9, 2006, Johnson, et al.
U.S. Appl. No. 60/812,078, filed Jun. 9, 2006, Johnson.
U.S. Appl. No. 60/842,669, filed Sep. 7, 2006, Johnson, et al.
U.S. Appl. No. 60/842,963, filed Sep. 8, 2006, Johnson, et al.
U.S. Appl. No. 60/845,171, filed Sep. 18, 2006, Johnson, et al.
U.S. Appl. No. 60/909,818, filed Apr. 3, 2007, Johnson, et al.
U.S. Appl. No. 60/978,887, filed Oct. 10, 2007, Boucher, et al.
U.S. Appl. No. 60/978,874, filed Oct. 10, 2007, Boucher, et al.
U.S. Appl. No. 60/987,663, filed Nov. 13, 2007, Johnson, et al.
U.S. Appl. No. 61/013,387, filed Dec. 13, 2007, Johnson, et al. U.S. Appl. No. 61/030,313, filed Feb. 21, 2008, Johnson.
U.S. Appl. No. 61/031,466, filed Feb. 26, 2008, Johnson.
U.S. Appl. No. 12/171,814, filed Jul. 11, 2008, Johnson. et al.
U.S. Appl. No. 12/171,867, filed Jul. 11, 2008, Johnson. et al.
U.S. Appl. No. 12/171,897, filed Jul. 11, 2008, Johnson. et al.
U.S. Appl. No. 12/190,022, filed Aug. 12, 2008, Johnson.
U.S. Appl. No. 61/079,989, filed Jul. 11, 2008, Boucher, et al.
U.S. Appl. No. 12/179,353, filed Jul. 24, 2008, Johnson.
U.S. Appl. No. 11/960,989, filed Dec. 20, 2007, Johnson, et al.
U.S. Appl. No. 11/950,674, filed Dec. 5, 2007, Johnson, et al.
U.S. Appl. No. 11/835,902, filed Aug. 8, 207, Johnson, et al.

(Continued)

*Primary Examiner* — Raymond J Henley, III
(74) *Attorney, Agent, or Firm* — Steven R. Eck

(57) ABSTRACT

The present invention relates to methods and compositions for treating diseases ameliorated by increased mucociliary clearance and mucosal hydration by administering an effective amount of a sodium channel blocker as defined herein and an osmolyte to a subject to a subject in need of increased mucociliary clearance and mucosal hydration.

16 Claims, 4 Drawing Sheets

OTHER PUBLICATIONS

U.S. Appl. No. 12/049,946, filed Mar. 17, 2008, Johnson, et al.
U.S. Appl. No. 12/049,968, filed Mar. 17, 2008, Johnson, et al.
U.S. Appl. No. 12/049,894, filed Mar. 17, 2008, Johnson, et al.
U.S. Appl. No. 12/050,010, filed Mar. 17, 2008, Johnson.
U.S. Appl. No. 12/049,993, filed Mar. 17, 2008, Johnson.
U.S. Appl. No. 12/050,019, filed Mar. 17, 2008, Johnson.
U.S. Appl. No. 12/061,837, filed Apr. 3, 2008, Johnson, et al.
U.S. Appl. No. 12/061,864, filed Apr. 3, 2008, Johnson, et al.
U.S. Appl. No. 12/098,581, filed Apr. 7, 2008, Johnson.
Bennett, W.D. et al. (1996) "Effect of Uridine 5'-Triphosphate Plus Amiloride on Mucociliary Clearance in Adult Cystic Fibrosis", *Am J Respir Crit Care Med.* vol. 153, pp. 1796-1801.
Boucher, R.C. (2007), "Airway Surface Dehydration In Cystic Fibrosis: Pathogenesis and Therapy", *Annu. Rev. Med.* vol. 58, pp. 157-170.
Boucher, R.C. (2007) "Evidence for airway surface dehydration as the inillating event in CF airway disease", *Journal of Internal Medicine*, vol. 261, pp. 5-16.
Boucher, R.C., (2007), "Cystic fibrosis: a disease of vulnerability to airway surface dehydration", *Trends in Molecular Medicine*, vol. 13(6), pp. 231-240.
Cline, D. et al. (2002), "Predicting the Quality of Powders for Inhalation from Surface Energy and Area", *Pharmaceutical Research*, vol. 19(9), pp. 1274-1277.
Clunes, M. et al. (2008), "Front-runners for pharmacotherapeutic correction of the airway ion transport defect in cystic fibrosis", *Current Opinion in Pharmacology*, vol. 8, pp. 292-299.
Donaldson, S.H. et al. (2006), "Mucus Clearance and Lung Fuction in Cystic Fibrosis with Hypertonic Saline", *The New England Journal of Medicine*, vol. 354, pp. 241-250.
Elkins. M.R. et al. (2006), "A Controlled Trial of Long-Term Inhaled Hypertonic Saline in Patients with Cystic Fibrosis", *The New England Journal of Medicine*, vol. 354(3), pp. 229-240.
Gowen, C.W. et al. (1986) "Increased nasal potential difference and amiloride sensitivity in neonates with cystic fibrosis", *The Journal of Pediatrics*, vol. 108(4), pp. 517-521.
Hirsh, A. J. et al. (2006) "Design, Synthesis, and Structure-Activity Relationships of Novel 2-Substituted Pyrazinoylguanidine Epithelial Sodium Channel Blockers: Drugs for Cystic Fibrosis and Chronic Bronchitis", *Journal of Medicinal Chemistry*, vol. 49, pp. 4098-4115.
Hirsh, A.J. et al. (2009) "Pharmacological Properties of $N$-(3,5-Diamino-6-chloropyrazine-2-carbonyl)-$N'$-4-[4-(2,3-dihydroxypropoxy)phenyl]butyl-guanidine Methanesulfonte (552-02), a Novel Epithelial Sodium Channel Blocker with Potential Clinical Efficacy for Cystic Fibrosis Lung Disease", *The Journal of Pharmacology and Experimental Therapeutics*, vol. 325(1), pp. 77-88.
Hirsh, A.J. et al. ((2004), "Evaluation of Second Generation Amiloride Analogs as Therapy for Cystic Fibrosis Lung Disease", *The Journal of Pharmacology and Experimental Therapeutics*, vol. 311(3), pp. 929-938.
Hofmann, T. et al. (1998), "Effects of Topically Delivered Benzamil and Amiloride on Nasal Potential Difference in Cystic Fibrosis", *Am. J. Resp. Crit. Care Med*, vol. 157, pp. 1844-1849.
Jones, K.M. et al. (1997), "Pharmacokinetics of Amiloride after Inhalation and Oral Administration in Adolescents and Adults with Cystic Fibrosis", *Pharmacotherapy*, vol. 17(2) pp. 263-270.
Knowles, M.R. et al. (1991) "Aerosolized Amiloride as Treatment of Cystic Fibrosis Lung Disease: A Pilot Study", *Adv. Exp. Med. Bio.* vol. 290, pp. 119-128, discussion 129-132.
Knowles, M.R. et al. (1990), "A Pilot Study of Aerosolized Amiloride for the Treatment of Lung Disease in Cystic Fibrosis", *The New England of Journal of Medicine*, vol. 322(17), pp. 1189-1194.
Mentz, W. M. et al. (1986). "Deposition, Clearance, and Effects of Aerosolized Amiloride in Sheep Airways[1-3]", *Am Rev. Respir. Dis.*, vol. 134(5), pp. 938-943.
Oliver, K.N. et al. (1996), "Acute Safety and Effects on Mucociliary Clearance of Aerosolized Uridine 5'-Triphosphate ± Amiloride in Normal Human Adults", *Am. J. Respir. Crit. Med.*, vol. 154, pp. 217-223.
Sood, N. et al., (2003), "Increasing Concentration of Inhaled Saline with or without Amiloride", *Am. J. Respir Crit. Care Med.*, vol. 167, pp. 158-163.
Tarran, R. et al. (2001), "The CF Salt Controversy: In vivo Observations and Therapeutics Approaches", *Molecular Cell*, vol. 8(7), pp. 149-158.
Tarran, R. et al, (2007), "Rationale for Hypertonic Saline Therapy for Cystic Fibrosis Lung Disease", *Seminars in Respiratory and Critical Care Medicine*, vol. 28(3), pp. 295-302.
Thelin, W.R. et al. (2007), "The epithelium as a target for therapy in cystic fibrosis", *Current Opinion in Pharmacology*, vol. 7, pp. 290-295.
Tomkiewicz, R.P. et al. (1993), "Amiloride Inhalation Therapy in Cystic Fibrosis", *Am. Rev. Respir. Dis.*, vol. 148, pp. 1002-1007.
Wark, P. et al. (2008), "Nebulised hypertonic saline for cystic fibrosis", *The Cochrane Collaboration, The Cochrane Library*, Issue 4, pp. 1-35.
Zhou, Z. et al. (2008), "Preventive but Not Late Amiloride Therapy Reduces Morbidity and Mortality of Lung Disease in βENaC-overexpressing Mice", *Am. J. Respir. Crit. Care Med.*, vol. 178, pp. 1245-1256.
Supplemental European Search Report for EP 07842074.
International Search Report for PCT/US07/77880, International Filing Date Sep. 7, 2007, mailed Sep. 15, 2008.
Supplemental European Search Report for EP 07842049.
Office Action for EA Application No. 200970258, Sep. 3, 2010.

Effect of an Osmolyte (Hypertonic Saline) With or Without Sodium channel blocker Compound 1 (10 µM) on Surface Liquid Volume after 8 h \* significance from Isotonic buffer (Vehicle) P<0.05
\*\* significance from HS (P<0.001)
† significance from Cmpd 1 (P<0.001)

Effect of Mannitol or compound 1 on Surface Liquid

METHODS OF ENHANCING MUCOSAL HYDRATION AND MUCOSAL CLEARANCE BY TREATMENT WITH SODIUM CHANNEL BLOCKERS AND OSMOLYTES

This application claims benefit of U.S. provisional application Ser. Nos. 60/842,669, filed on Sep. 7, 2006, and 60/842,963, filed Sep. 8, 2006, both incorporated herein by reference.

BACKGROUND OF THE INVENTION

1. Field of the Invention

The present invention relates to the use of sodium channel blockers with osmolytes, such as hypertonic sodium chloride, in producing more potent, durable and safe agents than either when used alone. The present invention also includes a variety of methods of treatment using these inventive sodium channel blocker-osmolyte combinations.

2. Description of the Background

The mucosal surfaces at the interface between the environment and the body have evolved a number of "innate defense", i.e., protective mechanisms. A principal form of such innate defense is to cleanse these surfaces with liquid. Typically, the quantity of the liquid layer on a mucosal surface reflects the balance between epithelial liquid secretion, often reflecting active anion ($Cl^-$ and/or $HCO_3^-$) secretion coupled with water (and a cation counter-ion), and epithelial liquid absorption, often reflecting active $Na^+$ absorption, coupled with water and counter anion ($Cl^-$ and/or $HCO_3^-$). Many diseases of mucosal surfaces are caused by too little protective liquid on those mucosal surfaces created by an imbalance between secretion (too little) and absorption (relatively too much). The defective salt transport processes that characterize these mucosal dysfunctions reside in the epithelial layer of the mucosal surface.

One approach to replenish the protective liquid layer on mucosal surfaces is to "re-balance" the system by blocking $Na^+$ channel and liquid absorption. The epithelial protein that mediates the rate-limiting step of $Na^+$ and liquid absorption is the epithelial $Na^+$ channel (ENaC). ENaC is positioned on the apical surface of the epithelium, i.e. the mucosal surface-environmental interface. Therefore, to inhibit ENaC mediated $Na^+$ and liquid absorption, an ENaC blocker of the amiloride class (which blocks from the extracellular domain of ENaC) must be delivered to the mucosal surface and, importantly, be maintained at this site, to achieve therapeutic utility. The present invention describes diseases characterized by too little liquid on mucosal surfaces and "topical" sodium channel blockers designed to exhibit the increased potency, reduced mucosal absorbtion, and slow dissociation ("unbinding" or detachment) from ENaC required for therapy of these diseases.

Chronic obstructive pulmonary diseases are characterized by dehydration of airway surfaces and the retention of mucous secretions in the lungs. Examples of such diseases include cystic fibrosis, chronic bronchitis, and primary or secondary ciliary dyskinesia. Such diseases affect approximately 15 million patients in the United States, and are the sixth leading cause of death. Other airway or pulmonary diseases characterized by the accumulation of retained mucous secretions include sinusitis (an inflammation of the paranasal sinuses associated with upper respiratory infection) and pneumonia.

U.S. Pat. No. 5,817,028 to Anderson describes a method for the provocation of air passage narrowing (for evaluating susceptibility to asthma) and/or the induction of sputum in subjects via the inhalation of mannitol. It is suggested that the same technique can be used to induce sputum and promote mucociliary clearance. Substances suggested include sodium chloride, potassium chloride, mannitol and dextrose.

Chronic bronchitis (CB), including the most common lethal genetic form of chronic bronchitis, cystic fibrosis (CF), a disease that reflects the body's failure to clear mucus normally from the lungs, which ultimately produces chronic airways infection. In the normal lung, the primary defense against chronic intrapulmonary airways infection (chronic bronchitis) is mediated by the continuous clearance of mucus from bronchial airway surfaces. This function in health effectively removes from the lung potentially noxious toxins and pathogens. Recent data indicate that the initiating problem, i.e., the "basic defect," in both CB and CF is the failure to clear mucus from airway surfaces. The failure to clear mucus reflects dehydration of airway surfaces that reflects an imbalance between the amount of liquid and mucin on airway surfaces. This "airway surface liquid" (ASL) is primarily composed of salt and water in proportions similar to plasma (i.e., isotonic). Mucin macromolecules organize into a well defined "mucus layer" which normally traps inhaled bacteria and is transported out of the lung via the actions of cilia which beat in a watery, low viscosity solution termed the "periciliary liquid" (PCL). In the disease state, there is an imbalance in the quantities of mucins (too much) and ASL (too little) on airway surfaces that produces airway surface dehydration. This dehydration leads to mucus concentration, reduction in the lubricant activity of the PCL, and a failure to clear mucus via ciliary activity to the mouth. The reduction in mechanical clearance of mucus from the lung leads to chronic airways inflammation and bacterial colonization of mucus adherent to airway surfaces. It is the chronic retention of bacteria, the failure of local antimicrobial substances to kill mucus-entrapped bacteria on a chronic basis, and the consequent chronic inflammatory responses of the body to this type of surface infection, that lead to the destruction of the lung in CB and CF.

The current afflicted population in the U.S. is 12,000,000 patients with the acquired (primarily from cigarette smoke exposure) form of chronic bronchitis and approximately 30,000 patients with the genetic form, cystic fibrosis. Approximately equal numbers of both populations are present in Europe. In Asia, there is little CF but the incidence of CB is high and, like the rest of the world, is increasing.

There is currently a large, unmet medical need for products that specifically treat CB and CF at the level of the basic defect that cause these diseases. The current therapies for chronic bronchitis and cystic fibrosis focus on treating the symptoms and/or the late effects of these diseases. Thus, for chronic bronchitis, β-agonists, inhaled steroids, anti-cholinergic agents, and oral theophyllines and phosphodiesterase inhibitors are all in development. However, none of these drugs treat effectively the fundamental problem of the failure to clear mucus from the lung. Similarly, in cystic fibrosis, the same spectrum of pharmacologic agents is used. These strategies have been complemented by more recent strategies designed to clear the CF lung of the DNA ("Pulmozyme"; Genentech) that has been deposited in the lung by neutrophils that have futilely attempted to kill the bacteria that grow in adherent mucus masses and through the use of inhaled antibiotics ("TOBI") designed to augment the lungs' own killing mechanisms to rid the adherent mucus plaques of bacteria. A general principle of the body is that if the initiating lesion is not treated, in this case mucus retention/obstruction, bacterial infections became chronic and increasingly refractory to antimicrobial therapy. Thus, a major unmet therapeutic need for both CB and CF lung diseases is an effective means of rehydrating airway mucus (i.e., restoring/expanding the volume of the ASL) and promoting its clearance, with bacteria, from the lung.

R. C. Boucher, in U.S. Pat. No. 6,264,975, describes the use of pyrazinoylguanidine sodium channel blockers for hydrating mucosal surfaces. These compounds, typified by the well-known diuretics amiloride, benzamil, and phenamil, are effective. However, these compounds suffer from the significant disadvantage that they are (1) relatively impotent, which is important because the mass of drug that can be inhaled by the lung is limited; (2) rapidly absorbed, which limits the half-life of the drug on the mucosal surface; and (3) are freely dissociable from ENaC. The sum of these disadvantages embodied in these well known diuretics produces compounds with insufficient potency and/or effective half-life on mucosal surfaces to have therapeutic benefit for hydrating mucosal surfaces.

R. C. Boucher, in U.S. Pat. No. 6,926,911, suggests the use of the relatively impotent sodium channel blockers such as amiloride, with osmolytes for the treatment of airway disesases. This combination gives no practical advantage over either treatment alone and is clinically not useful, see Donaldson et al, N Eng J Med 2006; 353:241-250. Amiloride was found to block the water permeability of airways and negate the potential benefit of concurrent use of hypertonic saline and amiloride.

Clearly, what is needed are treatments that are more effective at restoring the clearance of mucus from the lungs of patients with CB/CF. The value of these new therapies will be reflected in improvements in the quality and duration of life for both the CF and the CB populations.

Other mucosal surfaces in and on the body exhibit subtle differences in the normal physiology of the protective surface liquids on their surfaces but the pathophysiology of disease reflects a common theme, i.e., too little protective surface liquid. For example, in xerostomia (dry mouth) the oral cavity is depleted of liquid due to a failure of the parotid sublingual and submandibular glands to secrete liquid despite continued $Na^+$ (ENaC) transport mediated liquid absorption from the oral cavity. Similarly, keratoconjunctivitis sica (dry eye) is caused by failure of lacrimal glands to secrete liquid in the face of continued $Na^+$ dependent liquid absorption on conjunctional surfaces. In rhinosinusitis and otis media, there is an imbalance, as in CB, between mucin secretion and relative ASL depletion. Finally, in the gastrointestinal tract, failure to secrete $Cl^-$ (and liquid) in the proximal small intestine, combined with increased $Na^+$ (and liquid) absorption in the terminal ileum leads to the distal intestinal obstruction syndrome (DIOS). In older patients excessive $Na^+$ (and volume) absorption in the descending colon produces constipation and diverticulitis.

SUMMARY OF THE INVENTION

It is an object of the present invention to provide treatments comprising the use of osmolytes together with sodium channel blockers that are more potent, more specific, and/or absorbed less rapidly from mucosal surfaces, and/or are less reversible as compared to compounds such as amiloride, benzamil, and phenamil.

It is another aspect of the present invention to provide treatments using sodium channel blockers that are more potent and/or absorbed less rapidly and/or exhibit less reversibility, as compared to compounds such as amiloride, benzamil, and phenamil when administered with an osmotic enhancer. Therefore, such sodium channel blockers when used in conjunction with osmolytes will give a prolonged pharmacodynamic half-life on mucosal surfaces as compared to either compound used alone.

It is another object of the present invention to provide treatments using sodium channel blockers and osmolytes together which are absorbed less rapidly from mucosal surfaces, especially airway surfaces, as compared to compounds such as amiloride, benzamil, and phenamil.

It is another object of the invention to provide compositions which contain sodium channel blockers and osmolytes.

The objects of the invention may be accomplished with a method of treating a disease ameliorated by increased mucociliary clearance and mucosal hydration comprising administering an effective amount of a sodium channel blocker as defined herein and an osmolyte to a subject to a subject in need of increased mucociliary clearance and mucosal hydration.

The objects of the invention may also be accomplished with a method of inducing sputum for diagnostic purposes, comprising administering an effective amount of a sodium channel blocker as defined herein and an osmolyte to a subject in need thereof.

The objects of the invention may also be accomplished with a method of treating anthrax, comprising administering an effective amount of a sodium channel blocker as defined herein and an osmolyte to a subject in need thereof.

The objects of the invention may also be accomplished with a method of prophylactic, post-exposure prophylactic, preventive or therapeutic treatment against diseases or conditions caused by pathogens, particularly pathogens which may be used in bioterrorism, comprising administering an effective amount of a sodium channel blocker as defined herein and an osmolyte to a subject in need thereof.

The objects of the invention may also be accomplished with composition, comprising a sodium channel blocker as defined herein and an osmotically active compound.

A more complete appreciation of the invention and many of the attendant advantages thereof will be readily obtained as the same becomes better understood by reference to the following detailed description of the invention.

DETAILED DESCRIPTION OF THE INVENTION

Figure 1:
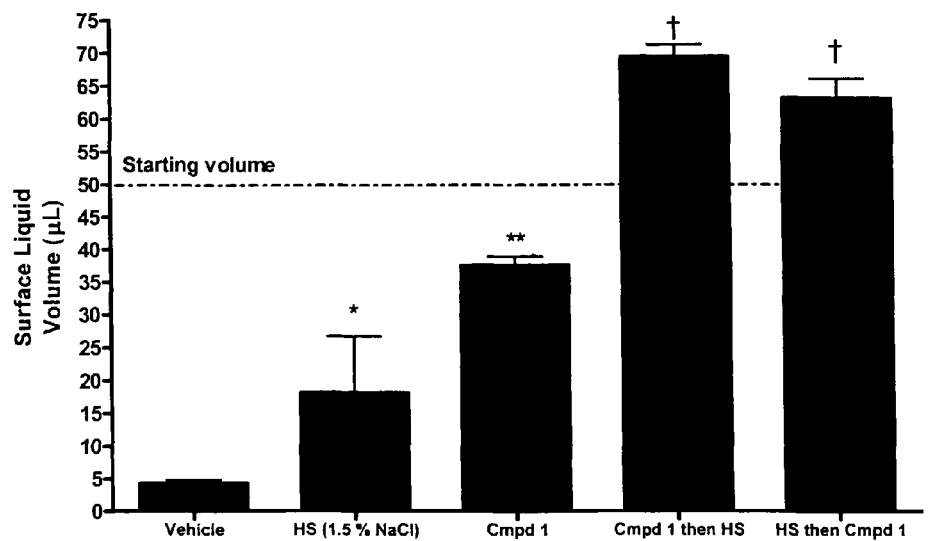
FIG. 1: Effect of an osmolyte with or without sodium channel blocker on surface liquid volume.
Figure 2:
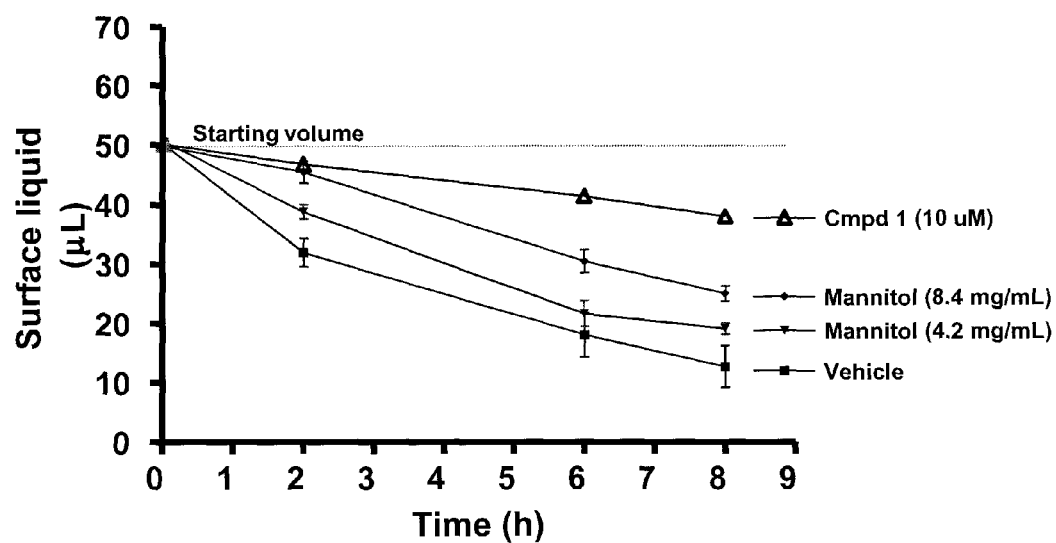
FIG. 2: Effect of mannitol or compound 1 on surface liquid.
Figure 3:
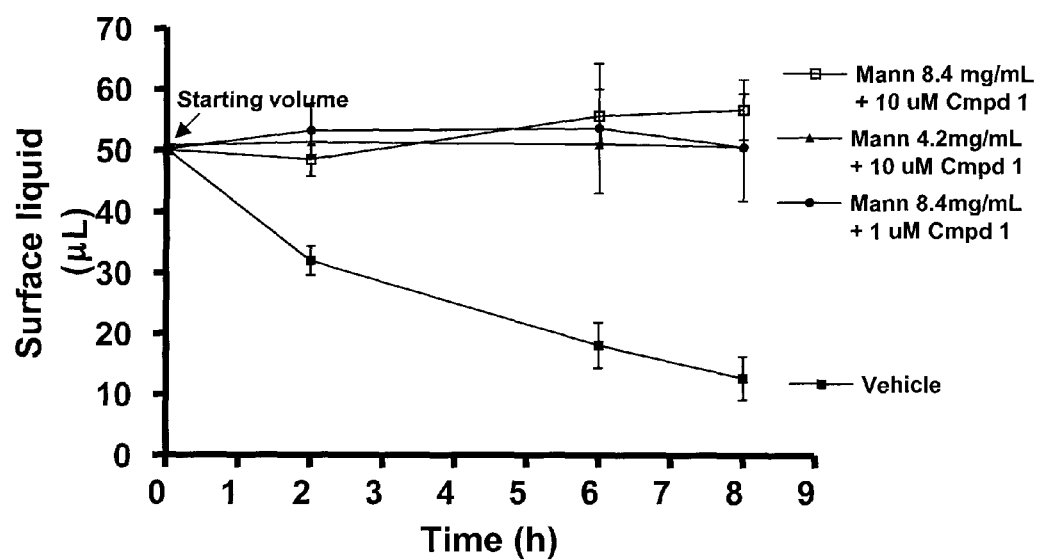
FIG. 3: Effect of mannitol and compound 1 on surface liquid.
Figure 4:
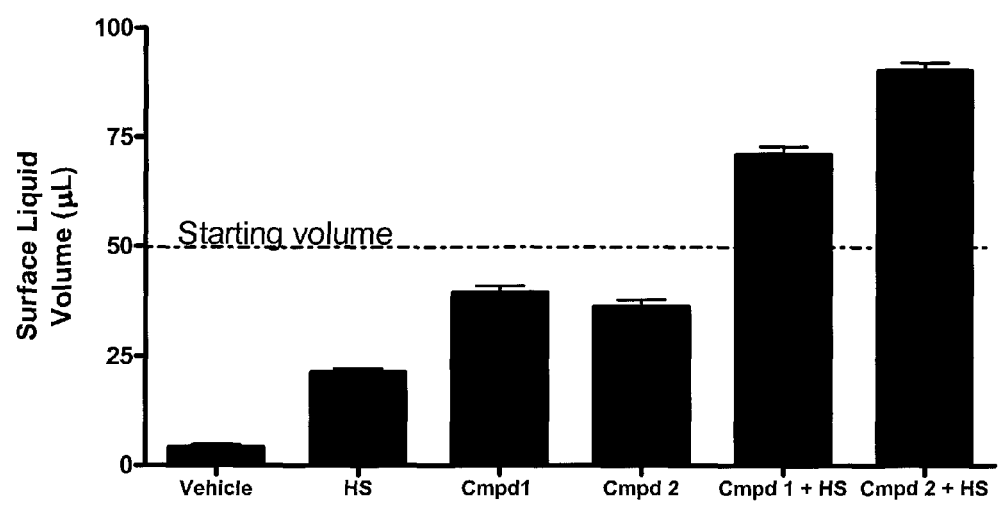
FIG. 4: Effect of hypertonic saline with or without compound 1 or compound 2 on surface liquid volume.

The term "sodium channel blocker as defined herein" as used herein refers to the sodium channel blockers described in U.S. patent application Ser. No. 10/076,551 (see pages 4-52), filed Feb. 19, 2002; U.S. Pat. No. 6,858,614 (see column 3, line 47 to column 29, line 64); WO 2004/073629 (see pages 5-107); U.S. patent application Ser. No. 10/367,947 (see pages 5-45, filed Feb. 19, 2003; U.S. Pat. No. 6,903,105 (see columns 4-33); U.S. patent application Ser. No. 10/920,410 (see pages 5-80), filed Aug. 18, 2004; U.S. Pat. No. 7,064,129 (see columns 4-76), U.S. patent application Ser. No. 10/920, 391 (see pages 5-91), filed Aug. 18, 2004, WO 2006/022935 (see pages 5-91), WO 2006/023573 (see pages 5-55), WO 2006/023617 (see pages 5-56), U.S. patent application Ser. No. 10/920,353 (see pages 5-68), filed Aug. 18, 2004; U.S.

patent application Ser. No. 10/920,418 (see pages 5-72), filed Aug. 18, 2004; and U.S. provisional application Ser. Nos. 60/495,725, 60/602,327, 60/495,720, 60/602,312, and 60/495,712, and U.S. patent application Ser. No. 11/195,758, each of which is incorporated herein by reference. All racemates, enantiomers, diastereomers, tautomers, polymorphs and pseudopolymorphs, salts and racemic mixtures of the sodium channel blockers are embraced by the present invention. The specific examples of sodium channel blockers described in those applications and patents are explicitly incorporated herein by reference. The sodium channel blockers may be synthesized as described in those applications and patents.

Thus, the sodium channel blockers useful in the present invention are represented by formula (I):

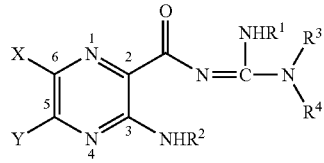
(I)

wherein

X is hydrogen, halogen, trifluoromethyl, lower alkyl, unsubstituted or substituted phenyl, lower alkyl-thio, phenyl-lower alkyl-thio, lower alkyl-sulfonyl, or phenyl-lower alkyl-sulfonyl;

Y is hydrogen, hydroxyl, mercapto, lower alkoxy, lower alkyl-thio, halogen, lower alkyl, unsubstituted or substituted mononuclear aryl, or $-N(R^2)_2$; and $R^1$ is hydrogen or lower alkyl.

In a first embodiment of the invention:

each $R^2$ is, independently, $-R^7$, $-(CH_2)_m-OR^8$, $-(CH_2)_m-NR^7R^{10}$, $-(CH_2)_n(CHOR^8)(CHOR^8)_n-CH_2OR^8$, $-(CH_2CH_2O)_m-R^8$, $-(CH_2CH_2O)_m-CH_2CH_2NR^7R^{10}$, $-(CH_2)_n-C(=O)NR^7R^{10}$, $-(CH_2)_n-Z_g-R^7$, $-(CH_2)_m-NR^{10}-CH_2(CHOR^8)(CHOR^8)_n-CH_2OR^8$, $-(CH_2)_n-CO_2R^7$, or

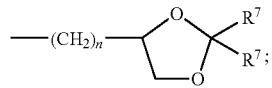

$R^3$ and $R^4$ are each, independently, hydrogen, a group represented by formula (A), lower alkyl, hydroxy lower alkyl, phenyl, phenyl-lower alkyl, (halophenyl)-lower alkyl, lower-(alkylphenylalkyl), lower (alkoxyphenyl)-lower alkyl, naphthyl-lower alkyl, or pyridyl-lower alkyl, with the proviso that at least one of $R^3$ and $R^4$ is a group represented by formula (A):

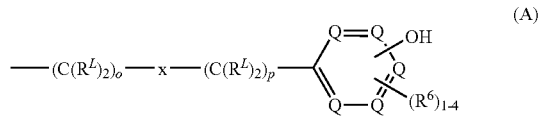
(A)

wherein each $R^L$ is, independently, $-R^7$, $-(CH_2)_n-OR^8$, $-O-(CH_2)_m-OR^8$, $-(CH_2)_n-NR^7R^{10}$, $-O-(CH_2)_m-NR^7R^{10}$, $-(CH_2)_n(CHOR^8)(CHOR^8)_n-CH_2OR^8$, $-O-(CH_2)_m(CHOR^8)(CHOR^8)_n-CH_2OR^8$, $-(CH_2CH_2O)_m-R^8$, $-O-(CH_2CH_2O)_m-R^8$, $-(CH_2CH_2O)_m-CH_2CH_2NR^7R^{10}$, $-O-(CH_2CH_2O)_m-CH_2CH_2NR^7R^{10}$, $-(CH_2)_n-C(=O)NR^7R^{10}$, $-O-(CH_2)_m-C(=O)NR^7R^{10}$, $-(CH_2)_n-(Z)_g-R^7$, $-O-(CH_2)_m-(Z)_g-R^7$, $-(CH_2)_n-NR^{10}-CH_2(CHOR^8)(CHOR^8)_n-CH_2OR^8$, $-O-(CH_2)_m-NR^{10}-CH_2(CHOR^8)(CHOR^8)_n-CH_2OR^8$, $-(CH_2)_n-CO_2R^7$, $-O-(CH_2)_m-CO_2R^7$, $-OSO_3H$, $-O$-glucuronide, $-O$-glucose,

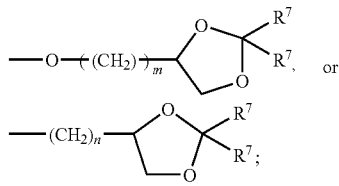

each o is, independently, an integer from 0 to 10;
each p is an integer from 0 to 10;
with the proviso that the sum of o and p in each contiguous chain is from 1 to 10;
each x is, independently, O, $NR^{10}$, $C(=O)$, CHOH, $C(=N-R^{10})$, $CHNR^7R^{10}$, or represents a single bond;
each $R^6$ is, independently, $-R^7$, $-OH$, $-OR^{11}$, $-N(R^7)_2$, $-(CH_2)_m-OR^8$, $-O-(CH_2)_m-OR^8$, $-(CH_2)_n-NR^7R^{10}$, $-O-(CH_2)_m-NR^7R^{10}$, $-(CH_2)_n(CHOR^8)(CHOR^8)_n-CH_2OR^8$, $-O-(CH_2)_m(CHOR^8)(CHOR^8)_n-CH_2OR^8$, $-(CH_2CH_2O)_m-R^8$, $-O-(CH_2CH_2O)_m-R^8$, $-(CH_2CH_2O)_m-CH_2CH_2NR^7R^{10}$, $-O-(CH_2CH_2O)_m-CH_2CH_2NR^7R^{10}$, $-(CH_2)_n-C(=O)NR^7R^{10}$, $-O-(CH_2)_m-C(=O)NR^7R^{10}$, $-(CH_2)_n-(Z)_g-R^7$, $-O-(CH_2)_m-(Z)_g-R^7$, $-(CH_2)_n-NR^{10}-CH_2(CHOR^8)(CHOR^8)_n-CH_2OR^8$, $-O-(CH_2)_m-NR^{10}-CH_2(CHOR^8)(CHOR^8)_n-CH_2OR^8$, $-(CH_2)-CO_2R^7$, $-O-(CH_2)_m-CO_2R^7$, $-OSO_3H$, $-O$-glucuronide, $-O$-glucose,

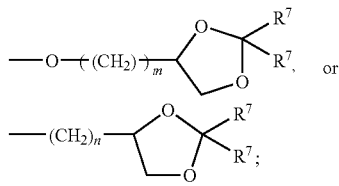

wherein when two $R^6$ are $-OR^{11}$ and are located adjacent to each other on a phenyl ring, the alkyl moieties of the two $R^6$ may be bonded together to form a methylenedioxy group;

each $R^7$ is, independently, hydrogen or lower alkyl;

each $R^8$ is, independently, hydrogen, lower alkyl, $-C(=O)-R^{11}$, glucuronide, 2-tetrahydropyranyl, or

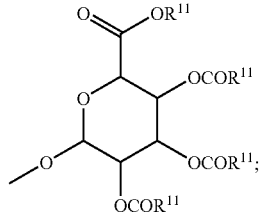

each $R^9$ is, independently, —$CO_2R^7$, —$CON(R^7)_2$, —$SO_2CH_3$, or —$C(=O)R^7$;

each $R^{10}$ is, independently, —H, —$SO_2CH_3$, —$CO_2R^7$, —$C(=O)NR^7R^9$, —$C(=O)R^7$, or —$CH_2$—(CHOH), —$CH_2OH$;

each Z is, independently, CHOH, C(=O), $CHNR^7R^{10}$, C=$NR^{10}$, or $NR^{10}$;

each $R^{11}$ is, independently, lower alkyl;

each g is, independently, an integer from 1 to 6;

each m is, independently, an integer from 1 to 7;

each n is, independently, an integer from 0 to 7;

each Q is, independently, C—OH, C—$R^6$ or a nitrogen atom, wherein one Q is C—OH and at most three Q in a ring are nitrogen atoms;

or a pharmaceutically acceptable salt thereof, and inclusive of all enantiomers, diastereomers, and racemic mixtures thereof.

In a second embodiment of the invention:

each $R^2$ is, independently, —$R^7$, —$(CH_2)_m$—$OR^8$, —$(CH_2)_m$—$NR^7R^{10}$, —$(CH_2)_n(CHOR^8)(CHOR^8)_n$—$CH_2OR^8$, —$(CH_2CH_2O)_m$—$R^8$, —$(CH_2CH_2O)_m$—$CH_2CH_2NR^7R^{10}$, —$(CH_2)_n$—$C(=O)NR^7R^{10}$, —$(CH_2)_n$—$Z_g$—$R^7$, —$(CH_2)_m$—$NR^{10}$—$CH_2(CHOR^8)(CHOR^8)_n$—$CH_2OR^8$, —$(CH_2)_n$—$CO_2R^7$, or

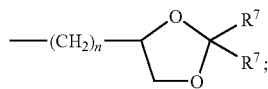

wherein when two —$CH_2OR^8$ groups are located 1,2- or 1,3- with respect to each other the $R^8$ groups may be joined to form a cyclic mono- or di-substituted 1,3-dioxane or 1,3-dioxolane;

$R^3$ and $R^4$ are each, independently, hydrogen, a group represented by formula (A), lower alkyl, hydroxy lower alkyl, phenyl, phenyl-lower alkyl, (halophenyl)-lower alkyl, lower-(alkylphenylalkyl), lower (alkoxyphenyl)-lower alkyl, naphthyl-lower alkyl, or pyridyl-lower alkyl, with the proviso that at least one of $R^3$ and $R^4$ is a group represented by formula (A):

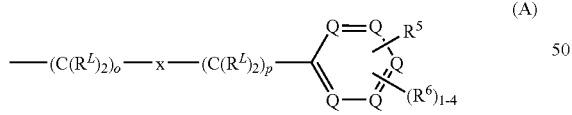

wherein each $R^L$ is, independently, —$R^7$, —$(CH_2)_n$—$OR^8$, —O—$(CH_2)_n$—$OR^8$, —$(CH_2)_n$—$NR^7R^{10}$, —O—$(CH_2)_m$—$NR^7R^{10}$, —$(CH_2)_n(CHOR^8)(CHOR^8)_n$—$CH_2OR^8$, —O—$(CH_2)_m(CHOR^8)(CHOR^8)_n$—$CH_2OR^8$, —$(CH_2CH_2O)_m$—$R^8$, —O—$(CH_2CH_2O)_m$—$R^8$, —$(CH_2CH_2O)_m$—$CH_2CH_2NR^7R^{10}$, —O—$(CH_2CH_2O)_m$—$CH_2CH_2NR^7R^{10}$, —$(CH_2)_n$—$C(=O)NR^7R^{10}$, —O—$(CH_2)_m$—$C(=O)NR^7R^{10}$, —$(CH_2)_n$—$(Z)_g$—$R^7$, —O—$(CH_2)_m$—$(Z)_g$—$R^7$, —$(CH_2)_n$—$NR^{10}$—$CH_2(CHOR^8)(CHOR^8)_n$—$CH_2OR^8$, —O—$(CH_2)_m$—$NR^{10}$—$CH_2(CHOR^8)(CHOR^8)_n$—$CH_2OR^8$, —$(CH_2)_n$—$CO_2R^7$, —O—$(CH_2)_m$—$CO_2R^7$, —$OSO_3H$, —O-glucuronide, —O-glucose,

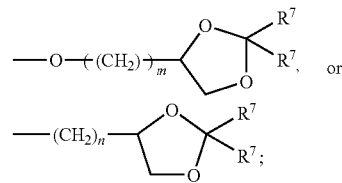

wherein when two —$CH_2OR^8$ groups are located 1,2- or 1,3- with respect to each other the $R^8$ groups may be joined to form a cyclic mono- or di-substituted 1,3-dioxane or 1,3-dioxolane;

each o is, independently, an integer from 0 to 10;

each p is an integer from 0 to 10;

with the proviso that the sum of o and p in each contiguous chain is from 1 to 10;

each x is, independently, O, $NR^{10}$, C(=O), CHOH, C(=N—$R^{10}$), $CHNR^7R^{10}$, or represents a single bond;

each $R^5$ is, independently, —$(CH_2)_n$—$NR^{12}R^{12}$, —O—$(CH_2)_m$—$NR^{12}R^{12}$, —O—$(CH_2)_n$—$NR^{12}R^{12}$, —O—$(CH_2)_m$—$(Z)_g R^{12}$, —$(CH_2)_n NR^{11}R^{11}$, —O—$(CH_2)_m NR^{11}R^{11}$, —$(CH_2)$, —$N^{\oplus}$-$(R^{11})_3$, —O—$(CH_2)_m$—$N^{\oplus}$—$(R^{11})_3$, —$(CH_2)_n$—$(Z)_g$—$(CH_2)_m$—$NR^{10}R^{10}$, —O—$(CH_2)_m$—$(Z)_g$—$(CH_2)_m$—$NR^{10}R^{10}$, —$(CH_2CH_2O)_m$—$CH_2CH_2NR^{12}R^{12}$, —O—$(CH_2CH_2O)_m$—$CH_2CH_2NR^{12}R^{12}$, $(CH_2)$, —(C=O)$NR^{12}R^{12}$, —O—$(CH_2)_m$—(C=O)$NR^{12}R^{12}$, —O—$(CH_2)_m$—$(CHOR^8)_m CH_2NR^{10}$-$(Z)_g$—$R^{10}$, —$(CH_2)_n$—$(CHOR^8)_m$—$CH_2$—$NR^{10}$, —$(CH_2)_n NR^{10}$—O$(CH_2)_m$ $(CHOR^8)_n CH_2NR^{10}$—$(Z)_g$—$R^{10}$, —$O(CH_2)_m$—$NR^{10}$—$(CH_2)_m$—$(CHOR^8)_n CH_2NR^{10}$-$(Z)_g$—$R^{10}$, -(Het)-$(CH_2)_m$—$OR^8$, -(Het)-$(CH_2)_m$—$NR^7R^{10}$, -(Het)-$(CH_2)_m(CHOR^8)(CHOR^8)_n$—$CH_2OR^8$, -(Het)-$(CH_2CH_2O)_m$—$R^8$, -(Het)-$(CH_2CH_2O)_m$—$CH_2CH_2NR^7R^{10}$, -(Het)-$(CH_2)_m$—$C(=O)NR^7R^{10}$, -(Het)-$(CH_2)_m$—$(Z)_g$—$R^7$, -(Het)-$(CH_2)_m$—$NR^{10}$—$CH_2(CHOR^8)(CHOR^8)_n$—$CH_2OR^8$, -(Het)-$(CH_2)_m$—$CO_2R^7$, -(Het)-$(CH_2)_m$—$NR^{12}R^{13}$, -(Het)-$(CH_2)_n$—$NR^{12}R^{12}$, -(Het)-$(CH_2)_m$—$(Z)_g R^{12}$, -(Het)-$(CH_2)_m NR^{11}R^{11}$, -(Het)-$(CH_2)_m$—$N^{\oplus}$—$(R^{11})_3$, -(Het)-$(CH_2)_m$—$(Z)_g$—$(CH_2)_m$—$NR^{10}R^{10}$, -(Het)-$(CH_2CH_2O)$, —$CH_2CH_2NR^{12}R^{12}$, -(Het)-$(CH_2)_m$—(C=O)$NR^{12}R^{12}$, -(Het)-$(CH_2)_m$—$(CHOR^8)_m CH_2NR^{10}$-$(Z)_g$—$R^{10}$, -(Het)-$(CH_2)_m$—$NR^{10}$—$(CH_2)_m$—$(CHOR^8)_n CH_2NR^{10}$—$(Z)_g$—$R^{10}$, wherein when two —$CH_2OR^8$ groups are located 1,2- or 1,3- with respect to each other the $R^8$ groups may be joined to form a cyclic mono- or di-substituted 1,3-dioxane or 1,3-dioxolane, —$(CH_2)_n(CHOR^8)(CHOR^8)_n$—$CH_2OR^8$, with the proviso that two —$CH_2OR^8$ groups are located 1,2- or 1,3- with respect to each other and the $R^8$ groups are joined to form a cyclic mono or disubstituted 1,3-dioxane or 1,3-dioxolane, —O—$(CH_2)_n(CHOR^8)(CHOR^8)_n$—$CH_2OR^8$, with the proviso that two —$CH_2OR^8$ groups are located 1,2- or 1,3- with respect to each other and the $R^8$ groups are joined to form a cyclic mono or disubstituted 1,3-dioxane or 1,3-dioxolane, —$(CH_2)_n$—$NR^{10}$—$CH_2(CHOR^8)(CHOR^8)_n$—$CH_2OR^8$, with the proviso that two —$CH_2OR^8$ groups are located 1,2- or 1,3- with respect to each other and the $R^8$ groups are joined to form a cyclic mono or disubstituted 1,3-dioxane or 1,3-dioxolane, or —O—$(CH_2)_n$—$NR^{10}$—$CH_2(CHOR^8)(CHOR^8)_n$—$CH_2OR^8$, with the proviso that two —$CH_2OR^8$ groups are located 1,2- or 1,3- with respect to each other and the $R^8$ groups are joined to form a cyclic mono or disubstituted 1,3-dioxane or 1,3-dioxolane; each $R^6$ is, independently, $-R^5$, $-R^7$, $-OR^8$, $-N(R^7)_2$, $-(CH_2)_m-OR^8$, $-O-(CH_2)_m-OR^8$, $-(CH_2)_n-NR^7R^{10}$, $-O-(CH_2)-NR^7R^{10}$, $-(CH_2)_n(CHOR^8)(CHOR^8)_n-CH_2OR^8$, $-O-(CH_2)_n(CHOR^8)(CHOR^8)_n-CH_2OR^8$, $-(CH_2CH_2O)_m-R^8$, $-O-(CH_2CH_2O)_m-R^8$, $-(CH_2CH_2O)_m-CH_2CH_2NR^7R^{10}$, $-O-(CH_2CH_2O)_m-CH_2CH_2NR^7R^{10}$, $-(CH_2)_n-C(=O)NR^7R^{10}$, $-O-(CH_2)_m-C(=O)NR^7R^{10}$, $-(CH_2)_n-(Z)_g-R^7$, $-O-(CH_2)_m-(Z)_g-R^7$, $-(CH_2)_n-NR^{10}-CH_2(CHOR^8)(CHOR^8)_n-CH_2OR^8$, $-O-(CH_2)_m-NR^{10}-CH_2(CHOR^8)(CHOR^8)_n-CH_2OR^8$, $-(CH_2)_n-CO_2R^7$, $-O-(CH_2)-CO_2R^7$, $-OSO_3H$, $-O$-glucuronide, $-O$-glucose,

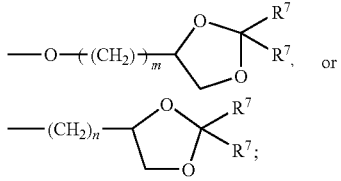

wherein when two $R^6$ are $-OR^{11}$ and are located adjacent to each other on a phenyl ring, the alkyl moieties of the two $R^6$ may be bonded together to form a methylenedioxy group and wherein when two $-CH_2OR^8$ groups are located 1,2- or 1,3- with respect to each other the $R^8$ groups may be joined to form a cyclic mono- or di-substituted 1,3-dioxane or 1,3-dioxolane;

each $R^7$ is, independently, hydrogen or lower alkyl;
each $R^8$ is, independently, hydrogen, lower alkyl, $-C(=O)-R^{11}$, glucuronide, 2-tetrahydropyranyl, or

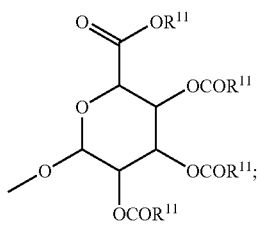

each $R^9$ is, independently, $-CO_2R^7$, $-CON(R^7)_2$, $-SO_2CH_3$, or $-C(=O)R^7$;
each $R^{10}$ is, independently, $-H$, $-SO_2CH_3$, $-CO_2R^7$, $-C(=O)NR^7R^9$, $-C(=O)R^7$, or $-CH_2-(CHOH)_n-CH_2OH$;
each Z is, independently, CHOH, C(=O), CHNR$^7$R$^{10}$, C=NR$^{10}$, or NR$^{10}$;
each $R^{11}$ is, independently, lower alkyl;
each $R^{12}$ is independently, $-SO_2CH_3$, $-CO_2R^7$, $-C(=O)NR^7R^9$, $-C(=O)R^7$, or $-CH_2-(CHOH)_n-CH_2OH$;
each Het is independently, $-NR^7$, $-NR^{10}$, $-S-$, $-SO-$, or $-SO_2-$;
each g is, independently, an integer from 1 to 6;
each m is, independently, an integer from 1 to 7;
each n is, independently, an integer from 0 to 7;
each Q is, independently, $C-R^5$, $C-R^6$, or a nitrogen atom, wherein one Q is $C-R^5$ and at most three Q in a ring are nitrogen atoms;
or a pharmaceutically acceptable salt thereof, and inclusive of all enantiomers, diastereomers, and racemic mixtures thereof.

In a third embodiment of the invention:
each $R^2$ is, independently, $-R^7$, $-(CH_2)_m-OR^8$, $-(CH_2)_m-NR^7R^{10}$, $-(CH_2)_n(CHOR^8)(CHOR^8)_n-CH_2OR^8$, $-(CH_2CH_2O)_m-R^8$, $-(CH_2CH_2O)_m-CH_2CH_2NR^7R^{10}$, $-(CH_2)$, $-C(=O)NR^7R^{10}$, $-(CH_2)_n-Z_g-R^7$, $-(CH_2)_m-NR^{10}-CH_2(CHOR^8)(CHOR^8)_n-CH_2OR^8$, $-(CH_2)_n-CO_2R^7$, or

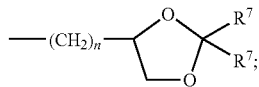

$R^3$ and $R^4$ are each, independently, hydrogen, a group represented by formula (A), lower alkyl, hydroxy lower alkyl, phenyl, phenyl-lower alkyl, (halophenyl)-lower alkyl, lower-(alkylphenylalkyl), lower (alkoxyphenyl)-lower alkyl, naphthyl-lower alkyl, or pyridyl-lower alkyl, with the proviso that at least one of $R^3$ and $R^4$ is a group represented by formula (A):

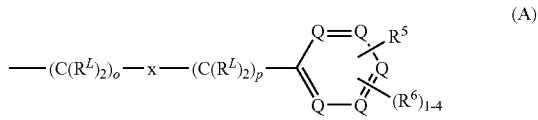

wherein
each $R^L$ is, independently, $-R^7$, $-(CH_2)-OR^8$, $-O-(CH_2)_m-OR^8$, $-(CH_2)_n$, $-NR^7R^{10}$, $-O-(CH_2)_m-NR^7R^{10}$, $-(CH_2)_n(CHOR^8)(CHOR^8)_n-CH_2OR^8$, $-O-(CH_2)_n(CHOR^8)(CHOR^8)$, $-CH_2OR^8$, $-(CH_2CH_2O)_m-R^8$, $-O-(CH_2CH_2O)_m-R^8$, $-(CH_2CH_2O)_m-CH_2CH_2NR^7R^{10}$, $-O-(CH_2CH_2O)_m-CH_2CH_2NR^7R^{10}$, $-(CH_2)$, $-C(=O)NR^7R^{10}$, $-O(CH_2)_m-C(=O)NR^7R^{10}$, $-(CH_2)_n-(Z)_g-R^7$, $-O-(CH_2)_m-(Z)_g-R^7$, $-(CH_2)_n-NR^{10}-CH_2(CHOR^8)(CHOR^8)_n$, $-CH_2OR^8$, $-O-(CH_2)_m-NR^{10}-CH_2(CHOR^8)(CHOR^8)_n-CH_2OR^8$, $-(CH_2)_n-CO_2R^7$, $-O-(CH_2)_m-CO_2R^7$, $-OSO_3H$, $-O$-glucuronide, $-O$-glucose,

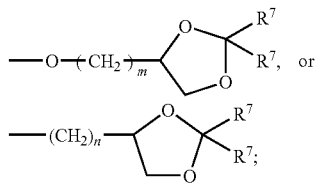

each o is, independently, an integer from 0 to 10;
each p is an integer from 0 to 10;
with the proviso that the sum of o and p in each contiguous chain is from 1 to 10;
each x is, independently, O, NR$^{10}$, C(=O), CHOH, C(=N-R$^{10}$), CHNR$^7$R$^{10}$, or represents a single bond;
wherein each $R^5$ is, independently, Link $-(CH_2)$, -CAP, Link $-(CH_2)_n(CHOR^8)(CHOR^8)_n$-CAP, Link $-(CH_2CH_2O)_m-CH_2$-CAP, Link $-(CH_2CH_2O)_m-CH_2CH_2$-CAP, Link $-(CH_2)_n-(Z)_g$-CAP, Link $-(CH_2)_n(Z)_g-(CH_2)_m$-CAP, Link $-(CH_2)$, $-NR^{13}-CH_2(CHOR^8)(CHOR^8)_n$-CAP, Link $-(CH_2)_n-(CHOR^8)_mCH_2-NR^{13}-(Z)_g$-CAP, Link $-(CH_2)_nNR^{13}-(CH_2)_m(CHOR^8)_nCH_2NR^{13}-(Z)_g$-CAP, Link $-(CH_2)_m-(Z)_g-(CH_2)_m$-CAP, Link NH$-C(=O)-NH-(CH_2)_m$-CAP, Link —$(CH_2)_m$—$C(=O)NR^{13}$—$(CH_2)_m$—$C(=O)NR^{10}R^{10}$, Link —$(CH_2)$, —$C(=O)NR^{13}$—$(CH_2)_m$-CAP, Link —$(CH_2)_m$—$C(=O)NR^{11}R^{11}$, Link —$(CH_2)_m$—$C(=O)NR^{12}R^{12}$, Link —$(CH_2)_n$—$(Z)_g$—$(CH_2)_m$—$(Z)_g$—CAP, Link -$Z_g$—$(CH_2)_m$-Het-$(CH_2)_m$-CAP;

each Link is, independently, —O—, —$(CH_2)_n$—, —$O(CH_2)_m$—, —$NR^{13}$—$C(=O)$—$NR^{13}$—, —$NR^{13}$—$C(=O)$—$(CH_2)_m$—, —$C(=O)NR^{13}$—$(CH_2)_m$—, —$(CH_2)_n$—$Z_g$—$(CH_2)_n$—, —S—, —SO—, —$SO_2$—, —$SO_2NR^7$—, —$SO_2NR^{10}$—, or -Het-;

each CAP is, independently, thiazolidinedione, oxazolidinedione, heteroaryl-$C(=O)N$ $R^{13}R^{13}$, heteroaryl-W, —CN, —O—$C(=S)NR^{13}R^{13}$, -$Z_gR^{13}$, —$CR^{10}(Z_gR^{13})(Z_gR^{13})$, —$C(=O)OAr$, —$C(=O)NR^{13}Ar$, imidazoline, tetrazole, tetrazole amide, —$SO_2NHR^{13}$, —$SO_2NH$—$C(R^{13}R^{13})$-$(Z)_g$—$R^{13}$, a cyclic sugar or oligosaccharide, a cyclic amino sugar or oligosaccharide,

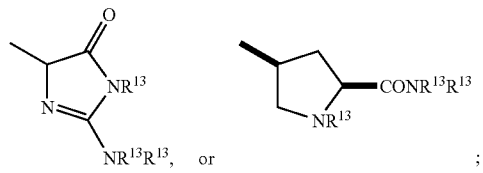

each Ar is, independently, phenyl, substituted phenyl, wherein the substituents of the substituted phenyl are 1-3 substituents independently selected from the group consisting of OH, $OCH_3$, $NR^{13}R^{13}$, Cl, F, and $CH_3$, or heteroaryl;

each W is independently, thiazolidinedione, oxazolidinedione, heteroaryl-$C(=O)NR^{13}R^{13}$—CN, —O—$C(=S)NR^{13}R^{13}$, -$Z_gR^{13}$, —$CR^{10}(Z_gR^{13})(Z_gR^{13})$, —$C(=O)OAr$, —$C(=O)NR^{13}Ar$, imidazoline, tetrazole, tetrazole amide, —$SO_2NHR^{13}$, —$SO_2NH$—$C(R^{13}R^{13})$-$(Z)_g$—$R^{13}$, a cyclic sugar or oligosaccharide, a cyclic amino sugar or oligosaccharide,

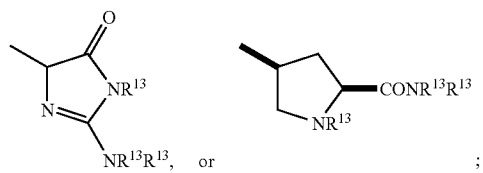

each $R^6$ is, independently, —$R^7$, —$OR^7$, —$OR^{11}$, —$N(R^7)_2$, —$(CH_2)_m$—$OR^8$, —O—$(CH_2)_m$—$OR^8$, —$(CH_2)_n$—$NR^7R^{10}$, —O—$(CH_2)_m$—$NR^7R^{10}$, —$(CH_2)_n$$(CHOR^8)(CHOR^8)_n$—$CH_2OR^8$, —O—$(CH_2)_m(CHOR^8)(CHOR^8)_n$—$CH_2OR^8$, —$(CH_2CH_2O)_m$—$R^8$, —O—$(CH_2CH_2O)_m$—$R^8$, —$(CH_2CH_2O)_m$—$CH_2CH_2NR^7R^{10}$, —O—$(CH_2CH_2O)_m$—$CH_2CH_2NR^7R^{10}$, —$(CH_2)_n$—$C(=O)NR^7R^{10}$, —O—$(CH_2)_m$—$C(=O)NR^7R^{10}$, —$(CH_2)_n$—$(Z)_g$—$R^7$, —O—$(CH_2)_n$—$(Z)_g$—$R^7$, —$(CH_2)_n$—$NR^{10}$—$CH_2(CHOR^8)(CHOR^8)_n$—$CH_2OR^8$, —O—$(CH_2)_m$—$NR^{10}$—$CH_2(CHOR^8)(CHOR^8)_n$—$CH_2OR^8$, —$(CH_2)$—$CO_2R^7$, —O—$(CH_2)_m$—$CO_2R^7$, —$OSO_3H$, —O-glucuronide, —O-glucose,

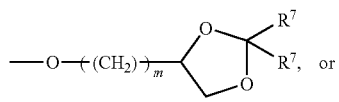

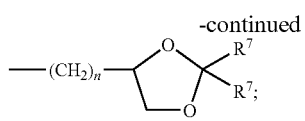

wherein when two $R^6$ are —$OR^{11}$ and are located adjacent to each other on a phenyl ring, the alkyl moieties of the two $R^6$ may be bonded together to form a methylenedioxy group; with the proviso that when at least two —$CH_2OR^8$ are located adjacent to each other, the $R^8$ groups may be joined to form a cyclic mono- or di-substituted 1,3-dioxane or 1,3-dioxolane, each $R^7$ is, independently, hydrogen lower alkyl, phenyl, or substituted phenyl;

each $R^8$ is, independently, hydrogen, lower alkyl, —$C(=O)$—$R^{11}$, glucuronide, 2-tetrahydropyranyl, or

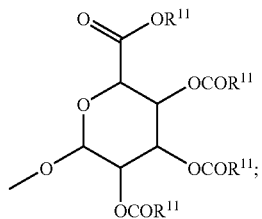

each $R^9$ is, independently, —$CO_2R^{13}$, —$CON(R^{13})_2$, —$SO_2CH_2R^{13}$, or —$C(=O)R^{13}$;

each $R^{10}$ is, independently, —H, —$SO_2CH_3$, —$CO_2R^7$, —$C(=O)NR^7R^9$, —$C(=O)R^7$, or —$CH_2$—(CHOH), —$CH_2OH$;

each Z is, independently, CHOH, $C(=O)$, —$(CH_2)_n$—, $CHNR^{13}R^{13}$, C=$NR^{13}$, or N13 each $R^{11}$ is, independently, lower alkyl;

each $R^{12}$ is independently, —$SO_2CH_3$, —$CO_2R^3$, —$C(=O)NR^{13}R^{13}$, —$C(=O)R^{13}$, or (CHOH), —$CH_2OH$;

each $R^{13}$ is, independently, hydrogen, $R^7$, $R^{10}$, —$(CH_2)_m$—$NR^7R^{10}$,

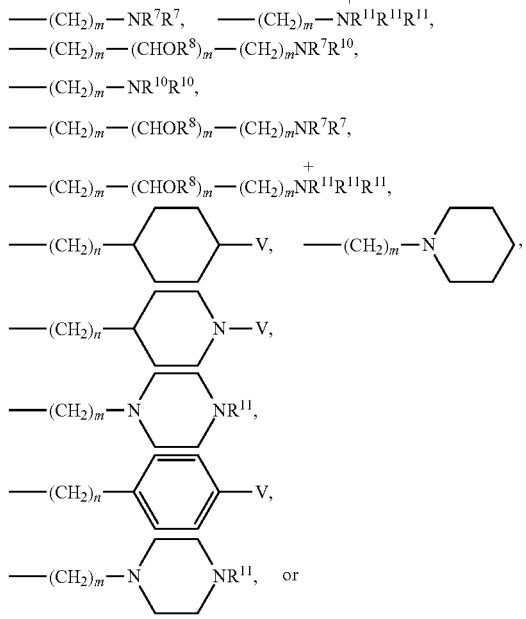

—(CH$_2$)$_m$—N⏜N—V;

with the proviso that NR$^{13}$R$^{13}$ can be joined on itself to form a ring comprising one of the following:

—N⏜NR$^{11}$,

—N⏜N—(CH$_2$)$_m$(CHOR$^8$)$_m$—(CH$_2$)$_n$R$^{11}$,

—N⏜N—(CH$_2$)$_m$(CHOR$^8$)$_m$—(CH$_2$)$_n$R$^{11}$;

each Het is independently, —NR$^3$, —S—, —SO—, —SO$_2$—, —O—, —SO$_2$NR$^{13}$—, —NHSO$_2$—, —NR$^{13}$CO—, or —CONR$^{13}$—;

each g is, independently, an integer from 1 to 6;
each m is, independently, an integer from 1 to 7;
each n is, independently, an integer from 0 to 7;
each Q is, independently, C—R$^5$, C—R$^6$, or a nitrogen atom, wherein one Q is C—R$^5$ and at most three Q in a ring are nitrogen atoms;
each V is, independently, —(CH$_2$)$_m$—NR$^7$R$^{10}$, —(CH$_2$)$_m$—NR$^7$R$^7$, —(CH$_2$)$_m$—

$\overset{+}{\text{NR}^{11}\text{R}^{11}\text{R}^{11}}$, —(CH$_2$)$_n$—(CHOR$^8$)$_m$—(CH$_2$)$_m$NR$^7$R$^{10}$, —(CH$_2$)$_n$—NR$^{10}$R$^{10}$, —(CH$_2$)$_n$—(CHOR$^8$)$_m$—(CH$_2$)$_m$NR$^7$R$^7$, —(CH$_2$)$_n$—(CHOR$^8$)$_m$—(CH$_2$)$_m\overset{+}{\text{NR}^{11}\text{R}^{11}\text{R}^{11}}$, with the proviso that when V is attached directly to a nitrogen atom, then V can also be, independently, R$^7$, R$^{10}$, or (R$^{11}$)$_2$;
wherein for any of the above compounds when two —CH$_2$OR$^8$ groups are located 1,2- or 1,3- with respect to each other the R$^8$ groups may be joined to form a cyclic mono- or di-substituted 1,3-dioxane or 1,3-dioxolane;
wherein any of the above compounds can be a pharmaceutically acceptable salt thereof, and wherein the above compounds are inclusive of all enantiomers, diastereomers, and racemic mixtures thereof.

In a fourth embodiment of the invention:
each R$^2$ is, independently, —R$^7$, —(CH$_2$)$_m$—OR$^8$, —(CH$_2$)$_m$—NR$^7$R$^{10}$, —(CH$_2$)$_n$(CHOR$^8$)(CHOR$^8$)$_n$—CH$_2$OR$^8$, —(CH$_2$CH$_2$O)$_m$—R$^8$, —(CH$_2$CH$_2$O), —CH$_2$CH$_2$NR$^7$R$^{10}$, —(CH$_2$)$_n$—C(=O)NR$^7$R$^{10}$, —(CH$_2$)$_n$—Z$_g$—R$^7$, —(CH$_2$)$_m$—NR$^{10}$—CH$_2$(CHOR$^8$)(CHOR$^8$)$_n$—CH$_2$OR$^8$, —(CH$_2$)$_n$—CO$_2$R$^7$, or —(CH$_2$)$_n$—[tetrahydrofuran ring with R$^7$, R$^7$];

wherein when two —CH$_2$OR$^8$ groups are located 1,2- or 1,3- with respect to each other the R$^8$ groups may be joined to form a cyclic mono- or di-substituted 1,3-dioxane or 1,3-dioxolane;

R$^3$ and R$^4$ are each, independently, hydrogen, a group represented by formula (A), lower alkyl, hydroxy lower alkyl, phenyl, phenyl-lower alkyl, (halophenyl)-lower alkyl, lower-(alkylphenylalkyl), lower (alkoxyphenyl)-lower alkyl, naphthyl-lower alkyl, or pyridyl-lower alkyl, with the proviso that at least one of R$^3$ and R$^4$ is a group represented by formula (A):

(A)
—(C(R$^L$)$_2$)$_o$—x—(C(R$^L$)$_2$)$_p$—[ring with Q=Q, Q—Q, R$^5$, (R$^6$)$_{1-4}$]

wherein
each R$^L$ is, independently, —R$^7$, —(CH$_2$)$_n$—OR$^8$, —O—(CH$_2$)$_m$—OR$^8$, —(CH$_2$)$_n$—NR$^7$R$^{10}$, —O—(CH$_2$)$_m$—NR$^7$R$^{10}$, —(CH$_2$)$_n$(CHOR$^8$)(CHOR$^8$)$_n$—CH$_2$OR$^8$, —O—(CH$_2$)$_m$(CHOR$^8$)(CHOR$^8$)$_n$—CH$_2$OR$^8$, —(CH$_2$CH$_2$O)$_m$—R$^8$, —O—(CH$_2$CH$_2$O)$_m$—R$^8$, —(CH$_2$CH$_2$O)$_m$—CH$_2$CH$_2$NR$^7$R$^{10}$, —O—(CH$_2$CH$_2$O), —CH$_2$CH$_2$NR$^7$R$^{10}$, —(CH$_2$), —C(=O)NR$^7$R$^{10}$, —O—(CH$_2$)$_m$—C(=O)NR$^7$R$^{10}$, —(CH$_2$)$_n$—(Z)$_g$—R$^7$, —O—(CH$_2$)$_m$—(Z)$_g$—R$^7$, —(CH$_2$)$_n$—NR$^{10}$—CH$_2$(CHOR$^8$)(CHOR$^8$)$_n$—CH$_2$OR$^8$, —O—(CH$_2$)$_m$—NR$^{10}$—CH$_2$(CHOR$^8$)(CHOR$^8$)$_n$—CH$_2$OR$^8$, —(CH$_2$)$_n$—CO$_2$R$^7$, —O—(CH$_2$)$_m$—CO$_2$R$^7$, —OSO$_3$H, —O-glucuronide, —O-glucose, —O—(CH$_2$)$_m$—[tetrahydrofuran ring with R$^7$, R$^7$], or —(CH$_2$)$_n$—[tetrahydrofuran ring with R$^7$, R$^7$];

wherein when two —CH$_2$OR$^8$ groups are located 1,2- or 1,3- with respect to each other the R$^8$ groups may be joined to form a cyclic mono- or di-substituted 1,3-dioxane or 1,3-dioxolane;
each o is, independently, an integer from 0 to 10;
each p is an integer from 0 to 10;
with the proviso that the sum of o and p in each contiguous chain is from 1 to 10;
each x is, independently, O, NR$^{10}$, C(=O), CHOH, C(=N—R$^{10}$), CHNR$^7$R$^{10}$, or represents a single bond;
each R$^5$ is independently, —(CH$_2$)$_n$—CO$_2$R$^{13}$, Het-(CH$_2$)$_m$—CO$_2$R$^{13}$, —(CH$_2$)$_n$—Z$_g$-CO$_2$R$^{13}$, Het-(CH$_2$)$_m$—Z$_g$—CO$_2$R$^{13}$, —(CH$_2$)$_n$—NR$^{10}$—(CH$_2$)$_n$(CHOR$^8$)$_n$—CO$_2$R$^{13}$, Het-(CH$_2$)$_m$—NR$^{10}$—(CH$_2$)$_m$(CHOR$^8$)$_n$—CO$_2$R$^{13}$, —(CH$_2$)$_n$—(CHOR$^8$)$_m$—CO$_2$R$^{13}$, Het-(CH$_2$)$_m$—(CHOR$^8$)$_m$—CO$_2$R$^{13}$, —(CH$_2$)$_n$—(CHOR$^8$)$_m$—Z$_g$—CO$_2$R$^{13}$, Het-(CH$_2$)$_n$—(CHOR$^8$)$_m$—Z$_g$-CO$_2$R$^{13}$, —(CH$_2$)$_n$—Z$_g$—(CH$_2$)$_m$—CO$_2$R$^{13}$, —(CH$_2$)$_n$—Z$_g$—(CH$_2$)$_m$—CO$_2$R$^{13}$, —(CH$_2$)$_n$-Z$_g$(CHOR$^8$)$_m$—Z$_g$—CO$_2$R$^{13}$, Het-(CH$_2$)$_n$—Z$_g$—(CHOR$^8$)$_n$—Z$_g$—CO$_2$R$^{13}$, —(CH$_2$)$_n$—CONH—C(=NR$^{13}$)—NR$^{13}$R$^{13}$, Het-(CH$_2$)$_n$—CO—NH—C(=NR$^{13}$)—NR$^{13}$R$^{13}$, —(CH$_2$)$_n$—Z$_g$—CONH—C(=NR$^{13}$)—NR$^{13}$R$^{13}$, Het-(CH$_2$)$_n$—Z$_g$—CONH—C (=NR¹³)—NR¹³R¹³, —(CH₂)ₙ—NR¹⁰—(CH₂)ₘ(CHOR⁸)ₙ—CONH—C(=NR¹³)—NR¹³R¹³, Het-(CH₂)ₙ—NR¹⁰—(CH₂)ₘ(CHOR⁸)ₙ—CONH—C(=NR¹³)ₙ—NR¹³R¹³, —(CH₂)ₙ—(CHOR⁸)ₘ—CONH—C(=NR¹³)—NR¹³R¹³, Het-(CH₂)ₙ—(CHOR⁸)ₘ—CONH—C(=NR¹³)—NR¹³R¹³, —(CH₂)ₙ—(CHOR⁸)ₘ—Z_g—CONH—C(=NR¹³)—NR¹³R¹³, Het-(CH₂)ₙ—(CHOR⁸)ₘ—Z_g—CONH—C(=NR¹³)NR¹³R¹³, —(CH₂)ₙ-Z_g—(CH₂)ₘ—CONH—C(=NR¹³)—NR¹³R¹³, Het-(CH₂)ₙ—Z_g—(CH₂)ₘ—CONH—C(=NR¹³)—NR¹³R¹³, —(CH₂)ₙ—Z_g—(CHOR⁸)ₘ—Z_g—CONH—C(=NR¹³)—NR¹³R¹³, Het-(CH₂)ₙ—Z_g-(CHOR⁸)ₘ—Z_g—CONH—C(=NR¹³)—NR¹³R¹³, —(CH₂)ₙ—CONR⁷—CONR¹³R¹³, Het-(CH₂)ₙ—CONR⁷—CON¹³R¹³, —(CH₂)ₙ—Z_g—CONR⁷—CONR¹³R¹³, —(CH₂)ₙ—Z_g—CONR⁷—CONR¹³R¹³, —(CH₂)—NR¹⁰—(CH₂)ₙ(CHOR⁸)ₙ—CONR⁷—CONR¹³R¹³, Het-(CH₂)ₙ—NR¹⁰—(CH₂)ₘ(CHOR⁸)—CONR⁷—CONR¹³R¹³, —(CH₂)ₙ—(CHOR⁸)ₘ—CONR⁷—CONR¹³R¹³, Het-(CH₂)ₙ—(CHOR⁸)ₘ—CONR⁷—CONR¹³R¹³, —(CH₂)ₙ—(CHOR⁸)ₘ—Z_g—CONR⁷—CONR¹³R¹³, Het-(CH₂)ₙ—(CHOR⁸)ₘ—Z_g—CNR⁷—CONR¹³R¹³, —(CH₂)ₙ—Z_g—(CH₂)ₘCONR⁷—CONR¹³R¹³, Het-(CH₂)ₙ—Z_g—(CH₂)ₘCONR⁷—CONR¹³R¹³, —(CH₂)ₙ-Z_g(CHOR⁸)ₘ—Z_g—CONR⁷—CONR¹³R¹³, Het-(CH₂)ₙ—Z_g(CHOR⁸)ₘ—Z_g—CONR⁷—CONR¹³R¹³, —(CH₂)ₙ—CONR⁷SO₂NR¹³R¹³, Het-(CH₂)ₘ—CONR⁷SO₂NR¹³R¹³, —(CH₂)ₙ-Z_g—CONR⁷SO₂NR¹³R¹³, Het-(CH₂)ₘ—Z_g—CONR⁷SO₂NR¹³R¹³, —(CH₂)ₙ—NR¹⁰—(CH₂)ₘ(CHOR⁸)ₙ—CONR⁷SO₂NR¹³R¹³, Het-(CH₂)ₘ—NR¹⁰—(CH₂)ₘ(CHOR⁸)ₙ—CONR⁷SO₂NR¹³R¹³, —(CH₂)ₙ—(CHOR⁸)ₘ—CONR⁷SO₂NR¹³R¹³, Het-(CH₂)ₘ—(CHOR⁸)ₘCONR⁷SO₂NR¹³R¹³—(CH₂)ₙ—(CHOR⁸)ₘ—Z_g—CONR⁷SO₂NR¹³R¹³, Het-(CH₂)ₙ—(CHOR⁸)ₘ—Z_g—CONR⁷SO₂NR¹³R¹³, —(CH₂)ₙ—Z_g—(CH₂)ₘCONR⁷SO₂NR¹³R¹³, Het-(CH₂)ₙ—Z_g—(CH₂)ₙCONR⁷SO₂NR¹³R¹³, —(CH₂)ₙ—Z_g—(CHOR⁸)ₘ—Z_g-CONR⁷SO₂NR¹³R¹³, Het-(CH₂)ₙ—Z_g—(CHOR⁸)ₘ—Z_g—CONR⁷SO₂NR¹³R¹³, —(CH₂)ₘ—SO₂NR¹³R¹³, Het-(CH₂)ₘ—SO₂N¹³R¹³, —(CH₂)ₙ—Z_g-SO₂NR¹³R¹³, Het-(CH₂)ₘ—Z_g—SO₂NR¹³R¹³, —(CH₂)ₙ—NR¹⁰—(CH₂)ₘ(CHOR⁸)ₙ—SO₂NR¹³R¹³, Het-(CH₂)ₙ—NR¹⁰—(CH₂)ₘ(CHOR⁸)ₙ—SO₂, NR¹³R¹³, —(CH₂)ₙ—(CHOR⁸)ₘ—SO₂NR¹³R¹³, Het-(CH₂)ₘ—(CHOR⁸)ₘ—SO₂NR¹³R¹³, —(CH₂)ₙ—(CHOR⁸)ₘ—Z_g-SO₂NR¹³R¹³, Het-(CH₂)ₙ—(CHOR⁸)ₘ-Z_g-SO₂NR¹³R¹³, —(CH₂)ₙ—Z_g—(CH₂)ₘ SO₂NR¹³R¹³, Het-(CH₂)ₙ—Z_g—(CH₂)ₘ SO₂NR¹³R¹³, —(CH₂)ₙ—Z_g—(CHOR⁸)ₘ—Z_g-SO₂NR¹³R¹³, Het-(CH₂)ₙ—Z_g—(CHOR⁸)ₘ—Z_g-SO₂NR¹³R¹³, —(CH₂)ₙ—CONR¹³R¹³, Het-(CH₂)ₘ—CONR¹³R¹³, —(CH₂)ₙ—Z_g—CONR¹³R¹³, Het-(CH₂)ₘ -Z_g—CONR¹³R¹³, —(CH₂)ₙ—NR¹⁰—(CH₂)ₘ(CHOR⁸)ₙ—CONR¹³R¹³, Het-(CH₂)ₘ—NR¹⁰—(CH₂)ₙ (CHOR⁸)ₙ—CONR¹³R¹³, —(CH₂)ₙ—(CHOR⁸)ₘ—CONR¹³R¹³, Het-(CH₂)ₘ—(CHOR⁸)ₘ—CONR¹³R¹³, —(CH₂)ₙ—(CHOR⁸)ₘ—Z_g—CONR¹³R¹³, Het-(CH₂)ₙ—(CHOR⁸)ₘ-Z_g—CONR¹³R¹³, —(CH₂)ₙ—Z_g—(CH₂)ₘCONR¹³R¹³, Het-(CH₂)ₙ—Z_g—(CH₂)ₘ CONR¹³R¹³, —(CH₂)ₙ—Z_g—(CHOR⁸)ₘ—Z_g—CONR¹³R¹³, Het-(CH₂)ₙ—Z_g—(CHOR⁸)ₘ—Z_g—CONR¹³R¹³, —(CH₂)ₙ—CONR⁷COR¹³, Het-(CH₂)ₙ—CONR⁷COR¹³, Het-(CH₂)ₘ—Z_g—CONR⁷COR³, —(CH₂)ₙ—NR¹⁰—(CH₂)ₘ(CHOR⁸)ₙ—CONR⁷COR¹³, Het-(CH₂)ₘ—NR¹⁰—(CH₂)ₙ(CHOR⁸)ₙ—CONR⁷COR¹³, —(CH₂)ₙ—(CHOR⁸)ₘ—CONR⁷COR¹³, —(CH₂)ₙ—(CHOR⁸)ₘ—CONR⁷COR¹³, Het-(CH₂)ₙ—(CHOR⁸)ₙ—CONR⁷COR¹³Het-(CH₂)ₙ—(CHOR⁸)ₘ—Z_g—CONR⁷COR¹³, Het-(CH₂)ₙ—(CHOR⁸)ₙ—Z_g—CONR⁷COR¹³, —(CH₂)ₙ—Z_g—(CH₂)ₘCONR⁷COR¹³, —(CH₂)ₙ—Z_g-(CH₂)ₘCONR⁷COR¹³, Het-(CH₂)ₙ—Z_g—(CHOR⁸)ₘ—Z_g—CONR⁷COR¹³, —(CH₂)ₙ—CONR⁷CO₂R¹³, —(CH₂)ₙ —Z_g—CONR⁷CO₂R¹³, Het-(CH₂)ₘZ_g—CONR⁷CO₂R¹³, —(CH₂)ₙ—NR¹⁰—(CH₂)ₘ(CHOR⁸)ₘ—CONR⁷CO₂R¹³, Het-(CH₂)ₘ—NR¹⁰—(CH₂)ₘ(CHOR⁸)ₙ—CO NR⁷CO₂R¹³, —(CH₂)ₙ—(CHOR⁸)ₘ—CONR⁷CO₂R¹³, Het-(CH₂)ₘ—(CHOR⁸)ₘ—CONR⁷CO₂R¹³, —(CH₂)ₙ—(CHOR⁸)ₙ—Z_g—CONR⁷CO₂R¹³, Het-(CH₂)ₙ—(CHOR⁸)ₘ—Z_g-CONR⁷CO₂R¹³, —-(CH₂)ₙ—Z_g—(CH₂)ₘCONR⁷CO₂R¹³, Het-(CH₂)ₙ—Z_g-(CH₂)ₘCONR⁷CO₂R¹³, —(CH₂)ₙ—Z_g—(CHOR⁸)ₘ—Z_g—CONR⁷CO₂R¹³, Het-(CH₂)ₙ—Z_g-(CHOR⁸)ₘ—Z_g—CONR⁷CO₂R¹³, —(CH₂)ₙ—NH—C(=NR¹³)—NR¹³R¹³, Het-(CH₂)ₘ—NH—C(=NR¹³)—NR¹³R¹³, —(CH₂)ₙ—Z_g-NH—C(=NR¹³)—NR¹³R¹³ Het-(CH₂)ₘ—Z_g-NH—C(=NR¹³)—NR¹³R¹³, —(CH₂)ₙ—NR¹⁰—(CH₂)ₘ(CHOR⁸)ₘ—NH—C(=NR¹³)—NR¹³R¹³, Het-(CH₂)ₘ—NR¹⁰—(CH₂)ₘ(CHOR⁸)ₙ—NH—C(=NR¹³)—NR¹³R¹³, —(CH₂)ₙ—(CHOR⁸)ₘ—NH—C(=NR¹³)NR¹³R¹³, Het-(CH₂)ₘ—(CHOR⁸)ₘ—NH—C(=NR¹³)—NR¹³R¹³, —(CH₂)ₙ—(CHOR⁸)ₘ—Z_g-NH—C(=NR¹³)—NR¹³R¹³, Het-(CH₂)ₙ—(CHOR⁸)ₘ—Z_g-NH—C(=NR¹³)—NR¹³R¹³, —(CH₂)ₙ—Z_g—(CH₂)ₘNH—C(=NR¹³)—NR¹³R¹³, Het-(CH₂)ₙ—Z_g—(CH₂)ₘNH—C(=NR¹³)—NR¹³R¹³, —(CH₂)ₙ—Z_g—(CHOR⁸)ₘ—Z_g-NH—C(=NR¹³)—NR¹³R¹³, Het-(CH₂)ₙ-Z_g—(CHOR⁸)ₘ—Z_g-NH—C(=NR¹³)—NR¹³R¹³, —(CH₂)ₙ—C(=NR¹³)—NR¹³R¹³, Het-(CH₂)ₘ—C(=NH)—NR¹³R¹³, —(CH₂)ₙ—Z_g—C(=NH)NR¹³R¹³, Het-(CH₂)ₘ—Z_g—C(=NH)—NR¹³R¹³, —(CH₂)ₙ—NR¹⁰—(CH₂)ₘ(CHOR⁸)ₙ—C(=NR¹³)—NR¹³R¹³, Het-(CH₂)ₘ—NR¹⁰—(CH₂)ₘ(CHOR⁸)ₙ—C(=NR¹³)—NR¹³R¹³, —(CH₂)ₘ—(CHOR⁸)ₘ—NH—C(=NR¹³)—NR¹³R¹³, Het-(CH₂)ₘ—(CHOR⁸)ₙ—C(=NR¹³)—NR¹³R¹³, —(CH₂)ₙ—(CHOR⁸)ₙ—Z_g—C(=NR¹³)—NR¹³R¹³, Het-(CH₂)ₙ—(CHOR⁸)ₘ—Z_g—C(=NR¹³)—NR¹³R¹³, —(CH₂)ₙ—Z_g—(CH₂)ₘ—C(=NHC(=NR¹³)—NR¹³R¹³, Het-(CH₂)ₙ—Z_g—(CH₂)ₘ—C(=NR¹³)—NR¹³R¹³, —(CH₂)ₙ—Z_g—(CHOR⁸)ₘ—Z_g-C(=NR¹³)—NR¹³R¹³, Het-(CH₂)ₙ—Z_g—(CHOR⁸)ₘ—Z_g—C(=NR¹³)—NR¹³R¹³;

wherein when two —CH₂OR⁸ groups are located 1,2- or 1,3- with respect to each other the R⁸ groups may be joined to form a cyclic mono- or di-substituted 1,3-dioxane or 1,3-dioxolane;

each R⁶ is, independently, —R⁵, —R⁷, —OR⁸, —N(R⁷)₂, —(CH₂)ₘ—OR⁸, —O—(CH₂)ₘ—OR⁸, —(CH₂)ₙ—NR⁷R¹⁰, —O—(CH₂)ₘ—NR⁷R¹⁰, —(CH₂)ₙ(CHOR⁸)(CHOR⁸)ₙ—CH₂OR⁸, —O—(CH₂)ₘ(CHOR⁸)(CHOR⁸)ₙ—CH₂OR⁸, —(CH₂CH₂O)ₘ—R⁸, —O—(CH₂CH₂O)ₘ—R⁸, —(CH₂CH₂O)ₘ—CH₂CH₂NR⁷R¹⁰, —O—(CH₂CH₂O)ₘ—CH₂CH₂NR⁷R¹⁰, —(CH₂)ₘ—C(=O)NR⁷R¹⁰, —O—(CH₂)ₘ—C(=O)NR⁷R¹⁰, —(CH₂)ₙ—(Z)_g—R⁷, —O—(CH₂)ₙ—(Z)_g—R⁷, —(CH₂)ₙ—NR¹⁰—CH₂(CHOR⁸)(CHOR⁸)ₙ—CH₂OR⁸, —O—(CH₂)ₘ—NR¹⁰—CH₂(CHOR⁸)(CHOR⁸)ₙ—CH₂OR⁸, —(CH₂)ₙ—CO₂R⁷, —O—(CH₂)ₘ—CO₂R⁷, —OSO₃H, —O-glucuronide, —O-glucose,

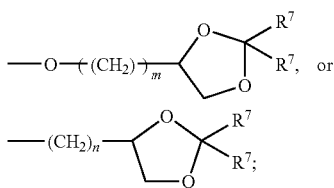

wherein when two R$^6$ are —OR$^{11}$ and are located adjacent to each other on a phenyl ring, the alkyl moieties of the two R$^6$ may be bonded together to form a methylenedioxy group, and wherein when two —CH$_2$OR$^8$ groups are located 1,2- or 1,3- with respect to each other the R$^8$ groups may be joined to form a cyclic mono- or di-substituted 1,3-dioxane or 1,3-dioxolane;

each R$^7$ is, independently, hydrogen lower alkyl, phenyl, or substituted phenyl;

each R$^8$ is, independently, hydrogen, lower alkyl, —C(=O)—R$^{11}$, glucuronide, 2-tetrahydropyranyl, or

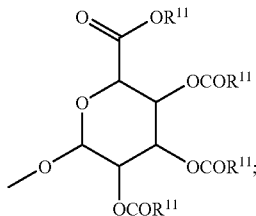

each R$^9$ is, independently, —CO$_2$R$^7$, —CON(R$^7$)$_2$, —SO$_2$CH$_3$, or —C(=O)R$^7$;

each R$^{10}$ is, independently, —H, —SO$_2$CH$_3$, —CO$_2$R$^7$, —C(=O)NR$^7$R$^9$, —C(=O)R$^7$, or —CH$_2$—(CHOH)$_n$—CH$_2$OH;

each Z is, independently, CHOH, C(=O), —(CH$_2$)$_n$—, CHNR$^7$R$^{10}$, C=NR$^{10}$, or NR$^{10}$;

each R$^{11}$ is, independently, lower alkyl;

each R$^{12}$ is independently, —SO$_2$CH$_3$, —CO$_2$R$^7$, —C(=O)NR$^7$R$^9$, —C(=O)R$^7$, or —CH$_2$—(CHOH)$_n$—CH$_2$OH;

each R$^{13}$ is, independently, hydrogen, R$^7$, R$^{10}$, —(CH$_2$)$_m$—NR$^7$R$^{10}$, —(CH$_2$)$_m$—NR$^7$R$^7$,    —(CH$_2$)$_m$—$\overset{+}{N}$R$^{11}$R$^{11}$R$^{11}$, —(CH$_2$)$_m$—(CHOR$^8$)$_m$—(CH$_2$)$_m$NR$^7$R$^{10}$, —(CH$_2$)$_m$—NR$^{10}$R$^{10}$, —(CH$_2$)$_m$—(CHOR$^8$)$_m$—(CH$_2$)$_m$NR$^7$R$^7$, —(CH$_2$)$_m$—(CHOR$^8$)$_m$—(CH$_2$)$_m$$\overset{+}{N}$R$^{11}$R$^{11}$R$^{11}$,

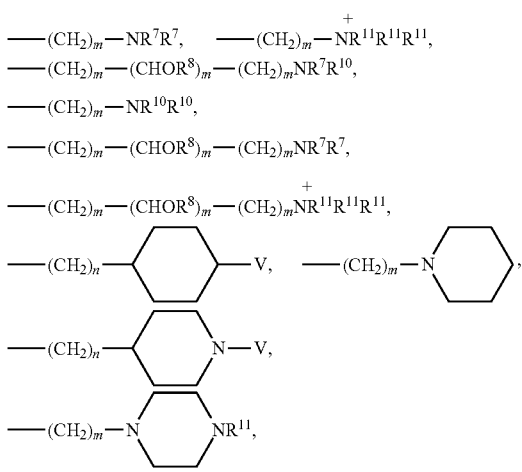

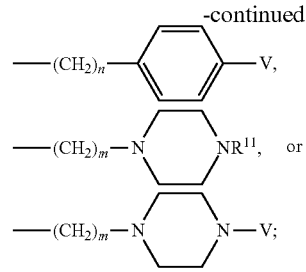

with the proviso that at least one R$^{13}$ must be a group other than hydrogen, R$^7$, or R$^{10}$;

with the further proviso that NR$^{13}$R$^{13}$ can be joined on itself to form a ring comprising one of the following:

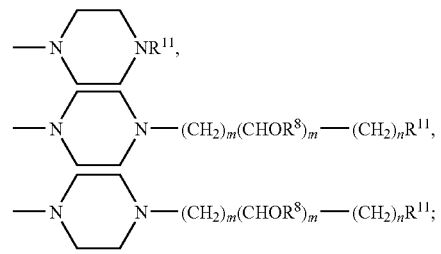

each Het is independently, —NR$^7$, —NR$^{10}$, —S—, —SO—, —SO$_2$—, —O—, —SO$_2$NH—, —NHSO$_2$—, —NR$^7$CO—, or —CONR$^7$—;

each g is, independently, an integer from 1 to 6;
each m is, independently, an integer from 1 to 7;
each n is, independently, an integer from 0 to 7;
each Q is, independently, C—R$^5$, C—R$^6$, or a nitrogen atom, wherein one Q is C—R$^5$ and at most three Q in a ring are nitrogen atoms;
each V is, independently, —(CH$_2$)$_m$—NR$^7$R$^{10}$, —(CH$_2$)$_m$—NR$^7$R$^7$, —(CH$_2$)$_m$ $\overset{+}{N}$R$^{11}$R$^{11}$R$^{11}$,    —(CH$_2$)$_n$—(CHOR$^8$)$_m$—(CH$_2$)$_m$NR$^7$R$^{10}$, —(CH$_2$)$_n$—NR$^{10}$R$^{10}$ —(CH$_2$)$_n$—(CHOR$^8$)$_m$—(CH$_2$)$_m$NR$^7$R$^7$, —(CH$_2$)$_n$—(CHOR$^8$)$_m$—(CH$_2$)$_m$$\overset{+}{N}$R$^{11}$R$^{11}$R$^{11}$ with the proviso that when V is attached directly to a nitrogen atom, then V can also be, independently, R$^7$, R$^{10}$, or (R$^{11}$)$_2$;

wherein for any of the above compounds when two —CH$_2$OR$^8$ groups are located 1,2- or 1,3- with respect to each other the R$^8$ groups may be joined to form a cyclic mono- or di-substituted 1,3-dioxane or 1,3-dioxolane;

wherein any of the above compounds can be a pharmaceutically acceptable salt thereof, and wherein the above compounds are inclusive of all enantiomers, diastereomers, and racemic mixtures thereof.

In a fifth embodiment of the invention:

each R$^2$ is, independently, —R$^7$, —(CH$_2$)$_n$—OR$^8$, —(CH$_2$)$_m$—NR$^7$R$^{10}$, —(CH$_2$)$_n$(CHOR$^8$)(CHOR$^8$)$_n$—CH$_2$OR$^8$, —(CH$_2$CH$_2$O)$_m$—R$^8$, —(CH$_2$CH$_2$O)$_m$—CH$_2$CH$_2$NR$^7$R$^{10}$, —(CH$_2$)$_n$—C(=O)NR$^7$R$^{10}$, —(CH$_2$)$_n$—

$Z_g$—$R^7$, —$(CH_2)_m$—$NR^{10}$—$CH_2(CHOR^8)(CHOR^8)_n$—$CH_2OR^8$, —$(CH_2)_n$—$CO_2R^7$, or

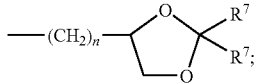

wherein when two —$CH_2OR^8$ groups are located 1,2- or 1,3- with respect to each other the $R^8$ groups may be joined to form a cyclic mono- or di-substituted 1,3-dioxane or 1,3-dioxolane; $R^3$ and $R^4$ are each, independently, hydrogen, a group represented by formula (A), lower alkyl, hydroxy lower alkyl, phenyl, phenyl-lower alkyl, (halophenyl)-lower alkyl, lower-(alkylphenylalkyl), lower (alkoxyphenyl)-lower alkyl, naphthyl-lower alkyl, or pyridyl-lower alkyl, with the proviso that at least one of $R^3$ and $R^4$ is a group represented by formula (A):

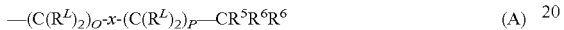

wherein
each $R^L$ is, independently, —$R^7$, —$(CH_2)_n$—$OR^8$, —O—$(CH_2)_m$—$OR^8$, —$(CH_2)_n$—$NR^7R^{10}$, —O—$(CH_2)_m$—$NR^7R^{10}$, —$(CH_2)_n(CHOR^8)(CHOR^8)_n$—$CH_2OR^8$, —O—$(CH_2)_m(CHOR^8)(CHOR^8)_n$—$CH_2OR^8$, —$(CH_2CH_2O)_m$—$R^8$, —O—$(CH_2CH_2O)_m$—$R^8$, —$(CH_2CH_2O)_m$—$CH_2CH_2NR^7R^{10}$, —O—$(CH_2CH_2O)_m$—$CH_2CH_2NR^7R^{10}$, —$(CH_2)_n$—C(=O)$NR^7R^{10}$, —O—$(CH_2)_m$—C(=O)$NR^7R^{10}$, —$(CH_2)_n$—$(Z)_g$—$R^7$, —O—$(CH_2)_m$—$(Z)_g$—$R^7$, —$(CH_2)_n$—$NR^{10}$—$CH_2(CHOR^8)(CHOR^8)_n$—$CH_2OR^8$, —O—$(CH_2)_m$—$NR^{10}$—$CH_2(CHOR^8)(CHOR^8)_n$—$CH_2OR^8$, —$(CH_2)_n$—$CO_2R^7$, —O—$(CH_2)_m$—$CO_2R^7$, —$OSO_3H$, —O-glucuronide, —O-glucose,

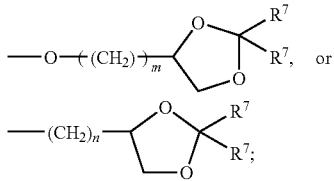

wherein when two —$CH_2OR^8$ groups are located 1,2- or 1,3- with respect to each other the $R^8$ groups may be joined to form a cyclic mono- or di-substituted 1,3-dioxane or 1,3-dioxolane;
each o is, independently, an integer from 0 to 10;
each p is an integer from 0 to 10;
with the proviso that the sum of o and p in each contiguous chain is from 1 to 10;
each x is, independently, O, $NR^{10}$, C(=O), CHOH, C(=N—$R^{10}$), $CHNR^7R^{10}$, or represents a single bond;
each $R^5$ is independently, —$(CH_2)_n$—$CO_2R^{13}$, Het-$(CH_2)_n$—$CO_2R^{13}$, —$(CH_2)_n$—$Z_g$-$CO_2R^{13}$, Het-$(CH_2)_m$—$Z_g$—$CO_2R^{13}$, —$(CH_2)_n$—$NR^{10}$—$(CH_2)_m(CHOR^8)_n$—$CO_2R^{13}$, Het-$(CH_2)_m$—$NR^{10}$—$(CH_2)_m(CHOR^8)_n$—$CO_2R^{13}$, —$(CH_2)_n$—$(CHOR^8)_n$—$CO_2R^{13}$, Het-$(CH_2)_m$—$(CHOR^8)_m$—$CO_2R^{13}$, —$(CH_2)_n$-$(CHOR^8)_mZ_g$—$CO_2R^{13}$, Het-$(CH_2)_n$—$(CHOR^8)_m$—$Z_g$-$CO_2R^{13}$, —$(CH_2)_m$—$Z_g$—$(CH_2)_m$—$CO_2R^{13}$, —$(CH_2)_n$—$Z_g$—$(CH_2)_m$—$CO_2R^{13}$, —$(CH_2)_n$-$Z_g(CHOR^8)_m$—$Z_g$—$CO_2R^{13}$, Het-$(CH_2)_n$—$Z_g$—$(CHOR^8)_m$—$Z_g$—$CO_2R^{13}$, —$(CH_2)_n$—CO—NH—C(=$NR^{13}$)—$NR^{13}R^{13}$, Het-$(CH_2)_n$—CO—NH—C(=$NR^{13}$)—$NR^{13}R^{13}$, —$(CH_2)_n$—$Z_g$—CONH—C(=$NR^{13}$)—$NR^{13}R^{13}$, Het-$(CH_2)_n$—$Z_g$—CONH—C(=$NR^{13}$)—$NR^{13}R^{13}$, —$(CH_2)_n$—$NR^{10}$—$(CH_2)_m(CHOR^8)_n$—CONH—C(=$NR^{13}$)—$NR^{13}R^{13}$, Het-$(CH_2)_n$—$NR^{10}$—$(CH_2)_m(CHOR^8)_n$—CONH—C(=$NR^{13}$)—$NR^{11}R^{11}$, —$(CH_2)_n$—$(CHOR^8)_m$—CONH—C(=$NR^{13}$)—$NR^{13}R^{13}$Het-$(CH_2)_n$—$(CHOR^8)_m$—CONH—C(=$NR^{13}$)_n—$NR^{13}R^{13}$, —$(CH_2)_n$—$(CHOR^8)_n$—$Z_g$—CONH—C(=$NR^{13}$)—$NR^{13}R^{13}$, Het-$(CH_2)_n$—$(CHOR^8)_m$—$Z_g$—CONH—C(=$NR^{13}$)—$NR^{13}R^{13}$, —$(CH_2)_m$-$Z_g$—$(CH_2)_m$CONH—C(=$NR^{13}$)$NR^{13}R^{13}$, Het-$(CH_2)_n$—$Z_g$—$(CH_2)_n$—CONH—C(=$NR^{13}$)—$NR^{13}R^{13}$, —$(CH_2)_n$—$Z_g$—$(CHOR^8)_m$—$Z_g$—CONH—C(=$NR^{13}$)$NR^{13}R^{13}$, Het-$(CH_2)_n$—$Z_g$-$(CHOR^8)_m$—$Z_g$—CONH—C(=$NR^{13}$)—$NR^{13}R^{13}$, —$(CH_2)$—$CONR^7$—$CONR^{13}R^{13}$, Het-$(CH_2)_n$—$CONR^7$—$CONR^{13}R^{13}$, —$(CH_2)_n$—$Z_g$—$CONR^7$—$CONR^{13}R^{13}$, —$(CH_2)_n$—$Z_g$—$CONR^7$—$CONR^{13}R^{13}$, —$(CH_2)_n$—$NR^{10}$—$(CH_2)_m(CHOR^8)_m$—$CONR^7$—$CONR^{13}R^{13}$, Het-$(CH_2)_n$—$NR^{10}$—$(CH_2)_m(CHOR^8)_n$—$CONR^7$—$CONR^{13}R^{13}$, —$(CH_2)_n$—$(CHOR^8)_m$—$CONR^7$—$CONR^{13}R^{13}$, Het-$(CH_2)_n$—$(CHOR^8)_m$—$CONR^7$—$CONR^{13}R^{13}$, —$(CH_2)_n$—$(CHOR^8)_m$—$Z_g$—$CONR^7$—$CONR^{13}R^{13}$, Het-$(CH_2)_n$—$(CHOR^8)_m$—$Z_g$—$CNR^7$—$CONR^{13}R^{13}$, —$(CH_2)_n$—$Z_g$-$(CH_2)_m$—$CONR^7$—$CONR^{13}R^{13}$, Het-$(CH_2)_n$—$Z_g$—$(CH_2)_m$—$CONR^7$—$CONR^{13}R^{13}$, —$(CH_2)_n$-$Z_g(CHOR^8)_m$—$Z_g$—$CONR^7$—$CONR^{13}R^{13}$, Het-$(CH_2)_n$—$Z_g(CHOR^8)_m$—$Z_g$—$CONR^7$—$CONR^{13}R^{13}$, —$(CH_2)_n$—$CONR^7SO_2N^3R^{13}$, Het-$(CH_2)_n$—$CONR^7SO_2NR^{13}R^{13}$, —$(CH_2)_n$-$Z_g$—$CONR^7SO_2NR^{13}R^{13}$, Het-$(CH_2)_m$—$Z_g$—$CONR^7SO_2NR^{13}R^{13}$, —$(CH_2)_n$—$NR^{10}$—$(CH_2)_m(CHOR^8)_n$—$CONR^7SO_2NR^{13}R^{13}$Het-$(CH_2)_m$—$NR^{13}$—$(CH_2)_m(CHOR^8)_n$—$CONR^7SO_2NR^{13}R^{13}$, —$(CH_2)_n$—$(CHOR^8)_m$—$CONR^7SO_2NR^{13}R^{13}$, Het-$(CH_2)_m$—$(CHOR^8)_m$—$CONR^7SO_2NR^{13}R^{13}$—$(CH_2)_3$—$(CHOR^3)_m$—$Z_g$—$CONR^7SO_2NR^{13}$ Het-$(CH_2)_n$—$(CHOR^8)_m$—$Z_g$—$CONR^7SO_2NR^{13}R^{13}$-$(CH_2)_n$—$Z_g$—$(CH_2)_m$$CONR^7SO_2NR^{13}R^{13}$, Het-$(CH_2)_n$—$Z_g$—$(CH_2)_m$$CONR^7SO_2NR^{13}R^{13}$, —$(CH_2)_n$—$Z_g$—$(CHOR^8)_m$—$Z_g$-$CONR^7SO_2NR^{13}R^{13}$, Het-$(CH_2)_n$—$Z_g$—$(CHOR^8)_m$—$Z_g$—$CONR^7SO_2NR^{13}R^{13}$, —$(CH_2)_n$—$SO_2NR^{13}R^{13}$, Het-$(CH_2)_m$—$SO_2NR^{13}R^{13}$, —$(CH_2)_nZ_g$-$SO_2NR^{13}R^{13}$Het-$(CH_2)_m$—$Z_g$-$SO_2NR^{13}R^{13}$—$(CH_2)_n$—$NR^{10}$—$(CH_2)_m(CHOR^8)_n$—$SO_2NR^{13}R^{13}$ Het-$(CH_2)_m$—$NR^{10}$—$(CH_2)_m(CHOR^8)_n$, —$SO_2NR^{13}R^{13}$, Het$(CH_2)_n$—$(CHOR^8)_m$$SO_2NR^{13}R^{13}$, Het-$(CH_2)_m$-$(CHOR^8)_m$—$SO_2NR^{13}R^{13}$, —$(CH_2)_n(CHOR^8)_m$—$Z_g$-$SO_2NR^{13}R^{13}$, Het-$(CH_2)_n$—$(CHOR^8)_m$-$Z_g$-$SO_2NR^{13}R^{13}$ $(CH_2)_n$—$Z_g$—$(CH_2)R"SO_2R^{13}R^{13}$, Het-$(CH_2)_n$—$Z_g$—$(CH_2)_mSO_2NR^{13}R^{13}$, —$(CH_2)_n$—$Z_g$—$(CHOR^8)_m$—$Z_g$-$SO_2NR^{13}R^{13}$, Het-$(CH_2)_n$—$Z_g$—$(CHOR^8)_m$—$Z_g$-$SO_2NR^{13}R^{13}$, —$(CH_2)_n$—$CONR^{13}R^{13}$, Het-$(CH_2)_m$—$CONR^{13}R^{13}$, Het$(CH_2)_n$—$Z_g$—$CONR^{13}R^{13}$, Het-$(CH_2)_m$-$Z_g$—$CONR^{13}R^{13}$, —$(CH_2)_n$—$NR^{10}$—$(CH_2)_m(CHOR^8)_n$$CONR^{13}R^{13}$, Het-$(CH_2)_n$—$NR^{10}$—$(CH_2)_m(CHOR^8)_n$—$Z_g$—$CONR^{13}R^{13}$, —$(CH_2)_n$—$(CHOR^8)_m$—$CONR^{13}R^{13}$, Het-$(CH_2)_m$—$(CHOR^8)_m$—$CONR^{13}R^{13}$, —$(CH_2)_n$—$(CHOR^8)_m$—$Z_g$—$CONR^{13}R^{13}$, Het-$(CH_2)_n$—$(CHOR^8)_m$-$Z_g$—$CONR^{13}R^{13}$, —$(CH_2)_n$—$Z_g$—$(CH_2)_mCONR^{13}R^{13}$, Het-$(CH_2)_n$—$Z_g$—$(CH_2)_mCONR^{13}R^{13}$, —$(CH_2)_n$—$Z_g$—$(CHOR^8)_m$—$Z_g$—$CONR^{13}R^{13}$Het-$(CH_2)_n$—$Z_g$—$(CHOR^8)_m$—$Z_g$—$CONR^{13}R^{13}$, —$(CH_2)$—$CONR^7COR^{13}$, Het-$(CH_2)_m$—$CONR^7COR^{13}$, —(CH$_2$)$_n$—Z$_g$—CONR$^7$COR$^3$, Het-(CH$_2$)$_m$—Z$_g$—CONR$^7$COR$^{13}$, —(CH$_2$)$_n$—NR$^{10}$—(CH$_2$)$_m$(CHOR$^8$)$_n$—CONR$^7$COR$^{13}$, Het-(CH$_2$)$_m$—NR$^{10}$—(CH$_2$)$_m$(CHOR$^8$)$_n$—CONR$^7$COR$^{13}$, —(CH$_2$)$_n$—(CHOR$^8$)$_m$—CONR$^7$COR$^{13}$, Het-(CH$_2$)$_m$—(CHOR$^8$)$_m$—CONR$^{13}$COR$^{13}$—(CH$_2$)$_n$-(CHOR$^8$)$_m$—Z$_g$—CONR$^7$COR$^{13}$, Het-(CH$_2$)$_n$—(CHOR$^8$)$_m$—Z$_g$—CONR$^7$COR$^{13}$, —(CH$_2$)$_n$—Z$_g$—(CH$_2$)$_m$ CONR$^7$COR$^{13}$, —(CH$_2$)$_n$—Z$_g$-(CH$_2$)$_m$CONR$^7$COR$^{13}$, Het-(CH$_2$)$_n$—Z$_g$—(CHOR$^8$)$_m$—Z$_g$—CONR$^7$COR$^{13}$, —(CH$_2$)$_n$, —CONR$^7$CO$_2$R$^{13}$, —(CH$_2$)$_n$ —Z$_g$—CONR$^7$CO$_2$R$^{13}$, Het-(CH$_2$)$_m$—Z$_g$—CONR$^7$CO$_2$R$^{13}$, —(CH$_2$)$_n$—NR$^{10}$—(CH$_2$)$_m$(CHOR$^8$)$_n$—CONR$^7$CO$_2$R$^{13}$, Het-(CH$_2$)$_m$—NR$^{10}$—(CH$_2$)$_m$(CHOR$^8$)$_n$—CO NR$^7$CO$_2$R$^{13}$, —(CH$_2$)$_n$—(CHOR$^8$)$_m$—CONR$^7$CO$_2$R$^{13}$, Het-(CH$_2$)$_m$—(CHOR$^8$)$_m$—CONR$^7$CO$_2$R$^{13}$, —(CH$_2$)$_n$—(CHOR$^8$)$_m$—Z$_g$—CONR$^7$CO$_2$R$^{13}$, Het-(CH$_2$)$_n$—(CHOR$^8$)$_m$—Z$_g$-CONR$^7$CO$_2$R$^{13}$, —(CH$_2$)$_n$—Z$_g$—(CH$_2$)$_m$ CONR$^7$CO$_2$R$^{13}$, Het-(CH$_2$)$_n$—Z$_g$-(CH$_2$)$_m$ CONR$^7$CO$_2$R$^{13}$, —(CH$_2$)$_n$—Z$_g$—(CHOR$^8$)$_m$—Z$_g$ CONR$^7$CO$_2$R$^{13}$, Het-(CH$_2$)$_n$—Z$_g$-(CHOR$^8$)$_m$—Z$_g$ CONR$^7$CO$_2$R$^{13}$, —(CH$_2$)$_n$—NH—C(=NR$^{13}$)—NR$^{13}$R$^{13}$, Het-(CH$_2$)$_m$—NH—C(=NR$^{13}$)—NR$^{13}$R$^{13}$, —(CH$_2$)$_n$—Z$_g$-NH—C(=NR$^{13}$)—NR$^{13}$R$^{13}$, Het-(CH$_2$)$_m$—Z$_g$-NH—C(=NR$^{13}$)—NR$^{13}$R$^{13}$, —(CH$_2$)$_n$—NR$^{13}$, —(CH$_2$)$_m$(CHOR$^8$)$_n$—NH—C(=NR$^{13}$)—NR$^{13}$R$^{13}$, Het-(CH$_2$)$_m$—NR$^{10}$—(CH$_2$)$_m$(CHOR$^8$)$_n$—NH—C(=NR$^{13}$)—NR$^{13}$R$^{13}$, —(CH$_2$)$_n$—(CHOR$^8$)$_m$—NH—C(=NR$^{13}$)—NR$^{13}$R$^{13}$, Het-(CH$_2$)$_m$—(CHOR$^8$)$_m$—NH—C(=NR$^{13}$)—NR$^{13}$R$^{13}$, —(CH$_2$)$_n$—(CHOR$^8$)$_m$—Z$_g$-NH—C(=NR$^{13}$)NR$^{13}$R$^{13}$, Het-(CH$_2$)$_n$—(CHOR$^8$)$_m$—Z$_g$-NH—C(=NR$^{13}$)—NR$^{13}$R$^{13}$, —(CH$_2$)$_n$—Z$_g$—(CH$_2$)$_m$NH—C(=NR$^{13}$)—NR$^{13}$R$^{13}$, Het-(CH$_2$)$_n$—Z$_g$—(CH$_2$)$_m$NH—C(=NR$^{13}$)—NR$^{13}$R$^{13}$, —(CH$_2$)$_n$—Z$_g$—(CHOR$^8$)$_m$—Z$_g$-NH—C(=NR$^{13}$)—NR$^{13}$R$^{13}$Het-(CH$_2$)$_n$-Z$_g$—(CHOR$^8$)$_m$—Z$_g$-NH—C(=NR$^{13}$)—NR$^{13}$R$^{13}$, —(CH$_2$)$_n$—C(=NR$^{13}$)—NR$^{13}$R$^{13}$, Het-(CH$_2$)$_m$—C(=NH)—NR$^{13}$R$^{13}$, —(CH$_2$)$_n$—Z$_g$—C(=NH)—NR$^{13}$R$^{13}$, Het-(CH$_2$)$_m$—Z$_g$—C(=NH)—NR$^{13}$R$^{13}$, —(CH$_2$)$_n$—NR$^{10}$—(CH$_2$)$_m$(CHOR$^8$)$_n$—C(=NR$^{13}$)—NR$^{13}$R$^{13}$, Het-(CH$_2$)$_m$—NR$^{10}$—(CH$_2$)$_m$(CHOR$^8$)$_n$—C(=NR$^{13}$)—NR$^{13}$R$^{13}$, —(CH$_2$)$_n$—(CHOR$^8$)$_m$—C(=NR$^{13}$)—NR$^{13}$R$^{13}$, Het-(CH$_2$)$_m$—(CHOR$^8$)$_m$—C(=NR$^{13}$)—NR$^{13}$R$^{13}$, —(CH$_2$)$_n$—(CHOR$^8$)$_m$—Z$_g$—C(=NR$^{13}$)—NR$^{13}$R$^{13}$, Het-(CH$_2$)$_n$—(CHOR$^8$)$_m$—Z$_g$—C(=NR$^{13}$)—NR$^{13}$R$^{13}$, —(CH$_2$)$_n$—Z$_g$—(CH$_2$)$_m$—C(=NHC(=NR$^{13}$)—NR$^{13}$R$^{13}$, Het-(CH$_2$)$_n$—Z$_g$—(CH$_2$)$_m$—C(=NR$^{13}$)NR$^{13}$R$^{13}$, —(CH$_2$)$_n$—Z$_g$—(CHOR$^8$)$_m$—Z$_g$-C(=NR$^{13}$)—NR$^{13}$R$^{13}$, Het-(CH$_2$)$_n$—Z$_g$—(CHOR$^8$)$_m$—Z$_g$—C(=NR$^{13}$)—NR$^{13}$R$^{13}$;

wherein when two —CH$_2$OR$^8$ groups are located 1,2- or 1,3- with respect to each other the R$^8$ groups may be joined to form a cyclic mono- or di-substituted 1,3-dioxane or 1,3-dioxolane;

each R$^6$ is, independently, —R$^5$, —R$^7$, —OR$^8$, —N(R$^7$)$_2$, —(CH$_2$)$_m$—OR$^8$, —O—(CH$_2$)$_m$—OR$^8$, —(CH$_2$)$_n$NR$^7$R$^{10}$, —O—(CH$_2$)$_m$—NR$^7$R$^{10}$, —(CH$_2$)$_n$(CHOR$^8$)(CHOR$^8$)$_n$—CH$_2$OR$^8$, —O—(CH$_2$)$_m$(CHOR$^8$)(CHOR$^8$)$_n$—CH$_2$OR$^8$, —(CH$_2$CH$_2$O)$_m$—R$^8$, —O—(CH$_2$CH$_2$O)$_m$—R$^8$, —(CH$_2$CH$_2$O)$_m$—CH$_2$CH$_2$NR$^7$R$^{10}$, —O—(CH$_2$CH$_2$O)$_m$—CH$_2$CH$_2$NR$^7$R$^{10}$, —(CH$_2$)$_m$—C(=O)NR$^7$R$^{10}$, —O—(CH$_2$)$_m$—C(=O)NR$^7$R$^{10}$, —(CH$_2$)$_n$—(Z)$_g$—R$^7$—O—(CH$_2$)$_m$—(Z)$_g$—R$^7$, —(CH$_2$)$_n$—NR$^{10}$—CH$_2$(CHOR$^8$)(CHOR$^8$)$_n$—CH$_2$OR$^8$, —O—(CH$_2$)$_n$—NR$^{10}$—CH$_2$(CHOR$^8$)(CHOR$^8$)$_n$—CH$_2$OR$^8$, —(CH$_2$)$_n$—CO$_2$R$^7$, —O—(CH$_2$)$_m$—CO$_2$R$^7$, —OSO$_3$H, —O-glucuronide, —O-glucose,

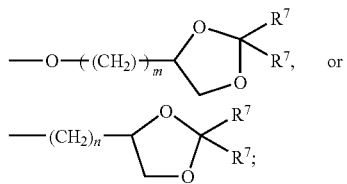

wherein when two R$^6$ are —OR$^{11}$ and are located adjacent to each other on a phenyl ring, the alkyl moieties of the two R$^6$ may be bonded together to form a methylenedioxy group, and wherein when two —CH$_2$OR$^8$ groups are located 1,2- or 1,3- with respect to each other the R$^8$ groups may be joined to form a cyclic mono- or di-substituted 1,3-dioxane or 1,3-dioxolane;

each R$^7$ is, independently, hydrogen lower alkyl, phenyl, or substituted phenyl;

each R$^8$ is, independently, hydrogen, lower alkyl, —C(=O)—R$^{11}$, glucuronide, 2-tetrahydropyranyl, or

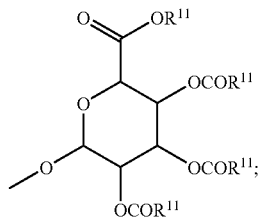

each R$^9$ is, independently, —CO$_2$R$^7$, —CON(R$^7$)$_2$, —SO$_2$CH$_3$, or —C(=O)R$^7$;

each R$^{10}$ is, independently, —H, —SO$_2$CH$_3$, —CO$_2$R$^7$—C(=O)NR$^7$R$^9$, —C(=O)R$^7$, or —CH$_2$—(CHOH)$_n$—CH$_2$OH;

each Z is, independently, CHOH, C(=O), —(CH$_2$)$_n$—, CHNR$^7$R$^{10}$, C=NR$^{10}$, or NR$^{10}$;

each R$^{11}$ is, independently, lower alkyl;

each R$^{12}$ is independently, —SO$_2$CH$_3$, —CO$_2$R$^7$, —C(=O)NR$^7$R$^9$, —C(=O)R$^7$, or —CH$_2$—(CHOH)$_n$—CH$_2$OH;

each R$^{13}$ is, independently, hydrogen, R$^7$, R$^{10}$, —(CH$_2$)$_m$—NR$^7$R$^{10}$,

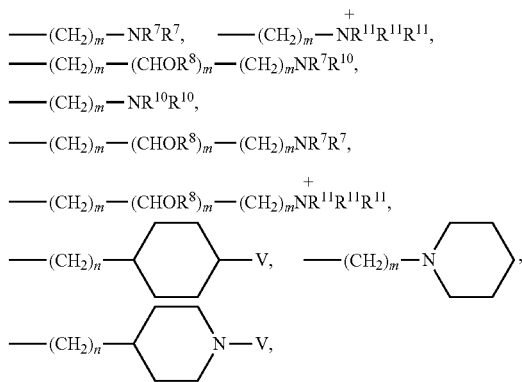

-continued

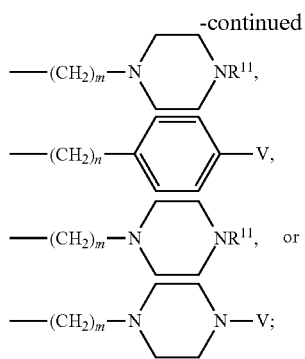

with the proviso that at least one $R^{13}$ must be a group other than hydrogen, $R^7$, or $R^{10}$;
with the further proviso that $NR^{13}R^{13}$ can be joined on itself to form a ring comprising one of the following:

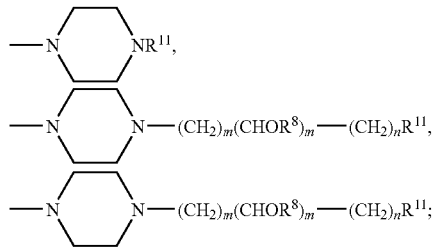

each Het is independently, $-NR^7-$, $-NR^{10}-$, $-S-$, $-SO-$, $-SO_2-$, $-O-$, $-SO_2NH-$, $-NHSO_2-$, $-NR^7CO-$, $-CONR^7-$;
each g is, independently, an integer from 1 to 6;
each m is, independently, an integer from 1 to 7;
each n is, independently, an integer from 0 to 7;
each V is, independently, $-(CH_2)_m-NR^7R^{10}$, $-(CH_2)_m-NR^7R^7$, $-(CH_2)_m-$

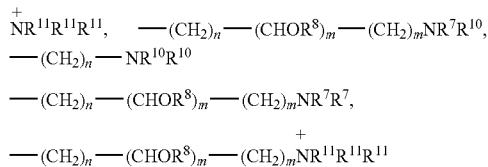

with the proviso that when V is attached directly to a nitrogen atom, then V can also be, independently, $R^7$, $R^{10}$, or $(R^{11})_2$;
  wherein for any of the above compounds when two $-CH_2OR^8$ groups are located 1,2- or 1,3- with respect to each other the $R^8$ groups may be joined to form a cyclic mono- or di-substituted 1,3-dioxane or 1,3-dioxolane;
wherein any of the above compounds can be a pharmaceutically acceptable salt thereof, and
wherein the above compounds are inclusive of all enantiomers, diastereomers, and racemic mixtures thereof.
In a sixth embodiment of the invention:
  each $R^2$ is, independently, $-R^7$, $-(CH_2)_m-OR^8$, $-(CH_2)_m-NR^7R^{10}$, $-(CH_2)_n(CHOR^8)(CHOR^8)_n-CH_2OR^8$, $-(CH_2CH_2O)_m-R^8$, $-(CH_2CH_2O)_m-CH_2CH_2NR^7R^{10}$, $-(CH_2)_n-C(=O)NR^7R^{10}$, $-(CH_2)_n-Z_g-R^7$, $-(CH_2)_m-NR^{10}-CH_2(CHOR^8)(CHOR^8)_n-CH_2OR^8$, $-(CH_2)_n-CO_2R^7$, or

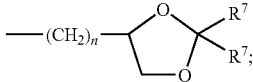

wherein when two $-CH_2OR^8$ groups are located 1,2- or 1,3- with respect to each other the $R^9$ groups may be joined to form a cyclic mono- or di-substituted 1,3-dioxane or 1,3-dioxolane;
  $R^3$ and $R^4$ are each, independently, hydrogen, a group represented by formula (A), lower alkyl, hydroxy lower alkyl, phenyl, phenyl-lower alkyl, (halophenyl)-lower alkyl, lower-(alkylphenylalkyl), lower (alkoxyphenyl)-lower alkyl, naphthyl-lower alkyl, or pyridyl-lower alkyl, with the proviso that at least one of $R^3$ and $R^4$ is a group represented by formula (A):

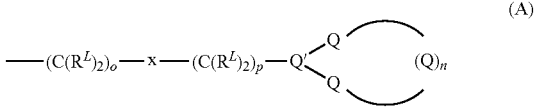

wherein
  each $R^L$ is, independently, $-R^7$, $-(CH_2)_n-OR^8$, $-O-(CH_2)_m-OR^8$, $-(CH_2)_n-NR^7R^{10}$, $-O-(CH_2)_m-NR^7R^{10}$, $-(CH_2)_n(CHOR^8)(CHOR^8)_n-CH_2OR^8$, $-O-(CH_2)_n(CHOR^8)(CHOR^8)_n-CH_2OR^8$, $-(CH_2CH_2O)_m-R^8$, $-O-(CH_2CH_2O)_m-R^8$, $-(CH_2CH_2O)_m-CH_2CH_2NR^7R^{10}$, $-O-(CH_2CH_2O)_m-CH_2CH_2NR^7R^{10}$, $-(CH_2)_n-C(=O)NR^7R^{10}$, $-O-(CH_2)_m-C(=O)NR^7R^{10}$, $-(CH_2)_n-(Z)_g-R^7$, $-O-(CH_2)_n-(Z)_g-R^7$, $-(CH_2)_n-NR^{10}-CH_2(CHOR^8)(CHOR^8)_n-CH_2OR^8$, $-O-(CH_2)_n-NR^{10}-CH_2(CHOR^8)(CHOR^8)_n-CH_2OR^8$, $-(CH_2)_n-CO_2R^7$, $-O-(CH_2)_m-CO_2R^7$, $-OSO_3H$, $-O$-glucuronide, $-O$-glucose,

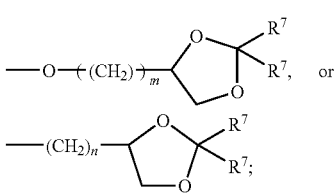

wherein when two $-CH_2OR^8$ groups are located 1,2- or 1,3- with respect to each other the $R^8$ groups may be joined to form a cyclic mono- or di-substituted 1,3-dioxane or 1,3-dioxolane;
  each o is, independently, an integer from 0 to 10;
  each p is an integer from 0 to 10;
  with the proviso that the sum of o and p in each contiguous chain is from 1 to 10;
  each x is, independently, O, $NR^{10}$, $C(=O)$, CHOH, $C(=N-R^{10})$, $CHNR^7R^{10}$, or represents a single bond;
  each $R^5$ is independently, $-(CH_2)_n-CO_2R^{13}$, Het-$(CH_2)_n-CO_2R^{13}$, $-(CH_2)_n-Z_g-CO_2R^{13}$, Het-$(CH_2)_m-Z_g-CO_2R^{13}$, $-(CH_2)_n-NR^{10}-(CH_2)_m(CHOR^8)_n-CO_2R^{13}$, Het-$(CH_2)_m-NR^{10}-(CH_2)_m(CHOR^8)_n-CO_2R^{13}$, $-(CH_2)_n-(CHOR^8)_m-CO_2R^{13}$, Het-$(CH_2)_m-(CHOR^8)_m-CO_2R^{13}$ $(CH_2)_n$ —$(CHOR^8)_m Z_g$—$CO_2R^{13}$, Het-$(CH_2)_n$—$(CHOR^8)_m$—$Z_g$-$CO_2R^{13}$, —$(CH_2)_n$—$Z_g$—$(CH_2)_m$ $CO_2R^{13}$, —$(CH_2)_n$—$Z_g$—$(CH_2)_m$—$CO_2R^{13}$, —$(CH_2)_n$ -$Z_g(CHOR^8)_m$—$Z_g$—$CO_2R^{13}$, Het-$(CH_2)_n$—$Z_g$— $(CHOR^8)_m$—$Z_g$—$CO_2R^{13}$, —$(CH_2)_n$—CONH—C $(=NR^{13})$—$NR^{13}R^{13}$, Het-$(CH_2)_n$—CO—NH—C $(=NR^{13})$—$NR^{13}R^{13}$, —$(CH_2)_n$—$Z_g$—CONH—C $(=NR^{13})$—$NR^{13}R^{13}$, Het-$(CH_2)_n$—$Z_g$—CONH—C $(=NR^{13})$—$NR^{13}R^{13}$, —$(CH_2)_n$—$NR^{13}$—$(CH_2)_m$ $(CHOR^8)_n$—CONH—C$(=NR^{13})$—$NR^{13}R^{13}$, Het-$(CH_2)_n$—$NR^{10}$—$(CH_2)_m(CHOR^8)_n$—CONH—C $(=NR^{13})$—$NR^{13}R^{13}$, —$(CH_2)_n$—$(CHOR^8)_m$— CONH—C$(=NR^{13})$—$NR^{13}R^{13}$, Het-$(CH_2)_n$— $(CHOR^8)_m$—CONH—C$(=NR^{13})$—$N^{13}R^{13}$, —$(CH_2)_n$ —$(CHOR^8)_m$—$Z_g$—CONH—C$(=NR^{13})$—$NR^{13}R^{13}$, Het-$(CH_2)_n$—$(CHOR^8)_n$—$Z_g$—CONH—C $(=NR^{13})$—$NR^{13}R^{13}$, —$(CH_2)_n$-$Z_g$—$(CH_2)_m$CONH— C$(=NR^{13})NR^{13}R^{13}$, Het-$(CH_2)_n$—$Z_g$—$(CH_2)_m$ CONH—C$(=NR^{13})$—$NR^{13}R^{13}$, —$(CH_2)_n$—$Z_g$— $(CHOR^8)_m$—$Z_g$—CONH—C$(=NR^{13})NR^{13}R^{13}$, Het-$(CH_2)_n$—$Z_g$-$(CHOR^8)_m$—$Z_g$—CONH—C$(=NR^{13})$— $NR^{13}R^{13}$, —$(CH_2)_n$—$CONR^{13}$—$CONR^{13}$, Het-$(CH_2)_n$ —$CONR^7$—$CONR^{13}R^{13}$, —$(CH_2)_n$—$Z_g$—$CONR^7$— $CONR^{13}R^{13}$, —$(CH_2)_n$—$Z_g$—$CONR^7$—$CONR^{13}R^{13}$, —$(CH_2)_n$—$NR^{13}$—$(CH_2)_m(CHOR^8)_n$—$CONR^7$— $CONR^{13}R^{13}$, Het-$(CH_2)_n$—$NR^{10}$—$(CH_2)_m(CHOR^8)_m$ —$CONR^7$—$CONR^{13}R^{13}$, —$(CH_2)_n$—$(CHOR^8)_m$— $CONR^7$—$CONR^{13}R^{13}$, Het-$(CH_2)_n$—$(CHOR^8)_m$— $CONR^7$—$CONR^{13}R^{13}$, —$(CH_2)_n$—$(CHOR^8)_m$—$Z_g$— $CONR^7$—$CONR^{13}R^{13}$, Het-$(CH_2)_n$—$(CHOR^8)_m$— $Z_g$—$CNR^7$—$CONR^{13}R^{13}$, —$(CH_2)_n$—$Z_g$-$(CH_2)_m$ $CONR^7$—$CONR^{13}R^{13}$, Het-$(CH_2)_n$—$Z_g$—$(CH_2)_m$ $CONR^7$—$CONR^{13}R^{13}$, —$(CH_2)_n$-$Z_g(CHOR^8)_m$— $Z_g$—$CONR^7$—$CONR^{13}R^{13}$, Het-$(CH_2)_n$—$Z_g$— $(CHOR^8)_m$—$Z_g$—$CONR^7$—$CONR^{13}R^{13}$, —$(CH_2)$— $CONR^7SO_2NR^{13}R^{13}$, Het-$(CH_2)_m$— $CONR^7SO_2NR^{13}R^{13}$, —$(CH_2)_n$-$Z_g$— $CONR^7SO_2NR^{13}R^{13}$, Het-$(CH_2)_m$—$Z_g$— $CONR^7SO_2NR^{13}R^{13}$, —$(CH_2)_n$—$NR^{10}$—$(CH_2)_m$ $(CHOR^8)_n$—$CONR^7SO_2NR^{13}R^{13}$, Het-$(CH_2)_m$— $NR^{10}$—$(CH_2)_m(CHOR^8)_n$—$CONR^7SO_2NR^{13}R^{13}$, —$(CH_2)_n$—$(CHOR^8)_m$—$CONR^7SO_2NR^{13}R^{13}$, Het-$(CH_2)_m$—$(CHOR^8)_m$—$CONR^7SO_2NR^{13}R^{13}$, —$(CH_2)_n$ —$(CHOR^8)_m$—$Z_g$—$CONR^7SO_2NR^{13}R^{13}$, Het-$(CH_2)_n$—$(CHOR^8)_m$—$Z_g$—$CONR^7SO_2NR^{13}R^{13}$, —$(CH_2)_n$—$Z_g$—$(CH_2)_m$$CONR^7SO_2NR^{13}R^{13}$, Het-$(CH_2)_n$—$Z_g$—$(CH_2)_m$$CONR^7SO_2NR^{13}R^{13}$, —$(CH_2)_n$ —$Z_g$—$(CHOR^8)_m$—$Z_g$-$CONR^7SO_2NR^{13}R^{13}$, Het-$(CH_2)_n$—$Z_g$—$(CHOR^8)_m$—$Z_g$—$CONR^7SO_2NR^{13}R^{13}$, —$(CH_2)_n$—$SO_2NR^{13}R^{13}$, Het-$(CH_2)_m$—$SO_2NR^{13}R^{13}$, —$(CH_2)_n$ —$Z_g$-$SO_2NR^{13}R^{13}$, Het-$(CH_2)_m$—$Z_g$-$SO_2NR^{13}R^{13}(CH_2)_n$—$NR^{10}$—$(CH_2)_m(CHOR^8)_m$— $SO_2NR^{13}R^{13}$, Het-$(CH_2)_m$-$NR^{10}$—$(CH_2)_m(CHOR^8)_n$ —$SO_2NR^{13}R^{13}$, —$(CH_2)_n$—$(CHOR^8)_m$— $SO_2NR^{13}R^{13}$, Het-$(CH_2)_m$—$(CHOR^8)_m$— $SO_2NR^{13}R^{13}$—$(CH_2)_n$—$(CHOR^8)_m$—$Z_g$- $SO_2NR^{13}R^{13}$, Het-$(CH_2)_n$—$(CHOR^8)_m$ -$Z_g$- $SO_2N^{13}R^{13}$, —$(CH_2)_n$—$Z_g$—$(CH_2)_m$ $SO_2NR^{13}R^{13}$, Het-$(CH_2)_n$—$Z_g$—$(CH_2)_m$ $SO_2NR^{13}R^{13}$, —$(CH_2)_n$— $Z_g$—$(CHOR^8)_m$—$Z_g$-$SO_2NR^{13}R^{13}$, Het-$(CH_2)_m$— $Z_g$—$(CHOR^8)_m$—$Z_g$-$SO_2NR^{13}R^{13}$, —$(CH_2)_n$— $CONR^{13}R^{13}$, Het-$(CH_2)_n$—$CON^{13}R^{13}$, —$(CH_2)_n$— $Z_g$—$CONR^{13}R^{13}$, Het-$(CH_2)_m$ -$Z_g$—$CONR^{13}R^{13}$, —$(CH_2)_n$—$NR^{13}$—$(CH_2)_m(CHOR^8)_n$—$CONR^{13}R^{13}$, Het-$(CH_2)_n$—$NR^{10}$—$(CH_2)_m$ $(CHOR^8)_n$ $CONR^{13}R^{13}$, —$(CH_2)_n$—$(CHOR^8)_m$—$CONR^{13}R^{13}$, Het-$(CH_2)_m$—$(CHOR^8)_m$—$CONR^{13}R^{13}$, —$(CH_2)_n$— $(CHOR^8)_m$—$Z_g$—$CONR^{13}R^{13}$, Het-$(CH_2)_n$ —$(CHOR^8)_n$-$Z_g$—$CONR^{13}R^{13}$, —$(CH_2)_n$—$Z_g$— $(CH_2)_m CONR^{13}R^{13}$, Het-$(CH_2)_n$—$Z_g$—$(CH_2)_m$ $CONR^{13}R^{13}$—$(CH_2)_n$—$Z_g$—$(CHOR^8)_m$—$Z_g$— $CONR^{13}R^{13}$, Het-$(CH_2)_n$—$Z_g$—$(CHOR^8)_m$—$Z_g$— $CONR^{13}R^{13}$, —$(CH_2)_n$—$CONR^7COR^{13}$, Het-$(CH_2)_m$ —$CONR^7COR^{13}$, —$(CH_2)_n$—$Z_g$—$CONR^7COR^{13}$, Het-$(CH_2)_m$—$Z_g$—$CONR^7COR^{13}$, —$(CH_2)_n$— $NR^{10}$—$(CH_2)_m(CHOR^8)_n$—$CONR^7COR^8$, Het-$(CH_2)_m$ —$NR^{10}$—$(CH_2)_m(CHOR^8)_n$—$CONR^7COR^{13}$, —$(CH_2)_n$—$(CHOR^8)_m$—$CONR^7COR^{13}$, Het-$(CH_2)_m$ —$(CHOR^8)_m$—$CONR^7COR^{13}$—$(CH_2)_n$—$(CHOR^8)_m$ —$Z_g$—$CONR^7COR^{13}$, Het-$(CH_2)_n$—$(CHOR^8)_m$— $Z_g$—$CONR^7COR^{13}$, —$(CH_2)_n$—$Z_g$—$(CH_2)_m$ $CONR^7COR^{13}$, —$(CH_2)_n$—$Z_g$-$(CH_2)_m CONR^7COR^{13}$, Het-$(CH_2)_n$—$Z_g$—$(CHOR^8)_m$—$Z_g$—$CONR^7COR^{13}$, —$(CH_2)_n$—$CONR^7CO_2R^{13}$, —$(CH_2)_n$ —$Z_g$— $CONR^7CO_2R^{13}$, Het-$(CH_2)_m$—$Z_g$—$CONR^7CO_2R^3$, —$(CH_2)_n$—$NR^{10}$—$(CH_2)_m(CHOR^8)_n$ —$CONR^7CO_2R^{13}$, Het-$(CH_2)_m$—$NR^{10}$—$(CH_2)_m$ $(CHOR^8)_n$—CO $NR^7CO_2R^{13}$, —$(CH_2)_n$—$(CHOR^8)_m$ —$CONR^7CO_2R^{13}$, Het-$(CH_2)_m$—$(CHOR^8)_m$— $CONR^7CO_2R^{13}$, —$(CH_2)_n$-$(CHOR^8)_m$—$Z_g$— $CONR^7CO_2R^{13}$, Het-$(CH_2)_n$—$(CHOR^8)_m$—$Z_g$- $CONR^7CO_2R^{13}$, —$(CH_2)_n$—$Z_g$—$(CH_2)_m$ $CONR^7CO_2R^{13}$, Het-$(CH_2)_n$—$Z_g$-$(CH_2)_m$ $CONR^7CO_2R^{13}$, —$(CH_2)_n$—$Z_g$—$(CHOR^8)_m$—$Z_g$— $CONR^7CO_2R^{13}$, Het-$(CH_2)_n$—$Z_g$-$(CHOR^8)_m$—$Z_g$— $CONR^7CO_2R^{13}$, —$(CH_2)_n$—NH—C$(=NR^{13})$— $NR^{13}R^{13}$, Het-$(CH_2)_m$—NH—C$(=NR^{13})$—$NR^{13}R^{13}$, —$(CH_2)_n$—$Z_g$-NH—C$(=NR^{13})$—$NR^{13}R^{13}$, Het-$(CH_2)_m$—$Z_g$-NH—C$(=NR^{13})$—$NR^{13}R^{13}$, —$(CH_2)_n$ —$NR^{10}$—$(CH_2)_m(CHOR^8)_n$—NH—C$(=NR^{13})$— $NR^{13}R^{13}$, Het-$(CH_2)_m$—$NR^{10}$—$(CH_2)_m(CHOR^8)_n$— NH—C$(=NR^{13})$—$NR^{13}R^{13}$, —$(CH_2)_n$—$(CHOR^8)_m$ —NH—C$(=NR^{13})$—$NR^{13}R^{13}$, Het-$(CH_2)_n$— $(CHOR^8)_m$—NH—C$(=NR^{13})$—$NR^{13}R^{13}$, —$(CH_2)_n$ —$(CHOR^8)_m$—$Z_g$-NH—C$(=NR^{13})$—$NR^{13}R^{13}$, Het-$(CH_2)_n$—$(CHOR^8)_m$—$Z_g$-NH—C$(=NR^{13})$— $NR^{13}R^{13}$, —$(CH_2)_n$—$Z_g$—$(CH_2)_m$NH—C$(=NR^{13})$— $NR^{13}R^{13}$, Het-$(CH_2)_n$—$Z_g$—$(CH_2)_m$NH—C $(=NR^{13})$—$NR^{13}R^{13}$, —$(CH_2)_n$—$Z_g$—$(CHOR^8)_m$— $Z_g$-NH—C$(=NR^{13})$—$NR^{13}R^{13}$, Het-$(CH_2)_n$-$Z_g$— $(CHOR^8)_m$—$Z_g$-NH—C$(=NR^{13})$—$NR^{13}R^{13}$, —$(CH_2)_n$—C$(=NH)$—$NR^{13}R^{13}$, Het-$(CH_2)_m$—C $(=NH)$—$NR^{13}R^{13}$, —$(CH_2)_n$—$Z_g$—C$(=NH)$— $NR^{13}R^{13}$, Het-$(CH_2)_m$—$Z_g$—C$(=NH)$—$NR^{13}R^{13}$, —$(CH_2)_n$—$NR^{10}$—$(CH_2)_m(CHOR^8)_n$—C$(=NR^{13})$— $NR^{13}R^{13}$, Het-$(CH_2)_m$—$NR^{10}$—$(CH_2)_m(CHOR^8)_n$—C $(=NR^{13})$—$NR^{13}R^{13}$, —$(CH_2)_n$—$(CHOR^8)_m$—C $(=NR^{13})$—$NR^{13}R^{13}$, Het-$(CH_2)_m$—$(CHOR^8)_m$—C $(=NR^{13})$—$NR^{13}R^{13}$, —$(CH_2)_n$—$(CHOR^8)_m$—$Z_g$—C $(=NR^{13})$—$NR^{13}R^{13}$, Het-$(CH_2)_n$—$(CHOR^8)_m$—$Z_g$— C$(=NR^{13})$—$NR^{13}R^{13}$, —$(CH_2)_n$—$Z_g$—$(CH_2)_m$—C $(=NHC(=NR^{13})$—$NR^{13}R^{13}$, Het-$(CH_2)_n$—$Z_g$— $(CH_2)_m$—C$(=NR^{13})$—$NR^{13}R^{13}$, —$(CH_2)_n$—$Z_g$— $(CHOR^8)_m$—$Z_g$-C$(=NR^{13})$—$NR^{13}R^{13}$, Het-$(CH_2)_n$— $Z_g$—$(CHOR^8)_m$—$Z_g$—C$(=NR^{13})$—$NR^{13}R^{13}$;

wherein when two —$CH_2OR^8$ groups are located 1,2- or 1,3- with respect to each other the $R^8$ groups may be joined to form a cyclic mono- or di-substituted 1,3-dioxane or 1,3-dioxolane;

each $R^6$ is, independently, —$R^5$, —$R^7$, —$OR^8$, —$N(R^7)_2$, —$(CH_2)_m$—$OR^8$, —O—$(CH_2)_m$—$OR^8$, —$(CH_2)_n$— $NR^7R^{10}$, —O—$(CH_2)_m$—$NR^7R^{10}$, —$(CH_2)_n(CHOR^8)$ $(CHOR^8)_n$—$CH_2OR^8$, —O—$(CH_2)_n(CHOR^8)(CHOR^8)_n$— $CH_2OR^8$, —$(CH_2CH_2O)_m$—$R^8$, —O—$(CH_2CH_2O)_m$—$R^8$, —(CH$_2$CH$_2$O)$_m$—CH$_2$CH$_2$NR$^7$R$^{10}$, —O—(CH$_2$CH$_2$O)$_m$—CH$_2$CH$_2$NR$^7$R$^{10}$, —(CH$_2$)$_n$—C(=O)NR$^7$R$^{10}$, —O—(CH$_2$)$_m$—C(=O)NR$^7$R$^{10}$, —(CH$_2$)$_n$—(Z)$_g$—R$^{71}$—O(CH$_2$)$_m$—(Z)$_g$R$^7$, —(CH$_2$)$_n$—NR$^{10}$—CH$_2$(CHOR$^8$)(CHOR$^8$)$_n$—CH$_2$OR$^8$, —O—(CH$_2$)$_m$—NR$^{10}$—CH$_2$(CHOR$^8$)(CHOR$^8$)$_n$—CH$_2$OR$^8$, —(CH$_2$)$_n$—CO$_2$R$^7$, —O—(CH$_2$)$_m$—CO$_2$R$^7$, —OSO$_3$H, —O-glucuronide, —O-glucose,

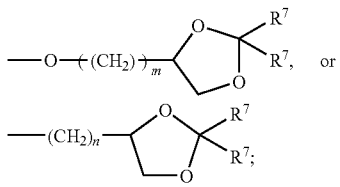

wherein when two R$^6$ are —OR$^{11}$ and are located adjacent to each other on a phenyl ring, the alkyl moieties of the two R$^6$ may be bonded together to form a methylenedioxy group, and wherein when two —CH$_2$OR$^8$ groups are located 1,2- or 1,3- with respect to each other the R$^8$ groups may be joined to form a cyclic mono- or di-substituted 1,3-dioxane or 1,3-dioxolane;

each R$^7$ is, independently, hydrogen lower alkyl, phenyl, or substituted phenyl;

each R$^8$ is, independently, hydrogen, lower alkyl, —C(=O)—R$^{11}$, glucuronide, 2-tetrahydropyranyl, or

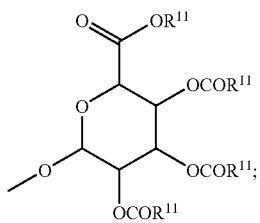

each R$^9$ is, independently, —CO$_2$R$^7$, —CON(R$^7$)$_2$, —SO$_2$CH$_3$, or —C(=O)R$^7$;

each R$^{10}$ is, independently, —H, —SO$_2$CH$_3$, —CO$_2$R$^7$, —C(=O)NR$^7$R$^9$, —C(=O)R$^7$, or —CH$_2$—(CHOH),—CH$_2$OH;

each Z is, independently, CHOH, C(=O), —(CH$_2$)$_n$—, CHNR$^7$R$^{10}$, C=NR$^{10}$, or NR$^{10}$;

each R$^{11}$ is, independently, lower alkyl;

each R$^{12}$ is independently, —SO$_2$CH$_3$, —CO$_2$R$^7$, —C(=O)NR$^7$R$^9$, —C(=O)R$^7$, or —CH$_2$—(CHOH),—CH$_2$OH;

each R$^{13}$ is, independently, hydrogen, R$^7$, R$^{10}$, —(CH$_2$)$_m$—NR$^7$R$^{10}$,

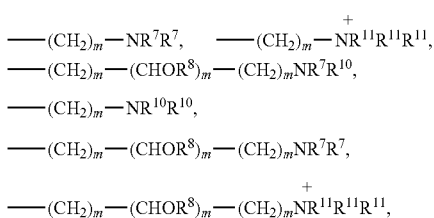

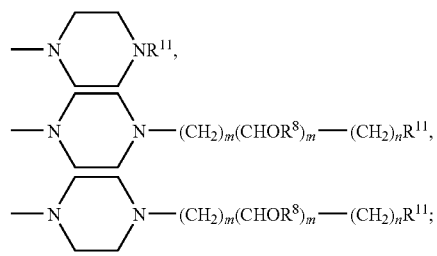

with the proviso that at least one R$^{13}$ must be a group other than hydrogen, R$^7$, or R$^{10}$;

with the further proviso that NR$^{13}$R$^{13}$ can be joined on itself to form a ring comprising one of the following:

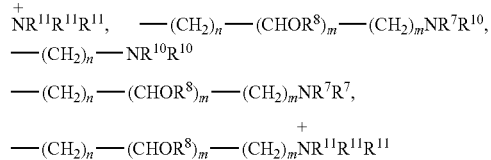

each Het is independently, —NR$^7$, —NR$^{10}$, —S—, —SO—, —SO$_2$—, —O—, —SO$_2$NH—, —NHSO$_2$—, —NR$^7$CO—, or —CONR$^7$—;

each g is, independently, an integer from 1 to 6;
each m is, independently, an integer from 1 to 7;
each n is, independently, an integer from 0 to 7;
each Q' is independently, CR$^6$ or N;
each Q is independently, —C(R$^6$R$^5$)—, —C(R$^6$R$^6$)—, —N(R$^{10}$)—, —N(R$^7$)—, —N(R$^5$)—, —S—, —SO—, or —SO$_2$—, with the proviso that at least one Q is —C(R$^5$R$^6$)— or —N(R$^5$)—, with the proviso that at most three Q in a ring is —N(R$^7$)—, —N(R$^5$)—, —S—, —SO—, or —SO$_2$—;

each V is, independently, —(CH$_2$)$_m$—NR$^7$R$^{10}$, —(CH$_2$)$_m$—NR$^7$R$^7$, —(CH$_2$)$_m$—$\overset{+}{N}$R$^{11}$R$^{11}$R$^{11}$, —(CH$_2$)$_n$—(CHOR$^8$)$_m$—(CH$_2$)$_m$NR$^7$R$^{10}$, —(CH$_2$)$_n$—NR$^{10}$R$^{10}$ —(CH$_2$)$_n$—(CHOR$^8$)$_m$—(CH$_2$)$_m$NR$^7$R$^7$, —(CH$_2$)$_n$—(CHOR$^8$)$_m$—(CH$_2$)$_m$$\overset{+}{N}$R$^{11}$R$^{11}$R$^{11}$ with the proviso that when V is attached directly to a nitrogen atom, then V can also be, independently, R$^7$, R$^{10}$, or (R$^{11}$)$_2$;

wherein for any of the above compounds when two —CH$_2$OR$^8$ groups are located 1,2- or 1,3- with respect to each other the $R^8$ groups may be joined to form a cyclic mono- or di-substituted 1,3-dioxane or 1,3-dioxolane;

wherein any of the above compounds can be a pharmaceutically acceptable salt thereof, and wherein the above compounds are inclusive of all enantiomers, diastereomers, and racemic mixtures thereof.

In a seventh embodiment of the invention:

each $R^2$ is, independently, —$R^7$, —$(CH_2)_m$—$OR^8$, —$(CH_2)_m NR^7R^{10}$, —$(CH_2)_n(CHOR^8)(CHOR^8)_n$—$CH_2OR^8$, —$(CH_2CH_2O)_m$—$R^8$, —$(CH_2CH_2O)_m$—$CH_2CH_2NR^7R^{10}$, —$(CH_2)_n$—$C(=O)NR^7R^{10}$, —$(CH_2)_n$—$Z_g$—$R^7$, —$(CH_2)_m$—$NR^{10}$—$CH_2(CHOR^8)(CHOR^8)_n$—$CH_2OR^8$, —$(CH_2)_n$—$CO_2R^7$, or

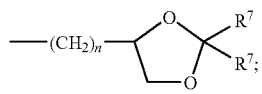

$R^3$ and $R^4$ are each, independently, hydrogen, a group represented by formula (A), lower alkyl, hydroxy lower alkyl, phenyl, phenyl-lower alkyl, (halophenyl)-lower alkyl, lower-(alkylphenylalkyl), lower (alkoxyphenyl)-lower alkyl, naphthyl-lower alkyl, or pyridyl-lower alkyl, with the proviso that at least one of $R^3$ and $R^4$ is a group represented by formula (A):

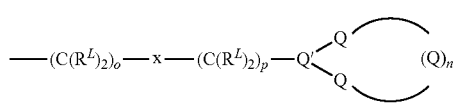

wherein each $R^L$ is, independently, —$R^7$, —$(CH_2)_n$—$OR^8$, O—$(CH_2)_m$—$OR^8$, —$(CH_2)_n$—$NR^7R^{10}$, —O—$(CH_2)_m$—$NR^7R^{10}$, —$(CH_2)_n(CHOR^8)(CHOR^8)_n$—$CH_2OR^8$, —O—$(CH_2)_m(CHOR^8)(CHOR^8)_n$—$CH_2OR^8$, —$(CH_2CH_2O)_m$—$R^8$, —O—$(CH_2CH_2O)_m$—$R^8$, —$(CH_2CH_2O)_m$—$CH_2CH_2NR^7R^{10}$, —O—$(CH_2CH_2O)_m$—$CH_2CH_2NR^7R^{10}$, —$(CH_2)_m$—$C(=O)NR^7R^{10}$, —O—$(CH_2)_m$—$C(=O)NR^7R^{10}$, —$(CH_2)_n$-$(Z)_g$—$R^7$, —O—$(CH_2)_m$—$(Z)_g$—$R^7$, —$(CH_2)_n$—$NR^{10}$—$CH_2(CHOR^8)(CHOR^8)_n$—$CH_2OR^8$, —O—$(CH_2)_m$—$NR^{10}$—$CH_2(CHOR^8)(CHOR^8)_n$—$CH_2OR^8$, —$(CH_2)_n$—$CO_2R^7$, —O—$(CH_2)_m$—$CO_2R^7$—$OSO_3H$, —O-glucuronide, —O-glucose,

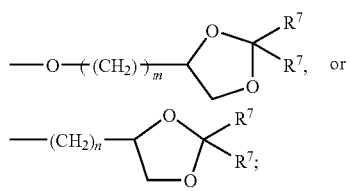

each o is, independently, an integer from 0 to 10;
each p is an integer from 0 to 10; with the proviso that the sum of o and p in each contiguous chain is from 1 to 10;
each x is, independently, O, $NR^{10}$, $C(=O)$, CHOH, $C(=N—R^{10})$, $CHNR^7R^{10}$, or represents a single bond;
each $R^5$ is, independently, —O—$(CH_2)_m$—$OR^8$, —$(CH_2)_n$—$NR^7R^{10}$, —O—$(CH_2)_m$—$NR^7R^{10}$, —$(CH_2)_n(CHOR^8)(CHOR^8)_n$—$CH_2OR^8$, —O—$(CH_2)_m(CHOR^8)(CHOR^8)_n$—$CH_2OR^8$, —$(CH_2CH_2O)_m$—$R^8$, —O—$(CH_2CH_2O)_m$—$R^8$, —$(CH_2CH_2O)_m$—$CH_2CH_2NR^7R^{10}$, —O—$(CH_2CH_2O)_m$—$CH_2CH_2NR^7R^{10}$, —$(CH_2)_n$—$C(=O)NR^7R^{10}$, —O—$(CH_2)_m$—$C(=O)NR^7R^{10}$, —$(CH_2)_n$—$(Z)_g$—$R^7$, —O—$(CH_2)_m$—$(Z)_g$—$R^7$, —$(CH_2)_n$—$NR^{10}$—$CH_2(CHOR^8)(CHOR^8)_n$—$CH_2OR^8$, —$(CH_2)_n$—$CO_2R^7$, —O—$(CH_2)_m$—$CO_2R^7$, —$OSO_3H$, —O-glucuronide, —O-glucose,

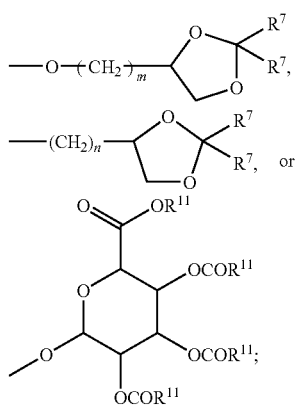

each $R^5$ may also be, independently, —$(CH_2)_n$—$NR^{12}R^{12}$, —O—$(CH_2)_m$—$NR^{12}R^{12}$, —O—$(CH_2)_n$—$NR^{12}R^{12}$, —O—$(CH_2)_m$—$(Z)_g R^{12}$, —$(CH_2)_n NR^{11}R^{11}$, —O—$(CH_2)_m NR^{11}R^{11}$, —$(CH_2)_n$—$N^{\oplus}$—$(R^{11})_3$, —O—$(CH_2)_m$—$N^{\oplus}$—$(R^{11})_3$, —$(CH_2)_n$—$(Z)_g$—$(CH_2)_m$—$NR^{10}R^{10}$, —O—$(CH_2)_m$—$(Z)_g$—$(CH_2)_m$—$NR^{10}R^{10}$, —$(CH_2CH_2O)_m$—$CH_2CH_2NR^{12}R^{12}$, —O—$(CH_2CH_2O)_m$—$CH_2CH_2NR^{12}R^{12}$, —$(CH_2)_n$—$(C=O)NR^{12}R^{12}$, —O—$(CH_2)$, —$(C=O)NR^{12}R^{12}$, —O—$(CH_2)_m$—$(CHOR^8)_m CH_2NR^{10}$—$(Z)_g$—$R^{10}$, —$(CH_2)_n$—$(CHOR^8)_m CH_2$—$NR^{10}$—$(Z)_g$—$R^{10}$, —$(CH_2)_n NR^{10}$—$(CH_2)_m (CHOR^8)_n CH_2 NR^{10}$—$(Z)_g$—$R^{10}$, —O$(CH_2)_m$—$NR^{10}$—$(CH_2)_m$—$(CHOR^{18})_n CH_2 NR^{10}$—$(Z)_g$—$R^{10}$, -(Het)-$(CH_2)_m$—$OR^8$, -(Het)-$(CH_2)_m$—$NR^7R^{10}$, -(Het)-$(CH_2)_m(CHOR^8)(CHOR^8)_n$—$CH_2OR^8$, -(Het)-$(CH_2CH_2O)_m$—$R^8$, -(Het)-$(CH_2CH_2O)_m$—$CH_2CH_2NR^7R^{10}$, -(Het)-$(CH_2)_m$—$C(=O)NR^7R^{10}$, -(Het)-$(CH_2)_m$—$(Z)_g$—$R^7$, -(Het)-$(CH_2)_m$—$NR^{10}$—$CH_2(CHOR^8)(CHOR^8)_n$—$CH_2OR^8$, -(Het)-$(CH_2)_m$—$CO_2R^7$, -(Het)-$(CH_2)_m$—$NR^{12}R^{12}$, -(Het)-$(CH_2)_n$—$NR^{12}R^{12}$, -(Het)-$(CH_2)_m$—$(Z)_g$—$R^{12}$, -(Het)-$(CH_2)_m$$NR^{11}R^{11}$, -(Het)-$(CH_2)_m$—$N^{\oplus}$—$(R^{11})_3$, -(Het)-$(CH_2)_m$—$(Z)_g$—$(CH_2)_m$—$NR^{10}R^{10}$, -(Het)-$(CH_2CH_2O)_m$—$CH_2CH_2NR^{12}R^{12}$, -(Het)-$(CH_2)_m$—$(C=O)NR^{12}R^{12}$, -(Het)-$(CH_2)_m$—$(CHOR^8)_n CH_2 NR^{10}$—$(Z)_g$-$R^{10}$, -(Het)-$(CH_2)_m$—$NR^{10}$—$(CH_2)_m$—$(CHOR^8)_n CH_2 NR^{10}$—$(Z)_g$—$R^{10}$, wherein when two —$CH_2OR^8$ groups are located 1,2- or 1,3- with respect to each other the $R^8$ groups may be joined to form a cyclic mono- or di-substituted 1,3-dioxane or 1,3-dioxolane, —$(CH_2)_n(CHOR^8)(CHOR^8)_n$—$CH_2OR^8$, with the proviso that at least two —$CH_2OR^8$ are located adjacent to each other and the $R^8$ groups are joined to form a cyclic mono- or di-substituted 1,3-dioxane or 1,3-dioxolane, —O—$(CH_2)_m(CHOR^8)(CHOR^8)_n$—$CH_2OR^8$, with the proviso that at least two —$CH_2OR^8$ are located adjacent to each other and the $R^8$ groups are joined to form a cyclic mono- or di-substituted 1,3-dioxane or 1,3-dioxolane, —$(CH_2)_m$—$NR^{10}$—$CH_2(CHOR^8)(CHOR^8)_n$—$CH_2OR^8$, with the proviso that at least two —$CH_2OR^8$ are located adjacent to each other and the $R^8$ groups are joined to form a cyclic mono- or di-substituted 1,3-dioxane or 1,3-dioxolane, or
—O—$(CH_2)_m$—$NR^{10}$—$CH_2(CHOR^8)(CHOR^8)_n$—$CH_2OR^8$, with the proviso that at least two —$CH_2OR^8$ are located adjacent to each other and the $R^5$ groups are joined to form a cyclic mono- or di-substituted 1,3-dioxane or 1,3-dioxolane;

each $R^5$ may also be, independently, Link-$(CH_2)_n$-CAP, Link-$(CH_2)_n(CHOR^8)(CHOR^8)_n$-CAP, Link—$(CH_2CH_2O)_m$—$CH_2$-CAP, Link-$(CH_2CH_2O)_m$—$CH_2CH_2$-CAP, Link-$(CH_2)_n$—$(Z)_g$—CAP, Link-$(CH_2)_n(Z)_g$—$(CH_2)_m$-CAP, Link-$(CH_2)_n$—$NR^{13}$—$CH_2(CHOR^8)(CHOR^8)_n$-CAP, Link-$(CH_2)_n$—$(CHOR^8)_mCH_2$—$NR^{13}$-$(Z)_g$—CAP, Link-$(CH_2)_n$ $NR^{13}$—$(CH_2)_m(CHOR^8)_n$$CH_2NR^{13}(Z)_g$—CAP, Link-$(CH_2)_m$—$(Z)_g$—$(CH_2)_m$-CAP, Link-NH—C(=O)—NH—$(CH_2)_m$-CAP, Link-$(CH_2)_m$—C(=O)$NR^{13}$—$(CH_2)_m$—C(=O)$NR^{10}R^{10}$, Link-$(CH_2)_m$—C(=O)$NR^{13}$—$(CH_2)_m$-CAP, Link-$(CH_2)_m$—C(=O)$NR^{11}R^{11}$, Link-$(CH_2)_m$—C(=O)$NR^{12}R^{12}$, Link-$(CH_2)_n$—$(Z)_g$—$(CH_2)_m$—$(Z)_g$—CAP, or Link-$Z_g$—$(CH_2)_m$-Het-$(CH_2)_m$-CAP;

each Link is, independently, —O—, —$(CH_2)_n$—, —$O(CH_2)_m$—, —$NR^{13}$—C(=O)—$NR^{13}$, —$NR^{13}$—C(=O)—$(CH_2)_m$—, —C(=O)$NR^{13}$—$(CH_2)_m$, —$(CH_2)_n$—$Z_g$—$(CH_2)_n$, —S—, —SO—, —$SO_2$—, —$SO_2NR^7$—, —$SO_2NR^{10}$—, or -Het-;

each CAP is, independently, thiazolidinedione, oxazolidinedione, heteroaryl-C(=O)N $R^{13}R^{13}$, heteroaryl-W, —CN, —O—C(=S)$NR^{13}R^{13}$, -$Z_gR^{13}$, —$CR^{10}(Z_gR^{13})(Z_gR^{13})$, —C(=O)OAr, —C(=O)$NR^{13}$Ar, imidazoline, tetrazole, tetrazole amide, —$SO_2NHR^{13}$, —$SO_2NH$—C$(R^{13}R^{13})$—$(Z)_g$—$R^{13}$, a cyclic sugar or oligosaccharide, a cyclic amino sugar or oligosaccharide,

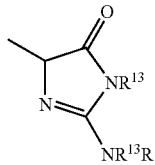 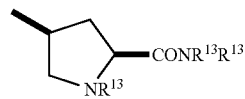

each Ar is, independently, phenyl, substituted phenyl, wherein the substituents of the substituted phenyl are 1-3 substituents independently selected from the group consisting of OH, $OCH_3$, $NR^{13}R^{13}$, Cl, F, and $CH_3$, or heteroaryl;

each W is independently, thiazolidinedione, oxazolidinedione, heteroaryl-C(=O)$NR^{13}R^{13}$—CN, —O—C(=S)$NR^{13}R^{13}$, -$Z_gR^{13}$, —$CR^{10}(Z_gR^{13})(Z_gR^{13})$, —C(=O)OAr, —C(=O)$NR^{13}$Ar, imidazoline, tetrazole, tetrazole amide, —$SO_2NHR^{13}$, —$SO_2NH$—C$(R^{13}R^{13})$-$(Z)_g$—$R^{13}$, a cyclic sugar or oligosaccharide, a cyclic amino sugar or oligosaccharide,

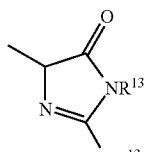 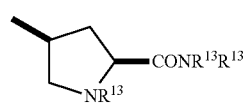

each $R^6$ is, independently, —$R^5$, —$R^7$, —$OR^8$, —$N(R^7)_2$, —$(CH_2)_m$—$OR^8$, —O—$(CH_2)_m$—$OR^8$, —$(CH_2)_n$—$NR^7R^{10}$, —O—$(CH_2)_m$—$NR^7R^{10}$, —$(CH_2)_n(CHOR^8)(CHOR^8)_n$—$CH_2OR^8$, —O—$(CH_2)_m(CHOR^8)(CHOR^8)_n$—$CH_2OR^8$, —$(CH_2CH_2O)_m$—$R^8$, —O—$(CH_2CH_2O)_m$—$R^8$, —$(CH_2CH_2O)_m$—$CH_2CH_2NR^7R^{10}$, —O—$(CH_2CH_2O)_m$—$CH_2CH_2NR^7R^{10}$, —$(CH_2)_n$—C(=O)$NR^7R^{10}$, —O—$(CH_2)_m$ —C(=O)$NR^7R^{10}$, —$(CH_2)_n$—$(Z)_g$—$R^7$, —O—$(CH_2)_m$—$(Z)_g$—$R^7$, —$(CH_2)_n$—$NR^{10}$—$CH_2(CHOR^8)$ $(CHOR^8)_n$—$CH_2OR^8$, —O—$(CH_2)_m$—$NR^{10}$—$CH_2$ $(CHOR^8)(CHOR^8)_n$—$CH_2OR^8$, —$(CH_2)_n$—$CO_2R^7$, —O—$(CH_2)_m$—$CO_2R^7$, —$OSO_3H$, —O-glucuronide, —O-glucose,

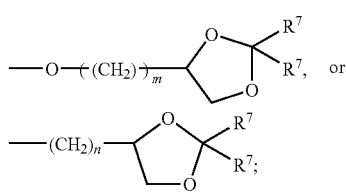

wherein when two —$CH_2OR^8$ groups are located 1,2- or 1,3- with respect to each other the $R^8$ groups may be joined to form a cyclic mono- or di-substituted 1,3-dioxane or 1,3-dioxolane;

each $R^7$ is, independently, hydrogen lower alkyl, phenyl, or substituted phenyl;

each $R^8$ is, independently, hydrogen, lower alkyl, —C(=O)—$R^{11}$, glucuronide, 2-tetrahydropyranyl, or

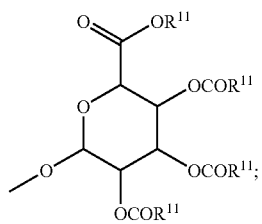

each $R^9$ is, independently, —$CO_2R^{13}$, —$CON(R^{13})_2$, —$SO_2CH_2R^{13}$, or —C(=O)$R^{13}$;

each $R^{10}$ is, independently, —H, —$SO_2CH_3$, —$CO_2R^7$, —C(=O)$NR^7R^9$, —C(=O)$R^7$, or —$CH_2$—(CHOH)$_n$—$CH_2OH$;

each Z is, independently, CHOH, C(=O), —$(CH_2)_n$—, $CHNR^{13}R^{13}$, C=$NR^{13}$, or $NR^{13}$;

each $R^{11}$ is, independently, lower alkyl;

each $R^{12}$ is independently, —$SO_2CH_3$, —$CO_2R^{13}$, —C(=O)$NR^{13}R^{13}$, —C(=O)$R^{13}$ or —$CH_2$—(CHOH)$_n$—$CH_2OH$;

each $R^{13}$ is, independently, hydrogen, $R^7$, $R^{10}$, —$(CH_2)_m$—$NR^7R^{10}$,

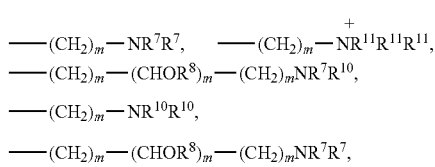

-continued

—(CH$_2$)$_m$—(CHOR$^8$)$_m$—(CH$_2$)$_m$NR$^{11}$R$^{11}$R$^{11}$,

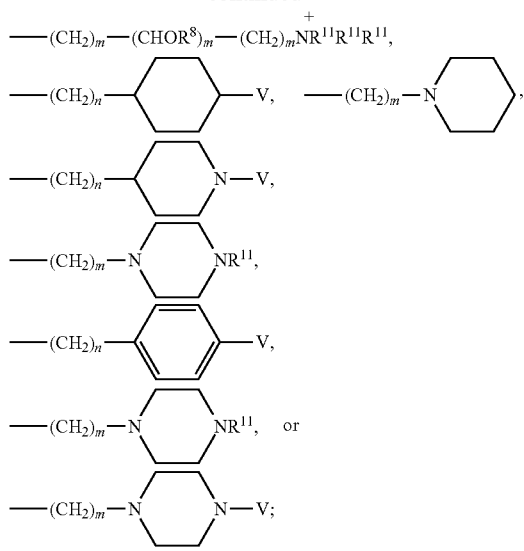

with the proviso that NR$^{13}$R$^{13}$ can be joined on itself to form a ring comprising one of the following:

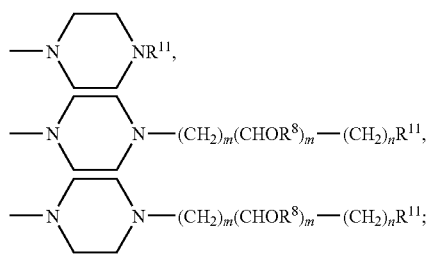

each Het is independently, —NR$^3$, —S—, —SO—, —SO$_2$—, —O—, —SO$_2$NR$^{13}$—, —NHSO$_2$—, —NR$^{13}$CO—, or —CONR$^{13}$—;

each g is, independently, an integer from 1 to 6;
each m is, independently, an integer from 1 to 7;
each n is, independently, an integer from 0 to 7;
each Q' is independently, CR$^6$ or N;
each Q is independently, —C(R$^6$R$^5$)—, —C(R$^6$R$^6$)—, —N(R$^{10}$)—, —N(R$^7$)—, —N(R$^5$)—, —S—, —SO—, or —SO$_2$—, with the proviso that at least one Q is —C(R$^5$R$^6$)— or —N(R$^5$)—, with the proviso that at most three Q in a ring is —N(R$^7$)—, —N(R$^5$)—, —S—, —SO—, or —SO$_2$—;

each V is, independently, —(CH$_2$)$_m$—NR$^7$R$^{10}$, —(CH$_2$)$_m$—NR$^7$R$^7$, —(CH$_2$)$_m$—

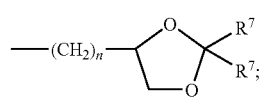

NR$^{11}$R$^{11}$R$^{11}$, —(CH$_2$)$_n$—(CHOR$^8$)$_m$—(CH$_2$)$_m$NR$^7$R$^{10}$,
—(CH$_2$)$_n$—NR$^{10}$R$^{10}$,
—(CH$_2$)$_n$—(CHOR$^8$)$_m$—(CH$_2$)$_m$NR$^7$R$^7$,
—(CH$_2$)$_n$—(CHOR$^8$)$_m$—(CH$_2$)$_m$NR$^{11}$R$^{11}$R$^{11}$, with the proviso that when V is attached directly to a nitrogen atom, then V can also be, independently, R$^7$, R$^{10}$, or (R$^{11}$)$_2$;

with the proviso that, when any two —CH$_2$OR$^8$ groups are located 1,2- or 1,3- with respect to each other, the R$^8$ groups may be joined to form a cyclic mono- or di-substituted 1,3-dioxane or 1,3-dioxolane;

or a pharmaceutically acceptable salt thereof, and
inclusive of all enantiomers, diastereomers, and racemic mixtures thereof.

In an eighth embodiment of the invention:
each R$^2$ is, independently, —R$^7$, —(CH$_2$)$_m$—OR$^8$, —(CH$_2$)$_m$—NR$^7$R$^{10}$, —(CH$_2$)$_n$(CHOR$^8$)(CHOR$^8$)$_n$—CH$_2$OR$^8$, —(CH$_2$CH$_2$O)$_m$—R$^8$, —(CH$_2$CH$_2$O)$_m$—CH$_2$CH$_2$NR$^7$R$^{10}$, —(CH$_2$)$_n$—C(=O)NR$^7$R$^{10}$, —(CH$_2$)$_n$—Z$_g$—R$^7$, —(CH$_2$)$_m$—NR$^{10}$—CH$_2$(CHOR$^8$)(CHOR$^8$)$_n$—CH$_2$OR$^8$, —(CH$_2$)$_n$—CO$_2$R$^7$, or —(CH$_2$)$_n$—[dioxolane ring with R$^7$, R$^7$];

R$^3$ and R$^4$ are each, independently, hydrogen, a group represented by formula (A), lower alkyl, hydroxy lower alkyl, phenyl, phenyl-lower alkyl, (halophenyl)-lower alkyl, lower-(alkylphenylalkyl), lower (alkoxyphenyl)-lower alkyl, naphthyl-lower alkyl, or pyridyl-lower alkyl, with the proviso that at least one of R$^3$ and R$^4$ is a group represented by formula (A):

—(C(R$^L$)$_2$)$_O$-x-(C(R$^L$)$_2$)$_P$—CR$^5$R$^6$R$^6$     (A)

each R$^L$ is, independently, —R$^7$, —(CH$_2$)$_n$—OR$^8$, —O—(CH$_2$)$_m$—OR$^8$, —(CH$_2$)$_n$—NR$^7$R$^{10}$, —O—(CH$_2$)$_m$—NR$^7$R$^{10}$, —(CH$_2$)$_n$(CHOR$^8$)(CHOR$^8$)$_n$—CH$_2$OR$^8$, —O—(CH$_2$)$_m$(CHOR$^8$)(CHOR$^8$)$_n$—CH$_2$OR$^8$, —(CH$_2$CH$_2$O)$_m$—R$^8$, —O—(CH$_2$CH$_2$O)$_m$—R$^8$, —(CH$_2$CH$_2$O)$_m$—CH$_2$CH$_2$NR$^7$R$^{10}$, —O—(CH$_2$CH$_2$O)$_m$—CH$_2$CH$_2$NR$^7$R$^{10}$, —(CH$_2$)$_n$—C(=O)NR$^7$R$^{10}$, —O—(CH$_2$)$_m$—C(=O)NR$^7$R$^{10}$, —(CH$_2$)$_n$-(Z)$_g$—R$^7$, —O—(CH$_2$)$_n$—(Z)$_g$—R$^7$, —(CH$_2$)$_n$—NR$^{10}$—CH$_2$(CHOR$^8$)(CHOR$^8$)$_n$—CH$_2$OR$^8$, —O—(CH$_2$)$_m$—NR$^{11}$—CH$_2$(CHOR$^8$)(CHOR$^8$)$_n$—CH$_2$OR$^8$, —(CH$_2$)$_n$—CO$_2$R$^7$, —O—(CH$_2$)$_m$—CO$_2$R$^7$, —OSO$_3$H, —O-glucuronide, —O-glucose,

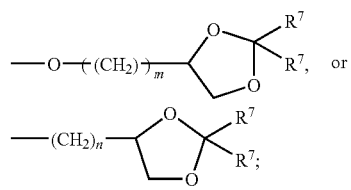

each o is, independently, an integer from 0 to 17;
each p is an integer from 0 to 17;
with the proviso that the sum of o and p in each contiguous chain is from 1 to 17;
each x is, independently, O, NR$^{10}$, C(=O), CHOH, C(=N—R$^{10}$), CHNR$^7$R$^{10}$, or represents a single bond, with the proviso that when x is a single bond the sum of o and p is from 7 to 17;
each R$^5$ is, independently, —O—(CH$_2$)$_m$—OR$^8$, —(CH$_2$)$_n$—NR$^7$R$^{10}$, —O—(CH$_2$)$_m$—NR$^7$R$^{10}$, —(CH$_2$)$_n$(CHOR$^8$)(CHOR$^8$)$_n$—CH$_2$OR$^8$, —O—(CH$_2$)$_m$(CHOR$^8$)(CHOR$^8$)$_n$—CH$_2$OR$^8$, —(CH$_2$CH$_2$O)$_m$—R$^8$, —O—(CH$_2$CH$_2$O)$_m$—R$^8$, —(CH$_2$CH$_2$O)$_m$—CH$_2$CH$_2$NR$^7$R$^{10}$, —O—(CH$_2$CH$_2$O)$_m$—CH$_2$CH$_2$NR$^7$R$^{10}$, —(CH$_2$)$_n$—C(=O)NR$^7$R$^{10}$, —O—(CH$_2$)$_m$—C(=O)NR$^7$R$^{10}$, —(CH$_2$)$_n$—(Z)$_g$—R$^7$, —O—

—(CH$_2$)$_n$—(Z)$_g$—R$^7$, (CHOR$^8$)$_n$—CH$_2$OR$^8$, (CHOR$^8$)(CHOR$^8$)$_n$ —CH$_2$OR$^8$, —(CH$_2$)$_m$—CO$_2$R$^7$, —OSO$_3$H, —O-glucuronide, —O-glucose, —(CH$_2$)$_n$—NR$^{10}$—CH$_2$(CHOR$^8$) —O—(CH$_2$)$_m$—NR$^{10}$—CH$_2$ —(CH$_2$)$_n$—CO$_2$R$^7$,

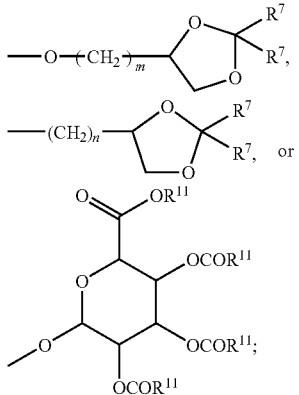

—(CH$_2$)$_n$—NR$^{12}$R$^{12}$, —O—(CH$_2$)$_m$—NR$^{11}$R$^{11}$, —O—(CH$_2$)$_m$—NR$^{11}$R$^{11}$, —O—(CH$_2$)$_m$—(Z)$_g$R$^{12}$, —(CH$_2$)$_n$NR$^{11}$R$^{11}$, —O—(CH$_2$)$_m$NR$^{11}$R$^{11}$, —(CH$_2$)$_n$—N$^\oplus$—(R$^{11}$)$_3$, —O—(CH$_2$)$_m$—N$^\oplus$-(R$^{11}$)$_3$, —(CH$_2$)$_n$—(Z)$_g$—(CH$_2$)$_m$—NR$^{10}$R$^{10}$, —O—(CH$_2$)$_m$—(Z)$_g$—(CH$_2$)$_m$—NR$^{10}$R$^{10}$, —(CH$_2$CH$_2$O)$_m$—CH$_2$CH$_2$NR$^{12}$R$^{12}$, —O—(CH$_2$CH$_2$O)$_m$ —CH$_2$CH$_2$NR$^{12}$R$^{12}$, —(CH$_2$)$_m$—(C=O)NR$^{12}$R$^{12}$, —O—(CH$_2$)$_m$—(C=O)NR$^{12}$R$^{12}$, —O—(CH$_2$)$_m$—(CHOR$^8$)$_m$ CH$_2$NR$^{10}$—(Z)$_g$—R$^{10}$, —(CH$_2$)$_n$—(CHOR$^8$)$_n$ —CH$_2$—NR$^{10}$—(Z)$_g$—R$^{10}$, —(CH$_2$)$_n$NR$^{10}$—O (CH$_2$)$_m$(CHOR$^8$)$_n$ CH$_2$NR$^{10}$—(Z)$_g$—R$^{10}$, —O(CH$_2$)$_m$—NR$^{10}$—(CH$_2$)$_n$—(CHOR$^8$)$_n$CH$_2$NR$^{10}$—(Z)$_g$—R$^{10}$, -(Het)-(CH$_2$)$_m$ —OR$^8$, -(Het)-(CH$_2$)$_m$—NR$^7$R$^{10}$, -(Het)-(CH$_2$)$_n$ (CHOR$^8$)(CHOR$^8$)$_n$—CH$_2$OR$^8$, -(Het)-(CH$_2$CH$_2$O)$_m$—R$^8$, -(Het)-(CH$_2$CH$_2$O)$_m$—CH$_2$CH$_2$NR$^7$R$^{10}$, -(Het)-(CH$_2$)$_m$—C(=O)NR$^7$R$^{10}$, -(Het)-(CH$_2$)$_m$—(Z)$_g$—R$^7$, -(Het)-(CH$_2$)$_m$—NR$^{10}$—CH$_2$(CHOR$^8$)(CHOR$^8$)$_n$—CH$_2$OR$^8$, -(Het)-(CH$_2$)$_m$ —CO$_2$R$^7$, -(Het)-(CH$_2$)$_m$—NR$^{12}$R$^{12}$, -(Het)-(CH$_2$)$_m$—NR$^{12}$R$^{12}$, -(Het)-(CH$_2$)$_m$—(Z)$_g$R$^{12}$, -(Het)-(CH$_2$)$_m$NR$^{11}$R$^{11}$, -(Het)-(CH$_2$)$_m$—N$^\oplus$-(R$^{11}$)$_3$, -(Het)-(CH$_2$)$_m$—(Z)$_g$—(CH$_2$)$_m$—NR$^{10}$R$^{10}$, -(Het)-(CH$_2$CH$_2$O)$_m$—CH$_2$CH$_2$NR$^{12}$R$^{12}$, -(Het)-(CH$_2$)$_m$—(C=O)NR$^{12}$R$^{12}$, -(Het)-(CH$_2$)$_m$—(CHOR$^8$)$_m$CH$_2$NR$^{10}$—(Z)$_g$—R$^{10}$, -(Het)-(CH$_2$)$_m$—NR$^{10}$—(CH$_2$)$_m$—(CHOR$^8$)$_n$CH$_2$NR$^{10}$—(Z)$_g$—R$^{10}$, —(CH$_2$)$_n$ (CHOR$^8$)(CHOR$^8$)$_n$—CH$_2$OR$^8$, with the proviso that at least two —CH$_2$OR$^8$ are located adjacent to each other and the R$^8$ groups are joined to form a cyclic mono- or di-substituted 1,3-dioxane or 1,3-dioxolane,
—O—(CH$_2$)$_m$(CHOR$^8$)(CHOR$^8$)$_n$—CH$_2$OR$^8$, with the proviso that at least two —CH$_2$OR$^8$ are located adjacent to each other and the R$^8$ groups are joined to form a cyclic mono- or di-substituted 1,3-dioxane or 1,3-dioxolane,
—(CH$_2$)$_n$—NR$^{10}$—CH$_2$(CHOR$^8$)(CHOR$^8$)$_n$—CH$_2$OR$^8$, with the proviso that at least two —CH$_2$OR$^8$ are located adjacent to each other and the R$^8$ groups are joined to form a cyclic mono- or di-substituted 1,3-dioxane or 1,3-dioxolane,
—O—(CH$_2$)$_m$—NR$^{10}$—CH$_2$(CHOR$^8$)(CHOR$^8$)$_n$—CH$_2$OR$^8$, with the proviso that at least two —CH$_2$OR$^8$ are located adjacent to each other and the R$^8$ groups are joined to form a cyclic mono- or di-substituted 1,3-dioxane or 1,3-dioxolane,
Link-(CH$_2$)$_n$-CAP, Link-(CH$_2$)$_n$(CHOR$^8$)(CHOR$^8$)$_n$-CAP, Link-(CH$_2$CH$_2$O)$_m$—CH$_2$-CAP, Link-(CH$_2$CH$_2$O)$_m$—CH$_2$CH$_2$-CAP, Link-(CH$_2$)$_n$—(Z)$_g$—CAP, Link-(CH$_2$)$_n$(Z)$_g$—(CH$_2$)$_m$-CAP, Link-(CH$_2$)$_n$—NR$^{13}$—CH$_2$(CHOR$^8$)(CHOR$^8$)$_n$-CAP, Link-(CH$_2$)$_n$—(CHOR$^8$)$_m$CH$_2$—NR$^{13}$-(Z)$_g$ -CAP, Link-(CH$_2$)$_n$—NR$^{13}$—(CH$_2$)$_m$(CHOR$^8$)$_n$CH$_2$NR$^{13}$-(Z)$_g$—CAP, Link-(CH$_2$)$_m$—(Z)$_g$—(CH$_2$)$_m$-CAP, Link-NH—C(=O)—NH—(CH$_2$)$_m$-CAP, Link-(CH$_2$)$_m$—C(=O)NR$^{13}$—(CH$_2$)$_m$—C(=O)NR$^{10}$R$^{10}$, Link-(CH$_2$)$_m$—C(=O)NR$^{13}$—(CH$_2$)$_m$-CAP, Link-(CH$_2$)$_m$—C(=O)NR$^{11}$R$^{11}$, Link-(CH$_2$)$_m$—C(=O)NR$^{12}$R$^{12}$, Link-(CH$_2$)$_n$—(Z)$_g$—(CH$_2$)$_m$—(Z)$_g$—CAP, or Link-Z$_g$—(CH$_2$)$_n$-Het-(CH$_2$)$_m$-CAP;

each Link is, independently, —O—, —(CH$_2$)$_n$—, —O(CH$_2$)$_m$—, —NR$^{13}$—C(=O)—NR$^{13}$, —NR$^{13}$—C(=O)—(CH$_2$)$_m$—, —C(=O)NR$^{13}$—(CH$_2$)$_m$, —(CH$_2$)$_n$—Z$_g$—(CH$_2$)$_n$, —S—, —SO—, —SO$_2$—, —SO$_2$NR$^7$—, —SO$_2$NR$^{10}$—, or -Het-;

each CAP is, independently, thiazolidinedione, oxazolidinedione, heteroaryl-C(=O)N R$^{13}$R$^{13}$, heteroaryl-W, —CN, —O—C(=S)NR$^{13}$R$^{13}$, -Z$_g$R$^{13}$, —CR$^{10}$(Z$_g$R$^{13}$)(Z$_g$R$^{13}$), —C(=O)OAr, —C(=O)NR$^{13}$Ar, imidazoline, tetrazole, tetrazole amide, —SO$_2$NHR$^{13}$, —SO$_2$NH—C(R$^{13}$R$^{13}$)-(Z)$_g$—R$^{13}$, a cyclic sugar or oligosaccharide, a cyclic amino sugar or oligosaccharide,

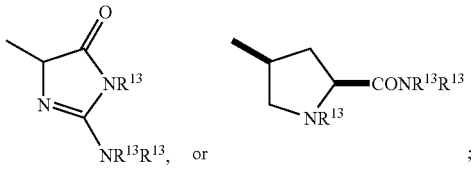

each Ar is, independently, phenyl, substituted phenyl, wherein the substituents of the substituted phenyl are 1-3 substituents independently selected from the group consisting of OH, OCH$_3$, NR$^{13}$R$^{13}$, Cl, F, and CH$_3$, or heteroaryl;

each W is independently, thiazolidinedione, oxazolidinedione, heteroaryl-C(=O)NR$^{13}$R$^{13}$, —CN, —O—C(=S)NR$^{13}$R$^{13}$, -Z$_g$R$^{13}$, —CR$^{10}$(Z$_g$R$^{13}$)(Z$_g$R$^{13}$), —C(=O)OAr, —C(=O)NR$^{13}$Ar, imidazoline, tetrazole, tetrazole amide, —SO$_2$NHR$^{13}$, —SO$_2$NH—C(R$^{13}$R$^{13}$)-(Z)$_g$—R$^{13}$, a cyclic sugar or oligosaccharide, a cyclic amino sugar or oligosaccharide,

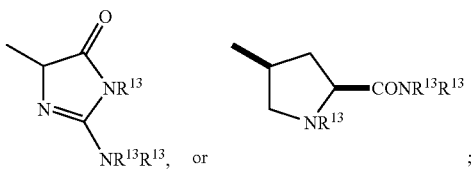

each R$^6$ is, independently, —R$^5$, —R$^7$, —OR$^8$, —N(R$^7$)$_2$, —(CH$_2$)$_m$—OR$^8$, —O—(CH$_2$)$_m$—OR$^8$, (CH$_2$)$_n$—NR$^7$R$^{10}$, —O—(CH$_2$)$_m$—NR$^7$R$^{10}$, —(CH$_2$)$_n$(CHOR$^8$)(CHOR$^8$)$_n$—CH$_2$OR$^8$, —O—(CH$_2$)$_n$(CHOR$^8$)(CHOR$^8$)$_n$—CH$_2$OR$^8$, —(CH$_2$CH$_2$O)$_m$—R$^8$, —O—(CH$_2$CH$_2$O)$_m$—R$^8$, —(CH$_2$CH$_2$O)$_m$—CH$_2$CH$_2$NR$^7$R$^{10}$, —O—(CH$_2$CH$_2$O)$_m$—CH$_2$ CH$_2$NR$^7$R$^{10}$, —(CH$_2$)$_n$—C(=O)NR$^7$R$^{10}$, —O—(CH$_2$)$_m$ —C(=O)NR$^7$R$^{10}$, —(CH$_2$)$_n$—(Z)$_g$—R$^7$, —O—(CH$_2$)$_m$—(Z)$_g$—R$^7$, —(CH$_2$)$_n$—NR$^{10}$—CH$_2$(CHOR$^8$)(CHOR$^8$)$_n$—CH$_2$OR$^8$, —O—(CH$_2$)$_m$—NR$^{10}$—CH$_2$(CHOR$^8$)(CHOR$^8$)$_n$—CH$_2$OR$^8$, —(CH$_2$)$_n$—CO$_2$R$^7$, —O—(CH$_2$)$_m$—CO$_2$R$^7$—OSO$_3$H, —O-glucuronide, —O-glucose,

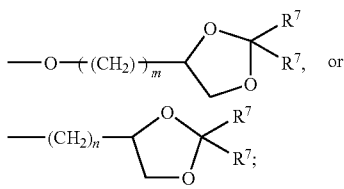

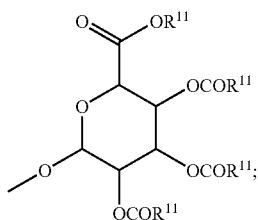

each $R^7$ is, independently, hydrogen lower alkyl, phenyl, or substituted phenyl;

each $R^8$ is, independently, hydrogen, lower alkyl, —C(=O)—$R^{11}$, glucuronide, 2-tetrahydropyranyl, or

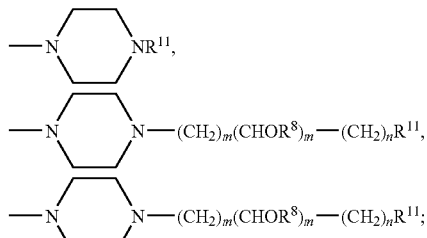

each $R^9$ is, independently, —$CO_2R^{13}$, —$CON(R^{13})_2$, —$SO_2CH_2R^{13}$, or —$C(=O)R^{13}$;

each $R^{10}$ is, independently, —H, —$SO_2CH_3$, —$CO_2R^7$, —C(=O)$NR^7R^9$, —C(=O)$R^7$, or —$CH_2$—(CHOH)$_n$—$CH_2OH$;

each Z is, independently, —CHOH, —C(=O), —(CH$_2$)$_n$—, —CHNR$^{13}$R$^{13}$, C=NR$^{13}$, or —NR$^{13}$;

each $R^{11}$ is, independently, lower alkyl;

each $R^{12}$ is, independently, —$SO_2CH_3$, —$CO_2R^{13}$, —C(=O)NR$^{13}$R$^{13}$, —C(=O)R$^{13}$, or —CH$_2$—(CHOH)$_n$—CH$_2$OH;

each $R^{13}$ is, independently, hydrogen, $R^7$, $R^{10}$, —(CH$_2$)$_m$—NR$^7$R$^{10}$, —(CH$_2$)$_m$—NR$^7$R$^7$, —(CH$_2$)$_m$—$\overset{+}{N}$R$^{11}$R$^{11}$R$^{11}$, —(CH$_2$)$_m$—(CHOR$^8$)$_m$—(CH$_2$)$_m$NR$^7$R$^{10}$, —(CH$_2$)$_m$—NR$^{10}$R$^{10}$, —(CH$_2$)$_m$—(CHOR$^8$)$_m$—(CH$_2$)$_m$NR$^7$R$^7$, —(CH$_2$)$_m$—(CHOR$^8$)$_m$—(CH$_2$)$_m$$\overset{+}{N}$R$^{11}$R$^{11}$R$^{11}$,

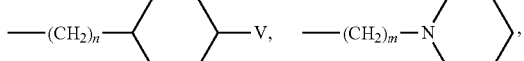

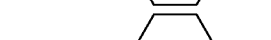

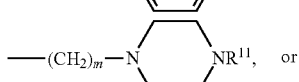

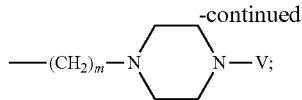

with the proviso that NR$^{13}$R$^{13}$ can be joined on itself to form a ring comprising one of the following:

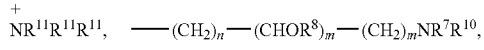

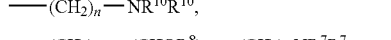

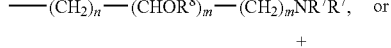

each Het is independently, —NR$^{13}$, —S—, —SO—, —SO$_2$—, —O—, —SO$_2$NR$^{13}$—, —NHSO$_2$—, —NR$^{13}$CO—, or —CONR$^{13}$—;

each g is, independently, an integer from 1 to 6;
each m is, independently, an integer from 1 to 7;
each n is, independently, an integer from 0 to 7;
each V is, independently, —(CH$_2$)$_m$—NR$^7$R$^{10}$, —(CH$_2$)$_m$—NR$^7$R$^7$, —(CH$_2$)$_m$ $\overset{+}{N}$R$^{11}$R$^{11}$R$^{11}$, —(CH$_2$)$_n$—(CHOR$^8$)$_m$—(CH$_2$)$_m$NR$^7$R$^{10}$, —(CH$_2$)$_n$—NR$^{10}$R$^{10}$, —(CH$_2$)$_n$—(CHOR$^8$)$_m$—(CH$_2$)$_m$NR$^7$R$^7$, or —(CH$_2$)$_n$—(CHOR$^8$)$_m$—(CH$_2$)$_m$$\overset{+}{N}$R$^{11}$R$^{11}$R$^{11}$, with the proviso that when V is attached directly to a nitrogen atom, then V can also be, independently, $R^7$, $R^{10}$, or $(R^{11})_2$;

with the proviso that, when any two —CH$_2$OR$^8$ groups in the compound are located 1,2- or 1,3- with respect to each other, the $R^9$ groups may be joined to form a cyclic mono- or di-substituted 1,3-dioxane or 1,3-dioxolane;

or a pharmaceutically acceptable salt thereof, and inclusive of all enantiomers, diastereomers, and racemic mixtures thereof.

In a ninth embodiment of the invention:

each $R^2$ is, independently, —$R^7$, —(CH$_2$)$_m$—OR$^8$, —(CH$_2$)$_m$—NR$^7$R$^{10}$, —(CH$_2$)$_n$(CHOR$^8$)(CHOR$^8$)$_n$—CH$_2$OR$^8$, —(CH$_2$CH$_2$O)$_m$—R$^8$, —(CH$_2$CH$_2$O)$_m$—CH$_2$CH$_2$NR$^7$R$^{10}$, —(CH$_2$)$_n$—C(=O)NR$^7$R$^{10}$, —(CH$_2$)$_n$—Z$_g$—R$^7$, —(CH$_2$)$_m$—NR$^{10}$—CH$_2$(CHOR$^8$)(CHOR$^8$)$_n$—CH$_2$OR$^8$, —(CH$_2$)$_n$—CO$_2$R$^7$, or

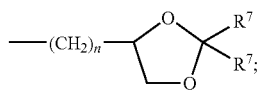

$R^3$ and $R^4$ are each, independently, hydrogen, a group represented by formula (A), lower alkyl, hydroxy lower alkyl, phenyl, phenyl-lower alkyl, (halophenyl)-lower alkyl, lower-(alkylphenylalkyl), lower (alkoxyphenyl)-lower alkyl, naphthyl-lower alkyl, or pyridyl-lower alkyl, with the proviso that at least one of $R^3$ and $R^4$ is a group represented by formula (A):

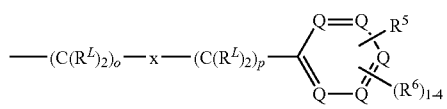

(A)

wherein
each $R^L$ is, independently, —$R^7$, —(CH$_2$)—OR$^8$, —O—(CH$_2$)$_m$—OR$^8$, —(CH$_2$)$_m$—NR$^7$R$^{10}$, —O—(CH$_2$)$_m$—NR$^7$R$^{10}$, —(CH$_2$)$_n$(CHOR$^8$)(CHOR$^8$)$_n$—CH$_2$OR$^8$, —O—(CH$_2$)$_m$(CHOR$^8$)(CHOR$^8$)$_n$—CH$_2$OR$^8$, —(CH$_2$CH$_2$O)$_m$—R$^8$, —O—(CH$_2$CH$_2$O)$_m$—R$^8$, —(CH$_2$CH$_2$O)$_m$—CH$_2$CH$_2$NR$^7$R$^{10}$, —O—(CH$_2$CH$_2$O)$_m$—CH$_2$CH$_2$NR$^7$R$^{10}$, —(CH$_2$)$_n$—C(=O)NR$^7$R$^{10}$, —O—(CH$_2$)$_m$—C(=O)NR$^7$R$^{10}$, —(CH$_2$)$_n$—(Z)$_g$—R$^7$, —O—(CH$_2$)$_m$—(Z)$_g$—R$^7$, —(CH$_2$)$_n$—NR$^{10}$—CH$_2$(CHOR$^8$)(CHOR$^8$)$_n$—CH$_2$OR$^8$, —O—(CH$_2$)$_m$—NR$^{10}$—CH$_2$(CHOR$^8$)(CHOR$^8$)$_n$—CH$_2$OR$^8$, —(CH$_2$)$_n$—CO$_2$R$^7$, —O—(CH$_2$)$_m$—CO$_2$R$^7$, —OSO$_3$H, —O-glucuronide, —O-glucose,

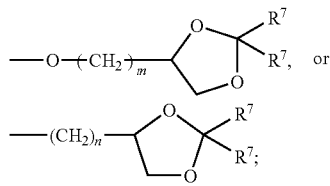

each o is, independently, an integer from 0 to 10;
each p is an integer from 0 to 10;
with the proviso that the sum of o and p in each contiguous chain is from 1 to 10;
each x is, independently, —O—, —NR$^{10}$—, —C(=O)—, —CHOH—, —C(=N—R$^{10}$)—, —CHNR$^7$R$^{10}$—, or represents a single bond;
each $R^5$ is, independently, -Link-(CH$_2$)$_m$-CAP, -Link-(CH$_2$)$_n$(CHOR$^8$)(CHOR$^8$)$_n$-CAP, -Link-(CH$_2$CH$_2$O)$_m$—CH$_2$-CAP, -Link-(CH$_2$CH$_2$O)$_m$—CH$_2$CH$_2$-CAP, -Link-(CH$_2$)$_m$—(Z)$_g$-CAP, -Link-(CH$_2$)$_n$(Z)$_g$—(CH$_2$)$_m$-CAP, -Link-(CH$_2$)$_n$—NR$^{13}$—CH$_2$(CHOR$^8$)(CHOR$^8$)$_n$-CAP, -Link-(CH$_2$)$_n$—(CHOR$^8$)$_m$CH$_2$—NR$^{13}$-(Z)$_g$—CAP, -Link-(CH$_2$)$_n$NR$^{13}$—(CH$_2$)$_m$(CHOR$^8$)$_n$CH$_2$NR$^{13}$-(Z)$_g$—CAP, -Link-(CH$_2$)$_m$—(Z)$_g$—(CH$_2$)$_m$-CAP, -Link-NH—C(=O)—NH—(CH$_2$)$_m$-CAP, -Link-(CH$_2$)$_m$—C(=O)NR$^{13}$-(CH$_2$)$_m$-CAP, -Link-(CH$_2$)$_m$—(Z)$_g$—(CH$_2$)$_m$—(Z)$_g$—CAP, or -Link-Z$_g$—(CH$_2$)$_m$-Het-(CH$_2$)$_m$-CAP;
each Link is, independently, —O—, —(CH$_2$)$_m$—, —O(CH$_2$)$_m$—, —NR$^{13}$—C(=O)—NR$^{13}$—, —NR$^{13}$—C(=O)—(CH$_2$)$_m$—, —C(=O)NR$^{13}$—(CH$_2$)$_m$—, —(CH$_2$)$_n$—Z$_g$—(CH$_2$)$_n$—, —S—, —SO—, —SO$_2$—, —SO$_2$NR$^7$—, —SO$_2$NR$^{10}$—, or -Het-;
each CAP is, independently, —CR$^{10}$(—(CH$_2$)$_m$—R$^9$)(—(CH$_2$)$_m$—R$^9$), —N(—(CH$_2$)$_m$—R$^9$)(—(CH$_2$), —R$^9$), or —NR$^{13}$(—(CH$_2$)$_n$—CO$_2$R$^{13}$);
each Ar is, independently, phenyl, substituted phenyl, wherein said substituent is 1-3 groups selected, independently, from the group consisting of —OH, —OCH$_3$, —NR$^{13}$R$^{13}$, —Cl, —F, and —CH$_3$, or heteroaryl;
wherein heteroaryl is selected from the group consisting of pyridine, pyrazine, tinazine, furyl, furfuryl-, thienyl, tetrazole, thiazolidinedione and imidazoyl

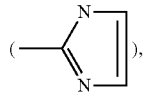

pyrrole, furan, thiophene, pyridine, quinoline, indole, adenine, pyrazole, imidazole, thiazole, isoxazole, indole, benzimidazole, purine, quinoline, isoquinoline, pyridazine, pyrimidine, pyrazine, 1,2,3-triazine, 1,2,4-triazine, 1,3,5-triazine, cinnoline, phthalazine, quinazoline, quinoxaline, and pterdine;
each $R^6$ is, independently, —$R^7$, —OR$^7$, —OR$^{11}$—N(R$^7$)$_2$, —(CH$_2$)$_m$—OR$^8$, —O—(CH$_2$)$_m$—OR$^8$, —(CH$_2$)$_n$—NR$^7$R$^{10}$, —O—(CH$_2$)$_n$—NR$^7$R$^{10}$, —(CH$_2$)$_n$(CHOR$^8$)(CHOR$^8$)$_n$—CH$_2$OR$^8$, —O—(CH$_2$)$_m$(CHOR$^8$)(CHOR$^8$)$_n$—CH$_2$OR$^8$, —(CH$_2$CH$_2$O)$_m$—R$^8$, —O—(CH$_2$CH$_2$O)$_m$—R$^8$, —(CH$_2$CH$_2$O)$_m$—CH$_2$CH$_2$NR$^7$R$^{10}$, —O—(CH$_2$CH$_2$O)$_m$—CH$_2$CH$_2$NR$^7$R$^{10}$, —(CH$_2$), —C(=O)NR$^7$R$^{10}$, —O—(CH$_2$)$_m$—C(=O)NR$^7$R$^{10}$, —(CH$_2$)$_n$—(Z)$_g$—R$^7$, —O—(CH$_2$)$_m$—(Z)$_g$—R$^7$, —(CH$_2$)$_n$—NR$^{10}$—CH$_2$(CHOR$^8$)(CHOR$^8$)$_n$—CH$_2$OR$^8$, —O—(CH$_2$)$_m$—NR$^{10}$—CH$_2$(CHOR$^8$)(CHOR$^8$)$_n$—CH$_2$OR$^8$, —(CH$_2$)$_n$—CO$_2$R$^7$, —O—(CH$_2$)$_m$—CO$_2$R$^7$—OSO$_3$H, —O-glucuronide, —O-glucose,

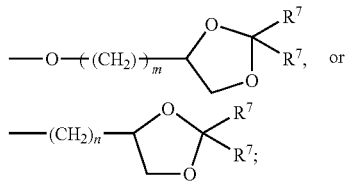

wherein when two $R^6$ are —OR$^{11}$ and are located adjacent to each other on a phenyl ring, the alkyl moieties of the two $R^6$ may be bonded together to form a methylenedioxy group;
with the proviso that when at least two —CH$_2$OR$^8$ are located adjacent to each other,
the $R^8$ groups may be joined to form a cyclic mono- or di-substituted 1,3-dioxane or 1,3-dioxolane,
each $R^7$ is, independently, hydrogen lower alkyl, phenyl, or substituted phenyl;
each $R^8$ is, independently, hydrogen, lower alkyl, —C(=O)—R$^{11}$, glucuronide, 2-tetrahydropyranyl, or

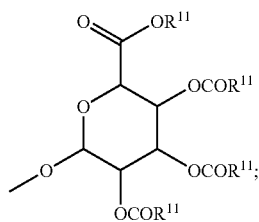

each $R^9$ is, independently, —CO$_2$R$^{13}$, —CON(R$^{13}$)$_2$, —SO$_2$CH$_2$R$^{13}$, —C(=O)R$^{13}$, thiazolidinedione, oxazolidinedione, heteroaryl-C(=O)NR$^{13}$R$^{13}$, heteroaryl-CAP, —CN, —O—C(=S)N$^{13}$R$^{13}$, -Z$_g$R$^{13}$, —C(=O)OAr, —C(=O)NR$^{13}$Ar, imidazoline, tetrazole, tetrazole amide, —SO$_2$NHR$^{13}$, —SO$_2$NH—C(R$^{13}$R$^{13}$)-(Z)$_g$—R$^{13}$, —C(=O)NR$^{10}$Ar, —SO$_2$NR$^7$R$^7$, cylic sugars and oligosaccharides, including cyclic amino sugars and oligosaccharides,

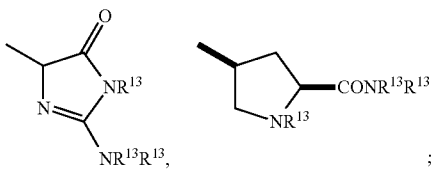

each $R^{10}$ is, independently, —H, —SO$_2$CH$_3$, —CO$_2$R$^7$, —C(=O)NR$^7$R$^9$, —C(=O)R$^7$, or —CH$_2$—(CHOH)$_n$—CH$_2$OH;

each Z is, independently, —CHOH—, —C(=O)—, —CHNR$^{13}$R$^{13}$—, —C=NR$^{13}$—, or —NR$^{13}$—;

each $R^{11}$ is, independently, lower alkyl;

each $R^{12}$ is independently, —SO$_2$CH$_3$, —CO$_2$R$^{13}$, —C(=O)NR$^{13}$R$^{13}$, —C(=O)R$^{13}$, or —CH$_2$—(CHOH)$_n$—CH$_2$OH;

each $R^{13}$ is, independently, —R$^7$ or —R$^{10}$;

each Het is independently, —NR$^3$—, —S—, —SO—, —SO$_2$—, —O—, —SO$_2$NR$^{13}$—, —NHSO$_2$—, —NR$^{13}$CO—, or —CONR$^{13}$—;

each g is, independently, an integer from 1 to 6;

each m is, independently, an integer from 1 to 7;

each n is, independently, an integer from 0 to 7;

each Q is, independently, C—R$^5$, C—R$^6$, or a nitrogen atom, wherein one Q is C—R$^5$ and at most three Q in a ring are nitrogen atoms;

each V is, independently, —(CH$_2$)$_m$—NR$^7$R$^{10}$, —(CH$_2$)$_m$—NR$^7$R$^7$, —(CH$_2$)$_m$—

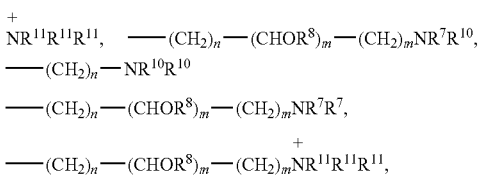

with the proviso that when V is attached directly to a nitrogen atom, then V can also be, independently, R$^7$, R$^{10}$, or (R$^{11}$)$_2$;

wherein when two —CH$_2$OR$^8$ groups are located 1,2- or 1,3- with respect to each other the R$^8$ groups may be joined to form a cyclic mono- or di-substituted 1,3-dioxane or 1,3-dioxolane;

or a pharmaceutically acceptable salt thereof, and inclusive of all enantiomers, diastereomers, and racemic mixtures thereof.

In the compounds represented by formula (I), X may be hydrogen, halogen, trifluoromethyl, lower alkyl, lower cycloalkyl, unsubstituted or substituted phenyl, lower alkyl-thio, phenyl-lower alkyl-thio, lower alkyl-sulfonyl, or phenyl-lower alkyl-sulfonyl. Halogen is preferred.

Examples of halogen include fluorine, chlorine, bromine, and iodine. Chlorine and bromine are the preferred halogens. Chlorine is particularly preferred. This description is applicable to the term "halogen" as used throughout the present disclosure.

As used herein, the term "lower alkyl" means an alkyl group having less than 8 carbon atoms. This range includes all specific values of carbon atoms and subranges there between, such as 1, 2, 3, 4, 5, 6, and 7 carbon atoms. The term "alkyl" embraces all types of such groups, e.g., linear, branched, and cyclic alkyl groups. This description is applicable to the term "lower alkyl" as used throughout the present disclosure. Examples of suitable lower alkyl groups include methyl, ethyl, propyl, cyclopropyl, butyl, isobutyl, etc.

Substituents for the phenyl group include halogens. Particularly preferred halogen substituents are chlorine and bromine.

Y may be hydrogen, hydroxyl, mercapto, lower alkoxy, lower alkyl-thio, halogen, lower alkyl, lower cycloalkyl, mononuclear aryl, or —N(R$^2$)$_2$. The alkyl moiety of the lower alkoxy groups is the same as described above. Examples of mononuclear aryl include phenyl groups. The phenyl group may be unsubstituted or substituted as described above. The preferred identity of Y is —N(R$^2$)$_2$. Particularly preferred are such compounds where each R$^2$ is hydrogen.

R$^1$ may be hydrogen or lower alkyl. Hydrogen is preferred for R$^1$.

Each R$^2$ may be, independently, —R$^7$, —(CH$_2$)$_m$—OR$^8$, —(CH$_2$)$_m$—NR$^7$R$^{10}$, —(CH$_2$)$_n$(CHOR$^8$)(CHOR$^8$)$_n$—CH$_2$OR$^8$, —(CH$_2$CH$_2$O)$_m$—R$^8$, —(CH$_2$CH$_2$O)$_m$—CH$_2$CH$_2$NR$^7$R$^{10}$, —(CH$_2$)$_n$—C(=O)NR$^7$R$^{10}$, —(CH$_2$)$_n$—Z$_g$—R$^7$, —(CH$_2$)$_m$—NR$^{10}$—CH$_2$(CHOR$^8$)(CHOR$^8$)$_n$—CH$_2$OR$^8$, —(CH$_2$)$_n$—CO$_2$R$^7$, or

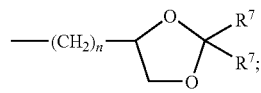

Hydrogen and lower alkyl, particularly C$_1$-C$_3$ alkyl are preferred for R$^2$. Hydrogen is particularly preferred.

R$^3$ and R$^4$ may be, independently, hydrogen, a group represented by formula (A), lower alkyl, hydroxy lower alkyl, phenyl, phenyl-lower alkyl, (halophenyl)-lower alkyl, lower-(alkylphenylalkyl), lower (alkoxyphenyl)-lower alkyl, naphthyl-lower alkyl, or pyridyl-lower alkyl, provided that at least one of R$^3$ and R$^4$ is a group represented by formula (A).

Preferred compounds are those where one of R$^3$ and R$^4$ is hydrogen and the other is represented by formula (A).

In formula (A), the moiety —(C(R$^L$)$_2$)$_o$-x-(C(R$^L$)$_2$)$_p$— defines an alkylene group bonded to the aromatic ring. The variables o and p may each be an integer from 0 to 10, subject to the proviso that the sum of o and p in the chain is from 1 to 10. Thus, o and p may each be 0, 1, 2, 3, 4, 5, 6, 7, 8, 9, or 10, or any subrange therebetween. Preferably, the sum of o and p is from 2 to 6. In a one preferred embodiment, the sum of o and p is 4.

The linking group in the alkylene chain, x, may be, independently, O, NR$^{10}$, C(=O), CHOH, C(=N—R$^{10}$), CHNR$^7$R$^{10}$, or represents a single bond;

Therefore, when x represents a single bond, the alkylene chain bonded to the ring is represented by the formula —(C(R$^L$)$_2$)$_{o+p}$—, in which the sum o+p is from 1 to 10.

Each R$^L$ may be, independently, —R$^7$, —(CH$_2$)$_n$—OR$^8$, —O—(CH$_2$)$_m$—OR$^8$, —(CH$_2$)$_n$—NR$^7$R$^{10}$, —O—(CH$_2$)$_m$—NR$^7$R$^{10}$, —(CH$_2$)$_n$(CHOR$^8$)(CHOR$^8$)$_n$—CH$_2$OR$^8$, —O—(CH$_2$)$_m$(CHOR$^8$)(CHOR$^8$)$_n$—CH$_2$OR$^8$, —(CH$_2$CH$_2$O)$_m$—R$^8$, —O—(CH$_2$CH$_2$O)$_m$—R$^8$, —(CH$_2$CH$_2$O)$_m$—CH$_2$CH$_2$NR$^7$R$^{10}$, —O—(CH$_2$CH$_2$O)$_m$—

CH₂CH₂NR⁷R¹⁰, —(CH₂), —C(=O)NR⁷R¹⁰, —O—(CH₂)ₘ—C(=O)NR⁷R¹⁰, —(CH₂)ₙ-(Z)g—R⁷, —O—(CH₂)ₘ—(Z)g—R⁷, —(CH₂)ₙ—NR¹⁰—CH₂(CHOR⁸)(CHOR⁸)ₙ—CH₂OR⁸, —O—(CH₂)ₘ, NR¹⁰—CH₂(CHOR⁸)(CHOR⁸)ₙ—CH₂OR⁸, —(CH₂)ₙ—CO₂R⁷, —O—(CH₂)ₘ—CO₂R⁷, —OSO₃H, —O-glucuronide, —O-glucose,

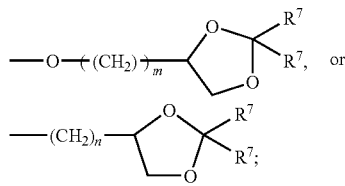

The preferred $R^L$ groups include —H, —OH, —N(R⁷)₂, especially where each R⁷ is hydrogen.

In the alkylene chain in formula (A), it is preferred that when one $R^L$ group bonded to a carbon atoms is other than hydrogen, then the other $R^L$ bonded to that carbon atom is hydrogen, i.e., the formula —CHR$^L$. It is also preferred that at most two $R^L$ groups in an alkylene chain are other than hydrogen, where in the other $R^L$ groups in the chain are hydrogens. Even more preferably, only one $R^L$ group in an alkylene chain is other than hydrogen, where in the other $R^K$ groups in the chain are hydrogens. In these embodiments, it is preferable that x represents a single bond.

In another particular embodiment of the invention, all of the $R^L$ groups in the alkylene chain are hydrogen. In these embodiments, the alkylene chain is represented by the formula

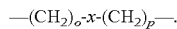

In the first embodiment of the invention described above, each Q in formula (A) is C—OH, C—R⁶ or a nitrogen atom, where at most three Q in a ring are nitrogen atoms. Of course, in each case, one Q must be C—OH. Thus, there may be 1, 2, or 3 nitrogen atoms in a ring. Preferably, at most two Q are nitrogen atoms. There may be 1-4 C—R⁶ groups in a ring, depending on the number of nitrogen atoms in a ring. That is, if there are zero, one, two or three nitrogen atoms in a ring, then there are four, three, two or one C—R⁶ groups in the ring respectively. More preferably, at most one Q is a nitrogen atom. In one particular embodiment, the nitrogen atom is at the 3-position of the ring. Of course, any such nitrogen atom in the ring is not substituted with either an —OH or R⁶ group. In another embodiment of the invention, each Q, other than the C—OH, is C—R⁶, i.e., there are no nitrogen atoms in the ring.

In the second, third, fourth and ninth embodiment of the invention described above, each Q in formula (A) is C—R⁵, C—R⁶, or a nitrogen atom, where at most three Q in a ring are nitrogen atoms. Of course, in each case, one Q is C—R⁵. Thus, there may be 1, 2, or 3 nitrogen atoms in a ring. There may be 1-4 C—R⁶ groups in a ring, depending on the number of nitrogen atoms in a ring. That is, if there are zero, one, two or three nitrogen atoms in a ring, then there are four, three, two or one C—R⁶ groups in the ring respectively. Preferably, at most two Q are nitrogen atoms. More preferably, at most one Q is a nitrogen atom. In one particular embodiment, the nitrogen atom is at the 3-position of the ring. In another embodiment of the invention, each Q is either C—R⁵ or C—R⁶, i.e., there are no nitrogen atoms in the ring.

In the sixth and seventh embodiment of the of the invention, each Q is independently, —C(R⁶R⁵)—, —C(R⁶R⁶)—, —N(R¹⁰)—, —N(R⁷)—, —N(R⁵)—, —S—, —SO—, or —SO₂—. At least one Q is —C(R⁵R⁶)— or —N(R⁵)—. In a preferred embodiment, at least one Q is —CHR⁵. In a particularly preferred embodiment each —C(R⁵R⁶) is —CHR⁶. At most three Q in a ring is —N(R⁷)—, —N(R⁵)—, —S—, —SO—, or —SO₂—. In a preferred embodiment, one or two Q is —N(R⁷)—, —N(R⁵)—, —S—, —SO—, or —SO₂—. In another embodiment, none of the Qs are —N(R⁷)—, —N(R⁵)—, —S—, —SO—, or —SO₂—, i.e., each Q is —C(R⁵R⁶).

In the second to ninth embodiments of the invention, preferred embodiments of R⁵ are:

—O—(CH₂)ₘZgR¹²,

-Het-(CH₂)ₘNH(C=NR¹³)NR¹³R¹³,

-Het-(CH₂)ₙZg(CH₂)ₘNH(C=NR¹³)NR¹³R¹³,

-Link-(CH₂)ₘ—(Z)g—(CH₂)ₘ-CAP,

-Het-(CH₂)ₘC(=O)NR¹³R¹³,

—(CH₂)ₙNR¹²R¹²,

—O—(CH₂)ₘNR¹¹R¹¹,

—O—(CH₂)ₘN⁺(R¹¹)₃,

—(CH₂)ₙZg(CH₂)ₘNR¹⁰R¹⁰, or

-Het-(CH₂)ₘZgNH(C=NR¹³)NR¹³R¹³.

Even more preferred embodiments are those found in the specific compounds described below.

In a preferred embodiment, the sodium channel blocker of formula I is

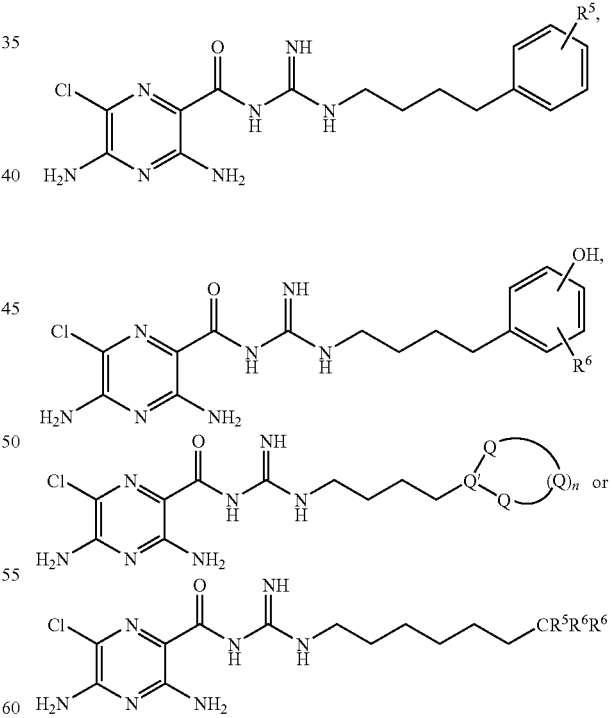

Preferred R⁵ groups of that embodiment are as described above and even more preferred embodiments are those found in the specific compounds described below.

Specific examples of sodium channel blockers that may be used in the present invention include:

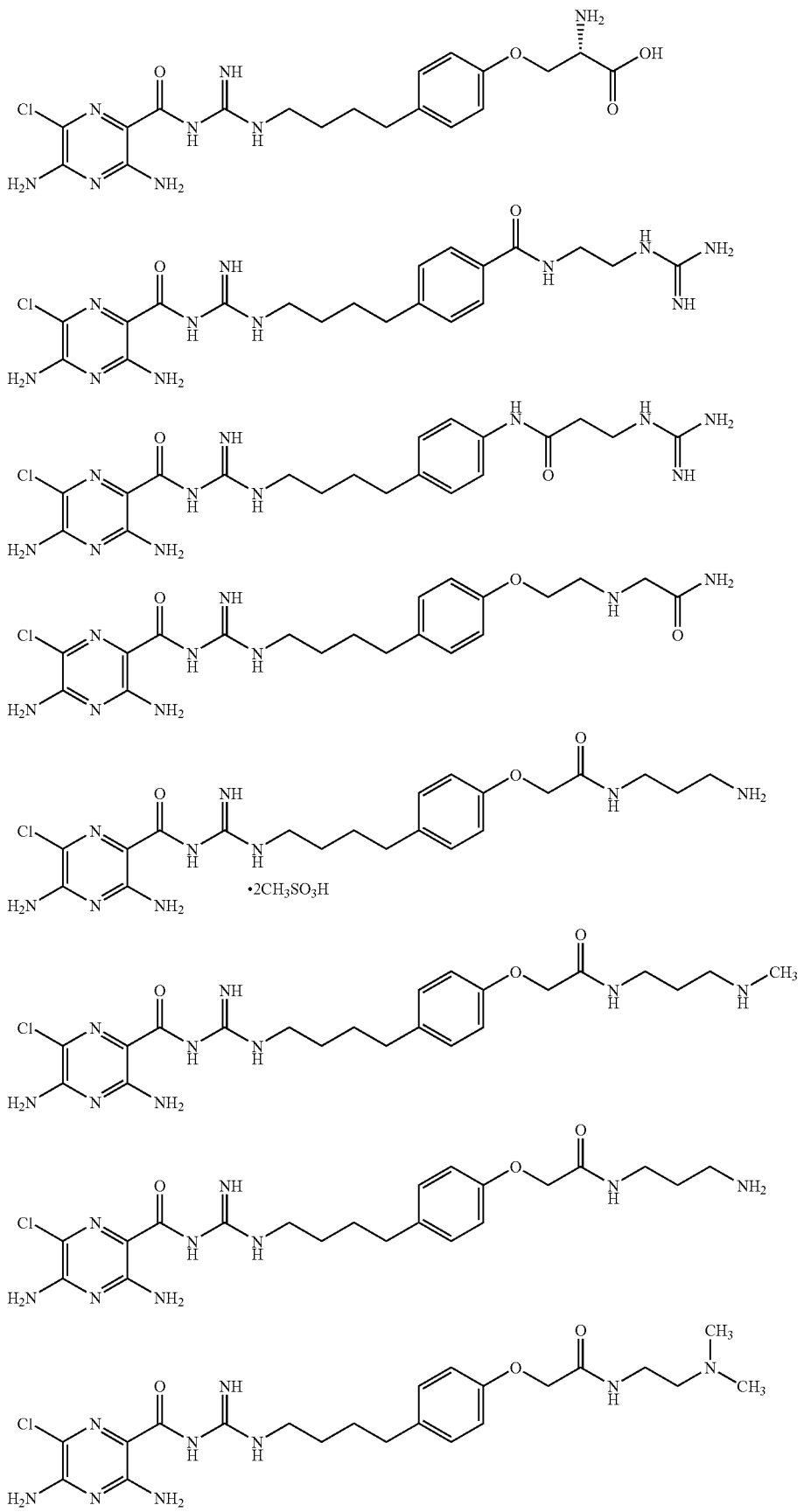

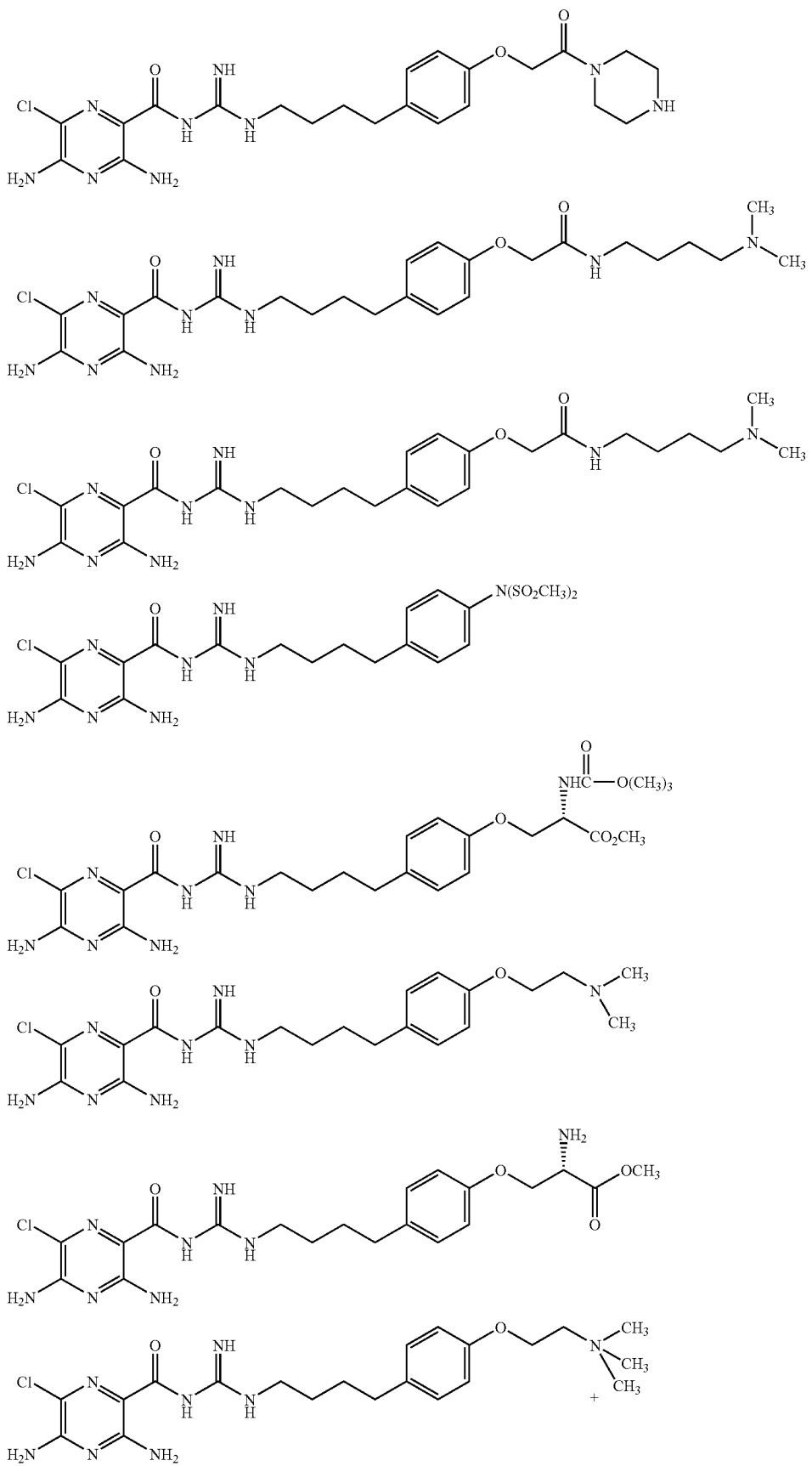

-continued

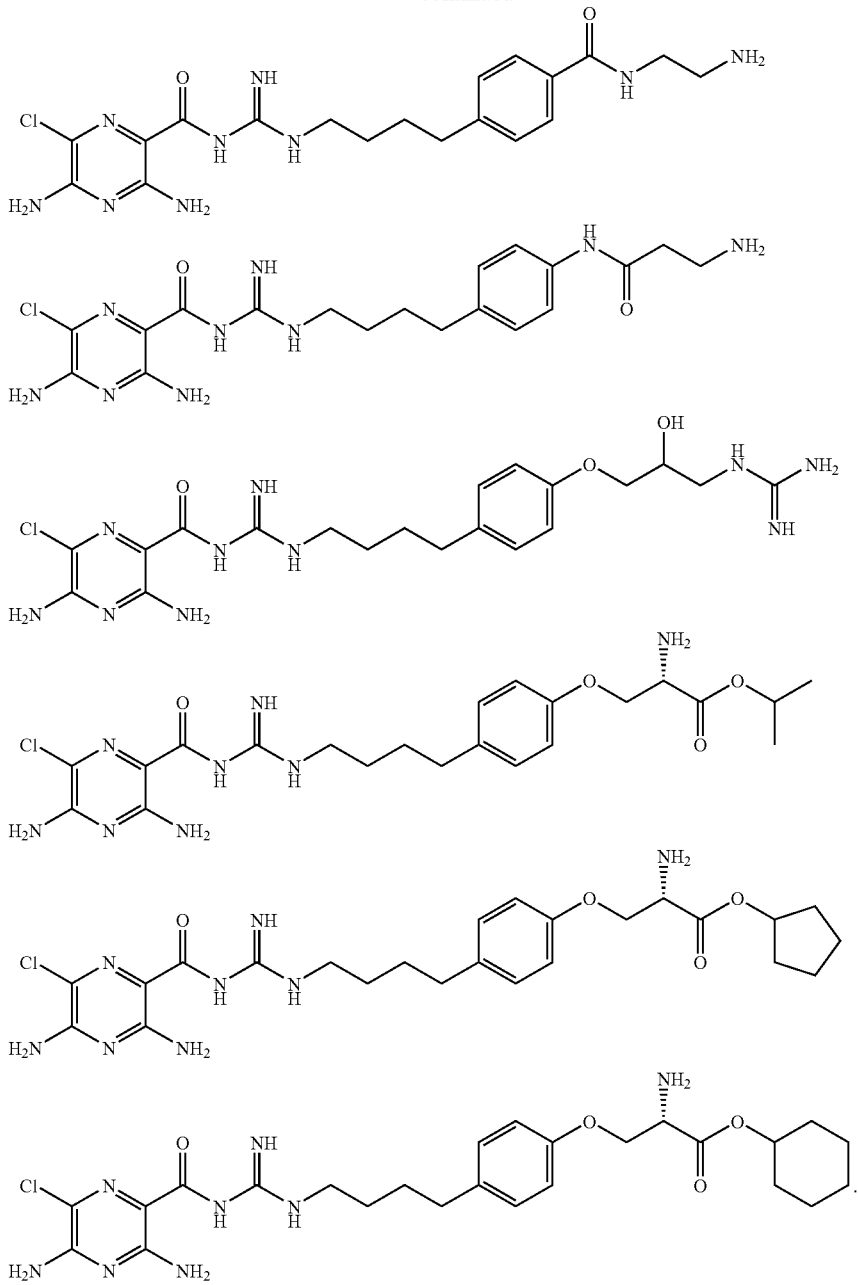

As discussed above, the present invention includes all racemates, enantiomers, diastereomers, tautomers, polymorphs and pseudopolymorphs, salts and racemic mixtures of the sodium channel blockers described above.

The present invention is based on the discovery that the sodium channel blockers identified above, which are more potent and/or, absorbed less rapidly from mucosal surfaces, especially airway surfaces, and/or less reversible from interactions with ENaC than amiloride, benzamil or phenamil, administered before, with or after an osmolyte to an airway surface, greatly improve the hydration of airway surfaces when compared to the sodium channel blocker, or osmolytes when used alone. As exemplified in FIG. 1, sodium channel blockers as defined herein when combined with osmolytes have a longer half-life on mucosal surfaces as compared to either compound alone.

The present invention is also based on the discovery that the sodium channel blocker described herein in combination with osmolytes can lower the dose of the sodium channel blocker needed to hydrate mucosal surfaces. This important property means that the sodium channel blocker will have a lower tendency to cause undesired side-effects by blocking sodium channels located at untargeted locations in the body of the recipient, e.g., in the kidneys when used in combination with an osmolyte.

The sodium channel blockers may be prepared and used as the free base. Alternatively, the compounds may be prepared and used as a pharmaceutically acceptable salt. Pharmaceutically acceptable salts are salts that retain or enhance the desired biological activity of the parent compound and do not impart undesired toxicological effects. Examples of such salts are (a) acid addition salts formed with inorganic acids, for example, hydrochloric acid, hydrobromic acid, sulfuric acid, phosphoric acid, nitric acid and the like; (b) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, malonic acid, sulfosalicylic acid, glycolic acid, 2-hydroxy-3-naphthoate, pamoate, salicylic acid, stearic acid, phthalic acid, mandelic acid, lactic acid and the like; and (c) salts formed from elemental anions for example, chlorine, bromine, and iodine.

The compounds of formula (I) may be synthesized according to procedures known in the art. A representative synthetic procedure is shown in the scheme below:

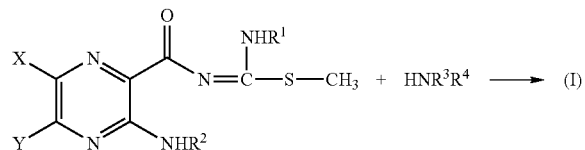

These procedures are described in, for example, E. J. Cragoe, "The Synthesis of Amiloride and Its Analogs" (Chapter 3) in *Amiloride and Its Analogs*, pp. 25-36, incorporated herein by reference. Other methods of preparing the compounds are described in, for example, U.S. Pat. No. 3,313,813, incorporated herein by reference. See in particular Methods A, B, C, and D described in U.S. Pat. No. 3,313,813. Several assays may be used to characterize the compounds of the present invention. Representative assays are discussed below.

Without being limited to any particular theory, it is believed that sodium channel blockers of the present invention block epithelial sodium channels present in mucosal surfaces the sodium channel blocker, described herein reduce the absorption of salt and water by the mucosal surfaces. This effect increases the volume of protective liquids on mucosal surfaces, rebalances the system, and thus treats disease. This effect is enhanced when used in combination with osmolytes.

Active osmolytes of the present invention are molecules or compounds that are osmotically active (i.e., are "osmolytes"). "Osmotically active" compounds of the present invention are membrane-impermeable (i.e., essentially non-absorbable) on the airway or pulmonary epithelial surface. The terms "airway surface" and "pulmonary surface," as used herein, include pulmonary airway surfaces such as the bronchi and bronchioles, alveolar surfaces, and nasal and sinus surfaces. Active compounds of the present invention may be ionic osmolytes (i.e., salts), or may be non-ionic osmolytes (i.e., sugars, sugar alcohols, and organic osmolytes). It is specifically intended that both racemic forms of the active compounds that are racemic in nature are included in the group of active compounds that are useful in the present invention. It is to be noted that all racemates, enantiomers, diastereomers, tautomers, polymorphs and pseudopolymorphs and racemic mixtures of the osmotically active compounds are embraced by the present invention.

Active osmolytes useful in the present invention that are ionic osmolytes include any salt of a pharmaceutically acceptable anion and a pharmaceutically acceptable cation. Preferably, either (or both) of the anion and cation are non-absorbable (i.e., osmotically active and not subject to rapid active transport) in relation to the airway surfaces to which they are administered. Such compounds include but are not limited to anions and cations that are contained in FDA approved commercially marketed salts, see, e.g., *Remington. The Science and Practice of Pharmacy*, Vol. II, pg. 1457 (19$^{th}$ Ed. 1995), incorporated herein by reference, and can be used in any combination including their conventional combinations.

Pharmaceutically acceptable osmotically active anions that can be used to carry out the present invention include, but are not limited to, acetate, benzenesulfonate, benzoate, bicarbonate, bitartrate, bromide, calcium edetate, camsylate (camphorsulfonate), carbonate, chloride, citrate, dihydrochloride, edetate, edisylate (1,2-ethanedisulfonate), estolate (lauryl sulfate), esylate (1,2-ethanedisulfonate), fumarate, gluceptate, gluconate, glutamate, glycollylarsanilate (p-glycollamidophenylarsonate), hexylresorcinate, hydrabamine (N,N'-Di(dehydroabietyl)ethylenediamine), hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, nitrte, pamoate (embonate), pantothenate, phosphate or diphosphate, polygalacturonate, salicylate, stearate, subacetate, succinate, sulfate, tannate, tartrate, teoclate (8-chlorotheophyllinate), triethiodide, bicarbonate, etc. Particularly preferred anions include chloride sulfate, nitrate, gluconate, iodide, bicarbonate, bromide, and phosphate.

Pharmaceutically acceptable cations that can be used to carry out the present invention include, but are not limited to, organic cations such as benzathine (N,N'-dibenzylethylenediamine), chloroprocaine, choline, diethanolamine, ethylenediamine, meglumine (N-methyl D-glucamine), procaine, D-lysine, L-lysine, D-arginine, L-arginine, triethylammonium, N-methyl D-glycerol, and the like. Particularly preferred organic cations are 3-carbon, 4-carbon, 5-carbon and 6-carbon organic cations. Metallic cations useful in the practice of the present invention include but are not limited to aluminum, calcium, lithium, magnesium, potassium, sodium, zinc, iron, ammonium, and the like. Particularly preferred cations include sodium, potassium, choline, lithium, meglumine, D-lysine, ammonium, magnesium, and calcium.

Specific examples of osmotically active salts that may be used with the sodium channel blockers described herein to carry out the present invention include, but are not limited to, sodium chloride, potassium chloride, choline chloride, choline iodide, lithium chloride, meglumine chloride, L-lysine chloride, D-lysine chloride, ammonium chloride, potassium sulfate, potassium nitrate, potassium gluconate, potassium iodide, ferric chloride, ferrous chloride, potassium bromide, etc. Either a single salt or a combination of different osmotically active salts may be used to carry out the present invention. Combinations of different salts are preferred. When different salts are used, one of the anion or cation may be the same among the differing salts.

Osmotically active compounds of the present invention also include non-ionic osmolytes such as sugars, sugar-alcohols, and organic osmolytes. Sugars and sugar-alcohols useful in the practice of the present invention include but are not limited to 3-carbon sugars (e.g., glycerol, dihydroxyacetone); 4-carbon sugars (e.g., both the D and L forms of erythrose, threose, and erythrulose); 5-carbon sugars (e.g., both the D and L forms of ribose, arabinose, xylose, lyxose, psicose, fructose, sorbose, and tagatose); and 6-carbon sugars (e.g., both the D and L forms of altose, allose, glucose, mannose, gulose, idose, galactose, and talose, and the D and L forms of allo-heptulose, allo-hepulose, gluco-heptulose, manno-heptulose, gulo-heptulose, ido-heptulose, galacto-heptulose, talo-heptulose). Additional sugars useful in the practice of the present invention include raffinose, raffinose series oligosaccharides, and stachyose. Both the D and L forms of the reduced form of each sugar/sugar alcohol useful in the present invention are also active compounds within the scope of the invention. For example, glucose, when reduced, becomes sorbitol; within the scope of the invention, sorbitol and other reduced forms of sugar/sugar alcohols (e.g., mannitol, dulcitol, arabitol) are accordingly active compounds of the present invention.

Osmotically active compounds of the present invention additionally include the family of non-ionic osmolytes termed "organic osmolytes." The term "organic osmolytes" is generally used to refer to molecules used to control intracellular osmolality in the kidney. See e.g., J. S. Handler et al., *Comp. Biochem. Physiol,* 117, 301-306 (1997); M. Burg, *Am. J. Physiol.* 268, F983-F996 (1995), each incorporated herein by reference. Although the inventor does not wish to be bound to any particular theory of the invention, it appears that these organic osmolytes are useful in controlling extracellular volume on the airway/pulmonary surface. Organic osmolytes useful as active compounds in the present invention include but are not limited to three major classes of compounds: polyols (polyhydric alcohols), methylamines, and amino acids. The polyol organic osmolytes considered useful in the practice of this invention include, but are not limited to, inositol, myo-inositol, and sorbitol. The methylamine organic osmolytes useful in the practice of the invention include, but are not limited to, choline, betaine, carnitine (L-, D- and DL forms), phosphorylcholine, lyso-phosphorylcholine, glycerophosphorylcholine, creatine, and creatine phosphate. The amino acid organic osmolytes of the invention include, but are not limited to, the D- and L-forms of glycine, alanine, glutamine, glutamate, aspartate, proline and taurine. Additional osmolytes useful in the practice of the invention include tihulose and sarcosine. Mammalian organic osmolytes are preferred, with human organic osmolytes being most preferred. However, certain organic osmolytes are of bacterial, yeast, and marine animal origin, and these compounds are also useful active compounds within the scope of the present invention.

Under certain circumstances, an osmolyte precursor may be administered to the subject; accordingly, these compounds are also useful in the practice of the invention. The term "osmolyte precursor" as used herein refers to a compound which is converted into an osmolyte by a metabolic step, either catabolic or anabolic. The osmolyte precursors of this invention include, but are not limited to, glucose, glucose polymers, glycerol, choline, phosphatidylcholine, lyso-phosphatidylcholine and inorganic phosphates, which are precursors of polyols and methylamines. Precursors of amino acid osmolytes within the scope of this invention include proteins, peptides, and polyamino acids, which are hydrolyzed to yield osmolyte amino acids, and metabolic precursors which can be converted into osmolyte amino acids by a metabolic step such as transamination. For example, a precursor of the amino acid glutamine is poly-L-glutamine, and a precursor of glutamate is poly-L-glutamic acid.

Also intended within the scope of this invention are chemically modified osmolytes or osmolyte precursors. Such chemical modifications involve linking to the osmolyte (or precursor) an additional chemical group which alters or enhances the effect of the osmolyte or osmolyte precursor (e.g., inhibits degradation of the osmolyte molecule). Such chemical modifications have been utilized with drugs or prodrugs and are known in the art. (See, for example, U.S. Pat. Nos. 4,479,932 and 4,540,564; Shek, E. et al., *J. Med. Chem.* 19:113-117 (1976); Bodor, N. et al., *J. Pharm. Sci.* 67:1045-1050 (1978); Bodor, N. et al., *J. Med. Chem.* 26:313-318 (1983); Bodor, N. et al., *J. Pharm. Sci.* 75:29-35 (1986), each incorporated herein by reference.

In general, osmotically active compounds of the present invention (both ionic and non-ionic) that do not promote, or in fact deter or retard bacterial growth are preferred.

The active compounds, methods and compositions of the present invention are useful as therapeutics for the treatment of chronic obstructive airway or pulmonary disease in subjects in need of such treatment. The active compounds, compositions and methods described herein may also be used to induce the production of a sputum or mucous sample in a patient. Additionally, the active compounds, compositions and methods described herein can be used for the lavage of the lungs and/or airways of a patient. The active compounds and compositions described herein may also be administered with other active agents that are to be introduced into airways of a subject, and in fact may function as vehicles or carriers for the other active agents.

Suitable subjects to be treated according to the present invention include both avian and mammalian subjects, preferably mammalian. Any mammalian subject in need of being treated according to the present invention is suitable, including dogs, cats and other animals for veterinary purposes. Human subjects are preferred. Human subjects of both genders and at any stage of development (i.e., neonate, infant, juvenile, adolescent, adult) can be treated according to the present invention. Preferred subjects include those humans afflicted with a chronic obstructive airway or pulmonary disease, including but not limited to cystic fibrosis, chronic bronchitis, emphysema, primary and secondary ciliary dyskinesia, sinusitis, and pneumonia. Human subjects afflicted with cystic fibrosis are particularly preferred.

The sodium channel blockers described herein and osmotically active compounds disclosed herein may be administered in any order and/or concurrently to mucousal surfaces such as the eye, the nose, and airway surfaces including the nasal passages, sinuses and lungs of a subject by any suitable means known in the art, such as by nose drops, mists, aerosols, continuous overnight nasal cannulation, etc. In one embodiment of the invention, sodium channel blockers and osmotically active compounds of the present invention are administered concurrently by transbronchoscopic lavage. In a preferred embodiment of the invention, active sodium channel blockers and osmotically active compounds of the present invention are deposited on lung airway surfaces by administering by inhalation an respirable aerosol respirable particles comprised of the sodium channel blocker and the osmotically active compounds, in which the sodium channel blocker can precede or follow the independent delivery of an osmotically active compound within a sufficiently short time for their effects to be additive. The respirable particles may be liquid or solid. Numerous inhalers for administering aerosol particles to the lungs of a subject are known. In another preferred embodiment of the invention, sodium channel blockers and osmotically active compounds can be given concurrently as defined herein.

The sodium channel blockers and osmotically active of the present invention are administered sequentially (in any order) or concurrently to the subject in need thereof. As used herein, the term "concurrently" means sufficiently close in time to produce a combined effect (that is, concurrently may be simultaneously, or it may be two or more events occurring within a short time period before or after each other). Concurrently also embraces the delivery of the sodium channel blockers and osmolytes as a mixture or solution of the two components as well as when delivered from two different nebulizers. An example of that would be the delivery of compound 1 in one nebulizer and hypertonic saline in a second nebulizer connected by a T-piece. When administered with other active agents, the active compounds of the present invention may function as a vehicle or carrier for the other active agent, or may simply be administered concurrently with the other active agent. The active compound of the present invention may be used as a dry or liquid vehicle for administering other active ingredients to airway surfaces. Such other active agents may be administered for treating the disease or disorder for which they are intended, in their conventional manner and dosages, in combination with the active compounds of the present invention, which may be thought of as serving as a vehicle or carrier for the other active agent. Any such other active ingredient may be employed, particularly where hydration of the airway surfaces (i.e., the activity of the osmotically active compounds of the present invention) facilitates the activity of the other active ingredient (e.g., by facilitating or enhancing uptake of the active ingredient, by contributing to the mechanism of action of the other active ingredient, or by any other mechanisms). In a preferred embodiment of the invention, when the active compound of the present invention is administered concurrently with another active agent, the active compound of the present invention has an additive effect in relation to the other active agent; that is, the desired effect of the other active agent is enhanced by the concurrent administration of the active compounds of the present invention.

Inhalers such as those developed by Inhale Therapeutic Systems (Nektar), Palo Alto, Calif., USA, may be employed, including but not limited to those disclosed in U.S. Pat. Nos. 5,740,794; 5,654,007; 5,458,135; 5,775,320; and 5,785,049. The Applicant specifically intends that the disclosures of all patent references cited herein be incorporated by reference herein in their entirety. Inhalers such as those developed by Dura Pharmaceuticals Inc, San Diego, Calif., USA, may also be employed, including but not limited to those disclosed in U.S. Pat. Nos. 5,622,166; 5,577,497; 5,645,051; and 5,492,112. Additionally, inhalers such as those developed by Aradigmn Corp., Hayward, Calif., USA, may be employed, including but not limited to those disclosed in U.S. Pat. Nos. 5,826,570; 5,813,397; 5,819,726; and 5,655,516. These apparatuses are particularly suitable as dry particle inhalers.

Aerosols of liquid particles comprising the active compound may be produced by any suitable means, such as with a pressure-driven aerosol nebulizer (L C Star) or an ultrasonic nebulizer (Pari eFlow). See, e.g., U.S. Pat. No. 4,501,729. Nebulizers are commercially available devices which transform solutions or suspensions of the active ingredient into a therapeutic aerosol mist either by means of acceleration of compressed gas, typically air or oxygen, through a narrow venturi orifice, by means of ultrasonic agitation or by means of a vibrating porous plate. Suitable formulations for use in nebulizers consist of the active ingredient in a liquid carrier, the active ingredient comprising up to 40% w/w of the formulation, but preferably less than 20% w/w. The carrier is typically water (and most preferably sterile, pyrogen-free water), a dilute aqueous alcoholic solution or propylene glycol. Perfluorocarbon carriers may also be used. Optional additives include preservatives if the formulation is not made sterile, for example, methyl hydroxybenzoate, antioxidants, flavoring agents, volatile oils, buffering agents and surfactants.

Aerosols of solid particles comprising the active compound may likewise be produced with any solid particulate medicament aerosol generator. Aerosol generators for administering solid particulate medicaments to a subject produce particles which are respirable, as explained above, and generate a volume of aerosol containing a predetermined metered dose of a medicament at a rate suitable for human administration. One illustrative type of solid particulate aerosol generator is an insufflator. Suitable formulations for administration by insufflation include finely comminuted powders which may be delivered by means of an insufflator or taken into the nasal cavity in the manner of a snuff. In the insufflator, the powder (e.g., a metered dose thereof effective to carry out the treatments described herein) is contained in capsules or cartridges, typically made of gelatin or plastic, which are either pierced or opened in situ and the powder delivered by air drawn through the device upon inhalation or by means of a manually-operated pump. The powder employed in the insufflator consists either solely of the active ingredient or of a powder blend comprising the active ingredient, a suitable powder diluent, such as lactose, and an optional surfactant. The active ingredient typically comprises from 0.1 to 100% w/w of the formulation. A second type of illustrative aerosol generator comprises a metered dose inhaler. Metered dose inhalers are pressurized aerosol dispensers, typically containing a suspension or solution formulation of the active ingredient in a liquified propellant. During use these devices discharge the formulation through a valve adapted to deliver a metered volume, typically from 10 to 150 µl, to produce a fine particle spray containing the active ingredient. Suitable propellants include certain chlorofluorocarbon compounds, for example, dichlorodifluoromethane, trichlorofluoromethane, dichlorotetrafluoroethane and mixtures thereof. The formulation may additionally contain one or more co-solvents, for example, ethanol, surfactants, such as oleic acid or sorbitan trioleate, antioxidants and suitable flavoring agents.

The aerosol, whether formed from solid or liquid particles, may be produced by the aerosol generator at a rate of from about 10 to 150 liters per minute, more preferably from about 30 to 150 liters per minute, and most preferably about 60 liters per minute. Aerosols containing greater amounts of medicament may be administered more rapidly.

The dosage of the sodium channel blockers and osmotically active compounds disclosed herein will vary depending on the condition being treated and the state of the subject, but generally may be from about 0.1 or 1 to about 30, 50, or 100 milliosmoles of the osmolyte, deposited on the airway surfaces. The daily dose may be divided among one or several unit dose administrations. The dosage of the sodium channel blockers compound will vary depending on the condition being treated and the state of the subject, but generally may be an amount sufficient to achieve dissolved concentrations of active compound on the nasal airway surfaces of the subject from about $10^{-9}$, $10^{-8}$, $10^{-7}$ to about $10^{-3}$, $10^{-2}$, or $10^{-1}$ moles/liter, and more preferably from about $10^{-7}$ to about $10^{-4}$ moles/liter. Depending upon the solubility of the particular formulation of active compound administered, the daily dose may be divided among one or several unit dose administrations. The daily dose by weight may range from about 0.01, 0.03, 0.1, 0.5 or 1.0 to 10 or 20 milligrams of active agent particles for a human subject, depending upon the age and condition of the subject. A currently preferred unit dose is about 0.5 milligrams of active agent given at a regimen of 2-10 administrations per day. The dosage may be provided as a prepackaged unit by any suitable means (e.g., encapsulating a gelatin capsule).

Other pharmacologically (e.g., bronchodilators) active agents ("third agents") may be administered concurrently to the subject in need thereof with the sodium channel blockers and osmotically active compounds of the present invention In particular, bronchodilators may be administered concurrently with the sodium channel blockers and osmotically active compounds of the present invention. Bronchodilators that can be used in the practice of the present invention include, but are not limited to, β-adrenergic agonists including but not limited to epinephrine, isoproterenol, fenoterol, albuterol, terbutaline, pirbuterol, bitolterol, metaproterenol, isoetharine, salmeterol, xinafoate, as well as anticholinergic agents including but not limited to ipratropium bromide, as well as compounds such as theophylline and aminophylline. These compounds may be administered in accordance with known techniques, either prior to or concurrently with the active compounds described herein.

Other active ingredients ("third agents") that may be administered with the sodium channel blockers and osmotically active compounds of the present invention include ion transport modulators and other active agents known to be useful in the treatment of the subject afflicted with a chronic obstructive pulmonary disease (e.g., DNase, antibiotics, disulfhydryl reducing compounds such as N-acetylcystene, etc.).

Ion transport modulators that can be administered as active agents along with the active compounds of the present invention herein include, purinoceptor (particularly P2Y2) receptor agonists such as UTP, UTP-γ-S, dinucleotide P2Y2 receptor agonists, and β-agonists.

The compounds of the present invention may also be used in conjunction with a P2Y2 receptor agonist or a pharmaceutically acceptable salt thereof (also sometimes referred to as an "active agent" herein). The composition may further comprise a P2Y2 receptor agonist or a pharmaceutically acceptable salt thereof (also sometimes referred to as an "active agent" herein). The P2Y2 receptor agonist is typically included in an amount effective to stimulate chloride and water secretion by airway surfaces, particularly nasal airway surfaces. Suitable P2Y2 receptor agonists are described in columns 9-10 of U.S. Pat. No. 6,264,975, U.S. Pat. No. 5,656,256, and U.S. Pat. No. 5,292,498, each of which is incorporated herein by reference.

Other active ingredients that can be administered in combination with the formulations described herein include nucleic acids or oligonucleotides; viral gene transfer vectors (including adenovirus, adeno-associated virus, and retrovirus gene transfer vectors); enzymes; and hormone drugs or physiologically active proteins or peptides such as insulin, somatostatin, oxytocin, desmopressin, leutinizing hormone releasing hormone, nafarelin, leuprolide, adrenocorticotrophic hormone, secretin, glucagon, calcitonin, growth hormone releasing hormone, growth hormone, etc. Enzyme drugs that may be used to carry out the present invention, include but are not limited to DNAse (for the treatment of, e.g., cystic fibrosis), $α_1$-antitrypsin (e.g., to inhibit elastase in the treatment of emphysema), etc. Suitable anti-inflammatory agents, including steroids, for use in the methods of the present invention include, but are not limited to, beclomethasone dipropionate, prednisone, flunisolone, dexamethasone, prednisolone, cortisone, theophylline, albuterol, cromolyn sodium, epinephrine, flunisolide, terbutaline sulfate, alpha-tocopherol (Vitamin E), dipalmitoylphosphatidylcholine, salmeterol and fluticasone dipropionate. Examples of antibiotics that may be employed include, but are not limited to tetracycline, choramphenicol, aminoglycosides, for example, tobramycin, beta-lactams, for example ampicillin, cephalosporins, erythromycin and derivatives thereof, clindamycin, phosphonic acid antibiotics, for example, fosfomycin, and the like. The antibiotics that may be employed may be used in combination, for example tobramycin and fosfomycin. Suitable anti-viral agents include acyclovir, ribavirin, ganciclovir and foscamet.

Suitable anti-neoplastic agents include, but are not limited to, etoposid, taxol, and cisplatin. Antihistamines include, but are not limited to, diphenhydramine and ranitadine. Anti-*Pneumocystis carinii* pneumonia drugs such as pentamidine and analogs thereof may also be used. Anti-tuberculosis drugs such as rifampin, erythromycin, chlorerythromycin, etc. Chelators of divalent cations (e.g., EGTA, EDTA), expectorants, and other agents useful in the loosening of mucous secretions (e.g., n-acetyl-L-cysteine) may also be administered as desired in the practice of the present invention.

The present invention is particularly useful for chronic treatments: that is, treatments wherein the administration is repeated two or more times in close proximity to one another, so that the multiple treatments achieve a combined therapeutic effect. For example, the administration may be carried out two, three, four, five, six or seven times a week, on separate days throughout the week. The treatment may be carried out for a period of two, four, or six days or more; daily for two or four weeks or more; daily for two or four months or more, etc. For example, the administering step may be carried out three, four, five or six times a day for the duration of the condition being treated, with chronic conditions receiving chronic treatments.

The compounds, compositions and methods described herein can be used for the lavage of a lung, or lung lobe, in a patient in need thereof by administering an effective therapeutic amount of the compositions to the lung of a subject. Lavage may be carried out with a bronchoscope by instilling a volume of fluid into a desired lobe of the lung (e.g., 30 milliliters to 3 liters, typically 300 milliliters) in accordance with known techniques. Lavage may be single administration or repetitive (e.g., three washings). A portion of the instilled fluid is removed or aspirated, after instillation, in accordance with known techniques. The lavage solution may be an aqueous solution, or may be a perfluorocarbon liquid such as used for blood substitutes.

Solid or liquid particulate pharmaceutical formulations containing active compounds of the present invention should include particles of respirable size: that is, particles of a size sufficiently small to pass through the mouth and larynx upon inhalation and into the bronchi, bronchioles, and (if necessary) the alveoli of the lungs. The bronchioles are a particularly preferred target for delivery to the airway surfaces. In general, particles ranging from about 1 to 5 or 6 microns in size (more particularly, less than about 4.7 microns in size) are respirable.

In a preferred embodiment, the geometric standard deviation of the particle size is about 1.7 or smaller. Particles of non-respirable size which are included in the aerosol tend to be deposited in the throat and swallowed, and the quantity of non-respirable particles in the aerosol is preferably minimized. For nasal administration, a particle size in the range of 10-500 μm is preferred to ensure retention in the nasal cavity.

In the manufacture of a formulation according to the invention, the sodium channel blockers and osmotically active compounds of the present invention may be admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a capsule, which may contain from 0.5% to 99% by weight of the active compound. One or more active compounds may be incorporated in the formulations of the invention, which formulations may be prepared by any of the well-known techniques of pharmacy consisting essentially of admixing the components.

Compositions containing respirable dry particles of active compound may be prepared by grinding the active compound with a mortar and pestle, and then passing the micronized composition through a 400 mesh screen to break up or separate out large agglomerates. For example, the grinding of sodium chloride would produce a micronized particle often referred to as a "round" salt.

The pharmaceutical composition may optionally contain a dispersant which serves to facilitate the formation of an aerosol. A suitable dispersant is lactose, which may be blended with the active agents in any suitable ratio (e.g., a 1 to 1 ratio by weight).

The term optionally as used herein means that the point of reference, for example the dispersant, pharmaceutical carrier, or additional component, may be present or absent.

The foregoing is illustrative of the present invention, and is not to be construed as limiting thereof. The invention is defined by the following claims, with equivalents of the claims to be included therein.

The present invention also provides methods of treatment that take advantage of the properties of the sodium channel blockers and osmotically active compounds discussed above. Thus, subjects that may be treated by the methods of the present invention include, but are not limited to, patients afflicted with cystic fibrosis, primary ciliary dyskinesia, bronchiectasis, chronic bronchitis, chronic obstructive airway disease, artificially ventilated patients, patients with acute pneumonia, etc. The present invention may be used to obtain a sputum sample from a patient by administering the active compounds to at least one lung of a patient, and then inducing or collecting a sputum sample from that patient. Typically, the invention will be administered to respiratory mucosal surfaces via aerosol (liquid or dry powders) or lavage.

Subjects that may be treated by the method of the present invention also include patients being administered supplemental oxygen nasally (a regimen that tends to dry the airway surfaces); patients afflicted with an allergic disease or response (e.g., an allergic response to pollen, dust, animal hair or particles, insects or insect particles, etc.) that affects nasal airway surfaces; patients afflicted with a bacterial infection e.g., staphylococcus infections such as *Staphylococcus aureus* infections, *Hemophilus influenza* infections, *Streptococcus pneumoniae* infections, *Pseudomonas aeuriginosa* infections, etc.) of the nasal airway surfaces; patients afflicted with an inflammatory disease that affects nasal airway surfaces; or patients afflicted with sinusitis (wherein the active agent or agents are administered to promote drainage of congested mucous secretions in the sinuses by administering an amount effective to promote drainage of congested fluid in the sinuses), or combined, Rhinosinusitis. The invention may be administered to rhino-sinal surfaces by topical delivery, including aerosols and drops.

The present invention may be used to hydrate mucosal surfaces other than airway surfaces. Such other mucosal surfaces include gastrointestinal surfaces, oral surfaces, genitourethral surfaces, ocular surfaces or surfaces of the eye, the inner ear and the middle ear. For example, the active compounds of the present invention may be administered by any suitable means, including locally/topically, orally, or rectally, in an effective amount.

The sodium channel blockers and osmotically active compounds of the present invention are also useful for treating airborne infections. Examples of airborne infections include, for example, RSV. The sodium channel blockers and osmotically active compounds of the present invention are also useful for treating an anthrax infection. The present invention relates to the use of sodium channel blockers and osmotically active compounds of the present invention for prophylactic, post-exposure prophylactic, preventive or therapeutic treatment against diseases or conditions caused by pathogens. In a preferred embodiment, the present invention relates to the use of sodium channel blockers and osmotically active compounds for prophylactic, post-exposure prophylactic, preventive or therapeutic treatment against diseases or conditions caused by pathogens which may be used in bioterrorism.

In recent years, a variety of research programs and biodefense measures have been put into place to deal with concerns about the use of biological agents in acts of terrorism. These measures are intended to address concerns regarding bioterrorism or the use of microorganisms or biological toxins to kill people, spread fear, and disrupt society. For example, the National Institute of Allergy and Infectious Diseases (NIAID) has developed a Strategic Plan for Biodefense Research which outlines plans for addressing research needs in the broad area of bioterrorism and emerging and reemerging infectious diseases. According to the plan, the deliberate exposure of the civilian population of the United States to *Bacillus anthracis* spores revealed a gap in the nation's overall preparedness against bioterrorism. Moreover, the report details that these attacks uncovered an unmet need for tests to rapidly diagnose, vaccines and immunotherapies to prevent, and drugs and biologics to cure disease caused by agents of bioterrorism.

Much of the focus of the various research efforts has been directed to studying the biology of the pathogens identified as potentially dangerous as bioterrorism agents, studying the host response against such agents, developing vaccines against infectious diseases, evaluating the therapeutics currently available and under investigation against such agents, and developing diagnostics to identify signs and symptoms of threatening agents. Such efforts are laudable but, given the large number of pathogens which have been identified as potentially available for bioterrorism, these efforts have not yet been able to provide satisfactory responses for all possible bioterrorism threats. Additionally, many of the pathogens identified as potentially dangerous as agents of bioterrorism do not provide adequate economic incentives for the development of therapeutic or preventive measures by industry. Moreover, even if preventive measures such as vaccines were available for each pathogen which may be used in bioterrorism, the cost of administering all such vaccines to the general population is prohibitive.

Until convenient and effective treatments are available against every bioterrorism threat, there exists a strong need for preventative, prophylactic or therapeutic treatments which can prevent or reduce the risk of infection from pathogenic agents.

The present invention provides such methods of prophylactic treatment. In one aspect, a prophylactic treatment method is provided comprising administering a prophylactically effective amount of a sodium channel blocker and an osmolyte to an individual in need of prophylactic treatment against infection from one or more airborne pathogens. A particular example of an airborne pathogen is anthrax.

In another aspect, a prophylactic treatment method is provided for reducing the risk of infection from an airborne pathogen which can cause a disease in a human, said method comprising administering an effective amount of a sodium channel blocker an osmolyte to the lungs of the human who may be at risk of infection from the airborne pathogen but is asymptomatic for the disease, wherein the effective amount of a sodium channel blocker and osmolye are sufficient to reduce the risk of infection in the human. A particular example of an airborne pathogen is anthrax.

In another aspect, a post-exposure prophylactic treatment or therapeutic treatment method is provided for treating infection from an airborne pathogen comprising administering an effective amount of a sodium channel blocker and an osmolyte to the lungs of an individual in need of such treatment against infection from an airborne pathogen. The pathogens which may be protected against by the prophylactic post exposure, rescue and therapeutic treatment methods of the invention include any pathogens which may enter the body through the mouth, nose or nasal airways, thus proceeding into the lungs. Typically, the pathogens will be airborne pathogens, either naturally occurring or by aerosolization. The pathogens may be naturally occurring or may have been introduced into the environment intentionally after aerosolization or other method of introducing the pathogens into the environment. Many pathogens which are not naturally transmitted in the air have been or may be aerosolized for use in bioterrorism. The pathogens for which the treatment of the invention may be useful includes, but is not limited to, category A, B and C priority pathogens as set forth by the NIAID. These categories correspond generally to the lists compiled by the Centers for Disease Control and Prevention (CDC). As set up by the CDC, Category A agents are those that can be easily disseminated or transmitted person-to-person, cause high mortality, with potential for major public health impact. Category B agents are next in priority and include those that are moderately easy to disseminate and cause moderate morbidity and low mortality. Category C consists of emerging pathogens that could be engineered for mass dissemination in the future because of their availability, ease of production and dissemination and potential for high morbidity and mortality. Particular examples of these pathogens are anthrax and plague. Additional pathogens which may be protected against or the infection risk therefrom reduced include influenza viruses, rhinoviruses, adenoviruses and respiratory syncytial viruses, and the like. A further pathogen which may be protected against is the coronavirus which is believed to cause severe acute respiratory syndrome (SARS).

The present invention is concerned primarily with the treatment of human subjects, but may also be employed for the treatment of other mammalian subjects, such as dogs and cats, for veterinary purposes.

As discussed above, the compounds used to prepare the compositions of the present invention may be in the form of a pharmaceutically acceptable free base. Because the free base of the compound is generally less soluble in aqueous solutions than the salt, free base compositions are employed to provide more sustained release of active agent to the lungs. An active agent present in the lungs in particulate form which has not dissolved into solution is not available to induce a physiological response, but serves as a depot of bioavailable drug which gradually dissolves into solution.

Another aspect of the present invention is a pharmaceutical composition, comprising a sodium channel blocker in a pharmaceutically acceptable carrier (e.g., an aqueous carrier solution). In general, the sodium channel blocker is included in the composition in an amount effective to inhibit the reabsorption of water by mucosal surfaces.

The compounds of the present invention may also be used in conjunction with a P2Y2 receptor agonist or a pharmaceutically acceptable salt thereof (also sometimes referred to as an "active agent" herein). The composition may further comprise a P2Y2 receptor agonist or a pharmaceutically acceptable salt thereof (also sometimes referred to as an "active agent" herein). The P2Y2 receptor agonist is typically included in an amount effective to stimulate chloride and water secretion by airway surfaces, particularly nasal airway surfaces. Suitable P2Y2 receptor agonists are described in columns 9-10 of U.S. Pat. No. 6,264,975, U.S. Pat. No. 5,656,256, and U.S. Pat. No. 5,292,498, each of which is incorporated herein by reference.

Bronchodiloators can also be used in combination with compounds of the present invention. These bronchodilators include, but are not limited to, β-adrenergic agonists including but not limited to epinephrine, isoproterenol, fenoterol, albutereol, terbutalin, pirbuterol, bitolterol, metaproterenol, iosetharine, salmeterol xinafoate, as well as anticholinergic agents including but not limited to ipratropium bromide, as well as compounds such as theophylline and aminophylline. These compounds may be administered in accordance with known techniques, either prior to or concurrently with the active compounds described herein.

Another aspect of the present invention is a pharmaceutical formulation, comprising sodium channel blockers and osmotically active compounds as described above in a pharmaceutically acceptable carrier (e.g., an aqueous carrier solution). In general, the sodium channel blocker is included in the composition in an amount effective to treat mucosal surfaces, such as inhibiting the reabsorption of water by mucosal surfaces, including airway and other surfaces.

The sodium channel blockers and osmotically active compounds disclosed herein may be administered to mucosal surfaces by any suitable means, including topically, orally, rectally, vaginally, ocularly and dermally, etc. For example, for the treatment of constipation, the active compounds may be administered orally or rectally to the gastrointestinal mucosal surface. The active compound may be combined with a pharmaceutically acceptable carrier in any suitable form, such as sterile physiological or dilute saline or topical solution, as a droplet, tablet or the like for oral administration, as a suppository for rectal or genito-urethral administration, etc. Excipients may be included in the formulation to enhance the solubility of the active compounds, as desired.

The sodium channel blockers and osmotically active compounds disclosed herein may be administered to the airway surfaces of a patient by any suitable means, including as a spray, mist, or droplets of the active compounds in a pharmaceutically acceptable carrier such as physiological or dilute saline solutions or distilled water. For example, the active compounds may be prepared as formulations and administered as described in U.S. Pat. No. 5,789,391 to Jacobus, the disclosure of which is incorporated by reference herein in its entirety.

Solid or liquid particulate active agents prepared for practicing the present invention could, as noted above, include particles of respirable or non-respirable size; that is, for respirable particles, particles of a size sufficiently small to pass through the mouth and larynx upon inhalation and into the bronchi and alveoli of the lungs, and for non-respirable particles, particles sufficiently large to be retained in the nasal airway passages rather than pass through the larynx and into the bronchi and alveoli of the lungs. In general, particles ranging from about 1 to 5 microns in size (more particularly, less than about 4.7 microns in size) are respirable. Particles of non-respirable size are greater than about 5 microns in size, up to the size of visible droplets. Thus, for nasal administration, a particle size in the range of 10-500 μm may be used to ensure retention in the nasal cavity.

In the manufacture of a formulation according to the invention, active agents or the physiologically acceptable salts or free bases thereof are typically admixed with, inter alia, an acceptable carrier. Of course, the carrier must be compatible with any other ingredients in the formulation and must not be deleterious to the patient. The carrier must be solid or liquid, or both, and is preferably formulated with the compound as a unit-dose formulation, for example, a capsule, that may contain 0.5% to 99% by weight of the active compound. One or more active compounds may be incorporated in the formulations of the invention, which formulations may be prepared by any of the well-known techniques of pharmacy consisting essentially of admixing the components.

Compositions containing respirable or non-respirable dry particles of micronized active agent may be prepared by grinding the dry active agent with a mortar and pestle, and then passing the micronized composition through a 400 mesh screen to break up or separate out large agglomerates.

The particulate active agent composition may optionally contain a dispersant which serves to facilitate the formulation of an aerosol. A suitable dispersant is lactose, which may be blended with the active agent in any suitable ratio (e.g., a 1 to 1 ratio by weight).

The sodium channel blockers and osmotically active compounds disclosed herein may be administered to airway surfaces including the nasal passages, sinuses and lungs of a subject by an suitable means know in the art, such as by nose drops, mists., etc. In one embodiment of the invention, the active compounds of the present invention and administered by transbronchoscopic lavage. In a preferred embodiment of the invention, sodium channel blockers and osmotically active compounds of the present invention are deposited on lung airway surfaces by administering an aerosol suspension of respirable particles comprised of the active compound, which the subject inhales. The respirable particles may be liquid or solid. Numerous inhalers for administering aerosol particles to the lungs of a subject are known.

The aerosol, whether formed from solid or liquid particles, may be produced by the aerosol generator at a rate of from about 10 to 150 liters per minute, more preferable from 30 to 150 liters per minute, and most preferably about 60 liters per minute. Aerosols containing greater amounts of medicament may be administered more rapidly.

The dosage of the active compounds disclosed herein will vary depending on the condition being treated and the state of the subject, but generally may be from about 0.01, 0.03, 0.05, 0.1 to 1, 5, 10 or 20 mg of the pharmaceutic agent, deposited on the airway surfaces. The daily dose may be divided among one or multiple unit dose administrations. The goal is to achieve a concentration of the pharmaceutic agents on lung airway surfaces of between $10^{-9}$-$10^4$ M.

In another embodiment, they are administered by administering an aerosol suspension of respirable or non-respirable particles (preferably non-respirable particles) comprised of active compound, which the subject inhales through the nose. The respirable or non-respirable particles may be liquid or solid. The quantity of active agent included may be an amount of sufficient to achieve dissolved concentrations of active agent on the airway surfaces of the subject of from about $10^{-9}$, $10^{-8}$, or $10^{-7}$ to about $10^{-3}$, $10^{-2}$, $10^{-1}$ moles/liter, and more preferably from about $10^{-9}$ to about $10^{-4}$ moles/liter.

In one embodiment of the invention, the particulate active agent composition may contain both a free base of active agent and a pharmaceutically acceptable salt to provide both early release and sustained release of active agent for dissolution into the mucus secretions of the nose. Such a composition serves to provide both early relief to the patient, and sustained relief over time. Sustained relief, by decreasing the number of daily administrations required, is expected to increase patient compliance with the course of active agent treatments.

Pharmaceutical formulations suitable for airway administration include formulations of solutions, emulsions, suspensions and extracts. See generally, J. Naim, Solutions, Emulsions, Suspensions and Extracts, in Remington: The Science and Practice of Pharmacy, chap. 86 ($19^{th}$ ed. 1995), incorporated herein by reference. Pharmaceutical formulations suitable for nasal administration may be prepared as described in U.S. Pat. Nos. 4,389,393 to Schor; 5,707,644 to Illum; 4,294,829 to Suzuki; and 4,835,142 to Suzuki, the disclosures of which are incorporated by reference herein in their entirety.

Mists or aerosols of liquid particles comprising the active compound may be produced by any suitable means, such as by a simple nasal spray with the active agent in an aqueous pharmaceutically acceptable carrier, such as a sterile saline solution or sterile water. Administration may be with a pressure-driven aerosol nebulizer or an ultrasonic nebulizer. See e.g. U.S. Pat. Nos. 4,501,729 and 5,656,256, both of which are incorporated herein by reference. Suitable formulations for use in a nasal droplet or spray bottle or in nebulizers consist of the active ingredient in a liquid carrier, the active ingredient comprising up to 40% w/w of the formulation, but preferably less than 20% w/w. Typically the carrier is water (and most preferably sterile, pyrogen-free water) or dilute aqueous alcoholic solution, preferably made in a 0.12% to 0.8% solution of sodium chloride. Optional additives include preservatives if the formulation is not made sterile, for example, methyl hydroxybenzoate, antioxidants, flavoring agents, volatile oils, buffering agents, osmotically active agents (e.g. mannitol, xylitol, erythritol) and surfactants.

Compositions containing respirable or non-respirable dry particles of micronized active agent may be prepared by grinding the dry active agent with a mortar and pestle, and then passing the micronized composition through a 400 mesh screen to break up or separate out large agglomerates.

The particulate composition may optionally contain a dispersant which serves to facilitate the formation of an aerosol. A suitable dispersant is lactose, which may be blended with the active agent in any suitable ratio (e.g., a 1 to 1 ratio by weight).

Several assays may be used to characterize the compounds of the present invention. Representative assays are discussed below.

In Vitro Measure of Sodium Channel Blocking Activity and Reversibility

One assay used to assess mechanism of action and/or potency of the compounds of the present invention involves the determination of lumenal drug inhibition of airway epithelial sodium currents measured under short circuit current ($I_{SC}$) using airway epithelial monolayers mounted in Ussing chambers. Cells obtained from freshly excised human, dog, sheep or rodent airways are seeded onto porous 0.4 micron Snapwell™ Inserts (CoStar), cultured at air-liquid interface (ALI) conditions in hormonally defined media, and assayed for sodium transport activity ($I_{SC}$) while bathed in Krebs Bicarbonate Ringer (KBR) in Using chambers. All test drug additions are to the lumenal bath with half-log dose addition protocols (from $1\times10^{-11}$ M to $3\times10^{-5}$ M), and the cumulative change in $I_{SC}$ (inhibition) recorded. All drugs are prepared in dimethyl sulfoxide as stock solutions at a concentration of $1\times10^{-2}$ M and stored at $-20°$ C. Six preparations are typically run in parallel; one preparation per run incorporates compound 1 as a positive control. After the maximal concentration ($5\times10^{-5}$ M) is administered, the lumenal bath is exchanged three times with fresh drug-free KBR solution, and the resultant $I_{SC}$ measured after each wash for approximately 5 minutes in duration. Reversibility is defined as the percent return to the baseline value for sodium current after the third wash. All data from the voltage clamps are collected via a computer interface and analyzed off-line.

Dose-effect relationships for all compounds are considered and analyzed by the Graphpad Prism V3.0 program. $IC_{50}$ values, maximal effective concentrations, and reversibility are calculated and compared to historical amiloride and benzamil data sets.

Pharmacological Assays of Absorption (1) Serosal Appearance Assay

Bronchial cells (dog, human, human CF, sheep, or rodent cells) are seeded at a density of $0.25 \times 10^6/cm^2$ on a porous Transwell-Col collagen-coated membrane with a growth area of 1.13 $cm^2$ or 4.7 $cm^2$ grown at an air-liquid interface in hormonally defined media that promotes a polarized epithelium or preseeded human tracheobronchial cells purchased from Mattek Corp are used. From 12 to 25 days after development of an air-liquid interface (ALI) the cultures are expected to be >90% ciliated, and mucins will accumulate on the cells. To ensure the integrity of primary airway epithelial cell preparations, the transepithelial resistance ($R_t$) and transepithelial potential differences (PD), which are indicators of the integrity of polarized nature of the culture, are measured. Human cell systems are preferred for studies of rates of absorption from apical surfaces. The serosal appearance assay is initiated by adding experimental sodium channel blockers or positive controls (amiloride, benzamil, phenamil) to the apical surface at an initial concentration of 100 µM. A series of samples (5 µl volume per sample) is collected at various time points, from both the apical and serosal bath. Concentrations are determined by measuring intrinsic fluorescence of each sodium channel blocker using HPLC. Quantitative analysis employs a standard curve generated from authentic reference standard materials of known concentration and purity. Data analysis of the rate of disappearance is performed using nonlinear regression, one phase exponential decay.

2. Confocal Microscopy Assay of ENaC Blocker Uptake and Airway Surface Liquid Volume/Height Changes.

Virtually all amiloride-like molecules fluoresce in the ultraviolet range. This property of these molecules may be used to directly measure cellular uptake using x-z confocal microscopy. Equimolar concentrations of experimental compounds and positive controls including amiloride and compounds that demonstrate rapid uptake into the cellular compartment (benzamil and phenamil) are placed on the apical surface of airway cultures on the stage of the confocal microscope. Serial x-z images are obtained with time and the magnitude of fluorescence accumulating in the cellular compartment is quantitated and plotted as a change in fluorescence versus time. Inert fluorescent dyes can be added to the surface liquid prior to the addition of novel sodium channel blockers with or without osmolytes and changes in surface liquid volume/height will be detected.

3. In Vitro Assays of Compound Metabolism

Airway epithelial cells have the capacity to metabolize drugs during the process of transepithelial absorption. Further, although less likely, it is possible that drugs can be metabolized on airway epithelial surfaces by specific ectoenzyme activities. Perhaps more likely as an ecto-surface event, compounds may be metabolized by the infected secretions that occupy the airway lumens of patients with lung disease, e.g. cystic fibrosis. Thus, a series of assays is performed to characterize the compound metabolism that results from the interaction of test osmolytes and novel sodium channel blockers with human airway epithelia and/or human airway epithelial lumenal products.

In the first series of assays, the interaction of test compounds in KBR as an "ASL" stimulant are applied to the apical surface of human airway epithelial cells grown in the T-Col insert system. For most compounds, metabolism (generation of new species) is tested for using high performance liquid chromatography (HPLC) to resolve chemical species and the endogenous fluorescence properties of these compounds to estimate the relative quantities of test compound and novel metabolites. For a typical assay, a test solution (25 µl KBR, containing 10 µM test compound) is placed on the epithelial lumenal surface. Sequential 5 to 10 µl samples are obtained from the lumenal and serosal compartments for HPLC analysis of (1) the mass of test compound permeating from the lumenal to serosal bath and (2) the potential formation of metabolites from the parent compound. In instances where the fluorescence properties of the test molecule are not adequate for such characterizations, radiolabeled compounds are used for these assays. From the HPLC data, the rate of disappearance and/or formation of novel metabolite compounds on the lumenal surface and the appearance of test compound and/or novel metabolite in the basolateral solution is quantitated. The data relating the chromatographic mobility of potential novel metabolites with reference to the parent compound are also quantitated.

To analyze the potential metabolism of test compounds by CF sputum, a "representative" mixture of expectorated CF sputum obtained from 10 CF patients (under IRB approval) has been collected. The sputum has been be solubilized in a 1:5 mixture of KBR solution with vigorous vortexing, following which the mixture was split into a "neat" sputum aliquot and an aliquot subjected to ultracentrifugation so that a "supernatant" aliquot was obtained (neat=cellular; supernatant=liquid phase). Typical studies of compound metabolism by CF sputum involve the addition of known masses of test compound to "neat" CF sputum and aliquots of CF sputum "supernatant" incubated at 37° C., followed by sequential sampling of aliquots from each sputum type for characterization of compound stability/metabolism by HPLC analysis as described above. As above, analysis of compound disappearance, rates of formation of novel metabolites, and HPLC mobilities of novel metabolites are then performed.

4. Durability of Novel ENaC Blockers with or without Osmolytes on Airway Surface Liquid on an in vitro Cell Culture Model.

Using a gravimetric (weighing) procedure, the luminal surface liquid (mass/volume) on primary bronchial epithelial cultures grown at an air/liquid interface on permeable membrane supports (Corning) are measured, and changes in luminal surface liquid volume are recorded for up to 8 h. An applied starting volume of buffer (Krebs-Henseleit Bicarbonate Buffer Solution) with and without equimolar concentrations (0.1-100 µM) of selected novel or commercially available sodium channel blockers with or without osmolytes are added and at which point the experiment is started. The permeable supports are then reweighted at select time points and the mass/volume recorded. The data is then analyzed determining the changes in surface liquid mass/volume form beginning to the end of the 8 hour time frame.

5. Pharmacological Effects and Mechanism of Action of the Drug in Animals

The effect of compounds for enhancing mucociliary clearance (MCC) immediately and over a long time frame (5 hours) can be measured using an in vivo model described by Sabater et al., Journal of Applied Physiology, 1999, pp. 2191-2196, incorporated herein by reference, and modified as described below.

Methods

Animal Preparation: Adult ewes weighing up to 75 Kg were placed in a restraint and positioned upright using a specialized body harness. The heads of the animals were immobilized, and local anesthesia of the nasal passage was provided (2% lidocaine) prior to nasal intubation (7.5 mm-I.D. endotracheal tube (ETT) (Mallinckrodt Medical, St. Louis, Mo.). The cuff of the ETT was placed just below the vocal cords. After intubation, the animals were allowed to equilibrate for approximately 20 min before MC measurements began.

Administration of Radio-aerosol: Aerosols of sulfur colloid radiolabled with technetium ($^{99m}$Tc-SC 3.1 mg/mL, ~10-15 mCi) were generated by a Raindrop Nebulizer (Nellcor Puritan Bennett, Pleasanton, Calif.) which produces a median aerodynamic droplet diameter of 3.6 μm. The nebulizer was connected to a dosimeter system consisting of a solenoid valve and a source of compressed air (20 psi). The output of the nebulizer was directed into a T piece, with one end attached to a respirator (Harvard apparatus, South Natick, Mass.). The system was activated for 1 second at the onset of the respirator's inspiratory cycle. The tidal volume was set at 300 mL, with an inspiratory-to-expiratory ratio of 1:1, and a rate of 20 breaths/min, to maximize central airway deposition. The sheep breathed the $^{99m}$Tc-SC aerosol for up to 5 min. Following tracer deposition, a gamma camera was used to measure the clearance of $^{99m}$Tc-SC from the airways. The camera was positioned above the animal's back with the sheep in its natural upright position in the harness. The field of the image was perpendicular to the animal's spinal cord. External radiolabled markers were placed on the sheep to facilitate proper alignment of the gamma camera. A region of interest was traced over the image corresponding to the right lung of the sheep and counts were recorded. The counts were corrected for decay and expressed as a percentage of radioactivity present in the baseline image. The left lung was excluded from the analysis because the outline of the lung was superimposed over the stomach and counts could be affected by swallowed $^{99m}$Tc-SC-labeled mucus. All deposition images were stored on a computer interfaced to the gamma camera. The protocol included a baseline deposition image obtained immediately post radio aerosol administration. After acquisition of baseline images, either 4 mL of $H_2O$ (vehicle), amiloride (3 mM), or NCE (3 mM) were aerosolized using the Pari LC JetPlus nebulizer to free-breathing sheep using two separate protocols.

Treatment Protocol (Assessment of activity at t-zero immediate activity): A baseline deposition image was obtained immediately after radio-aerosol administration. At time zero, after acquisition of the baseline image, vehicle control (distilled water), positive control (amiloride), or experimental compounds were aerosolized from a 4 ml volume using a Pari LC JetPlus nebulizer to free-breathing animals. The nebulizer was driven by compressed air with a flow of 8 liters per minute. The time to deliver the solution was 10 to 12 minutes. Animals were extubated immediately following delivery of the total dose in order to prevent false elevations in counts caused by aspiration of excess radio-tracer from the ETT. Serial images of the lung were obtained at 15-minute intervals during the first 2 hours after dosing and hourly for the next 6 hours after dosing for a total observation period of 8 hours. A washout period of at least 7 days separated dosing sessions with different experimental agents.

Treatment Protocol (Assessment of Activity at t-4 hours durability): The following variation of the standard protocol was used to assess the durability of response following a single exposure to vehicle control (distilled water), positive control compounds (amiloride or benzamil), or investigational agents. At time zero, vehicle control (distilled water), positive control (amiloride), or investigational compounds were aerosolized from a 4 ml volume using a Pari LC JetPlus nebulizer to free-breathing animals. The nebulizer was driven by compressed air with a flow of 8 liters per minute. The time to deliver the solution was 10 to 12 minutes. Animals were restrained in an upright position in a specialized body harness for 4 hours. At the end of the 4-hour period animals received a single dose of aerosolized $^{99m}$Tc-Human serum albumin (3.1 mg/ml; containing approximately 20 mCi) from a Raindrop Nebulizer. Animals were extubated immediately following delivery of the total dose of radio-tracer. A baseline deposition image was obtained immediately after radio-aerosol administration. Serial images of the lung were obtained at 15-minute intervals during the first 2 hours after administration of the radio-tracer (representing hours 4 through 6 after drug administration) and hourly for the next 2 hours after dosing for a total observation period of 4 hours. A washout period of at least 7 days separated dosing sessions with different experimental agents.

Statistics: Data from the in vivo sheep MC assays were analyzed using a two way ANOVA with repeated measures, followed by slope analysis of the regression of the retention vs time plot using an ANCOVA to compare slopes. If needed, a multiple comparison test (Newman-Keuls) will also be performed on the slope data. The percent activity retained can be calculated by dividing the measured slope from protocol 2, by the measured slope obtained in protocol 1 and then multiplying by 100%.

EXAMPLES

Having generally described this invention, a further understanding can be obtained by reference to certain specific examples which are provided herein for purposes of illustration only and are not intended to be limiting unless otherwise specified.

Example 1

To measure the effects of novel sodium channel blockers with or without osmotically active agents on surface liquid volume on airway surface liquid an in vitro cell culture model was used as described above, Assay #4. The effects of an ionic osmolyte, 1.5% NaCl (hypertonic saline), with or without 10 μM of compound 1 before and after adding 1.5% NaCl and compared it to isotonic buffer (vehicle) (FIG. 1) on surface liquid volume was measured over 8 hours. Using the same method (Assay #4) the effects of a non-ionic osmolyte mannitol at 4.2 and 8.4 mg/mL were compared to compound 1 and isotonic buffer (vehicle) (FIG. 2), and also by combining mannitol (4.2 and 8.4 mg/mL) with compound 1 at 1 and 10 μM (FIG. 3) on surface liquid volume was measured. The effects of compound 2 with an ionic osmolyte, 1.5% NaCl (hypertonic saline), was compared to compound 1 and hypertonic saline (1.5% NaCl), compound 1 in isotonic buffer, compound 2 in isotonic buffer, 1.5% NaCl, and isotonic buffer (vehicle) (FIG. 4) on changes in surface liquid over 8 hours.

Compound 1 is

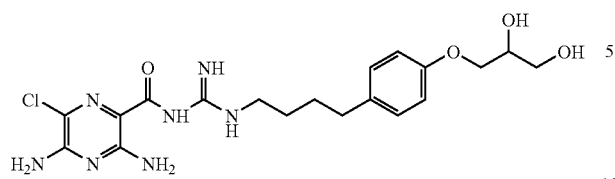

Compound 2 is

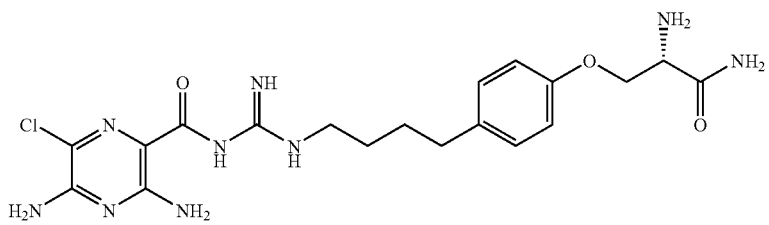

Example 2

A pathophysiological model of CF lung disease based on the abnormal epithelial ion channel defects (CFTR and ENaC), describes depletion of airway surface liquid (ASL) that results in reduced mucociliary clearance (MCC) as the primary cause for chronic respiratory infections. Recently, an aerosol therapy consisting of 7% hypertonic saline three to four times a day in CF patients has been shown to be safe, to transiently increase ASL, enhance MCC, and improve lung function.[1,2] The hypothesis that inhibiting sodium absorption using Compound 1 described above, combined with hypertonic saline, would significantly improve duration of action of hypertonic saline by prolonging the increased ASL volume was tested. Primary canine bronchial epithelia (CBE) were grown at an air-liquid interface on permeable membrane supports and a gravimetric method was used to measure changes in volume of buffer on the surface of the epithelium. After adding 50 μL of isotonic buffer to the apical surface of CBE, 85+12% (n=27) was absorbed within 8 hours. Addition of 50 μL of a 1.5% NaCl solution on the surface of CBE caused a transient osmotic expansion that resulted in an increased volume of 108+6.3% (n=4), that within 8 hours decreased to 50.2+19% (n=4) of the initial volume added. Using Compound 1 alone at 10 μM, significantly inhibited volume depletion (74.7+8.7%) for over 8 hours. However, combining Compound 1 (10 μM) with a pre or post administration of a 1.5% NaCl solution produced a volume expansion of 132+13% (n=12), that was maintained for 8 hours. In summary, it was found that by combining hypertonic saline with Compound 1 did not only lead to an increase in the ASL volume but also significantly increased the duration of this effect for greater than 8 h. Based on this result, a combined hypertonic saline/Compound 1 aerosol therapy may be a useful therapeutic approach for the treatment of CF and other conditions as described herein.

1. Elkins et al (2006) N Engl J Med 354, 229-240.
2. Donaldson et al (2006) N Engl J Med 354, 241-250.

The compounds used in the Examples described above are not within the scope of the genuses defined herein. The results obtained with those compounds suggest that similar results would be obtained with the sodium channel blockers within the scope of the genuses defined herein. Moreover, the assays are illustrative of the general methodology which can be used to assess the sodium channel blockers within the scope of the genuses defined herein.

The invention claimed is:

1. A method for improving the duration of action of an osmolyte in a patient in need of increased mucocilliary clearance or mucosal hydration, said method comprising co-administering an effective amount of said osmolyte with an effective amount of a sodium channel blocker represented by formula (I):

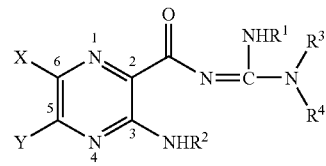

wherein
X is hydrogen, halogen, trifluoromethyl, lower alkyl, unsubstituted or substituted phenyl, lower alkyl-thio, phenyl-lower alkyl-thio, lower alkyl-sulfonyl, or phenyl-lower alkyl-sulfonyl;
Y is hydrogen, hydroxyl, mercapto, lower alkoxy, lower alkyl-thio, halogen, lower alkyl, unsubstituted or substituted mononuclear aryl, or —N($R^2$)$_2$; and
$R^1$ is hydrogen or lower alkyl,
wherein $R^2$, $R^3$ and $R^4$ are as defined in (1), (2), (3), (4), (5), (6), (7), (8) or (9) below:

(1)
each $R^2$ is, independently, —$R^7$, —(CH$_2$)$_n$—OR$^8$, —(CH$_2$)$_m$—NR$^7$R$^{10}$, —(CH$_2$)$_n$(CHOR$^8$)(CHOR$^8$)$_n$—CH$_2$OR$^8$, —(CH$_2$CH$_2$O), —R$^8$, —(CH$_2$CH$_2$O), —CH$_2$CH$_2$NR$^7$R$^{10}$, —(CH$_2$)$_n$—C(=O)NR$^7$R$^{10}$, —(CH$_2$)$_n$—Z$_g$—R$^7$—(CH$_2$)$_m$—NR$^{10}$—CH$_2$(CHOR$^8$)(CHOR$^8$)$_n$—CH$_2$OR$^8$, —(CH$_2$)$_n$—CO$_2$R$^7$, or

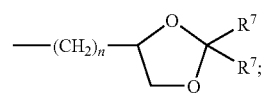

$R^3$ and $R^4$ are each, independently, hydrogen, a group represented by formula (A), lower alkyl, hydroxy lower alkyl, phenyl, phenyl-lower alkyl, (halophenyl)-lower alkyl, lower-(alkylphenylalkyl), lower (alkoxyphenyl)-lower alkyl, naphthyl-lower alkyl, or pyridyl-lower alkyl, with the proviso that at least one of $R^3$ and $R^4$ is a group represented by formula (A):

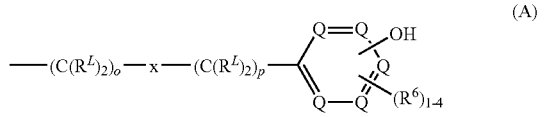
(A)

wherein
each $R^L$ is, independently, —$R^7$, —$(CH_2)_n$—$OR^8$, —O—$(CH_2)_m$—$OR^8$, —$(CH_2)_n$—$NR^7R^{10}$, —$O(CH_2)_m$—$NR^7R^{10}$, —$(CH_2)_n(CHOR^8)(CHOR^8)_n$—$CH_2OR^8$, —O—$(CH_2)_m(CHOR^8)(CHOR^8)_n$—$CH_2OR^8$, —$(CH_2CH_2O)_m$—$R^8$, —O—$(CH_2CH_2O)_m$—$R^8$, —$(CH_2CH_2O)_m$—$CH_2CH_2NR^7R^{10}$, —O—$(CH_2CH_2O)_m$—$CH_2CH_2NR^7R^{10}$, —$(CH_2)_n$—$C(=O)NR^7R^{10}$, —O—$(CH_2)_m$—$C(=O)NR^7R^{10}$, —$(CH_2)_n$—$(Z)_g$—$R^7$, —O—$(CH_2)_m$—$(Z)_g$—$R^7$, —$(CH_2)_n$—$NR^{10}$—$CH_2(CHOR^8)(CHOR^8)_n$—$CH_2OR^8$, —O—$(CH_2)_n$—$NR^{10}$—$CH_2(CHOR^8)(CHOR^8)_n$—$CH_2OR^8$, —$(CH_2)_n$—$CO_2R^7$, —O—$(CH_2)_m$—$CO_2R^7$, —$OSO_3H$, —O-glucuronide, —O-glucose,

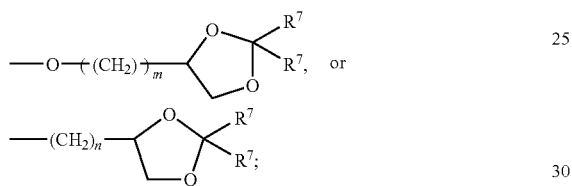

each o is, independently, an integer from 0 to 10;
each p is an integer from 0 to 10;
with the proviso that the sum of o and p in each contiguous chain is from 1 to 10;
each x is, independently, O, $NR^{10}$, $C(=O)$, CHOH, $C(=N—R^{10})$, $CHNR^7R^{10}$, or represents a single bond;
each $R^6$ is, independently, —$R^7$, —OH, —$OR^{11}$, —$N(R^7)_2$, —$(CH_2)_m$—$OR^8$, —O—$(CH_2)_m$—$OR^8$, —$(CH_2)_m$—$NR^7R^{10}$, —O—$(CH_2)_m$—$NR^7R^{10}$, —$(CH_2)_n(CHOR^8)(CHOR^8)_n$—$CH_2OR^8$, —O—$(CH_2)_m(CHOR^8)(CHOR^8)_n$—$CH_2OR^8$, —$(CH_2CH_2O)_m$—$R^8$, —O—$(CH_2CH_2O)_m$—$R^8$, —$(CH_2CH_2O)_m$—$CH_2CH_2NR^7R^{10}$, —O—$(CH_2CH_2O)_m$—$CH_2CH_2NR^7R^{10}$, —$(CH_2)_n$—$C(=O)NR^7R^{10}$, —O—$(CH_2)_m$—$C(=O)NR^7R^{10}$, —$(CH_2)_n$—$(Z)_g$—$R^7$, —O—$(CH_2)_m$—$(Z)_g$—$R^7$, —$(CH_2)_n$—$NR^{10}$—$CH_2(CHOR^8)(CHOR^8)_n$—$CH_2OR^8$, —O—$(CH_2)_m$—$NR^{10}$—$CH_2(CHOR^8)(CHOR^8)_n$—$CH_2OR^8$, —$(CH_2)_n$—$CH_2R^7$, —O—$(CH_2)_m$—$CO_2R^7$, —$OSO_3H$, —O-glucuronide, —O-glucose,

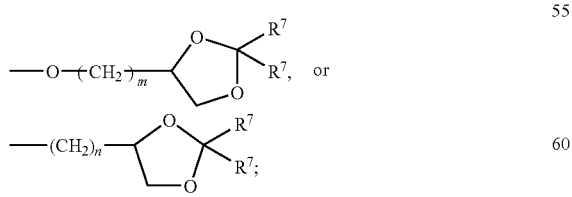

wherein when two $R^6$ are —$OR^{11}$ and are located adjacent to each other on a phenyl ring, the alkyl moieties of the two $R^6$ may be bonded together to form a methylenedioxy group;

each $R^7$ is, independently, hydrogen or lower alkyl;
each $R^8$ is, independently, hydrogen, lower alkyl, —$C(=O)$—$R^{11}$, glucuronide, 2-tetrahydropyranyl, or

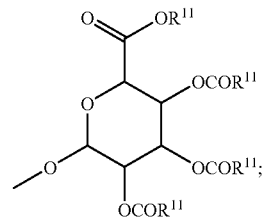

each $R^9$ is, independently, —$CO_2R^7$, —$CON(R^7)_2$, —$SO_2CH_3$, or —$C(=O)R^7$;
each $R^{10}$ is, independently, —H, —$SO_2CH_3$, —$CO_2R^7$, —$C(=O)NR^7R^9$, —$C(=O)R^7$, or —$CH_2$—$(CHOH)_n$—$CH_2OH$;
each Z is, independently, CHOH, $C(=O)$, $CHNR^7R^{10}$, $C=NR^{10}$, or $NR^{10}$;
each $R^{11}$ is, independently, lower alkyl;
each g is, independently, an integer from 1 to 6;
each m is, independently, an integer from 1 to 7;
each n is, independently, an integer from 0 to 7;
each Q is, independently, C—OH, C—$R^6$ or a nitrogen atom, wherein one Q is C—OH and at most three Q in a ring are nitrogen atoms;
or a pharmaceutically acceptable salt thereof, and inclusive of all enantiomers, diastereomers, and racemic mixtures thereof;

(2) each $R^2$ is, independently, —$R^7$, —$(CH_2)_m$—$OR^8$, —$(CH_2)_m$—$NR^7R^{10}$, —$(CH_2)_n(CHOR^8)(CHOR^8)_n$—$CH_2OR^8$, —$(CH_2CH_2O)_m$—$R^8$, —$(CH_2CH_2O)_m$—$CH_2CH_2NR^7R^{10}$, —$(CH_2)_n$—$C(=O)NR^7R^{10}$, —$(CH_2)_n$—$Z_g$—$R^7$, —$(CH_2)_m$—$NR^{10}$—$CH_2(CHOR^8)(CHOR^8)_n$—$CH_2OR^8$, —$(CH_2)_n$—$CO_2R^7$, or

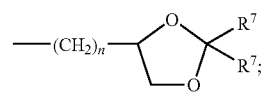

wherein when two —$CH_2OR^8$ groups are located 1,2- or 1,3- with respect to each other the $R^8$ groups may be joined to form a cyclic mono- or di-substituted 1,3-dioxane or 1,3-dioxolane;

$R^3$ and $R^4$ are each, independently, hydrogen, a group represented by formula (A), lower alkyl, hydroxy lower alkyl, phenyl, phenyl-lower alkyl, (halophenyl)-lower alkyl, lower-(alkylphenylalkyl), lower (alkoxyphenyl)-lower alkyl, naphthyl-lower alkyl, or pyridyl-lower alkyl, with the proviso that at least one of $R^3$ and $R^4$ is a group represented by formula (A):

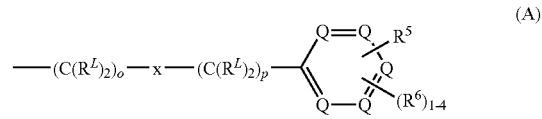
(A)

wherein each $R^L$ is, independently, $-R^7$, $-(CH_2)-OR^8$, $-O-(CH_2)_m-OR^8$, $-(CH_2)_n-NR^7R^{10}$, $-O-(CH_2)_m-NR^7R^{10}$, $-(CH_2)_n(CHOR^8)(CHOR^8)_n-CH_2OR^8$, $-O-(CH_2)_m(CHOR^8)(CHOR^8)_n-CH_2OR^8$, $-(CH_2CH_2O)_m-R^8$, $-O-(CH_2CH_2O)_m-R^8$, $-(CH_2CH_2O)_m-CH_2CH_2NR^7R^{10}$, $-O-(CH_2CH_2O)_m-CH_2CH_2NR^7R^{10}$, $-(CH_2)_n-C(=O)NR^7R^{10}$, $-O-(CH_2)_m-C(=O)NR^7R^{10}$, $-(CH_2)_n-(Z)_gR^7$, $-O-(CH_2)_m-(Z)_g-R^7$, $-(CH_2)_n-NR^{10}-CH_2(CHOR^8)(CHOR^8)_n-CH_2OR^8$, $-O-(CH_2)_m-NR^{10}-CH_2(CHOR^8)(CHOR^8)_n-CH_2OR^8$, $-(CH_2)_n-CO_2R^7$, $-O-(CH_2)_m-CO_2R^7$, $-OSO_3H$, $-O$-glucuronide, $-O$-glucose,

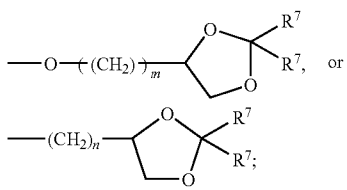

wherein when two $-CH_2OR^8$ groups are located 1,2- or 1,3- with respect to each other the $R^8$ groups may be joined to form a cyclic mono- or di-substituted 1,3-dioxane or 1,3-dioxolane;

each o is, independently, an integer from 0 to 10;

each p is an integer from 0 to 10;

with the proviso that the sum of o and p in each contiguous chain is from 1 to 10;

each x is, independently, O, $NR^{10}$, C(=O), CHOH, C(=N—$R^{10}$), $CHNR^7R^{10}$, or represents a single bond;

each $R^5$ is, independently, $-(CH_2)_n-NR^{12}R^{12}$, $-O-(CH_2)_m-NR^{12}R^{12}$, $-O-(CH_2)_n-NR^{12}R^{12}$, $-O-(CH_2)_m-(Z)_gR^{12}$, $-(CH_2)_nNR^{11}R^{11}$, $-O-(CH_2)_mNR^{11}R^{11}$, $-(CH_2)_n-N^{\oplus}-(R^{11})_3$, $-O-(CH_2)_m-N^{\oplus}-(R^{11})_3$, $-(CH_2)_n-(Z)_g-(CH_2)_m-NR^{10}R^{10}$, $-O-(CH_2)_m-(Z)_g-(CH_2)_m-NR^{10}R^{10}$, $-(CH_2CH_2O)_m-CH_2CH_2NR^{12}R^{12}$, $-O-(CH_2CH_2O)_m-CH_2CH_2NR^{12}R^{12}$, $-(CH_2)_n-(C=O)NR^{12}R^{12}$, $-O-(CH_2)_m-(C=O)NR^{12}R^{12}$, $-O-(CH_2)_n-(CHOR^8)_mCH_2NR^{10}-(Z)_g-R^{10}$, $-(CH_2)_n-(CHOR^8)_mCH_2-NR^{10}-(Z)_g-R^{10}$, $-(CH_2)_mNR^{10}-O(CH_2)_m(CHOR^8)_nCH_2NR^{10}-(Z)_g-R^{10}$, $-O(CH_2)_m-NR^{10}-(CH_2)_m-(CHOR^8)_nCH_2NR^{10}-(Z)_g-R^{10}$, -(Het)-$(CH_2)_m-OR^8$, -(Het)-$(CH_2)_m-NR^7R^{10}$, -(Het)-$(CH_2)_m(CHOR^8)(CHOR^8)_n-CH_2OR^8$, -(Het)-$(CH_2CH_2O)_m-R^8$, -(Het)-$(CH_2CH_2O)_m-CH_2CH_2NR^7R^{10}$, -(Het)-$(CH_2)_m-C(=O)NR^7R^{10}$, -(Het)-$(CH_2)_m-(Z)_g-R^7$, -(Het)-$(CH_2)_m-NR^{10}-CH_2(CHOR^8)(CHOR^8)_n-CH_2OR^8$, -(Het)-$(CH_2)_m-CO_2R^7$, -(Het)-$(CH_2)_m-NR^{12}R^{12}$, -(Het)-$(CH_2)_n-NR^{12}R^{12}$, -(Het)-$(CH_2)_m-(Z)_gR^{12}$, -(Het)-$(CH_2)_m-NR^{11}R^{11}$, -(Het)-$(CH_2)_m-N^{\oplus}-(R^{11})_3$, -(Het)-$(CH_2)_m-(Z)_g-(CH_2)_m-NR^{10}R^{10}$, -(Het)-$(CH_2CH_2O)_m-CH_2CH_2NR^{12}R^{12}$, -(Het)-$(CH_2)_m-(C=O)NR^{12}R^{12}$, -(Het)-$(CH_2)_m-(CHOR^8)_mCH_2NR^{10}-(Z)_g-R^{10}$, -(Het)-$(CH_2)_m-NR^{10}-$ $(CH_2)_m-(CHOR^8)_nCH_2NR^{10}-(Z)_g-R^{10}$, wherein when two $-CH_2OR^8$ groups are located 1,2- or 1,3- with respect to each other the $R^8$ groups may be joined to form a cyclic mono- or di-substituted 1,3-dioxane or 1,3-dioxolane, $-(CH_2)_n(CHOR^8)(CHOR^8)_n-CH_2OR^8$, with the proviso that two $-CH_2OR^8$ groups are located 1,2- or 1,3- with respect to each other and the $R^8$ groups are joined to form a cyclic mono or disubstituted 1,3-dioxane or 1,3-dioxolane, $-O-(CH_2)_m(CHOR^8)(CHOR^8)_n-CH_2OR^8$, with the proviso that two $-CH_2OR^8$ groups are located 1,2- or 1,3- with respect to each other and the $R^8$ groups are joined to form a cyclic mono or disubstituted 1,3-dioxane or 1,3-dioxolane, $-(CH_2)_n-NR^{10}-CH_2(CHOR^8)(CHOR^8)_n-CH_2OR^8$, with the proviso that two $-CH_2OR^8$ groups are located 1,2- or 1,3- with respect to each other and the $R^8$ groups are joined to form a cyclic mono or disubstituted 1,3-dioxane or 1,3-dioxolane, or $-O-(CH_2)_m-NR^{10}-CH_2(CHOR^8)(CHOR^8)_n-CH_2OR^8$, with the proviso that two $-CH_2OR^8$ groups are located 1,2- or 1,3- with respect to each other and the $R^8$ groups are joined to form a cyclic mono or disubstituted 1,3-dioxane or 1,3-dioxolane;

each $R^6$ is, independently, $-R^5$, $-R^7$, $-OR^8$, $-N(R^7)_2$, $-(CH_2)_m-OR^8$, $-O-(CH_2)_m-OR^8$, $-(CH_2)_n-NR^7R^{10}$, $-O-(CH_2)_m-NR^7R^{10}$, $-(CH_2)_n(CHOR^8)(CHOR^8)_n-CH_2OR^8$, $-O-(CH_2)_n(CHOR^8)(CHOR^8)_n-CH_2OR^8$, $-(CH_2CH_2O)_m-R^8$, $-O-(CH_2CH_2O)_m-R^8$, $-(CH_2CH_2O)_m-CH_2CH_2NR^7R^{10}$, $-O-(CH_2CH_2O)_m-CH_2CH_2NR^7R^{10}$, $-(CH_2)_n-C(=O)NR^7R^{10}$, $-O-(CH_2)_m-C(=O)NR^7R^{10}$, $-(CH_2)_n-(Z)_g-R^7$, $-O-(CH_2)_m-(Z)_g-R^7$, $-(CH_2)_n-NR^{10}-CH_2(CHOR^8)(CHOR^8)_n-CH_2OR^8$, $-O-(CH_2)_m-NR^{10}-CH_2(CHOR^8)(CHOR^8)_n-CH_2OR^8$, $-(CH_2)_n-CO_2R^7$, $-O-(CH_2)_m-CO_2R^7$, $-OSO_3H$, $-O$-glucuronide, $-O$-glucose,

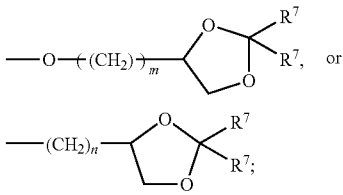

wherein when two $R^6$ are $-OR^{11}$ and are located adjacent to each other on a phenyl ring, the alkyl moieties of the two $R^6$ may be bonded together to form a methylenedioxy group and wherein when two $-CH_2OR^8$ groups are located 1,2- or 1,3- with respect to each other the $R^8$ groups may be joined to form a cyclic mono- or di-substituted 1,3-dioxane or 1,3-dioxolane;

each $R^7$ is, independently, hydrogen or lower alkyl;

each $R^8$ is, independently, hydrogen, lower alkyl, $-C(=O)-R^{11}$, glucuronide, 2-tetrahydropyranyl, or

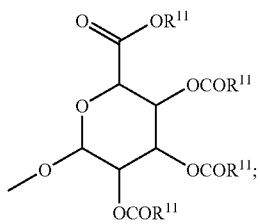

each $R^9$ is, independently, $-CO_2R^7$, $-CON(R^7)_2$, $-SO_2CH_3$, or $-C(=O)R^7$;

each $R^{10}$ is, independently, $-H$, $-SO_2CH_3$, $-CO_2R^7$, $-C(=O)NR^7R^9$, $-C(=O)R^7$, or $-CH_2-(CHOH)_n-CH_2OH$;

each Z is, independently, CHOH, C(=O), CHNR$^7$R$^{10}$, C=NR$^{10}$, or NR$^{10}$;

each $R^{11}$ is, independently, lower alkyl;

each $R^{12}$ is independently, $-SO_2CH_3$, $-CO_2R^7$, $-C(=O)NR^7R^9$, $-C(=O)R^7$, or $-CH_2-(CHOH)_n-CH_2OH$;

each Het is independently, $-NR^7$, $-NR^{10}$, $-S-$, $-SO-$, or $-SO_2-$;

each g is, independently, an integer from 1 to 6;
each m is, independently, an integer from 1 to 7;
each n is, independently, an integer from 0 to 7;
each Q is, independently, $C-R^5$, $C-R^6$, or a nitrogen atom, wherein one Q is $C-R^5$ and at most three Q in a ring are nitrogen atoms;

or a pharmaceutically acceptable salt thereof, and
inclusive of all enantiomers, diastereomers, and racemic mixtures thereof;

(3) each $R^2$ is, independently, $-R^7$, $-(CH_2)_m-OR^8$, $-(CH_2)_m-NR^7R^{10}$, $-(CH_2)_n(CHOR^8)(CHOR^8)_n-CH_2OR^8$, $-(CH_2CH_2O)_m-R^8$, $-(CH_2CH_2O)_m-CH_2CH_2NR^7R^{10}$, $-(CH_2)_n-C(=O)NR^7R^{10}$, $-(CH_2)_n-Z_g-R^7$, $-(CH_2)_m-NR^{10}-CH_2(CHOR^8)(CHOR^8)_n-CH_2OR^8$, $-(CH_2)_n-CO_2R^7$, or

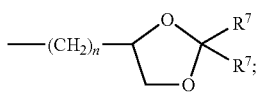

$R^3$ and $R^4$ are each, independently, hydrogen, a group represented by formula (A), lower alkyl, hydroxy lower alkyl, phenyl, phenyl-lower alkyl, (halophenyl)-lower alkyl, lower-(alkylphenylalkyl), lower (alkoxyphenyl)-lower alkyl, naphthyl-lower alkyl, or pyridyl-lower alkyl, with the proviso that at least one of $R^3$ and $R^4$ is a group represented by formula (A):

(A)

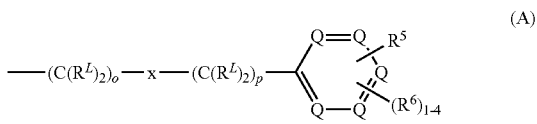

wherein
each $R^L$ is, independently, $-R^7$, $-(CH_2)_n-OR^8$, $-O-(CH_2)_m-OR^8$, $-(CH_2)_m-NR^7R^{10}$, $-O-(CH_2)_m-NR^7R^{10}$, $-(CH_2)_n(CHOR^8)(CHOR^8)_n-CH_2OR^8$, $-O-(CH_2)_m(CHOR^8)(CHOR^8)_n-CH_2OR^8$, $-(CH_2CH_2O)_m-R^8$, $-O(CH_2CH_2O)_m-R^8$, $-(CH_2CH_2O)_m-CH_2CH_2NR^7R^{10}$, $-O-(CH_2CH_2O)_m-CH_2CH_2NR^7R^{10}$, $-(CH_2)_n-C(=O)NR^7R^{10}$, $-O-(CH_2)_m-C(=O)NR^7R^{10}$, $-(CH_2)_n-(Z)_g-R^7$, $-O-(CH_2)_m-(Z)_g-R^7$, $-(CH_2)_n-NR^{10}-CH_2(CHOR^8)(CHOR^8)_n-CH_2OR^8$, $-O-(CH_2)_m-NR^{10}-CH_2(CHOR^8)(CHOR^8)_n-CH_2OR^8$, $-(CH_2)_n-CO_2R^7$, $-O-(CH_2)_m-CO_2R^7$, $-OSO_3H$, $-O$-glucuronide, $-O$-glucose,

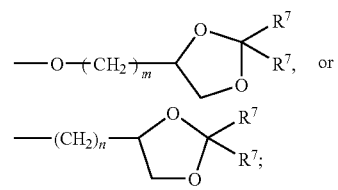

each o is, independently, an integer from 0 to 10;
each p is an integer from 0 to 10;
with the proviso that the sum of o and p in each contiguous chain is from 1 to 10;
each x is, independently, O, NR$^{10}$, C(=O), CHOH, C(=N—R$^{10}$), CHNR$^7$R$^{10}$, or represents a single bond;
wherein each $R^5$ is, independently, Link $-(CH_2)_n$-CAP, Link $-(CH_2)_n(CHOR^8)(CHOR^8)_n$-CAP, Link $-(CH_2CH_2O)_m-CH_2$-CAP, Link $-(CH_2CH_2O)_n-CH_2CH_2$-CAP, Link $-(CH_2)_n-(Z)_g$-CAP, Link $-(CH_2)_n(Z)_g-(CH_2)_m$-CAP, Link $-(CH_2)_n-NR^{13}-CH_2(CHOR^8)(CHOR^8)_n$-CAP, Link $-(CH_2)_n-(CHOR^8)_mCH_2-NR^{13}-Z_g$-CAP, Link $-(CH_2)_n-NR^{13}-(CH_2)_m(CHOR^8)_nCH_2NR^{13}-(Z)_g$-CAP, Link $-(CH_2)_m-(Z)_g-(CH_2)_m$-CAP, Link NH—C(=O)—NH—$(CH_2)_m$-CAP, Link $-(CH_2)_m-C(=O)NR^{13}-(CH_2)_m-C(=O)NR^{10}R^{10}$, Link $-(CH_2)_m-C(=O)NR^{13}-(CH_2)_m$-CAP, Link $-(CH_2)_m-C(=O)NR^{11}R^{11}$, Link $-(CH_2)_m-C(=O)NR^{12}R^{12}$, Link $-(CH_2)_n-(Z)_g-(CH_2)_m-(Z)_g$-CAP, Link $-Z_g-(CH_2)_m$-Het-$(CH_2)_m$-CAP;

each Link is, independently, $-O-$, $-(CH_2)_n-$, $-O(CH_2)_m-$, $-NR^{13}-C(=O)-NR^{13}$, $-NR^{13}-C(=O)-(CH_2)_m-$, $-C(=O)NR^{13}-(CH_2)_m-$, $-(CH_2)_n-Z_g-(CH_2)_n-$, $-S-$, $-SO-$, $-SO_2-$, $-SO_2NR^7-$, $-SO_2NR^{10}-$, or -Het-;

each CAP is, independently, thiazolidinedione, oxazolidinedione, heteroaryl-C(=O)N R$^{13}$R$^{13}$, heteroaryl-W, $-CN$, $-O-C(=S)NR^{13}R^{13}$, $-Z_gR^{13}$, $-CR^{10}(Z_gR^{13})(Z_gR^{13})$, $-C(=O)OAr$, $-C(=O)NR^{13}Ar$, imidazoline, tetrazole, tetrazole amide, $-SO_2NHR^{13}$, $-SO_2NH-C(R^{13}R^{13})-(Z)_g-R^{13}$, a cyclic sugar or oligosaccharide, a cyclic amino sugar or oligosaccharide,

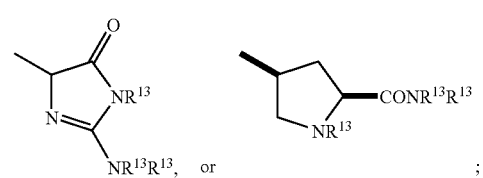

each Ar is, independently, phenyl, substituted phenyl, wherein the substituents of the substituted phenyl are 1-3 substituents independently selected from the group consisting of OH, OCH$_3$, NR$^{13}$R$^{13}$, Cl, F, and CH$_3$, or heteroaryl;

each W is independently, thiazolidinedione, oxazolidinedione, heteroaryl-C(=O)NR$^{13}$R$^{13}$, —CN, —O—C(=S) NR$^{13}$R$^{13}$, —Z$_g$R$^{13}$, —CR$^{10}$(Z$_g$R$^{13}$)(Z$_g$R$^{13}$), —C(=O) OAr, —C(=O)NR$^{13}$Ar, imidazoline, tetrazole, tetrazole amide, —SO$_2$NHR$^{13}$, —SO$_2$NH—C(R$^{13}$R$^{13}$)—(Z)$_g$—R$^{13}$, a cyclic sugar or oligosaccharide, a cyclic amino sugar or oligosaccharide,

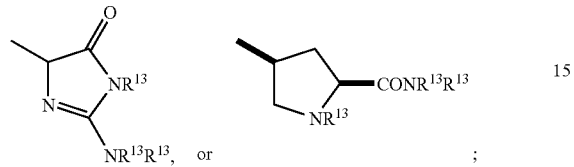

each R$^6$ is, independently, —R$^7$, —OR$^7$, —OR$^{11}$, —N(R$^7$)$_2$, —(CH$_2$)$_m$—OR$^8$, —O—(CH$_2$)$_m$—OR$^8$, —(CH$_2$)$_n$—NR$^7$R$^{10}$, —O—(CH$_2$)$_m$—NR$^7$R$^{10}$, —(CH$_2$)$_n$(CHOR$^8$)(CHOR$^8$)$_n$—CH$_2$OR$^8$, —O—(CH$_2$)$_m$(CHOR$^8$)(CHOR$^8$)$_n$—CH$_2$OR$^8$, —(CH$_2$CH$_2$O)$_m$—R$^8$, —O—(CH$_2$CH$_2$O)$_n$—R$^8$, —(CH$_2$CH$_2$O)$_m$—CH$_2$CH$_2$NR$^7$R$^{10}$, —O—(CH$_2$CH$_2$O)$_m$—CH$_2$CH$_2$NR$^7$R$^{10}$, —(CH$_2$)$_n$—C(=O)NR$^7$R$^{10}$, —O—(CH$_2$)$_m$—C(=O)NR$^7$R$^{10}$, —(CH$_2$)$_n$—(Z)$_g$—R$^7$, —O—(CH$_2$)$_m$—(Z)$_g$—R$^7$, —(CH$_2$)$_n$—NR$^{10}$—CH$_2$(CHOR$^8$)(CHOR$^8$)$_n$—CH$_2$OR$^8$, —O—(CH$_2$)$_m$—NR$^{10}$—CH$_2$(CHOR$^8$)(CHOR$^8$)$_n$—CH$_2$OR$^8$, —(CH$_2$)$_n$—CO$_2$R$^7$, —O—(CH$_2$)$_m$—CO$_2$R$^7$, —OSO$_3$H, —O-glucuronide, —O-glucose,

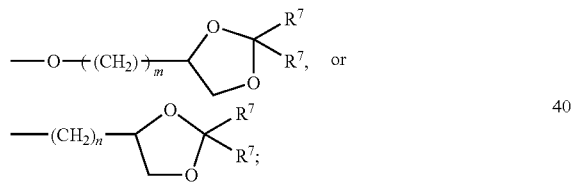

wherein when two R$^6$ are —OR$^{11}$ and are located adjacent to each other on a phenyl ring, the alkyl moieties of the two R$^6$ may be bonded together to form a methylenedioxy group;

with the proviso that when at least two —CH$_2$OR$^8$ are located adjacent to each other, the R$^8$ groups may be joined to form a cyclic mono- or di-substituted 1,3-dioxane or 1,3-dioxolane, each R$^7$ is, independently, hydrogen lower alkyl, phenyl, or substituted phenyl;

each R$^8$ is, independently, hydrogen, lower alkyl, —C(=O)—R$^{11}$, glucuronide, 2-tetrahydropyranyl, or

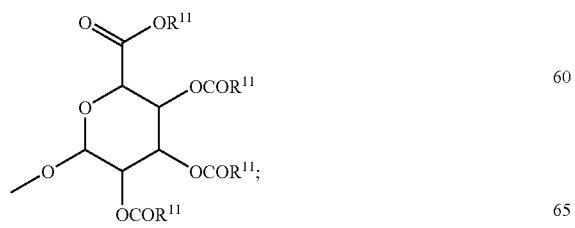

each R$^9$ is, independently, —CO$_2$R$^{13}$, —CON(R$^{13}$)$_2$, —SO$_2$CH$_2$R$^{13}$, or —C(=O)R$^{13}$;

each R$^{10}$ is, independently, —H, —SO$_2$CH$_3$, —CO$_2$R$^7$, —C(=O)NR$^7$R$^9$, —C(=O)R$^7$, or —CH$_2$—(CHOH)$_n$—CH$_2$OH;

each Z is, independently, CHOH, C(=O), —(CH$_2$)$_n$—, CHNR$^{13}$R$^{13}$, C=NR$^{13}$, or NR$^{13}$;

each R$^{11}$ is, independently, lower alkyl;

each R$^{12}$ is independently, —SO$_2$CH$_3$, —CO$_2$R$^{13}$, —C(=O)NR$^{13}$R$^{13}$, —C(=O)R$^{13}$, or —CH$_2$—(CHOH)$_n$—CH$_2$OH;

each R$^{13}$ is, independently, hydrogen, R$^7$, R$^{10}$, —(CH$_2$)—NR$^7$R$^{10}$, —(CH$_2$)$_m$—NR$^7$R$^7$, —(CH$_2$)$_m$—NR$^{11}$R$^{11}$R$^{11}$$^+$,
—(CH$_2$)$_m$—(CHOR$^8$)$_m$—(CH$_2$)$_m$NR$^7$R$^{10}$,
—(CH$_2$)$_m$—NR$^{10}$R$^{10}$,
—(CH$_2$)$_m$—(CHOR$^8$)$_m$—(CH$_2$)$_m$NR$^7$R$^7$,
—(CH$_2$)$_m$—(CHOR$^8$)$_m$—(CH$_2$)$_m$NR$^{11}$R$^{11}$R$^{11}$$^+$,

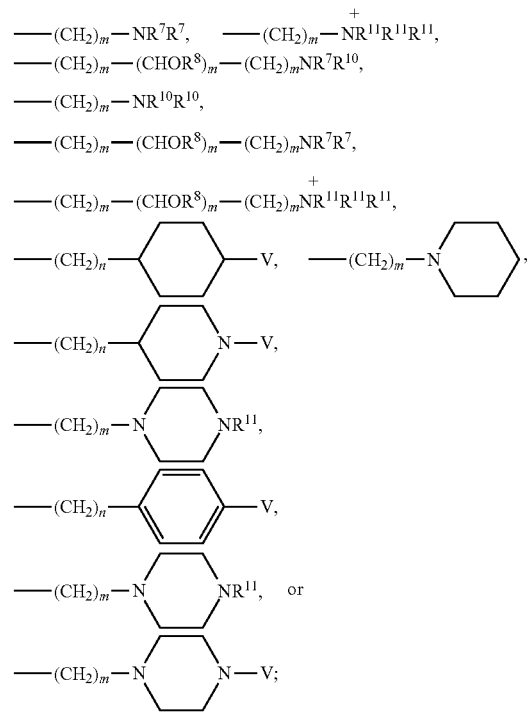

with the proviso that NR$^{13}$R$^{13}$ can be joined on itself to form a ring comprising one of the following:

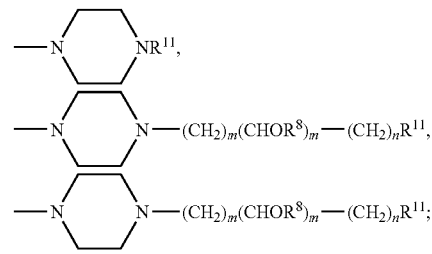

each Het is independently, —NR$^{13}$, —S—, —SO—, —SO$_2$—, —O—, —SO$_2$NR$^{13}$—, —NHSO$_2$—, —NR$^{13}$CO—, or —CONR$^{13}$—;

each g is, independently, an integer from 1 to 6;
each m is, independently, an integer from 1 to 7;
each n is, independently, an integer from 0 to 7;
each Q is, independently, C—R$^5$, C—R$^6$, or a nitrogen atom, wherein one Q is C—R$^5$ and at most three Q in a ring are nitrogen atoms;

each V is, independently, —(CH$_2$)$_m$—NR$^7$R$^{10}$, —(CH$_2$)$_m$—NR$^7$R$^7$, —(CH$_2$)$_m$—

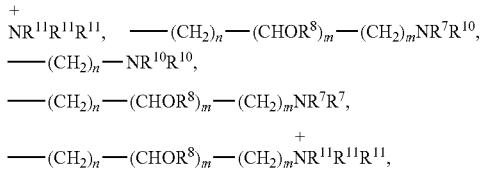

with the proviso that when V is attached directly to a nitrogen atom, then V can also be, independently, R$^7$, R$^{10}$, or (R$^{11}$)$_2$;
  wherein for any of the above compounds when two —CH$_2$OR$^8$ groups are located 1,2- or 1,3- with respect to each other the R$^8$ groups may be joined to form a cyclic mono- or di-substituted 1,3-dioxane or 1,3-dioxolane;
  wherein any of the above compounds can be a pharmaceutically acceptable salt thereof, and wherein the above compounds are inclusive of all enantiomers, diastereomers, and racemic mixtures thereof, (4)
  each R$^2$ is, independently, —R$^7$, —(CH$_2$)$_m$—OR$^8$, —(CH$_2$)$_m$—NR$^7$R$^{10}$, —(CH$_2$)$_n$(CHOR$^8$)(CHOR$^8$)$_n$—CH$_2$OR$^8$, (CH$_2$CH$_2$O)$_m$—R$^8$, —(CH$_2$CH$_2$O)$_m$—CH$_2$CH$_2$NR$^7$R$^{10}$, —(CH$_2$)$_n$—C(═O)NR$^7$R$^{10}$, —(CH$_2$)$_n$—Z$_g$—R$^7$, —(CH$_2$)$_m$—NR$^{10}$—CH$_2$(CHOR$^8$)(CHOR$^8$)$_n$—CH$_2$OR$^8$, —(CH$_2$)$_n$—CO$_2$R$^7$, or

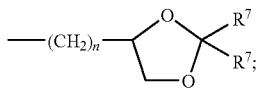

wherein when two —CH$_2$OR$^8$ groups are located 1,2- or 1,3- with respect to each other the R$^8$ groups may be joined to form a cyclic mono- or di-substituted 1,3-dioxane or 1,3-dioxolane;
  R$^3$ and R$^4$ are each, independently, hydrogen, a group represented by formula (A), lower alkyl, hydroxy lower alkyl, phenyl, phenyl-lower alkyl, (halophenyl)-lower alkyl, lower-(alkylphenylalkyl), lower (alkoxyphenyl)-lower alkyl, naphthyl-lower alkyl, or pyridyl-lower alkyl, with the proviso that at least one of R$^3$ and R$^4$ is a group represented by formula (A):

(A)

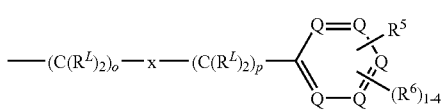

wherein
  each R$^L$ is, independently, —R$^7$, —(CH$_2$)$_n$—OR$^8$, —O—(CH$_2$)—OR$^8$, —(CH$_2$)$_n$—NR$^7$R$^{10}$, —O—(CH$_2$)$_m$—NR$^7$R$^{10}$, —(CH$_2$)$_n$(CHOR$^8$)(CHOR$^8$)$_n$—CH$_2$OR$^8$, —O—(CH$_2$)$_m$(CHOR$^8$)(CHOR$^8$)$_n$—CH$_2$OR$^8$, —(CH$_2$CH$_2$O)$_m$—R$^8$, —O—(CH$_2$CH$_2$O)$_m$—R$^8$, —(CH$_2$CH$_2$O)$_m$—CH$_2$CH$_2$NR$^7$R$^{10}$, —O—(CH$_2$CH$_2$O)$_m$—CH$_2$CH$_2$NR$^7$R$^{10}$, —(CH$_2$)$_n$—C(═O)NR$^7$R$^{10}$, —O—(CH$_2$)$_m$—C(═O)NR$^7$R$^{10}$, —(CH$_2$)$_n$—(Z)$_g$—R$^7$, —O—(CH$_2$)$_n$—(Z)$_g$—R$^7$, —(CH$_2$)$_n$—NR$^{10}$—CH$_2$(CHOR$^8$)(CHOR$^8$)$_n$—CH$_2$OR$^8$, —O—(CH$_2$)$_m$—NR$^{10}$—CH$_2$(CHOR$^8$)(CHOR$^8$)$_n$—CH$_2$OR$^8$, —(CH$_2$)$_n$—CO$_2$R$^7$, —O—(CH$_2$)$_m$—CO$_2$R$^7$, —OSO$_3$H, —O-glucuronide, —O-glucose,

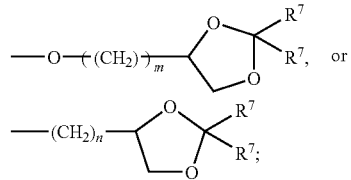

wherein when two —CH$_2$OR$^8$ groups are located 1,2- or 1,3- with respect to each other the R$^8$ groups may be joined to form a cyclic mono- or di-substituted 1,3-dioxane or 1,3-dioxolane;
  each o is, independently, an integer from 0 to 10;
  each p is an integer from 0 to 10;
  with the proviso that the sum of o and p in each contiguous chain is from 1 to 10;
  each x is, independently, O, NR$^{10}$, C(═O), CHOH, C(═N—R$^{10}$), CHNR$^7$R$^{10}$, or represents a single bond;
each R$^5$ is independently, —(CH$_2$)$_n$—CO$_2$R$^{13}$, Het-(CH$_2$)$_m$—CO$_2$R$^{13}$, —(CH$_2$)$_n$—Z$_g$—CO$_2$R$^{13}$, Het-(CH$_2$)$_m$—Z$_g$—CO$_2$R$^{13}$, —(CH$_2$)$_n$—NR$^{10}$—(CH$_2$)$_m$(CHOR$^8$)$_n$—CO$_2$R$^{13}$, Het-(CH$_2$)$_m$—NR$^{10}$—(CH$_2$)$_m$(CHOR$^8$)$_n$—CO$_2$R$^{13}$, —(CH$_2$)$_n$—(CHOR$^8$)$_m$—CO$_2$R$^{13}$, Het-(CH$_2$)—(CHOR$^8$)$_m$—CO$_2$R$^{13}$, —(CH$_2$)$_n$—(CHOR$^8$)$_m$ Z$_g$—CO$_2$R$^{13}$, Het-(CH$_2$)$_n$—(CHOR$^8$)$_m$—Z$_g$—CO$_2$R$^{13}$ —(CH$_2$)$_n$—Z$_g$—(CH$_2$)$_m$—CO$_2$R$^{13}$, —(CH$_2$)$_n$—Z$_g$—(CH$_2$)$_m$—CO$_2$R$^{13}$, —(CH$_2$)$_n$—Z$_g$—(CHOR$^8$)$_m$—Z$_g$—CO$_2$R$^{13}$, Het-(CH$_2$)$_n$—Z$_g$—(CHOR$^8$)$_m$—Z$_g$—CO$_2$R$^3$, —(CH$_2$)$_n$—CONH—C(═NR$^{13}$)—NR$^{13}$R$^{13}$, Het-(CH$_2$)$_n$—CO—NH—C(═NR$^{13}$)—NR$^{13}$R$^{13}$, —(CH$_2$)$_n$—Z$_g$—CONH—C(═NR$^{13}$)—NR$^{13}$R$^{13}$, Het-(CH$_2$)$_n$—Z$_g$—CONH—C(═NR$^{13}$)$_n$—NR$^{13}$R$^{13}$—(CH$_2$)$_n$—NR$^{10}$—(CH$_2$)$_m$(CHOR$^8$)$_n$—CONH—C(═NR$^{13}$)—NR$^{13}$R$^{13}$, Het-(CH$_2$)$_n$—NR$^{10}$—(CH$_2$)$_m$(CHOR$^8$)$_n$—CONH—C(═NR$^{13}$)—NR$^{13}$R$^{13}$, —(CH$_2$)$_n$—(CHOR$^8$)$_m$—CONH—C(═NR$^{13}$)—NR$^{13}$R$^{13}$, Het-(CH$_2$)$_n$—(CHOR$^8$)$_m$—CONH—C(═NR$^{13}$)—NR$^{13}$R$^{13}$, —(CH$_2$)$_n$—(CHOR$^8$)$_m$—Z$_g$—CONH—C(═NR$^{13}$)—NR$^{13}$R$^{13}$, Het-(CH$_2$)$_n$—(CHOR$^8$)$_m$—Z$_g$—CONH—C(═NR$^{13}$)—NR$^{13}$R$^{13}$, —(CH$_2$)$_n$—Z$_g$—(CH$_2$)$_m$CONH—C(═NR$^{13}$)NR$^{13}$R$^{13}$, Het-(CH$_2$)$_n$—Z$_g$—(CH$_2$)$_m$—CONH—C(═NR$^3$)—NR$^{13}$R$^{13}$, —(CH$_2$)$_n$—Z$_g$—(CHOR$^8$)$_m$—Z$_g$—CONH—C(═NR$^{13}$R$^{13}$, Het-(CH$_2$)$_n$—Z$_g$—(CHOR$^8$)$_n$—Z$_g$—CONH—C(═NR$^{13}$)—NR$^{13}$R$^{13}$, —(CH$_2$)$_n$—CONR$^{13}$—CONR$^{13}$R$^{13}$, Het-(CH$_2$)$_n$—CONR$^7$—CONR$^{13}$R$^{13}$, —(CH$_2$)$_n$—Z$_g$—CONR$^7$—CONR$^{13}$R$^{13}$, —(CH$_2$)$_n$—Z$_g$—CONR$^7$—CONR$^{13}$R$^{13}$, —(CH$_2$)$_n$—NR$^{10}$—(CH$_2$)$_m$(CHOR$^8$)$_n$—CONR$^7$—CONR$^{13}$R$^{13}$, Het-(CH$_2$)$_n$—NR$^{10}$—(CH$_2$)$_m$(CHOR$^8$)$_n$—CONR$^7$—CONR$^{13}$R$^{13}$, —(CH$_2$)$_n$—(CHOR$^8$)$_m$—CONR$^7$—CONR$^{13}$R$^{13}$, Het-(CH$_2$)$_n$—(CHOR$^8$)$_m$—CONR$^7$—CONR$^{13}$R$^{13}$, —(CH$_2$)$_n$—(CHOR$^8$)$_m$—Z$_g$—CONR$^7$—CONR$^{13}$R$^{13}$, Het-(CH$_2$)$_n$—(CHOR$^8$)$_m$—Z$_g$—CONR$^7$—CONR$^{13}$R$^{13}$, —(CH$_2$)$_n$—Z$_g$—(CH$_2$)$_m$CONR$^7$—CONR$^{13}$R$^{13}$, Het-(CH$_2$)$_n$—Z$_g$—(CH$_2$)$_m$CONR$^7$—CONR$^{13}$R$^{13}$, —(CH$_2$)$_n$—Z$_g$—(CHOR$^8$)$_m$—Z$_g$—CONR$^7$—CONR$^{13}$R$^{13}$, Het-(CH$_2$)$_n$—Z$_g$(CHOR$^8$)$_m$—Z$_g$—CONR$^7$—CONR$^{13}$R$^{13}$, —(CH$_2$)$_n$—CONR$^7$SO$_2$NR$^{13}$R$^{13}$, Het-(CH$_2$)$_m$—

CONR$^7$SO$_2$NR$^{13}$R$^{13}$, —(CH$_2$)$_n$—Z$_g$—CONR$^7$SO$_2$NR$^{13}$R$^{13}$, Het-(CH$_2$)$_m$—Z$_g$—CONR$^7$SO$_2$NR$^{13}$R$^{13}$, —(CH$_2$)$_n$—NR$^{10}$—(CH$_2$)$_m$(CHOR$^8$)$_n$—CONR$^7$SO$_2$NR$^{13}$R$^{13}$, Het-(CH$_2$)$_m$—NR$^{10}$—(CH$_2$)$_m$(CHOR$^8$)$_n$—CONR$^7$SO$_2$NR$^{13}$R$^{13}$, —(CH$_2$)$_n$—(CHOR$^8$)$_m$—CONR$^7$SO$_2$NR$^{13}$R$^{13}$, Het-(CH$_2$)$_m$—(CHOR$^8$)$_m$—CONR$^7$SO$_2$NR$^{13}$R$^{13}$, —(CH$_2$)$_n$—(CHOR$^8$)$_m$—Z$_g$—CONR$^7$SO$_2$NR$^{13}$R$^{13}$, Het-(CH$_2$)$_n$—(CHOR$^8$)$_m$—Z$_g$—CONR$^7$SO$_2$NR$^{13}$R$^{13}$, —(CH$_2$)$_n$—Z$_g$—(CH$_2$)$_m$CONR$^7$SO$_2$NR$^{13}$R$^{13}$, Het-(CH$_2$)$_n$—Z$_g$—(CH$_2$)$_m$CONR$^7$SO$_2$NR$^{13}$R$^{13}$, —(CH$_2$)$_n$—Z$_g$—(CHOR$^8$)$_m$—Z$_g$—CONR$^7$SO$_2$NR$^{13}$R$^{13}$, Het-(CH$_2$)$_n$—Z$_g$—(CHOR$^8$)$_m$—Z$_g$—CONR$^7$SO$_2$NR$^{13}$R$^{13}$, —(CH$_2$)$_n$—SO$_2$NR$^{13}$R$^{13}$, Het-(CH$_2$)$_m$—SO$_2$NR$^{13}$R$^{13}$, —(CH$_2$)$_n$—Z$_g$—SO$_2$NR$^{13}$R$^{13}$, Het-(CH$_2$)$_m$—Z$_g$—SO$_2$NR$^{13}$R$^{13}$, —(CH$_2$)$_n$—NR$^{10}$—(CH$_2$)$_m$(CHOR$^8$)$_n$—SO$_2$NR$^{13}$R$^{13}$, Het-(CH$_2$)$_m$—NR$^{10}$—(CH$_2$)$_m$(CHOR$^8$)$_n$—SO$_2$NR$^{13}$R$^{13}$, —(CH$_2$)$_n$—(CHOR$^8$)$_m$—SO$_2$NR$^{13}$R$^{13}$, Het-(CH$_2$)$_m$—(CHOR$^8$)$_m$—SO$_2$NR$^{13}$R$^{13}$, —(CH$_2$)$_n$—(CHOR$^8$)$_m$—Z$_g$—SO$_2$NR$^{13}$R$^{13}$Het-(CH$_2$)$_n$—(CHOR$^8$)$_m$—Z$_g$—SO$_2$NR$^{13}$R$^{13}$, —(CH$_2$)$_n$—Z$_g$—(CH$_2$)$_m$SO$_2$NR$^{13}$R$^{13}$, Het-(CH$_2$)$_n$—Z$_g$—(CH$_2$)$_m$SO$_2$NR$^{13}$R$^{13}$, —(CH$_2$)$_n$—Z$_g$—(CHOR$^8$)$_m$—Z$_g$—SO$_2$NR$^{13}$R$^{13}$, Het-(CH$_2$)$_n$—Z$_g$—(CHOR$^8$)$_n$—Z$_g$—SO$_2$NR$^{13}$R$^{13}$, —(CH$_2$)$_n$—CONR$^{13}$R$^{13}$, -Het-(CH$_2$)$_m$—CONR$^{13}$R$^{13}$, —(CH$_2$)$_n$—Z$_g$—CONR$^{13}$R$^{13}$, Het-(CH$_2$)$_m$—Z$_g$—CONR$^{13}$R$^{13}$, —(CH$_2$)$_n$—NR$^{10}$—(CH$_2$)$_m$(CHOR$^8$)$_n$—CONR$^{13}$R$^{13}$, Het-(CH$_2$)$_m$—NR$^{10}$—(CH$_2$)$_m$(CHOR$^8$)$_n$—CONR$^{13}$R$^{13}$, —(CH$_2$)$_n$—(CHOR$^8$)$_m$—CONR$^{13}$R$^{13}$, Het-(CH$_2$)$_m$—(CHOR$^8$)$_n$—CONR$^{13}$R$^{13}$—(CH$_2$)$_n$—(CHOR$^8$)$_n$—Z$_g$—CONR$^{13}$R$^{13}$, Het-(CH$_2$)$_n$—(CHOR$^8$)$_m$—Z$_g$—CONR$^{13}$R$^{13}$, —(CH$_2$)$_n$—Z$_g$—(CH$_2$)$_m$CONR$^{13}$R$^{13}$, Het-(CH$_2$)$_n$—Z$_g$—(CH$_2$)$_m$CONR$^{13}$R$^{13}$(CH$_2$)$_n$—Z$_g$—(CHOR$^8$)$_m$Z$_g$—CONR$^{13}$R$^{13}$, Het-(CH$_2$)$_n$—Z$_g$—(CHOR$^8$)$_m$—Z$_g$—CONR$^{13}$R$^{13}$, —(CH$_2$)$_n$—CONR$^7$COR$^{13}$, Het-(CH$_2$)$_n$—CONR$^7$COR$^{13}$, —(CH$_2$)$_n$—Z$_g$—CONR$^7$COR$^{13}$, Het-(CH$_2$)$_m$—Z$_g$—CONR$^7$COR$^{13}$—(CH$_2$)$_n$—NR$^{10}$—(CH$_2$)$_m$(CHOR$^8$)$_n$—CONR$^7$COR$^{13}$, Het-(CH$_2$)$_m$—NR$^{10}$—(CH$_2$)$_m$(CHOR$^8$)$_m$—CONR$^7$COR$^{13}$, —(CH$_2$)$_n$—(CHOR$^8$)$_m$—CONR$^7$COR$^{13}$, Het-(CH$_2$)$_m$—(CHOR$^8$)$_m$—CONR$^7$COR$^{13}$, —(CH$_2$)$_n$—(CHOR$^8$)$_m$—Z$_g$—CONR$^7$COR$^{13}$, Het-(CH$_2$)$_n$—(CHOR$^8$)$_m$—Z$_g$—CONR$^7$COR$^{13}$, —(CH$_2$)$_n$—Z$_g$—(CH$_2$)$_m$CONR$^7$COR$^{13}$, Het-(CH$_2$)$_n$—Z$_g$—(CHOR$^8$)$_m$—Z$_g$—CONR$^7$COR$^{13}$, —(CH$_2$)$_n$—CONR$^7$CO$_2$R$^{13}$, Het-(CH$_2$)$_m$—Z$_g$—CONR$^7$CO$_2$R$^{13}$, —(CH$_2$)$_n$—NR$^{10}$—(CH$_2$)$_m$(CHOR$^8$)$_m$—CONR$^7$CO$_2$R$^{13}$, Het-(CH$_2$)$_n$—NR$^{10}$—(CH$_2$)$_n$(CHOR$^8$)$_m$—CONR$^7$CO$_2$R$^{13}$, —(CH$_2$)$_n$—(CHOR$^8$)$_m$—CONR$^7$CO$_2$R$^{13}$, Het-(CH$_2$)$_m$—(CHOR$^8$)$_m$—CONR$^7$CO$_2$R$^{13}$, —(CHOR$^8$)$_n$—Z$_g$—CONR$^7$CO$_2$R$^{13}$, Het-(CH$_2$)$_n$—(CHOR$^8$)$_m$—Z$_g$—CONR$^7$CO$_2$R$^{13}$(CH$_2$)$_n$—Z$_g$—(CH$_2$)$_m$CONR$^7$CO$_2$R$^{13}$, Het-(CH$_2$)$_n$—Z$_g$—(CH$_2$)$_m$CONR$^7$CO$_2$R$^{13}$, —(CH$_2$)$_n$—Z$_g$(CHOR$^8$)$_m$—Z$_g$—CONR$^7$CO$_2$R$^{13}$, Het-(CH$_2$)$_n$—Z$_g$—(CHOR$^8$)$_m$—Z$_g$—CONR$^7$CO$_2$R$^{13}$, —(CH$_2$)$_n$—NH—C(=NR$^{13}$)—NR$^{13}$R$^{13}$, Het-(CH$_2$)$_m$—NH—C(=NR$^3$)—NR$^{13}$R$^{13}$, —(CH$_2$)$_n$—Z$_g$-NH—C(=NR$^{13}$)—NR$^{13}$R$^{13}$, Het-(CH$_2$)$_m$—Z$_g$-NH—C(=NR$^{13}$)—NR$^{13}$R$^{13}$, —(CH$_2$)$_n$—NR$^{10}$—(CH$_2$)$_m$(CHOR$^8$)$_n$—NH—C(=NR$^{13}$)—NR$^{13}$R$^{13}$, Het-(CH$_2$)$_m$—NR$^{10}$—(CH$_2$)$_m$(CHOR$^8$)$_n$—NH—C(=NR$^{13}$)—NR$^{13}$R$^{13}$, —(CH$_2$)$_n$—(CHOR$^8$)$_n$—NH—C(=NR$^{13}$)—NR$^{13}$R$^{13}$, Het-(CH$_2$)$_m$—

(CHOR$^8$)$_m$—NH—C(=NR$^{13}$)—NR$^{13}$R$^{13}$, —(CH$_2$)$_n$—(CHOR$^8$)$_m$—Z$_g$—NH—C(=NR$^{13}$)—NR$^{13}$R$^{13}$, Het-(CH$_2$)$_n$—(CHOR$^8$)$_n$—Z$_g$—NH—C(=NR$^{13}$)—NR$^{13}$R$^{13}$, —(CH$_2$)$_n$—Z$_g$—(CH$_2$)$_m$NH—C(=NR$^{13}$)—NR$^{13}$R$^{13}$, Het-(CH$_2$)$_n$—Z$_g$—(CH$_2$)$_m$NH—C(=NR$^{13}$)—NR$^{13}$R$^{13}$, —(CH$_2$)$_n$—Z$_g$—(CHOR$^8$)$_m$—Z$_g$—NH—C(=NR$^{13}$)—NR$^{13}$R$^{13}$, Het-(CH$_2$)$_n$—Z$_g$—(CHOR$^8$)$_m$—Z$_g$-NH—C(=NR$^{13}$)—NR$^{13}$R$^{13}$, —(CH$_2$),—C(=NR$^{13}$)—NR$^{13}$R$^{13}$, Het-(CH$_2$)$_n$—C(=NH)—NR$^{13}$R$^{13}$, —(CH$_2$)$_n$—Z$_g$—C(=NH)—NR$^{13}$R$^{13}$, Het-(CH$_2$)$_m$—Z$_g$—C(=NH)—NR$^{13}$R$^{13}$, —(CH$_2$)$_n$—NR$^{10}$—(CH$_2$)$_n$(CHOR$^8$)$_m$—C(=NR$^{13}$)—NR$^{13}$R$^{13}$, Het-(CH$_2$)$_m$—NR$^{10}$—(CH$_2$)$_m$(CHOR$^8$)$_n$—C(=NR$^{13}$)—NR$^{13}$R$^{13}$, —(CH$_2$)$_n$—(CHOR$^8$)$_m$—C(=NR$^{13}$)—NR$^{13}$R$^{13}$, Het-(CH$_2$)$_m$—(CHOR$^8$)$_m$—C(=NR$^{13}$)—NR$^{13}$R$^{13}$, —(CH$_2$)$_n$—(CHOR$^8$)$_n$—Z$_g$—C(=NR$^{13}$)—NR$^{13}$R$^{13}$, Het-(CH$_2$)$_n$—(CHOR$^8$)$_m$—Z$_g$—C(=NR$^{13}$)—NR$^{13}$R$^{13}$, —(CH$_2$)$_n$—Z$_g$—(CH$_2$)$_m$—C(=NHC(=NR$^{13}$)—NR$^{13}$R$^{13}$, Het-(CH$_2$)$_n$—Z$_g$—(CH$_2$)$_m$—C(=NR$^{13}$)—NR$^{13}$R$^{13}$, —(CH$_2$)$_n$—Z$_g$—(CHOR$^8$)$_m$—Z$_g$—C(=NR$^{13}$)—NR$^{13}$R$^{13}$, Het-(CH$_2$)$_n$—Z$_g$—(CHOR$^8$)$_m$—Z$_g$—C(=NR$^{13}$)—NR$^{13}$R$^{13}$;

wherein when two —CH$_2$OR$^8$ groups are located 1,2- or 1,3- with respect to each other the R$^8$ groups may be joined to form a cyclic mono- or di-substituted 1,3-dioxane or 1,3-dioxolane;

each R$^6$ is, independently, —R$^5$, —R$^7$, —OR$^8$, —N(R$^7$)$_2$, —(CH$_2$)$_m$—OR$^8$, —O—(CH$_2$)$_m$—OR$^8$, —(CH$_2$)$_m$—NR$^7$R$^{10}$, —O—(CH$_2$)$_m$—NR$^7$R$^{10}$, —(CH$_2$)$_n$(CHOR$^8$)(CHOR$^8$)$_n$—CH$_2$OR$^8$, —O—(CH$_2$)$_m$(CHOR$^8$)(CHOR$^8$)$_n$—CH$_2$OR$^8$, —(CH$_2$CH$_2$O)$_m$—R$^8$, —O—(CH$_2$CH$_2$O)$_m$—R$^8$, —(CH$_2$CH$_2$O)$_m$—CH$_2$CH$_2$NR$^7$R$^{10}$, —O—(CH$_2$CH$_2$O)$_m$—CH$_2$CH$_2$NR$^7$R$^{10}$, —(CH$_2$)$_n$—C(=O)NR$^7$R$^{10}$, —O—(CH$_2$)$_m$—C(=O)NR$^7$R$^{10}$, —(CH$_2$)$_n$—(Z)$_g$—R$^7$, —O—(CH$_2$)$_m$—(Z)$_g$—R$^7$, —(CH$_2$)$_n$—NR$^{10}$—CH$_2$(CHOR$^8$)(CHOR$^8$)$_n$—CH$_2$OR$^8$, —O—(CH$_2$)$_m$—NR$^{10}$—CH$_2$(CHOR$^8$)(CHOR$^8$)$_n$—CH$_2$OR$^8$, —(CH$_2$)$_n$—CO$_2$R$^7$, —O—(CH$_2$)$_m$—CO$_2$R$^7$—OSO$_3$H, —O-glucuronide, —O-glucose,

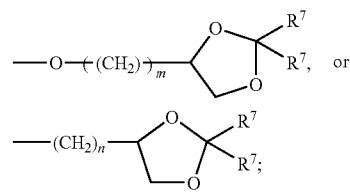

wherein when two R$^6$ are —OR$^{11}$ and are located adjacent to each other on a phenyl ring, the alkyl moieties of the two R$^6$ may be bonded together to form a methylenedioxy group, and wherein when two —CH$_2$OR$^8$ groups are located 1,2- or 1,3- with respect to each other the R$^8$ groups may be joined to form a cyclic mono- or di-substituted 1,3-dioxane or 1,3-dioxolane;

each R$^7$ is, independently, hydrogen lower alkyl, phenyl, or substituted phenyl;

each R$^8$ is, independently, hydrogen, lower alkyl, —C(=O)—R$^{11}$, glucuronide, 2-tetrahydropyranyl, or

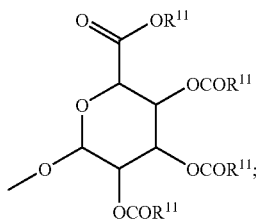

each $R^9$ is, independently, $-CO_2R^7$, $-CON(R^7)_2$, $-SO_2CH_3$, or $-C(=O)R^7$;

each $R^{10}$ is, independently, $-H$, $-SO_2CH_3$, $-CO_2R^7$, $-C(=O)NR^7R^9$, $-C(=O)R^7$, or $-CH_2-(CHOH)_n-CH_2OH$;

each Z is, independently, CHOH, $C(=O)$, $-(CH_2)_n-$, $CHNR^7R^{10}$, $C=NR^{10}$, or $NR^{10}$;

each $R^{11}$ is, independently, lower alkyl;

each $R^{12}$ is independently, $-SO_2CH_3$, $-CO_2R^7$, $-C(=O)NR^7R^9$, $-C(=O)R^7$, or $CH_2-(CHOH)_n-CH_2OH$;

each $R^{13}$ is, independently, hydrogen, $R^7$, $R^{10}$, $-(CH_2)_m-NR^7R^{10}$,

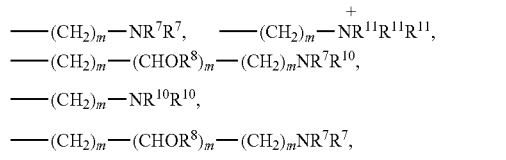

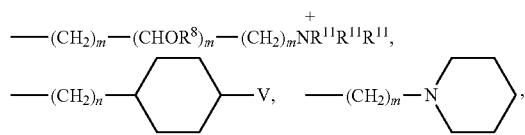

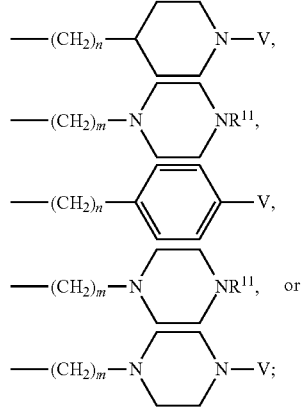

with the proviso that at least one $R^{13}$ must be a group other than hydrogen, $R^7$, or $R^{10}$;

with the further proviso that $NR^{13}R^{13}$ can be joined on itself to form a ring comprising one of the following:

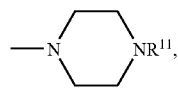

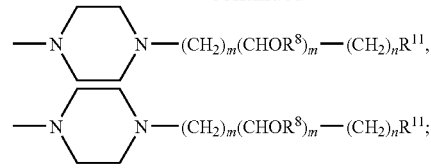

each Het is independently, $-NR^7$, $-NR^{10}$, $-S-$, $-SO-$, $-SO_2-$, $-O-$, $-SO_2NH-$, $-NHSO_2-$, $-NR^7CO-$, or $-CONR^7-$;

each g is, independently, an integer from 1 to 6;
each m is, independently, an integer from 1 to 7;
each n is, independently, an integer from 0 to 7;
each Q is, independently, $C-R^5$, $C-R^6$, or a nitrogen atom, wherein one Q is $C-R^5$ and at most three Q in a ring are nitrogen atoms;
each V is, independently, $-(CH_2)_m-NR^7R^{10}$, $-(CH_2)_m-NR^7R^{10}$, $-(CH_2)_m-$

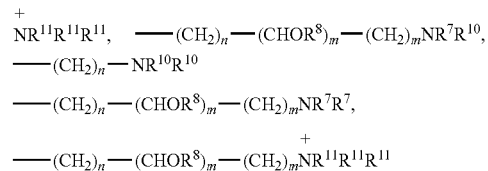

with the proviso that when V is attached directly to a nitrogen atom, then V can also be, independently, $R^7$, $R^{10}$, or $(R^{11})_2$;

wherein for any of the above compounds when two $-CH_2OR^8$ groups are located 1,2- or 1,3- with respect to each other the $R^8$ groups may be joined to form a cyclic mono- or di-substituted 1,3-dioxane or 1,3-dioxolane;

wherein any of the above compounds can be a pharmaceutically acceptable salt thereof, and wherein the above compounds are inclusive of all enantiomers, diastereomers, and racemic mixtures thereof;

(5) each $R^2$ is, independently, $-R^7$, $-(CH_2)_m-OR^8$, $-(CH_2)_m-NR^7R^{10}$, $-(CH_2)_n(CHOR^8)(CHOR^8)_n-CH_2OR^8$, $-(CH_2CH_2O)_m-R^8$, $-(CH_2CH_2O)_m-CH_2CH_2NR^7R^{10}$, $-(CH_2)$, $-C(=O)NR^7R^{10}$, $-(CH_2)_n-Z_g-R^7$, $-(CH_2)_m-NR^{10}-CH_2(CHOR^8)(CHOR^8)_n-CH_2OR^8$, $-(CH_2)_n-CO_2R^7$, or

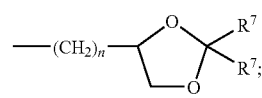

wherein when two $-CH_2OR^8$ groups are located 1,2- or 1,3- with respect to each other the $R^8$ groups may be joined to form a cyclic mono- or di-substituted 1,3-dioxane or 1,3-dioxolane; $R^3$ and $R^4$ are each, independently, hydrogen, a group represented by formula (A), lower alkyl, hydroxy lower alkyl, phenyl, phenyl-lower alkyl, (halophenyl)-lower alkyl, lower-(alkylphenylalkyl), lower (alkoxyphenyl)-lower alkyl, naphthyl-lower alkyl, or pyridyl-lower alkyl, with the proviso that at least one of $R^3$ and $R^4$ is a group represented by formula (A):

wherein
each $R^L$ is, independently, $—R^7$, $—(CH_2)_n—OR^8$, $—O—(CH_2)_m—OR^8$, $—(CH_2)_n—NR^7R^{10}$, $—O—(CH_2)_m—NR^7R^{10}$, $—(CH_2)_n(CHOR^8)(CHOR^8)_n—CH_2OR^8$, $—O—(CH_2)_n(CHOR^8)(CHOR^8)_n—CH_2OR^8$, $—(CH_2CH_2O)_m—R^8$, $—O—(CH_2CH_2O)_m—R^8$, $—(CH_2CH_2O)_m—CH_2CH_2NR^7R^{10}$, $—O—(CH_2CH_2O)_m—CH_2CH_2NR^7R^{10}$, $—(CH_2)_n—C(=O)NR^7R^{10}$, $—O—(CH_2)_n—C(=O)NR^7R^{10}$, $—(CH_2)_n—(Z)_g—R^7$, $—O—(CH_2)_m—(Z)_g—R^7$, $—(CH_2)_n—NR^{10}—CH_2(CHOR^8)(CHOR^8)_n—CH_2OR^8$, $—O—(CH_2)_m—NR^{10}—CH_2(CHOR^8)(CHOR^8)_n—CH_2OR^8$, $—(CH_2)_n—CO_2R^7$, $—O—(CH_2)_m—CO_2R^7—OSO_3H$, —O-glucuronide, —O-glucose,

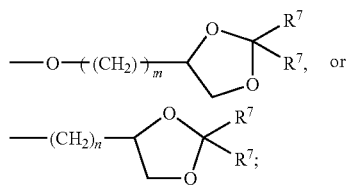

or wherein when two $—CH_2OR^8$ groups are located 1,2- or 1,3- with respect to each other the $R^8$ groups may be joined to form a cyclic mono- or di-substituted 1,3-dioxane or 1,3-dioxolane;
each o is, independently, an integer from 0 to 10;
each p is an integer from 0 to 10;
with the proviso that the sum of o and p in each contiguous chain is from 1 to 10;
each x is, independently, O, $NR^{10}$, $C(=O)$, CHOH, $C(=N—R^{10})$, $CHNR^7R^{10}$, or represents a single bond;
each $R^5$ is independently, $—(CH_2)_n—CO_2R^{13}$, Het-$(CH_2)_m—CO_2R^{13}$, $—(CH_2)_n-Z_g CO_2R^{13}$, Het-$(CH_2)_m—Z_g—CO_2R^{13}$, $—(CH_2)_n—NR^{10}—(CH_2)_m(CHOR^8)_n—CO_2R^{13}$, Het-$(CH_2)_m—NR^{10}—(CH_2)_m(CHOR^8)_n—CO_2R^{13}$, $—(CH_2)_n—(CHOR^8)_m—CO_2R^{13}$, Het-$(CH_2)_m—(CHOR^8)_m—CO_2R^{13}$, $—(CH_2)_n—(CHOR^8)_m Z_g—CO_2R^{13}$, Het-$(CH_2)_n—(CHOR^8)_m—Z_g—CO_2R^{13}$, $—(CH_2)_n—Z_g—(CH_2)_m—CO_2R^{13}$, $—(CH_2)_n—Z_g(CHOR^8)_m—Z_g—CO_2R^{13}$, Het-$(CH_2)_n—Z_g—(CHOR^8)_m—Z_g-CO_2R^{13}$, $—(CH_2)_n—CONH—C(=NR^{13})—NR^{13}R^{13}$Het-$(CH_2)_n—CO—NH—C(=NR^{13})—NR^{13}R^{13}$, $—(CH_2)_n—Z_g—CONH—C(=NR^{13})—NR^{13}R^{13}$, Het-$(CH_2)_n—Z_g—CONH—C(=NR^{13})—NR^{13}R^{13}$, $—(CH_2)_n—NR^{10}—(CH_2)_m(CHOR^8)_n—CONH—C(=NR^{13})—NR^{13}R^{13}$, Het-$(CH_2)_n—NR^{10}—(CH_2)_m(CHOR^8)_n—CONH—C(=NR^{13})—NR^{13}R^{13}$, $—(CH_2)_n—(CHOR^8)_m CONH—C(=NR^{13})—NR^{13}R^{13}$, Het-$(CH_2)_n—(CHOR^8)_m—CONH—C(=NR^{13})—NR^{13}R^{13}$, $—(CH_2)_n—(CHOR^8)_m—Z_g—CONH—C(=NR^{13})—NR^{13}R^{13}$, Het-$(CH_2)_n—(CHOR^8)_m—Z_g—CONH—C(=NR^{13})—NR^{13}R^{13}$, $—(CH_2)_n—Z_g-(CH_2)_m CONH—C(=NR^{13})—NR^{13}R^{13}$, Het-$(CH_2)_n—Z_g—(CH_2)_m CONH—C(=NR^{13})—NR^{13}R^{13}$, $—(CH_2)_n—Z_g—(CHOR^8)_m—Z_g—CONH—C(=NR^{13})—NR^{13}R^{13}$, Het-$(CH_2)_n—Z_g—(CHOR^8)_m—Z_g—CONH—C(=NR^{13})—NR^{13}R^{13}$, $—(CH_2)_n—CONR^7—CONR^{13}R^{13}$, Het-$(CH_2)_n—CONR^7—CONR^{13}R^{13}$, $—(CH_2)_n—Z_g—CONR^7—CONR^{13}R^{13}$, $—(CH_2)_n—Z_g—CONR^7—CONR^{13}R^{13}$, $—(CH_2)_n—NR^{10}—(CH_2)_m(CHOR^8)_n—CONR^7—CONR^{13}R^{13}$, Het-$(CH_2)_n—NR^{10}—(CH_2)_m(CHOR^8)_n—CONR^7—CONR^{13}R^{13}$, $—(CH_2)_n—(CHOR^8)_m—CONR^7—CONR^{13}R^{13}$, Het-$(CH_2)_n—(CHOR^8)_m—CONR^7—CONR^{13}R^{13}$, $—(CH_2)_n—(CHOR^8)_m—Z_g—CONR^7—CONR^{13}R^{13}$, Het-$(CH_2)_n—(CHOR^8)_m—Z_g—CNR^7—CONR^{13}R^{13}$, $—(CH_2)_n—Z_g—(CH_2)_m CONR^7—CONR^{13}R^{13}$, Het-$(CH_2)_n—Z_g—(CH_2)_m CONR^7—CONR^{13}R^{13}$, $—(CH_2)_n—Z_g(CHOR^8)_m—Z_g CONR^7—CONR^{13}R^{13}$, Het-$(CH_2)_n—Z_g(CHOR^8)_m—Z_g—CONR^7—CONR^{13}R^{13}$, $—(CH_2)_n—CONR^7SO_2NR^{13}R^{13}$, Het-$(CH_2)_m—CONR^7SO_2NR^{13}R^{13}$, $—(CH_2)_n—Z_g-CONR^7SO_2NR^{13}R^{13}$, Het-$(CH_2)_m—Z_g—CONR^7SO_2NR^{13}R^{13}$, $—(CH_2)_n—NR^{10}—(CH_2)_m(CHOR^8)_n—CONR^7SO_2NR^{13}R^{13}$, Het-$(CH_2)_m—NR^{10}—(CH_2)_m(CHOR^8)_n—CONR^7SO_2NR^{13}R^{13}$, $—(CH_2)_n—(CHOR^8)—CONR^7SO_2NR^{13}R^{13}$, Het-$(CH_2)_m—(CHOR^8)_m—CONR^7SO_2NR^{13}R^{13}$, $—(CH_2)_n—(CHOR^8)_m—Z_g—CONR^7SO_2NR^{13}R^{13}$, Het-$(CH_2)_n—(CHOR^8)_m—Z_g—CONR^7SO_2NR^{13}R^{13}$, $—(CH_2)_n—Z_g—(CH_2)_m CONR^7SO_2NR^{13}R^{13}$, Het-$(CH_2)_n—Z_g—(CH_2)_m CONR^7SO_2NR^{13}R^{13}$, $—(CH_2)_n—Z_g—(CHOR^8)_m—Z_g—CONR^7SO_2NR^{13}R^{13}$, Het-$(CH_2)_n—Z_g—(CHOR^8)_m—Z_g—CONR^7SO_2NR^{13}R^{13}$, $—(CH_2)_m—SO_2NR^{13}R^{13}$, Het-$(CH_2)_m—SO_2NR^{13}R^{13}$, $—(CH_2)_n-Z_g-SO_2NR^{13}R^{13}$, Het-$(CH_2)_m—Z_g-SO_2NR^{13}R^{13}$, $—(CH_2)_n—NR^{10}—(CH_2)_m(CHOR^8)_n—SO_2NR^{13}R^{13}$, Het-$(CH_2)_m—NR^{10}—(CH_2)_m(CHOR^8)_n—SO_2NR^{13}R^{13}$, $—(CH_2)_n—(CHOR^8)_m—SO_2NR^{13}R^{13}$, Het-$(CH_2)_m—(CHOR^8)_m—SO_2NR^{13}R^{13}$, $—(CH_2)_n—(CHOR^8)_m—Z_g-SO_2NR^{13}R^{13}$, Het-$(CH_2)_n—(CHOR^8)_m—Z_g-SO_2NR^{13}R^{13}$, $—(CH_2)_n—Z_g—(CH_2)_m SO_2NR^{13}R^{13}$, Het-$(CH_2)_n—Z_g-(CH_2)_m SO_2NR^{13}R^{13}$, $—(CH_2)_n—Z_g—(CHOR^8)_m—Z_g-SO_2NR^{13}R^{13}$, Het-$(CH_2)_n—Z_g-(CHOR^8)_m—Z_g-SO_2NR^{13}R^{13}$, $—(CH_2)_n—CONR^{13}R^{13}$, Het-$(CH_2)_m—CONR^{13}R^{13}$, $—(CH_2)_n—Z_g—CONR^{13}R^{13}$, Het-$(CH_2)_m—Z_g—CONR^{13}R^{13}$, $—(CH_2)_n—NR^{10}—(CH_2)_m(CHOR^8)_n—CONR^{13}R^{13}$, Het-$(CH_2)_m—NR^{10}—(CH_2)_m(CHOR^8)_n—CONR^{13}R^{13}$, $—(CH_2)_n—(CHOR^8)_m—CONR^{13}R^{13}$, Het-$(CH_2)_m—(CHOR^8)_m—CONR^{13}R^{13}$, $—(CH_2)_n—(CHOR^8)_m—Z_g—CONR^{13}R^{13}$, Het-$(CH_2)_n—(CHOR^8)_m—Z_g—CONR^{13}R^{13}$, $—(CH_2)_n—Z_g—(CH_2)_m CONR^{13}R^{13}$, Het-$(CH_2)_n—Z_g-(CH_2)_m CONR^{13}R^{13}$, $1(CH_2)_n—Z_g—(CHOR^8)_m—Z_g—CONR^{13}R^{13}$, Het-$(CH_2)_n—Z_g-(CHOR^8)_m—Z_g—CONR^{13}R^{13}$, $—(CH_2)_n—CONR^7COR^{13}$, Het-$(CH_2)_m—CONR^7COR^{13}$, $—(CH_2)_n—Z_g—CONR^7COR^{13}$, Het-$(CH_2)_m—Z_g—CONR^7COR^{13}$, $—(CH_2)_n—NR^{10}—(CH_2)_m(CHOR^8)_n—CONR^7COR^{13}$, Het-$(CH_2)_m—NR^{10}—(CH_2)_m(CHOR^8)—CONR^7COR^{13}$, $—(CH_2)_n—(CHOR^8)_m—CONR^7COR^{13}$, Het-$(CH_2)_m—(CHOR^8)_m—CONR^7COR^{13}$, $—(CH_2)_n—(CHOR^8)_m—Z_g—CONR^7COR^{13}$, Het-$(CH_2)_n—(CHOR^8)_m—Z_g—CONR^7COR^{13}$, $—(CH_2)_n—Z_g—(CH_2)_m CONR^7COR^{13}$, $—(CH_2)_n—Z_g—(CH_2)_m CONR^7COR^{13}$, Het-$(CH_2)_n—Z_g—(CHOR^8)_m—Z_g-CONR^7COR^{13}$, $—(CH_2)_n—CONR^7CO_2R^{13}$, $—(CH_2)_n—Z_g—CONR^7CO_2R^{13}$, Het-$(CH_2)_m—Z_g—CONR^7CO_2R^{13}$, $—(CH_2)_n—NR^{10}—(CH_2)_m(CHOR^8)_n—CONR^7CO_2R^{13}$ Het-$(CH_2)_m—NR^{10}—(CH_2)_m(CHOR^8)_n—CO NR^7CO_2R^{13}$, $—(CH_2)_n—$ (CHOR⁸), —CONR⁷CO₂R¹³, Het-(CH₂)ₙ—(CHOR⁸)ₘ—CONR⁷CO₂R¹³, —(CH₂)ₙ—(CHOR⁸)ₘ-Z_g—CONR⁷CO₂R¹³, Het-(CH₂)ₙ—(CHOR⁸)ₘ—Z_g—CONR⁷CO₂R¹³, —(CH₂)ₙ—Z_g-(CH₂)ₘ CONR⁷CO₂R¹³, Het-(CH₂)ₙ—Z_g—(CH₂)ₘ CONR⁷CO₂R¹³, —(CH₂)ₙ—Z_g-(CHOR⁸)ₘ—Z_g CONR⁷CO₂R¹³, Het-(CH₂)ₙ—(CHOR⁸)ₘ—Z_g—CONR⁷CO₂R¹³, —(CH₂)ₙ—NH—C(═NR¹³)—NR¹³R¹³, Het-(CH₂)ₘ—NH—C(═NR¹³)—NR¹³R¹³, —(CH₂)ₙ-Z_g-NH—C(═NR¹³)—NR¹³R¹³, Het-(CH₂)ₘ—Z_g-NH—C(═NR¹³)—NR¹³R¹³, —(CH₂)ₙ—NR¹⁰—(CH₂)ₘ(CHOR⁸)ₙ—NH—C(═NR¹³)—NR¹³R¹³, Het-(CH₂)ₘ—NR¹⁰—(CH₂)ₘ(CHOR⁸)ₘ—NH—C(═NR¹³)—NR¹³R¹³, —(CH₂)ₙ—(CHOR⁸)ₘ—NH—C(═NR¹³)—NR¹³R¹³, Het-(CH₂)ₘ—(CHOR⁸)ₘ—NH—C(═NR¹³)—NR¹³R¹³, —(CH₂)ₙ—(CHOR⁸)ₘ-Z_g-NH—C(═NR¹³)—NR¹³R¹³, Het-(CH₂)ₙ—(CHOR⁸)ₘ—Z_g-NH—C(═NR¹³)—NR¹³R¹³, —(CH₂)ₙ—Z_g—(CH₂)ₘ NH—C(═NR¹³)—NR¹³R¹³, Het-(CH₂)ₙ—Z_g-(CH₂)ₘ NH—C(═NR¹³)—NR¹³R¹³, —(CH₂)ₙ—Z_g—(CHOR⁸)ₘ—Z_g-NH—C(═NR¹³)—NR¹³R¹³, Het-(CH₂)ₙ—Z_g—(CHOR⁸)ₘ—Z_g-NH—C(═NR¹³)—NR¹³R¹³, —(CH₂)ₙ—C(═NR¹³)—NR¹³R¹³, Het-(CH₂)ₘ—C(═NH)—NR¹³R¹³, —(CH₂)ₙ—Z_g—C(═NH)—NR¹³R¹³, Het-(CH₂)ₘ—Z_g—C(═NH)—NR¹³R¹³, —(CH₂)ₙ—NR¹⁰(CH₂)ₘ(CHOR⁸)ₙ—C(═NR¹³)—NR¹³R¹³, Het-(CH₂)ₘ—NR¹⁰—(CH₂)ₘ(CHOR⁸)ₘ—C(═NR¹³)—NR¹³R¹³, —(CH₂)ₙ—(CHOR⁸)ₘ—C(═NR¹³)—NR¹³R¹³, Het-(CH₂)ₙ—(CHOR⁸)ₘ—C(═NR¹³)—NR¹³R¹³, —(CH₂)ₙ—(CHOR⁸)ₘ—Z_g—C(═NH)—NR¹³R¹³, Het-(CH₂)ₙ—(CHOR⁸)ₘ- Z_g—C(═NR¹³)—NR¹³R¹³, —(CH₂)ₙ—Z_g—(CH₂)ₘ—C(═NHC(═NR¹³)—NR¹³R¹³, Het-(CH₂)ₙ—Z_g—(CH₂)ₘ—C(═NR¹³)—NR¹³R¹³, —(CH₂)ₙ—Z_g—(CHOR⁸)ₘ —Z_g—C(═NR¹³)—NR¹³R¹³, Het-(CH₂)ₙ—Z_g—(CHOR⁸)ₘ—Z_g—C(═NR¹³)—NR¹³R¹³;

wherein when two —CH₂OR⁸ groups are located 1,2- or 1,3- with respect to each other the R⁸ groups may be joined to form a cyclic mono- or di-substituted 1,3-dioxane or 1,3-dioxolane;

each R⁶ is, independently, —R⁵, —R⁷, —OR⁸, —N(R⁷)₂, —(CH₂)ₘ—OR⁸, —O—(CH₂)ₘ—OR⁸, —(CH₂)ₙ—NR⁷R¹⁰, —O(CH₂)ₘ—NR⁷R¹⁰, —(CH₂)ₙ(CHOR⁸)(CHOR⁸)ₙ—CH₂OR⁸, O—(CH₂)ₘ(CHOR⁸)(CHOR⁸)ₙ—CH₂OR⁸, —(CH₂CH₂O)ₘ—R⁸, —O—(CH₂CH₂O)ₘ—R⁸, —(CH₂CH₂O)ₘ—CH₂CH₂NR⁷R¹⁰, —O—(CH₂CH₂O)ₘ—CH₂CH₂NR⁷R¹⁰, —(CH₂)ₙ—C(═O)NR⁷R¹⁰, —O—(CH₂)ₘ—C(═O)NR⁷R¹⁰, —(CH₂)ₙ—(Z)_g—R⁷, —O—(CH₂)ₘ—(Z)_g—R⁷, —(CH₂)ₙ—NR¹⁰—CH₂(CHOR⁸)(CHOR⁸)ₙ—CH₂OR⁸, —O—(CH₂)ₘ—NR¹⁰—CH₂(CHOR⁸)(CHOR⁸)ₙ—CH₂OR⁸, —(CH₂)ₙ—CO₂R⁷, —O—(CH₂)ₘ—CO₂R⁷, —OSO₃H, —O-glucuronide, —O-glucose,

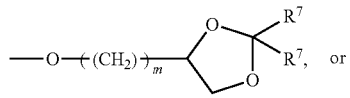, or

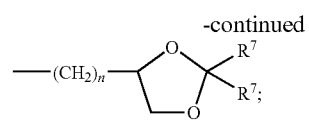

wherein when two R⁶ are —OR¹¹ and are located adjacent to each other on a phenyl ring, the alkyl moieties of the two R⁶ may be bonded together to form a methylenedioxy group, and wherein when two —CH₂OR⁸ groups are located 1,2- or 1,3- with respect to each other the R⁸ groups may be joined to form a cyclic mono- or di-substituted 1,3-dioxane or 1,3-dioxolane;

each R⁷ is, independently, hydrogen lower alkyl, phenyl, or substituted phenyl;

each R⁸ is, independently, hydrogen, lower alkyl, —C(═O)—R¹¹, glucuronide, 2-tetrahydropyranyl, or

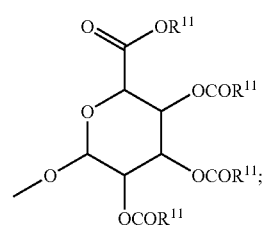

each R⁹ is, independently, —CO₂R⁷, —CON(R⁷)₂, —SO₂CH₃, or —C(═O)R⁷;

each R¹⁰ is, independently, —H, —SO₂CH₃, —CO₂R⁷, —C(═O)NR⁷R⁹, —C(═O)R⁷, or —CH₂—(CHOH), —CH₂OH;

each Z is, independently, CHOH, C(═O), —(CH₂)ₙ—, CHNR⁷R¹⁰, C═NR¹⁰, or NR¹⁰;

each R¹¹ is, independently, lower alkyl;

each R¹² is independently, —SO₂CH₃, —CO₂R⁷, —C(═O)NR⁷R⁹, —C(═O)R⁷, or —CH₂—(CHOH), —CH₂OH;

each R¹³ is, independently, hydrogen, R⁷, R¹⁰, —(CH₂)ₘ—NR⁷R¹⁰,

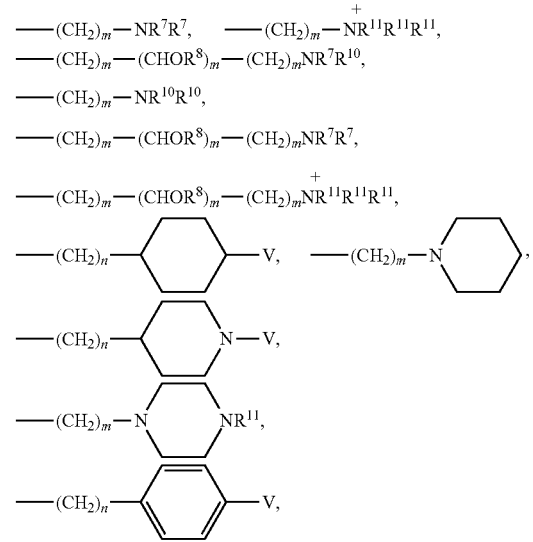

-continued

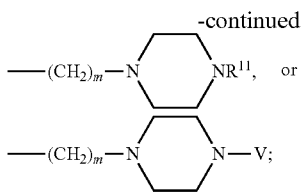

with the proviso that at least one $R^{13}$ must be a group other than hydrogen, $R^7$, or $R^{10}$; with the further proviso that $NR^{13}R^{13}$ can be joined on itself to form a ring comprising one of the following:

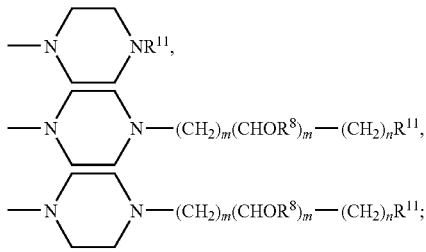

each Het is independently, $NR^7$, $-NR^{10}$, $-S-$, $-SO-$, $-SO_2-$, $-O-$, $-SO_2NH-$, $-NHSO_2-$, $-NR^7CO-$, $-CONR^7-$;

each g is, independently, an integer from 1 to 6;

each m is, independently, an integer from 1 to 7;

each n is, independently, an integer from 0 to 7;

each V is, independently, $-(CH_2)_m-NR^7R^{10}$, $-(CH_2)_m-NR^7R^7$, $-(CH_2)_m$

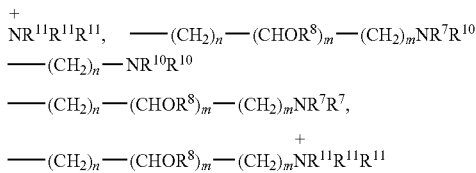

$NR^{11}R^{11}R^{11}{}^{+}$, $-(CH_2)_n-(CHOR^8)_m-(CH_2)_mNR^7R^{10}$, $-(CH_2)_n-NR^{10}R^{10}$ $-(CH_2)_n-(CHOR^8)_m-(CH_2)_mNR^7R^7$, $-(CH_2)_n-(CHOR^8)_m-(CH_2)_mNR^{11}R^{11}R^{11}{}^{+}$ with the proviso that when V is attached directly to a nitrogen atom, then V can also be, independently, $R^7$, $R^{10}$, or $(R^{11})_2$;

wherein for any of the above compounds when two $-CH_2OR^8$ groups are located 1,2- or 1,3- with respect to each other the $R^9$ groups may be joined to form a cyclic mono- or di-substituted 1,3-dioxane or 1,3-dioxolane;

wherein any of the above compounds can be a pharmaceutically acceptable salt thereof, and wherein the above compounds are inclusive of all enantiomers, diastereomers, and racemic mixtures thereof;

(6)

each $R^2$ is, independently, $-R^7$, $-(CH_2)-OR^8$, $-(CH_2)_m-NR^7R^{10}$, $-(CH_2)_n(CHOR^8)(CHOR^8)_n-CH_2OR^8$, $-(CH_2CH_2O)_m-R^8$, $-(CH_2CH_2O)_m-CH_2CH_2NR^7R^{10}$, $-(CH_2)-$, $-C(=O)NR^7R^{10}$, $-(CH_2)_n-Z_g-R^7$, $-(CH_2)_mNR^{10}-CH_2(CHOR^8)(CHOR^8)_n-CH_2OR^8$, $-(CH_2)_n-CO_2R^7$, or

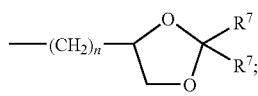

wherein when two $-CH_2OR^8$ groups are located 1,2- or 1,3- with respect to each other the $R^8$ groups may be joined to form a cyclic mono- or di-substituted 1,3-dioxane or 1,3-dioxolane;

$R^3$ and $R^4$ are each, independently, hydrogen, a group represented by formula (A), lower alkyl, hydroxy lower alkyl, phenyl, phenyl-lower alkyl, (halophenyl)-lower alkyl, lower-(alkylphenylalkyl), lower (alkoxyphenyl)-lower alkyl, naphthyl-lower alkyl, or pyridyl-lower alkyl, with the proviso that at least one of $R^3$ and $R^4$ is a group represented by formula (A):

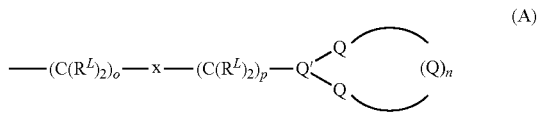

wherein each $R^L$ is, independently, $-R^7$, $-(CH_2)_n-OR^8$, $-O-(CH_2)_m-OR^8$, $-(CH_2)_n-NR^7R^{10}$, $-O-(CH_2)_m-NR^7R^{10}$, $-(CH_2)_n(CHOR^8)(CHOR^8)_n-CH_2OR^8$, $-O-(CH_2)_m(CHOR^8)(CHOR^8)_n-CH_2OR^8$, $-(CH_2CH_2O)_m-R^8$, $-O-(CH_2CH_2O)_m-R^8$, $-(CH_2CH_2O)_m-CH_2CH_2NR^7R^{10}$, $-O-(CH_2CH_2O)_m-CH_2CH_2NR^7R^{10}$, $-(CH_2)$, $-C(=O)NR^7R^{10}$, $-O-(CH_2)_m-C(=O)NR^7R^{10}$, $-(CH_2)_n-(Z)_g-R^7$, $-O-(CH_2)_m-(Z)_g-R^7$, $-(CH_2)_n-NR^{10}-CH_2(CHOR^8)(CHOR^8)_n-CH_2OR^8$, $-O-(CH_2)_m-NR^{10}-CH_2(CHOR^8)(CHOR^8)_n-CH_2OR^8$, $-(CH_2)_n-CO_2R^7$, $-O-(CH_2)_m-CO_2R^7$, $-OSO_3H$, $-O$-glucuronide, $-O$-glucose,

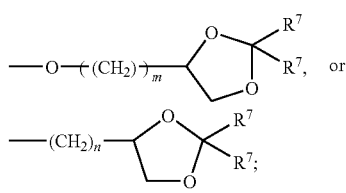

wherein when two $-CH_2OR^8$ groups are located 1,2- or 1,3- with respect to each other the $R^8$ groups may be joined to form a cyclic mono- or di-substituted 1,3-dioxane or 1,3-dioxolane;

each o is, independently, an integer from 0 to 10;

each p is an integer from 0 to 10;

with the proviso that the sum of o and p in each contiguous chain is from 1 to 10;

each x is, independently, O, $NR^{10}$, $C(=O)$, CHOH, $C(=N-R^{10})$, $CHNR^7R^{10}$, or represents a single bond;

each $R^5$ is independently, $-(CH_2)_n-CO_2R^{13}$, Het-$(CH_2)_m-CO_2R^{13}$, $-(CH_2)_n-Z_g-CO_2R^{13}$, Het-$(CH_2)_m-Z_g-CO_2R^{13}$, $-(CH_2)_n-NR^{10}-(CH_2)_m(CHOR^8)_n-CO_2R^{13}$, Het-$(CH_2)_m-NR^{10}-(CH_2)_m(CHOR^8)_n-CO_2R^{13}$, $-(CH_2)_n-(CHOR^8)_n-CO_2R^{13}$, Het-$(CH_2)_m-(CHOR^8)_m-CO_2R^{13}$, $-(CH_2)_n-(CHOR^8)_nZ_g-CO_2R^{13}$, Het-$(CH_2)_n-$ $(CHOR^8)_n$—$Z_g$-$CO_2R^{13}$, —$(CH_2)_n$—$Z_g$—$(CH_2)_m$—$CO_2R^{13}$, —$(CH_2)_n$—$Z_g$—$(CH_2)_m$—$CO_2R^{13}$, —$(CH_2)_n$—$Z_g$$(CHOR^8)_n$—$Z_g$—$CO_2R^{13}$, Het-$(CH_2)_n$—$Z_g$—$(CHOR^8)_m$—$Z_g$—$CO_2R^{13}$, —$(CH_2)_n$—CONH—C($=NR^{13}$)—$NR^{13}R^{13}$, Het-$(CH_2)_n$—CO—NH—C($=NR^{13}$)—$NR^{13}R^{13}$, —$(CH_2)_n$—$Z_g$—CONH—C($=NR^{13}$)—$NR^{13}R^{13}$, Het-$(CH_2)_n$—$Z_g$—CONH—C($=NR^{13}$)—$NR^{13}R^{13}$, —$(CH_2)_n$—$NR^{10}$—$(CH_2)_m(CHOR^8)_n$—CONH—C($=NR^{13}$)—$NR^{13}R^{13}$, Het-$(CH_2)_n$—$NR^{10}$—$(CH_2)_m(CHOR^8)_n$—CONH—C($=NR^{13}$)—$NR^{13}R^{13}$, —$(CH_2)_n$—$(CHOR^8)_n$—CONH—C($=NR^{13}$)—$NR^{13}R^{13}$, Het-$(CH_2)_n$—$(CHOR^8)_m$—CONH—C($=NR^{13}$)—$NR^{13}R^{13}$, —$(CH_2)_n$—$(CHOR^8)_n$—$Z_g$—CONH—C($=NR^{13}$)—$NR^{13}R^{13}$, Het-$(CH_2)_n$—$(CHOR^8)_m$—$Z_g$—CONH—C($=NR^{13}$)—$NR^{13}R^{13}$, —$(CH_2)_n$—$Z_g$—$(CH_2)_m$CONH—C($=NR^{13}$)—$NR^{13}R^{13}$, Het-$(CH_2)_n$—$Z_g$—$(CH_2)_m$CONH—C($=NR^{13}$)—$NR^{13}R^{13}$, —$(CH_2)_n$—$Z_g$—$(CHOR^8)_m$—$Z_g$-CONH—C($=NR^{13}$)—$NR^{13}R^{13}$, Het-$(CH_2)_n$—$Z_g$-$(CHOR^8)_m$—$Z_g$—CONH—C($=NR^{13}$)—$NR^{13}R^{13}$, —$(CH_2)_n$—$CONR^7$—$CONR^{13}R^{13}$, Het-$(CH_2)$,—$CONR^7$—$CONR^{13}R^{13}$, —$(CH_2)_n$—$Z_g$—$CONR^7$—$CONR^{13}R^{13}$, —$(CH_2)_n$—$Z_g$—$CONR^7$—$CONR^{13}R^{13}$, —$(CH_2)_n$—$NR^{10}$—$(CH_2)_m(CHOR^8)_n$—$CONR^7$—$CONR^{13}R^{13}$, Het-$(CH_2)_n$—$NR^{10}$—$(CH_2)_m(CHOR^8)_n$—$CONR^7$—$CONR^{13}R^{13}$, —$(CH_2)_n$—$(CHOR^8)_m$—$CONR^7$—$CONR^{13}R^{13}$, Het-$(CH_2)_n$—$(CHOR^8)$—$CONR^7$—$CONR^{13}R^{13}$, —$(CH_2)_n$—$(CHOR^8)_n$—$Z_g$—$CONR^7$—$CONR^{13}R^{13}$, Het-$(CH_2)_n$—$(CHOR^8)_m$—$Z_g$—$CNR^7$—$CNR^{13}R^{13}$, —$(CH_2)_nZ_g$—$(CH_2)_m$$CONR^7$—$CONR^{13}R^{13}$, Het-$(CH_2)_n$—$Z_g$—$(CH_2)_m$$CONR^7$—$CONR^{13}R^{13}$, —$(CH_2)_n$—$Z_g$$(CHOR^8)_m$—$Z_g$—$CONR^7$—$CONR^{13}R^{13}$, Het-$(CH_2)_n$—$Z_g$$(CHOR^8)_m$—$Z_g$—$CONR^7$—$CONR^{13}R^{13}$, —$(CH_2)$—$CONR^7SO_2NR^{13}R^{13}$, Het-$(CH_2)_m$—$CONR^7SO_2NR^{13}R^{13}$, —$(CH_2)_n$—$Z_g$—$CONR^7SO_2NR^{13}R^{13}$, Het-$(CH_2)_m$—$Z_g$—$CONR^7SO_2NR^{13}R^{13}$, —$(CH_2)_n$—$NR^{10}$—$(CH_2)_m(CHOR^8)_n$—$CONR^7SO_2NR^{13}R^{13}$, Het-$(CH_2)_m$—$NR^{10}$—$(CH_2)_m(CHOR^8)_n$—$CONR^7SO_2NR^{13}R^{13}$, —$(CH_2)_n$—$(CHOR^8)_m$—$CONR^7SO_2NR^{13}R^{13}$, Het-$(CH_2)_m$—$(CHOR^8)_m$—$CONR^7SO_2NR^{13}R^{13}$—$(CH_2)_n$—$(CHOR^8)_m$—$Z_g$—$CONR^7SO_2NR^{13}R^{13}$, Het-$(CH_2)_n$—$(CHOR^8)_m$—$Z_g$—$CONR^7SO_2NR^{13}R^{13}$, —$(CH_2)_n$—$Z_g$—$(CH_2)_m$$CONR^7SO_2NR^{13}R^{13}$, Het-$(CH_2)_n$—$Z_g$—$(CH_2)_m$$CONR^7SO_2NR^{13}R^{13}$, —$(CH_2)_n$—$Z_g$—$(CHOR^8)_m$—$Z_g$—$CONR^7SO_2NR^{13}R^{13}$, Het-$(CH_2)_n$—$Z_g$—$(CHOR^8)_m$—$Z_g$—$CONR^7SO_2NR^{13}R^{13}$, —$(CH_2)_n$—$SO_2NR^{13}R^{13}$, Het-$(CH_2)_m$—$SO_2NR^{13}R^{13}$, —$(CH_2)_n$—$Z_g$—$SO_2NR^{13}R^{13}$, Het-$(CH_2)_m$—$Z_g$—$SO_2NR^{13}R^{13}$, —$(CH_2)_n$—$NR^{10}$—$(CH_2)_m(CHOR^8)_n$—$SO_2NR^{13}R^{13}$, Het-$(CH_2)_m$—$NR^{10}$—$(CH_2)_m(CHOR^8)_n$—$SO_2NR^{13}R^{13}$—$(CH_2)_n$—$(CHOR^8)_m$—$SO_2NR^{13}R^{13}$, Het-$(CH_2)_m$—$(CHOR^8)_m$—$SO_2NR^{13}R^{13}$—$(CH_2)_n$—$(CHOR^8)_m$—$Z_g$—$SO_2NR^{13}R^{13}$, Het-$(CH_2)_n$—$(CHOR^8)_m$—$Z_g$-$SO_2NR^{13}R^{13}$, —$(CH_2)_n$—$Z_g$—$(CH_2)_m$$SO_2NR^{13}R^{13}$, Het-$(CH_2)_n$—$Z_g$—$(CH_2)_m$$SO_2NR^{13}R^{13}$, —$(CH_2)_n$—$Z_g$—$(CHOR^8)_m$—$Z_g$—$SO_2NR^{13}R^{13}$, Het-$(CH_2)_n$—$Z_g$—$(CHOR^8)_m$—$Z_g$—$SO_2NR^{13}R^{13}$, Het-$(CH_2)_n$—$CONR^{13}R^{13}$, Het-$(CH_2)_n$—$CONR^{13}R^{13}$, —$(CH_2)_m$—$Z_g$—$CONR^{13}R^{13}$, —$(CH_2)_n$—$NR^{10}$—$(CH_2)_m$ $(CHOR^8)_n$—$CONR^{13}R^{13}$, Het-$(CH_2)_m$—$NR^{10}$—$(CH_2)_m(CHOR^8)_n$—$CONR^{13}R^{13}$, —$(CH_2)_n$—$(CHOR^8)_m$—$CONR^{13}R^{13}$, Het-$(CH_2)_m$—$(CHOR^8)_m$—$CONR^{13}R^{13}$, —$(CH_2)_n$—$(CHOR^8)_m$—$Z_g$—$CONR^{13}R^{13}$, Het-$(CH_2)_n$—$(CHOR^8)_m$-$Z_g$—$CONR^{13}R^{13}$, —$(CH_2)_n$—$Z_g$—$(CH_2)_m$$CONR^{13}R^{13}$, Het-$(CH_2)_n$—$Z_g$—$(CH_2)_m$$CONR^{13}R^{13}$, —$(CH_2)_n$—$Z_g$—$(CHOR^8)_m$—$Z_g$—$CONR^{13}R^{13}$, Het-$(CH_2)_n$—$Z_g$—$(CHOR^8)_m$—$Z_g$—$CONR^{13}R^{13}$, —$(CH_2)_n$—$CONR^7COR^{13}$, Het-$(CH_2)_m$—$CONR^7COR^{13}$, —$(CH_2)_n$—$Z_g$—$CONR^7COR^{13}$, Het-$(CH_2)_m$—$Z_g$—$CONR^7COR^{13}$, —$(CH_2)_n$—$NR^{10}$—$(CH_2)_m(CHOR^8)_n$—$CONR^7COR^{13}$, Het-$(CH_2)_m$—$NR^{10}$—$(CH_2)_m(CHOR^8)_m$—$CONR^7COR^{13}$, —$(CH_2)_n$—$(CHOR^8)_m$—$CONR^7COR^{13}$, Het-$(CH_2)_n$—$(CHOR^8)_m$—$CONR^7COR^{13}$, —$(CH_2)_n$—$(CHOR^8)_m$—$Z_g$—$CONR^7COR^{13}$, Het-$(CH_2)_n$—$(CHOR^8)_m$—$Z_g$—$CONR^7COR^{13}$, —$(CH_2)_n$—$Z_g$—$(CH_2)_m$ $CONR^7COR^{13}$, —$(CH_2)_n$—$Z_g$—$(CH_2)_m$$CONR^7COR^{13}$, Het-$(CH_2)_n$—$Z_g$—$(CHOR^8)_m$—$Z_g$—$CONR^7COR^{13}$, —$(CH_2)_n$—$CONR^7CO_2R^{13}$, —$(CH_2)_n$—$Z_g$—$CONR^7CO_2R^{13}$, Het-$(CH_2)_m$—$Z_g$—$CONR^7CO_2R^{13}$, —$(CH_2)$—$NR^{10}$—$(CH_2)_m$ $(CHOR^8)_m$—$CONR^7CO_2R^{13}$, Het-$(CH_2)_n$—$NR^{10}$—$(CH_2)_m(CHOR^8)_n$—CO $NR^7CO_2R^{13}$, —$(CH_2)_n$—$(CHOR^8)_m$—$CONR^7CO_2R^{13}$, Het-$(CH_2)_m$—$(CHOR^8)_m$—$CONR^7CO_2R^{13}$, —$(CH_2)_n$—$(CHOR^8)_m$—$Z_g$—$CONR^7CO_2R^{13}$, Het-$(CH_2)_n$—$(CHOR^8)_m$—$Z_g$—$CONR^7CO_2R^{13}$, —$(CH_2)_n$—$Z_g$—$(CH_2)_m$ $CONR^7CO_2R^{13}$, Het-$(CH_2)_n$—$Z_g$—$(CH_2)_m$ $CONR^7CO_2R^{13}$, —$(CH_2)_n$—$Z_g$—$(CHOR^8)_m$—$Z_g$—$CONR^7CO_2R^{13}$, Het-$(CH_2)_n$—$Z_g$—$(CHOR^8)_m$—$Z_g$—$CONR^7CO_2R^{13}$, —$(CH_2)_n$—NH—C($=NR^{13}$)—$NR^{13}R^{13}$, Het-$(CH_2)_m$—NH—C($=NR^{13}$)—$NR^{13}R^{13}$, —$(CH_2)_n$—$Z_g$—NH—C($=NR^{13}$)—$NR^{13}R^{13}$, Het-$(CH_2)_m$—$Z_g$—NH—C($=NR^{13}$)—$NR^{13}R^{13}$, —$(CH_2)_n$—$NR^{11}$—$(CH_2)_m(CHOR^8)_n$—NH—C($=NR^{13}$)—$NR^{13}R^{13}$, Het-$(CH_2)_n$—$NR^{10}$—$(CH_2)_m(CHOR^8)_n$—NH—C($=NR^{13}$)—$NR^{13}R^{13}$, —$(CH_2)_n$—$(CHOR^8)_m$—NH—C($=NR^{13}$)—$NR^{11}R^{13}$, Het-$(CH_2)_m$—$(CHOR^8)$—NH—C($=NR^{13}$)—$NR^{13}R^{13}$, —$(CH_2)_n$—$(CHOR^8)_m$-NH—C($=NR^{13}$)—$NR^{13}R^{13}$, Het-$(CH_2)_n$—$(CHOR^8)_m$—$Z_g$-NH—C($=NR^{13}$)—$NR^{13}R^{13}$, —$(CH_2)_n$—$Z_g$—$(CH_2)_m$NH—C($=NR^{13}$)—$NR^{13}R^{13}$, Het-$(CH_2)_n$—$Z_g$—$(CH_2)_n$NH—C($=NR^{13}$)—$NR^{13}$, —$(CH_2)_n$—$Z_g$—$(CHOR^8)_m$—$Z_g$—NH—C($=NR^{13}$)—$NR^{13}R^{13}$Het-$(CH_2)_n$—$Z_g$—$(CHOR^8)_m$—$Z_g$—NH—C($=NR^{13}$)—$NR^{13}R^{13}$, —$(CH_2)_m$—C($=NH$)—$NR^{13}R^{13}$, Het-$(CH_2)_m$—C($=NH$)—$NR^{13}R^{13}$, —$(CH_2)_n$—$Z_g$—C($=NH$)$_m$—$NR^{13}R^{13}$, Het-$(CH_2)_m$—$Z_g$—C($=NH$)—$NR^{13}R^{13}$, —$(CH_2)_n$—$NR^{10}$—$(CH_2)_m(CHOR^8)_n$—C($=NR^{13}$)—$NR^{13}R^{13}$, Het-$(CH_2)_m$—$NR^{10}$—$(CH_2)_m(CHOR^8)_n$—C($=NR^{13}$)—$NR^{13}R^{13}$, —$(CH_2)_n$—$(CHOR^8)_m$—C($=NR^{13}$)—$NR^{13}R^{13}$, Het-$(CH_2)_m$—$(CHOR^8)_m$—C($=NR^{13}$)—$NR^{13}R^{13}$, —$(CH_2)_n$—$(CHOR^8)_m$—$Z_g$—C($=NR^{13}$)—$NR^{13}R^{13}$, Het-$(CH_2)_n$—$(CHOR^8)_m$—$Z_g$C($=NR^{13}$)—$NR^{13}R^{13}$, —$(CH_2)_n$—$Z_g$—$(CH_2)_m$—C($=NHC(=NR^{13})$—$NR^{13}R^{13}$, Het-$(CH_2)_n$—$Z_g$—$(CH_2)_m$—C($=NR^{13}$)—$NR^{13}R^{13}$, —$(CH_2)_n$—$Z_g$—$(CHOR^8)_m$—$Z_g$—C($=NR^{13}$)—$NR^{13}R^{13}$, Het-$(CH_2)_n$—$Z_g$—$(CHOR^8)_m$—$Z_g$—C($=NR^{13}$)—$NR^{13}R^{13}$;

wherein when two —CH$_2$OR$^8$ groups are located 1,2- or 1,3- with respect to each other the R$^8$ groups may be joined to form a cyclic mono- or di-substituted 1,3-dioxane or 1,3-dioxolane;

each R$^6$ is, independently, —R$^5$, —R$^7$, —OR$^8$, —N(R$^7$)$_2$, —(CH$_2$)$_m$—OR$^8$, —O—(CH$_2$)$_n$—OR$^8$, —(CH$_2$)$_n$—NR$^7$R$^{10}$, —O—(CH$_2$)$_m$—NR$^7$R$^{10}$, —(CH$_2$)$_n$(CHOR$^8$)(CHOR$^8$)$_n$—CH$_2$OR$^8$, —O—(CH$_2$)$_n$(CHOR$^8$)(CHOR$^8$)$_n$—CH$_2$OR$^8$, —(CH$_2$CH$_2$O)$_m$—R$^8$, —O—(CH$_2$CH$_2$O)—R$^8$, —(CH$_2$CH$_2$O)$_m$—CH$_2$CH$_2$NR$^7$R$^{10}$, —O—(CH$_2$CH$_2$O)$_m$—CH$_2$CH$_2$NR$^7$R$^{10}$, —(CH$_2$), —C(=O)NR$^7$R$^{10}$, —O—(CH$_2$), —C(=O)NR$^7$R$^{10}$, —(CH$_2$)$_n$—(Z)$_g$—R$^7$—O—(CH$_2$)$_m$—(Z)$_g$—R$^7$, —(CH$_2$)$_m$—NR$^{10}$—CH$_2$(CHOR$^8$)(CHOR$^8$)$_m$—CH$_2$OR$^8$, —O—(CH$_2$)$_m$—NR$^{10}$—CH$_2$(CHOR$^8$)(CHOR$^8$)$_n$—CH$_2$OR$^8$, —(CH$_2$)$_n$—CO$_2$R$^7$, —O—(CH$_2$)$_m$—CO$_2$R$^7$, —OSO$_3$H, —O-glucuronide, —O-glucose,

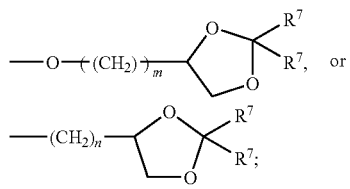

wherein when two R$^6$ are —OR$^{11}$ and are located adjacent to each other on a phenyl ring, the alkyl moieties of the two R$^6$ may be bonded together to form a methylenedioxy group, and wherein when two —CH$_2$OR$^8$ groups are located 1,2- or 1,3- with respect to each other the R$^8$ groups may be joined to form a cyclic mono- or di-substituted 1,3-dioxane or 1,3-dioxolane;

each R$^7$ is, independently, hydrogen lower alkyl, phenyl, or substituted phenyl;

each R$^8$ is, independently, hydrogen, lower alkyl, —C(=O)—R$^{11}$, glucuronide, 2-tetrahydropyranyl, or

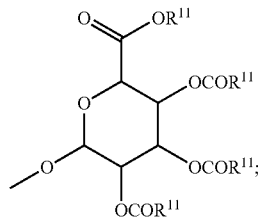

each R$^9$ is, independently, —CO$_2$R$^7$, —CON(R$^7$)$_2$, —SO$_2$CH$_3$, or —C(=O)R$^7$;

each R$^{10}$ is, independently, —H, —SO$_2$CH$_3$, —CO$_2$R$^7$, —C(=O)NR$^7$R$^9$, —C(=O)R$^7$, or —CH$_2$—(CHOH)$_n$—CH$_2$OH;

each Z is, independently, CHOH, C(=O), —(CH$_2$)$_n$—, CHNR$^7$R$^{10}$, C=NR$^{10}$, or NR$^{11}$;

each R$^{11}$ is, independently, lower alkyl;

each R$^{12}$ is independently, —SO$_2$CH$_3$, —CO$_2$R$^7$—C(=O)NR$^7$R$^9$, —C(=O)R$^7$ or —CH$_2$—(CHOH)$_n$—CH$_2$OH;

each R$^{13}$ is, independently, hydrogen, R$^7$, R$^{10}$, —(CH$_2$)$_n$—NR$^7$R$^{10}$,

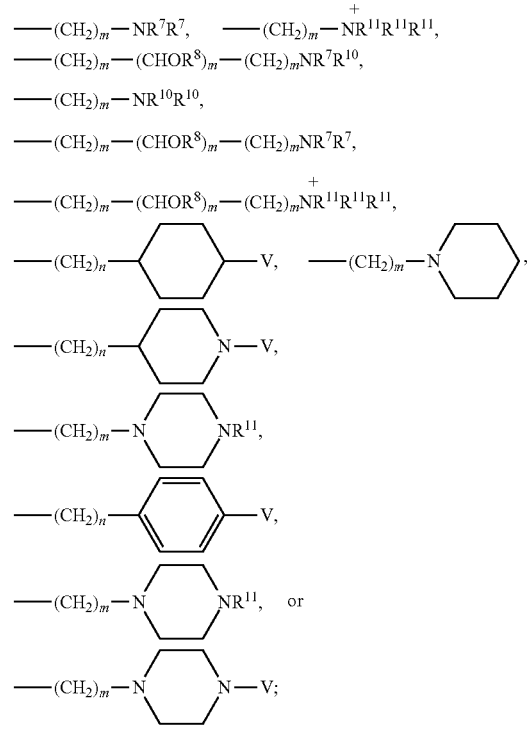

with the proviso that at least one R$^{13}$ must be a group other than hydrogen, R$^7$, or R$^{10}$;

with the further proviso that NR$^{13}$R$^{13}$ can be joined on itself to form a ring comprising one of the following:

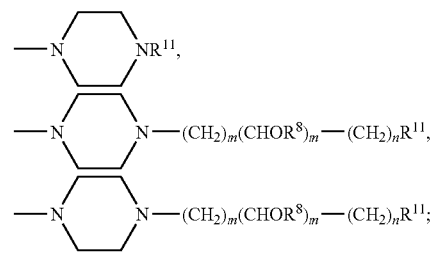

each Het is independently, —NR$^7$, —NR$^{10}$, —S—, —SO—, —SO$_2$—, —O—, —SO$_2$NH—, —NHSO$_2$—, —NR$^7$CO—, or —CONR$^7$—;

each g is, independently, an integer from 1 to 6;

each m is, independently, an integer from 1 to 7;

each n is, independently, an integer from 0 to 7;

each Q' is independently, CR$^6$ or N;

each Q is independently, —C(R$^6$R$^5$)—, —C(R$^6$R$^6$)—, —N(R$^{10}$)—, —N(R$^7$)—, —N(R$^5$)—, —S—, —SO—, or —SO$_2$—, with the proviso that at least one Q is —C(R$^5$R$^6$)— or —N(R$^5$)—, with the proviso that at most three Q in a ring is —N(R$^7$)—, —N(R$^5$)—, —S—, —SO—, or —SO$_2$—;

each V is, independently, —(CH$_2$)$_m$—NR$^7$R$^{10}$, —(CH$_2$)$_m$—NR$^7$R$^7$, —(CH$_2$)$_m$—

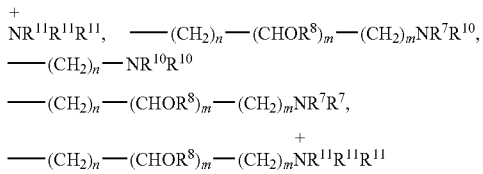

$-NR^{11}R^{11}R^{11}$, $-(CH_2)_n-(CHOR^8)_m-(CH_2)_mNR^7R^{10}$,
$-(CH_2)_n-NR^{10}R^{10}$
$-(CH_2)_n-(CHOR^8)_m-(CH_2)_mNR^7R^7$,
$-(CH_2)_n-(CHOR^8)_m-(CH_2)_mNR^{11}R^{11}R^{11}$ with the proviso that when V is attached directly to a nitrogen atom, then V can also be, independently, $R^7$, $R^{10}$, or $(R^{11})_2$;

wherein for any of the above compounds when two $-CH_2OR^8$ groups are located 1,2- or 1,3- with respect to each other the $R^8$ groups may be joined to form a cyclic mono- or di-substituted 1,3-dioxane or 1,3-dioxolane;

wherein any of the above compounds can be a pharmaceutically acceptable salt thereof, and wherein the above compounds are inclusive of all enantiomers, diastereomers, and racemic mixtures thereof;

(7)
each $R^2$ is, independently, $-R^7$, $-(CH_2)-OR^8$, $-(CH_2)_m-NR^7R^{10}$, $-(CH_2)_n(CHOR^8)(CHOR^8)_n-CH_2OR^8$, $-(CH_2CH_2O)_m-R^8$, $-(CH_2CH_2O)_m-CH_2CH_2NR^7R^{10}$, $-(CH_2)$, $-C(=O)NR^7R^{10}$, $-(CH_2)_n-Z_g-R^7$, $-(CH_2)_m-NR^{10}-CH_2(CHOR^8)(CHOR^8)_n-CH_2OR^8$, $-(CH_2)_n-CO_2R^7$, or

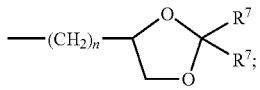

$R^3$ and $R^4$ are each, independently, hydrogen, a group represented by formula (A), lower alkyl, hydroxy lower alkyl, phenyl, phenyl-lower alkyl, (halophenyl)-lower alkyl, lower-(alkylphenylalkyl), lower (alkoxyphenyl)-lower alkyl, naphthyl-lower alkyl, or pyridyl-lower alkyl, with the proviso that at least one of $R^3$ and $R^4$ is a group represented by formula (A):

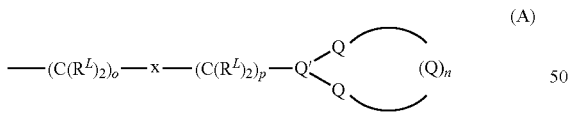
(A)

wherein
each $R^L$ is, independently, $-R^7$, $-(CH_2)_n-OR^8$, $-O-(CH_2)_m-OR^8$, $-(CH_2)_n-NR^7R^{10}$, $-(CH_2)_m-NR^7R^{10}$, $-(CH_2)_n(CHOR^8)(CHOR^8)_n-CH_2OR^8$, $-O-(CH_2)_m(CHOR^8)(CHOR^8)_n-CH_2OR^8$, $-(CH_2CH_2O)_m-R^8$, $-O-(CH_2CH_2O)_m-R^8$, $-(CH_2CH_2O)_m-CH_2CH_2NR^7R^{10}$, $-O-(CH_2CH_2O)_n-CH_2CH_2NR^7R^{10}$, $-(CH_2)$, $-C(=O)NR^7R^{10}$, $-O-(CH_2)_m-C(=O)NR^7R^{10}$, $-(CH_2)_n-(Z)_g-R^7$, $-O-(CH_2)_m-(Z)_g-R^7$, $-(CH_2)_n-NR^{10}-CH_2(CHOR^8)(CHOR^8)_n-CH_2OR^8$, $-(CH_2)_m-NR^{10}-CH_2(CHOR^8)(CHOR^8)_n-CH_2OR^8$, $-(CH_2)_n-CO_2R^7$, $-O-(CH_2)_m-CO_2R^7$, $-OSO_3H$, $-O$-glucuronide, $-O$-glucose,

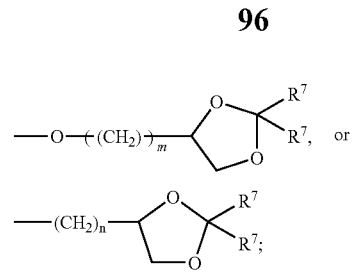

each o is, independently, an integer from 0 to 10;

each p is an integer from 0 to 10;

with the proviso that the sum of o and p in each contiguous chain is from 1 to 10;

each x is, independently, O, $NR^{11}$, $C(=O)$, CHOH, $C(=N-R^{10})$, $CHNR^7R^{10}$, or represents a single bond;

each $R^5$ is, independently, $-O-(CH_2)_m-OR^8$, $-(CH_2)_n-NR^7R^{10}$, $-O-(CH_2)_n-NR^7R^{10}$, $-(CH_2)_n(CHOR^8)(CHOR^8)_n-CH_2OR^8$, $-O-(CH_2)_m(CHOR^8)(CHOR^8)_n-CH_2OR^8$, $-(CH_2CH_2O)_m-R^8$, $-O-(CH_2CH_2O)_m-R^8$, $-(CH_2CH_2O)_m-CH_2CH_2NR^7R^{10}$, $-O-(CH_2CH_2O)_m-CH_2CH_2NR^7R^{10}$, $-(CH_2)_n-C(=O)NR^7R^{10}$, $-O-(CH_2)_m-C(=O)NR^7R^{10}$, $-(CH_2)_n-(Z)_g-R^7$, $-O-(CH_2)_m-(Z)_g-R^7$, $-(CH_2)_n-NR^{10}-CH_2(CHOR^8)(CHOR^8)_n-CH_2OR^8$, $-O-(CH_2)_m-NR^{10}-CH_2(CHOR^8)(CHOR^8)_n-CH_2OR^8$, $-(CH_2)_n-CO_2R^7$, $-O-(CH_2)_n-CO_2R^7$, $-OSO_3H$, $-O$-glucuronide, $-O$-glucose,

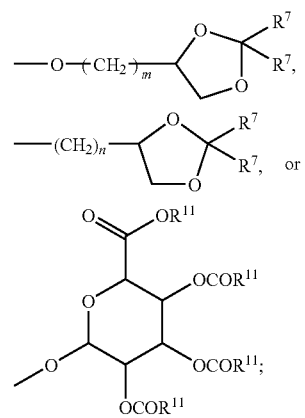

each $R^5$ may also be, independently, $-(CH_2)_n-NR^{12}R^{12}$, $-O-(CH_2)-NR^{12}R^{12}$, $-O-(CH_2)-NR^{12}R^{12}$, $-O-(CH_2)_m-(Z)_gR^{12}$, $-(CH_2)_nNR^{11}$, $-O-(CH_2)_m$ $NR^{11}R^{11}$, $-(CH_2)_n-N^6-(R^{11})_3$, $-O-(CH_2)_m-N^6-(R^{11})_3$, $-(CH_2)_n-(Z)_g-(CH_2)_m-NR^{10}R^{10}$, $-O-(CH_2)_m-(Z)_g-(CH_2)_m-NR^{10}R^{10}$, $-(CH_2CH_2O)_m-CH_2CH_2NR^{12}R^{12}$, $-O-(CH_2CH_2O)_m-CH_2CH_2NR^{12}R^{12}$, $-(CH_2)_n-(C=O)NR^{12}R^{12}$, $-O-(CH_2)_m-(C=O)NR^{12}R^{12}$, $-O-(CH_2)_m-(CHOR^8)_mCH_2NR^{10}-(Z)_g-R^{10}$, $-(CH_2)_n-(CHOR^8)_nCH_2-NR^{10}-(Z)_g-R^{10}$, $-(CH_2)_n-NR^{10}-O(CH_2)_m(CHOR^8)_nCH_2NR^{10}-(Z)_g-R^{10}$, $-O(CH_2)_m-NR^{10}-(CH_2)_m-(CHOR^8)_n$ $CH_2NR^{10}-(Z)_g-R^{10}$, -(Het)-$(CH_2)_m-OR^8$, -(Het)-

$-(CH_2)_m-NR^7R^{10}$, $-(Het)-(CH_2)_m(CHOR^8)(CHOR^8)_n-CH_2OR^8$, $-(Het)-(CH_2CH_2O)_m-R^8$, $-(Het)-(CH_2CH_2O)_m-CH_2CH_2NR^7R^{10}$, $-(Het)-(CH_2)_m-C(=O)NR^7R^{10}$, $-(Het)-(CH_2)_m-(Z)_g-R^7$, $-(Het)-(CH_2)_m-NR^{10}-CH_2(CHOR^8)(CHOR^8)_n-CH_2OR^8$, $-(Het)-(CH_2)_m-CO_2R^7$, $-(Het)-(CH_2)_m-NR^{12}R^{12}$, $-(Het)-(CH_2)_n-NR^{12}R^{12}$, $-(Het)-(CH_2)_m-(Z)_gR^{12}$, $-(Het)-(CH_2)_mNR^{11}R^{11}$, $-(Het)-(CH_2)_m-N^{\oplus}-(R^{11})_3$, $-(Het)-(CH_2)_m-(Z)_g-(CH_2)_m-NR^{10}R^{10}$, $-(Het)-(CH_2CH_2O)_m-CH_2CH_2NR^{12}R^{12}$, $-(Het)-(CH_2)_m-(C=O)NR^{12}R^{12}$, $-(Het)-(CH_2)_n-(CHOR^8)_m CH_2NR^{10}-(Z)_g-R^{10}$, $-(Het)-(CH_2)_m-NR^{10}-(CH_2)_m-(CHOR^8)_nCH_2NR^{10}-(Z)_g-R^{10}$, wherein when two $-CH_2OR^8$ groups are located 1,2- or 1,3- with respect to each other the $R^8$ groups may be joined to form a cyclic mono- or di-substituted 1,3-dioxane or 1,3-dioxolane, $-(CH_2)_n(CHOR^8)(CHOR^8)_n-CH_2OR^8$, with the proviso that at least two $-CH_2OR^8$ are located adjacent to each other and the $R^8$ groups are joined to form a cyclic mono- or di-substituted 1,3-dioxane or 1,3-dioxolane, $-O-(CH_2)_m(CHOR^8)(CHOR^8)_n-CH_2OR^8$, with the proviso that at least two $-CH_2OR^8$ are located adjacent to each other and the $R^5$ groups are joined to form a cyclic mono- or di-substituted 1,3-dioxane or 1,3-dioxolane, $-(CH_2)_n-NR^{10}-CH_2(CHOR^8)(CHOR^8)_n-CH_2OR^8$, with the proviso that at least two $-CH_2OR^8$ are located adjacent to each other and the $R^8$ groups are joined to form a cyclic mono- or di-substituted 1,3-dioxane or 1,3-dioxolane, or $-O-(CH_2)_m-NR^{10}-CH_2(CHOR^8)(CHOR^8)_n-CH_2OR^8$, with the proviso that at least two $-CH_2OR^8$ are located adjacent to each other and the $R^8$ groups are joined to form a cyclic mono- or di-substituted 1,3-dioxane or 1,3-dioxolane;

each $R^5$ may also be, independently, Link-$(CH_2)$, -CAP, Link-$(CH_2)_n(CHOR^8)(CHOR^8)_n$-CAP, Link-$(CH_2CH_2O)_m-CH_2$-CAP, Link-$(CH_2CH_2O)_m-CH_2CH_2$-CAP, Link-$(CH_2)_n-(Z)_g$-CAP, Link-$(CH_2)_n$ $(Z)_g-(CH_2)_m$-CAP, Link-$(CH_2)_n-NR^{13}-CH_2(CHOR^8)(CHOR^8)_n$-CAP, Link-$(CH_2)_n-(CHOR^8)_n$ $CH_2-NR^{13}-(Z)_g$-CAP, Link-$(CH_2)_n$ $NR^{13}-(CH_2)_m$ $(CHOR^8)_nCH_2NR^{13}-(Z)_g$-CAP, Link-$(CH_2)_m-(Z)_g-(CH_2)_m$-CAP, Link-NH-C(=O)-NH-$(CH_2)_m$- CAP, Link-$(CH_2)_m-C(=O)NR^{13}(CH_2)_m-C(=O)NR^{10}R^{10}$, Link-$(CH_2)_m-C(=O)NR^{13}-(CH_2)$, CAP, Link-$(CH_2)_m-C(=O)NR^{11}R^{11}$, Link-$(CH_2)_m-C(=O)NR^{12}R^{12}$, Link-$(CH_2)_n$ $-(Z)_g-(CH_2)_m-(Z)_g$-CAP, or Link-$Z_g-(CH_2)_m$-Het-$(CH_2)_m$-CAP;

each Link is, independently, $-O-$, $-(CH_2)_n-$, $-O(CH_2)_m-$, $-NR^{13}-C(=O)-NR^{13}$, $-NR^{13}-C(=O)-(CH_2)_m-$, $-C(=O)NR^{13}(CH_2)_m$, $-(CH_2)_n$ $-Z_g-(CH_2)_n$, $-S-$, $-SO-$, $-SO_2-$, $-SO_2NR^7-$, $-SO_2NR^{10}-$, or -Het-;

each CAP is, independently, thiazolidinedione, oxazolidinedione, heteroaryl-C(=O)N$R^{13}R^{13}$, heteroaryl-W, $-CN$, $-O-C(=S)NR^{13}R^{13}$, $-Z_gR^{13}$, $-CR^{10}(Z_gR^{13})(Z_gR^{13})$, $-C(=O)OAr$, $-C(=O)NR^{13}Ar$, imidazoline, tetrazole, tetrazole amide, $-SO_2NHR^{13}$, $-SO_2NH-C(R^{13}R^{13})-(Z)_g-R^{13}$, a cyclic sugar or oligosaccharide, a cyclic amino sugar or oligosaccharide,

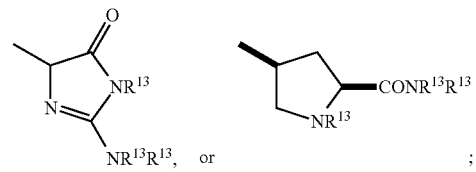

each Ar is, independently, phenyl, substituted phenyl, wherein the substituents of the substituted phenyl are 1-3 substituents independently selected from the group consisting of OH, OCH$_3$, NR$^{13}$R$^{13}$, Cl, F, and CH$_3$, or heteroaryl;

each W is independently, thiazolidinedione, oxazolidinedione, heteroaryl-C(=O)NR$^{13}$R$^{13}$, $-CN$, $-O-C(=S)NR^{13}R^{13}$, $-Z_gR^{13}$, $-CR^{10}(Z_gR^{13})(Z_gR^{13})$, $-C(=O)OAr$, $-C(=O)NR^{13}Ar$, imidazoline, tetrazole, tetrazole amide, $-SO_2NHR^{13}$, $-SO_2NH-C(R^{13}R^{13})-(Z)_g-R^{13}$, a cyclic sugar or oligosaccharide, a cyclic amino sugar or oligosaccharide,

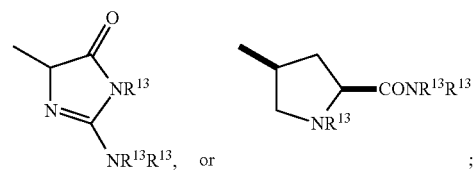

each $R^6$ is, independently, $-R^5$, $-R^7$, $-OR^8$, $-N(R^7)_2$, $-(CH_2)_m-OR^8$, $-O-(CH_2)_m-OR^8$, $-(CH_2)_n-NR^7R^{10}$, $-O-(CH_2)_n-NR^7R^{10}$, $-(CH_2)_n(CHOR^8)(CHOR^8)_n-CH_2OR^8$, $-O-(CH_2)_m(CHOR^8)(CHOR^8)_n-CH_2OR^8$, $-(CH_2CH_2O)_m-R^8$, $-O-(CH_2CH_2O)_m-R^8$, $-(CH_2CH_2O)_m-CH_2CH_2NR^7R^{10}$, $-O-(CH_2CH_2O)_m-CH_2CH_2NR^7R^{10}$, $-(CH_2)$, $-C(=O)NR^7R^{10}$, $-O-(CH_2)_m-C(=O)NR^7R^{10}$, $-(CH_2)_n-(Z)_g-R^7$, $-O-(CH_2)_m-(Z)_g-R^7$, $-(CH_2)_n-NR^{10}-CH_2(CHOR^8)(CHOR^8)_n-CH_2OR^8$, $-O-(CH_2)_m-NR^{10}-CH_2(CHOR^8)(CHOR^8)_n-CH_2OR^8$, $-(CH_2)_n-CO_2R^7$, $-O-(CH_2)_m-CO_2R^7$, $-OSO_3H$, $-O$-glucuronide, $-O$-glucose,

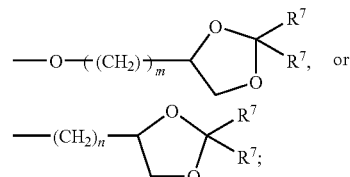

wherein when two $-CH_2OR^8$ groups are located 1,2- or 1,3- with respect to each other the $R^8$ groups may be joined to form a cyclic mono- or di-substituted 1,3-dioxane or 1,3-dioxolane;

each $R^7$ is, independently, hydrogen lower alkyl, phenyl, or substituted phenyl;

each $R^8$ is, independently, hydrogen, lower alkyl, $-C(=O)-R^{11}$, glucuronide, 2-tetrahydropyranyl, or

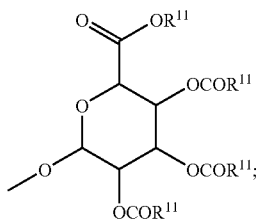

each R⁹ is, independently, —CO₂R¹³, —CON(R¹³)₂, —SO₂CH₂R¹³, or —C(=O)R¹³;

each R¹⁰ is, independently, —H, —SO₂CH₃, —CO₂R⁷, —C(=O)NR⁷R⁹, —C(=O)R⁷, or —CH₂—(CHOH)ₙ—CH₂OH;

each Z is, independently, CHOH, C(=O), —(CH₂)ₙ—, CHNR¹³R¹³, C=NR¹³, or NR¹³;

each R¹¹ is, independently, lower alkyl;

each R¹² is independently, —SO₂CH₃, —CO₂R¹³, —C(=O)N³R¹³, —C(=O)R¹³, or CH₂—(CHOH)ₙ—CH₂OH;

each R¹³ is, independently, hydrogen, R⁷, R¹⁰, —(CH₂)ₘ—NR⁷R¹⁰,

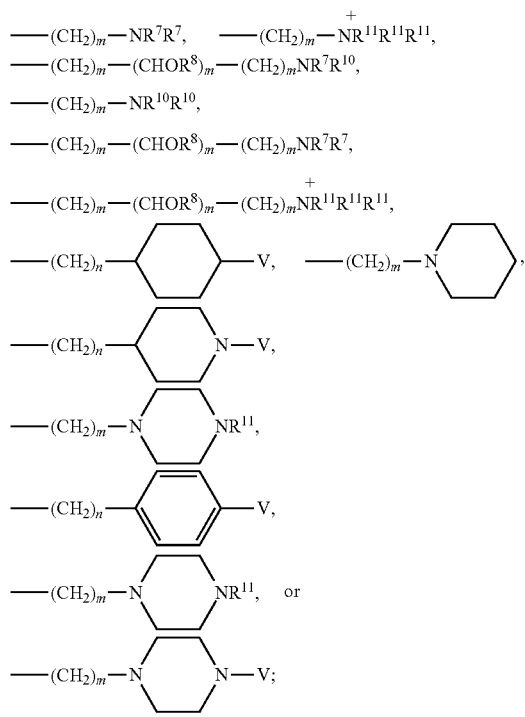

with the proviso that NR¹³R¹³ can be joined on itself to form a ring comprising one of the following:

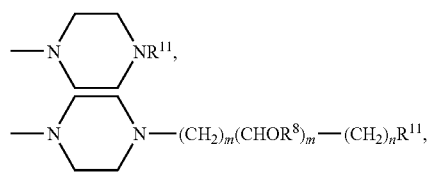

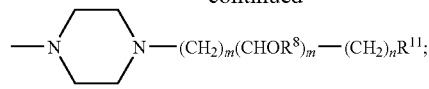

each Het is independently, —NR¹³, —S—, —SO—, —SO₂—, —O—, —SO₂NR¹³—, —NHSO₂—, NR¹³CO—, or —CONR¹³—;

each g is, independently, an integer from 1 to 6;
each m is, independently, an integer from 1 to 7;
each n is, independently, an integer from 0 to 7;
each Q' is independently, CR⁶ or N;
each Q is independently, —C(R⁶R⁵)—, —C(R⁶R⁶)—, —N(R¹⁰)—, —N(R⁷)—, —N(R⁵)—, —S—, —SO—, or —SO₂—,
with the proviso that at least one Q is —C(R⁵R⁶)— or —N(R⁵)—,
with the proviso that at most three Q in a ring is —N(R⁷)—, —N(R⁵)—, —S—, —SO—, or —SO₂—;
each V is, independently, —(CH₂)ₘ—NR⁷R¹⁰, —(CH₂)ₘ—NR⁷R⁷, —(CH₂)ₘ

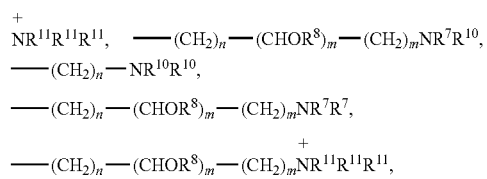

with the proviso that when V is attached directly to a nitrogen atom, then V can also be, independently, R⁷, R¹⁰, or (R¹¹)₂;

with the proviso that, when any two —CH₂OR⁸ groups are located 1,2- or 1,3- with respect to each other, the R⁸ groups may be joined to form a cyclic mono- or di-substituted 1,3-dioxane or 1,3-dioxolane;

or a pharmaceutically acceptable salt thereof, and inclusive of all enantiomers, diastereomers, and racemic mixtures thereof;

(8)
each R² is, independently, —R⁷, —(CH₂)ₘ—OR⁸, —(CH₂)ₘ—NR⁷R¹⁰, —(CH₂)ₙ(CHOR⁸)(CHOR⁸)ₙ—CH₂OR⁸, —(CH₂CH₂O)ₘ—R⁸, —(CH₂CH₂O)ₘ—CH₂CH₂NR⁷R¹⁰, —(CH₂), —C(=O)NR⁷R¹⁰, —(CH₂)ₙ—Zg—R⁷, —(CH₂)ₘ—NR¹⁰—CH₂(CHOR⁸)(CHOR⁸)ₙ—CH₂OR⁸, —(CH₂)ₙ—CO₂R⁷, or

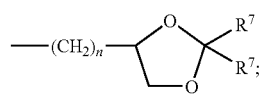

R³ and R⁴ are each, independently, hydrogen, a group represented by formula (A), lower alkyl, hydroxy lower alkyl, phenyl, phenyl-lower alkyl, (halophenyl)-lower alkyl, lower-(alkylphenylalkyl), lower (alkoxyphenyl)-lower alkyl, naphthyl-lower alkyl, or pyridyl-lower alkyl, with the proviso that at least one of R³ and R⁴ is a group represented by formula (A):

—(C(Rᴸ)₂)ₒ-x-(C(Rᴸ)₂)ₚ—CR⁵R⁶R⁶        (A)

each Rᴸ is, independently, —R⁷, —(CH₂)ₙ—OR⁸, —O—(CH₂)ₘ—OR⁸, —(CH₂)ₙ—NR⁷R¹⁰, —O—(CH₂)ₘ—NR⁷R¹⁰, —(CH₂)ₙ(CHOR⁸)(CHOR⁸)ₙ—CH₂OR⁸, —O—(CH$_2$)$_m$(CHOR$^8$)(CHOR$^8$)$_n$—CH$_2$OR$^8$, —(CH$_2$CH$_2$O)$_m$—R$^8$, —O—(CH$_2$CH$_2$O)$_m$—R$^8$, —(CH$_2$CH$_2$O)$_m$, —CH$_2$CH$_2$NR$^7$R$^{10}$, —O—(CH$_2$CH$_2$O)$_m$—CH$_2$CH$_2$NR$^7$R$^{10}$, —(CH$_2$)$_n$—C(=O)NR$^7$R$^{10}$, —O(CH$_2$)$_m$—C(=O)NR$^7$R$^{10}$, —(CH$_2$)$_n$-Z$_g$—R$^7$, O—(CH$_2$)$_m$—(Z)$_g$—R$^7$—(CH$_2$)$_n$—NR$^{10}$—CH$_2$(CHOR$^8$)(CHOR$^8$)$_n$—CH$_2$OR$^8$, —O—(CH$_2$)$_m$—NR$^{10}$—CH$_2$(CHOR$^8$)(CHOR$^8$)$_n$—CH$_2$OR$^8$, —(CH$_2$)—CO$_2$R$^7$, —O—(CH$_2$)$_m$—CO$_2$R$^7$—OSO$_3$H, —O-glucuronide, —O-glucose,

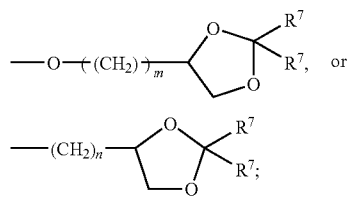

each o is, independently, an integer from 0 to 17;

each p is an integer from 0 to 17;

with the proviso that the sum of o and p in each contiguous chain is from 1 to 17;

each x is, independently, O, NR$^{10}$, C(=O), CHOH, C(=N—R$^{10}$), CHNR$^7$R$^{10}$, or represents a single bond, with the proviso that when x is a single bond the sum of o and p is from 7 to 17;

each R$^5$ is, independently, —O—(CH$_2$)$_m$—OR$^8$, —(CH$_2$)$_n$—NR$^7$R$^{10}$, —O(CH$_2$)$_m$—NR$^7$R$^{10}$, —(CH$_2$)$_n$(CHOR$^8$)(CHOR$^8$)$_n$—CH$_2$OR$^8$, O—(CH$_2$)$_m$(CHOR$^8$)(CHOR$^8$)$_n$—CH$_2$OR$^8$, —(C$_2$H$_2$O)$_m$—R$^8$, —O—(CH$_2$CH$_2$O)$_m$—R$^8$, —(CH$_2$CH$_2$O)$_m$—CH$_2$CH$_2$NR$^7$R$^{10}$, —O—(CH$_2$CH$_2$O)$_m$—CH$_2$CH$_2$NR$^7$R$^{10}$, —(CH$_2$)$_n$—C(=O)NR$^7$R$^{10}$, —O—(CH$_2$)$_m$—C(=O)NR$^7$R$^{10}$, —(CH$_2$)$_n$—(Z)$_g$—R$^7$, —O—(CH$_2$)$_m$—(Z)$_g$—R$^7$, —(CH$_2$)$_n$—NR$^{10}$—CH$_2$(CHOR$^8$)(CHOR$^8$)$_n$—CH$_2$OR$^8$, —O—(CH$_2$)$_m$—NR$^{10}$—CH$_2$(CHOR$^8$)(CHOR$^8$)$_n$—CH$_2$OR$^8$, —(CH$_2$)$_n$—CO$_2$R$^7$, —O—(CH$_2$)$_m$—CO$_2$R$^7$—OSO$_3$H, —O-glucuronide, —O-glucose,

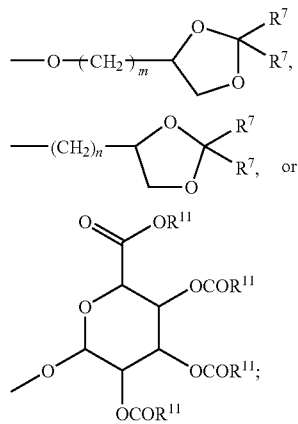

—(CH$_2$)$_n$—NR$^{12}$R$^{12}$, —O—(CH$_2$)$_m$—NR$^{12}$R$^{12}$, —O—(CH$_2$)$_n$—NR$^{12}$R$^{12}$, —O—(CH$_2$)$_m$—(Z)$_g$R$^{12}$, —(CH$_2$)$_n$NR$^{11}$R$^{11}$, —O—(CH$_2$)$_m$NR$^{11}$R$^{11}$, —(CH$_2$)$_n$—N$^\oplus$—(R$^{11}$)$_3$, —O—(CH$_2$)$_m$—N$^\oplus$—(R$^{11}$)$_3$, —(CH$_2$)$_n$—(Z)$_g$—(CH$_2$)$_m$—NR$^{10}$R$^{10}$, —O—(CH$_2$)$_m$—(Z)$_g$—(CH$_2$)$_m$—NR$^{10}$R$^{10}$, —(CH$_2$CH$_2$O)$_m$—CH$_2$CH$_2$NR$^{12}$R$^{12}$, —O—(CH$_2$CH$_2$O)$_m$—CH$_2$CH$_2$NR$^{12}$R$^{12}$, —(CH$_2$)$_n$—(C=O)NR$^{12}$R$^{12}$, —O—(CH$_2$)$_m$—(C=O)NR$^{12}$R$^{12}$, —O—(CH$_2$)$_m$—(CHOR$^8$)$_m$CH$_2$NR$^{10}$—(Z)$_g$—R$^{10}$, —(CH$_2$)$_n$—(CHOR$^8$)$_m$CH$_2$—NR$^{10}$—(Z)$_g$—R$^{10}$, —(CH$_2$)$_n$NR$^{10}$—O—(CH$_2$)$_m$(CHOR$^8$)$_n$CH$_2$NR$^{10}$—(Z)$_g$—R$^{10}$, —O(CH$_2$)$_m$—NR$^{10}$—(CH$_2$)$_m$—(CHOR$^8$)$_n$CH$_2$NR$^{10}$—(Z)$_g$—R$^{10}$, -(Het)-(CH$_2$)$_m$—OR$^8$, -(Het)-(CH$_2$)$_m$—NR$^7$R$^{10}$, -(Het)-(CH$_2$)$_m$(CHOR$^8$)(CHOR$^8$)$_n$—CH$_2$OR$^8$, -(Het)-(CH$_2$CH$_2$O)$_m$—R$^8$, -(Het)-(CH$_2$CH$_2$O)$_m$—CH$_2$CH$_2$NR$^7$R$^{10}$, -(Het)-(CH$_2$)$_m$—C(=O)NR$^7$R$^{10}$, (Het)-(CH$_2$)—(Z)$_g$—R$^7$, -(Het)-(CH$_2$)$_m$—NR$^{10}$—CH$_2$(CHOR$^8$)(CHOR$^8$)$_n$—CH$_2$OR$^8$, -(Het)-(CH$_2$)$_m$—CO$_2$R$^7$, -(Het)-(CH$_2$)$_m$—NR$^{12}$R$^{12}$, -(Het)-(CH$_2$)$_n$—NR$^{12}$R$^{12}$, -(Het)-(CH$_2$)$_m$—(Z)$_g$R$^{12}$, -(Het)-(CH$_2$)$_m$NR$^{11}$R$^{11}$, -(Het)-(CH$_2$)$_m$—N$^\oplus$—(R$^{11}$)$_3$, -(Het)-(CH$_2$)$_m$—(Z)$_g$—(CH$_2$)$_m$—NR$^{10}$R$^{10}$, -(Het)-(CH$_2$CH$_2$O)$_m$—CH$_2$CH$_2$NR$^{12}$R$^{12}$, -(Het)-(CH$_2$)$_m$—(C=O)NR$^{12}$R$^{12}$, -(Het)-(CH$_2$)$_m$—(CHOR$^8$)$_m$CH$_2$NR$^{10}$—(Z)$_g$—R$^{10}$, -(Het)-(CH$_2$)$_m$—NR$^{10}$—(CH$_2$)$_m$—(CHOR$^8$)$_n$CH$_2$NR$^{10}$—(Z)$_g$—R$^{10}$, —(CH$_2$)$_n$(CHOR$^8$)(CHOR$^8$)$_n$—CH$_2$OR$^8$, with the proviso that at least two —CH$_2$OR$^8$ are located adjacent to each other and the R$^8$ groups are joined to form a cyclic mono- or di-substituted 1,3-dioxane or 1,3-dioxolane, —O—(CH$_2$)$_m$(CHOR$^8$)(CHOR$^8$)$_n$—CH$_2$OR$^8$, with the proviso that at least two —CH$_2$OR$^8$ are located adjacent to each other and the R$^8$ groups are joined to form a cyclic mono- or di-substituted 1,3-dioxane or 1,3-dioxolane, —(CH$_2$)$_n$—NR$^{10}$—CH$_2$(CHOR$^8$)(CHOR$^8$)$_n$—CH$_2$OR$^8$, with the proviso that at least two —CH$_2$OR$^8$ are located adjacent to each other and the R$^8$ groups are joined to form a cyclic mono- or di-substituted 1,3-dioxane or 1,3-dioxolane, —O—(CH$_2$)$_m$—NR$^{10}$—CH$_2$(CHOR$^8$)(CHOR$^8$)$_p$—CH$_2$OR$^8$, with the proviso that at least two —CH$_2$OR$^8$ are located adjacent to each other and the R$^8$ groups are joined to form a cyclic mono- or di-substituted 1,3-dioxane or 1,3-dioxolane, Link-(CH$_2$)$_n$-CAP, Link-(CH$_2$)$_n$(CHOR$^8$)(CHOR$^8$)$_n$-CAP, Link-(CH$_2$CH$_2$O)$_m$—CH$_2$-CAP, Link-(CH$_2$CH$_2$O)$_m$—CH$_2$CH$_2$-CAP, Link-(CH$_2$)$_n$—(Z)$_g$—CAP, Link-(CH$_2$)$_n$(Z)$_g$—(CH$_2$)$_m$-CAP, Link-(CH$_2$)$_n$—NR$^{13}$—CH$_2$(CHOR$^8$)(CHOR$^8$)$_n$-CAP, Link-(CH$_2$)$_n$—(CHOR$^8$)$_m$CH$_2$—NR$^{13}$—(Z)$_g$-CAP, Link-(CH$_2$)$_n$NR$^{13}$—(CH$_2$)$_m$(CHOR$^8$)$_n$CH$_2$NR$^{13}$-(Z)$_g$—CAP, Link-(CH$_2$)$_m$—(Z)$_g$—(CH$_2$)$_m$-CAP, Link-NH—C(=O)—NH—(CH$_2$)$_m$-CAP, Link-(CH$_2$)$_m$—C(=O)NR$^{13}$—(CH$_2$)$_m$—C(=O)NR$^{10}$R$^{10}$, Link-(CH$_2$)$_m$—C(=O)NR$^{13}$—(CH$_2$)$_m$-CAP, Link-(CH$_2$)$_m$—C(=O)NR$^{11}$R$^{11}$, Link-(CH$_2$)$_m$—C(=O)NR$^{12}$R$^{12}$, Link-(CH$_2$)$_n$—(Z)$_g$—(CH$_2$)$_m$(Z)$_g$—CAP, or Link-Z$_g$—(CH$_2$)$_m$-Het-(CH$_2$)$_m$-CAP;

each Link is, independently, —O—, —(CH$_2$)$_n$—, —O(CH$_2$)$_m$—, —NR$^{13}$—C(=O)—NR$^{13}$, —NR$^{13}$—C(=O)—(CH$_2$)$_m$—, —C(=O)NR$^{13}$—(CH$_2$)$_m$—, —(CH$_2$)$_n$—Z$_g$—(CH$_2$)$_n$, —S—, —SO—, —SO$_2$—, —SO$_2$NR$^7$—, —SO$_2$NR$^{10}$, or -Het-;

each CAP is, independently, thiazolidinedione, oxazolidinedione, heteroaryl-C(=O)NR$^{13}$R$^{13}$, heteroaryl-W, —CN, —O—C(=S)NR$^{13}$R$^{13}$, —Z$_g$R$^{13}$, —CR$^{10}$(Z$_g$R$^{13}$)(Z$_g$R$^{13}$), —C(=O)OAr, —C(=O)NR$^{13}$Ar, imidazoline, tetrazole, tetrazole amide, —SO$_2$NHR$^{13}$, —SO$_2$NH—C(R$^{13}$R$^{13}$)—(Z)$_g$—R$^{13}$, a cyclic sugar or oligosaccharide, a cyclic amino sugar or oligosaccharide,

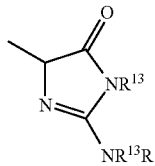 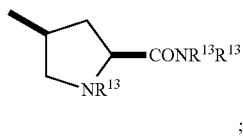

each Ar is, independently, phenyl, substituted phenyl, wherein the substituents of the substituted phenyl are 1-3 substituents independently selected from the group consisting of OH, OCH$_3$, NR$^{13}$R$^{13}$, Cl, F, and CH$_3$, or heteroaryl;

each W is independently, thiazolidinedione, oxazolidinedione, heteroaryl-C(=O)NR$^{13}$R$^{13}$—CN, —O—C(=S)NR$^{13}$R$^{13}$, —Z$_g$R$^{13}$, —CR$^{10}$(Z$_g$R$^{13}$)(Z$_g$R$^{13}$), —C(=O)OAr, —C(=O)NR$^{13}$Ar, imidazoline, tetrazole, tetrazole amide, —SO$_2$NHR$^{13}$, SO$_2$NH—C(R$^{13}$R$^{13}$)—(Z)$_g$—R$^{13}$, a cyclic sugar or oligosaccharide, a cyclic amino sugar or oligosaccharide,

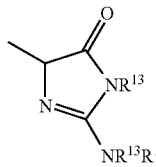 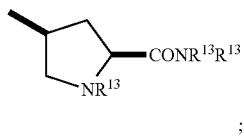

each R$^6$ is, independently, —R$^5$, —R$^7$, —OR$^8$, —N(R$^7$)$_2$, —(CH$_2$)$_m$—OR$^8$, —O—(CH$_2$)$_m$—OR$^8$, —(CH$_2$)$_n$—NR$^7$R$^{10}$, —O—(CH$_2$)$_m$—NR$^7$R$^{10}$, —(CH$_2$)$_n$(CHOR$^8$)(CHOR$^8$)$_n$—CH$_2$OR$^8$, —O—(CH$_2$)$_n$(CHOR$^8$)(CHOR$^8$)$_n$—CH$_2$OR$^8$, —(CH$_2$CH$_2$O)$_m$—R$^8$, —O—(CH$_2$CH$_2$O)—R$^8$, —(CH$_2$CH$_2$O)$_m$—CH$_2$CH$_2$NR$^7$R$^{10}$, —O—(CH$_2$CH$_2$O)$_m$—CH$_2$CH$_2$NR$^7$R$^{10}$, —(CH$_2$), —C(=O)NR$^7$R$^{10}$, —O—(CH$_2$)$_m$—C(=O)NR$^7$R$^{10}$, —(CH$_2$)$_n$—(Z)$_g$—R$^7$, —O—(CH$_2$)$_m$—(Z)$_g$—R$^7$, —(CH$_2$)$_n$—NR$^{10}$—CH$_2$(CHOR$^8$)(CHOR$^8$)$_n$—CH$_2$OR$^8$, —O—(CH$_2$)$_m$—NR$^{10}$—CH$_2$(CHOR$^8$)(CHOR$^8$)$_n$—CH$_2$OR$^8$, —(CH$_2$)$_n$—CO$_2$R$^{77}$—O—(CH$_2$)$_m$—CO$_2$R$^7$, —OSO$_3$H, —O-glucuronide, —O-glucose,

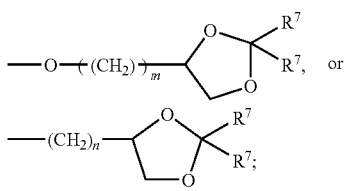

each R$^7$ is, independently, hydrogen lower alkyl, phenyl, or substituted phenyl;
each R$^8$ is, independently, hydrogen, lower alkyl, —C(=O)—R$^{11}$, glucuronide, 2-tetrahydropyranyl, or

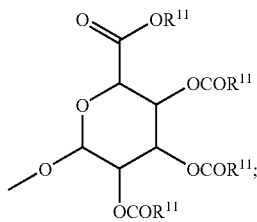

each R$^9$ is, independently, —CO$_2$R$^{13}$, —CON(R$^{13}$)$_2$, —SO$_2$CH$_2$R$^{13}$, or —C(=O)R$^{13}$;

each R$^{10}$ is, independently, —H, —SO$_2$CH$_3$, —CO$_2$R$^7$, —C(=O)NR$^7$R$^9$, —C(=O)R$^7$, or —CH$_2$—(CHOH), —CH$_2$OH;

each Z is, independently, —CHOH, —C(=O), —(CH$_2$)$_n$—, —CHNR$^{13}$R$^{13}$, C=NR$^{13}$, or —NR$^{13}$;

each R$^{11}$ is, independently, lower alkyl;

each R$^{12}$ is, independently, —SO$_2$CH$_3$, —CO$_2$R$^{13}$, —C(=O)NR$^{13}$R$^{13}$, —C(=O)R$^{13}$, or —CH$_2$—(CHOH), —CH$_2$OH;

each R$^{13}$ is, independently, hydrogen, R$^7$, R$^{10}$, —(CH$_2$)$_m$—NR$^7$R$^{10}$,

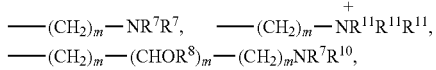
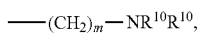
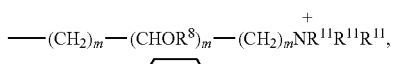
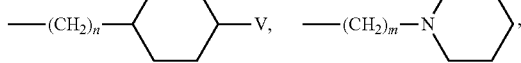
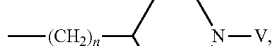
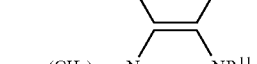
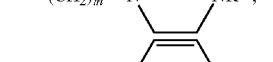
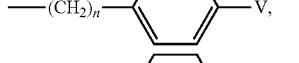
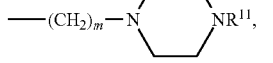
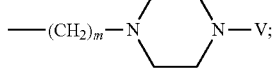

with the proviso that NR$^{13}$R$^{13}$ can be joined on itself to form a ring comprising one of the following:

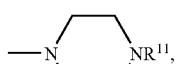
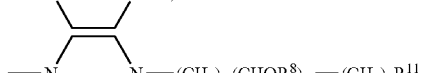

-continued

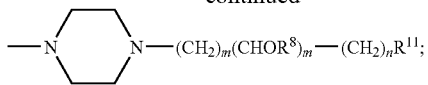

each Het is independently, —NR$^{13}$—, —S—, —SO—, —SO$_2$—, —O—, —SO$_2$NR$^{13}$—, —NHSO$_2$—, —NR$^{13}$CO—, or —CONR$^{13}$—;
each g is, independently, an integer from 1 to 6;
each m is, independently, an integer from 1 to 7;
each n is, independently, an integer from 0 to 7;
each V is, independently, —(CH$_2$)$_m$—NR$^7$R$^{10}$, —(CH$_2$)$_m$—NR$^7$R$^7$, —(CH$_2$)$_m$

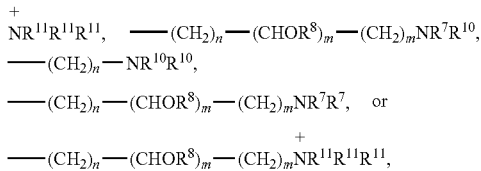

$\overset{+}{N}R^{11}R^{11}R^{11}$, —(CH$_2$)$_n$—(CHOR$^8$)$_m$—(CH$_2$)$_m$NR$^7$R$^{10}$, —(CH$_2$)$_n$—NR$^{10}$R$^{10}$, —(CH$_2$)$_n$—(CHOR$^8$)$_m$—(CH$_2$)$_m$NR$^7$R$^7$, or —(CH$_2$)$_n$—(CHOR$^8$)$_m$—(CH$_2$)$_m$$\overset{+}{N}$R$^{11}$R$^{11}$R$^{11}$, with the proviso that when V is attached directly to a nitrogen atom, then V can also be, independently, R$^7$, R$^{10}$, or (R$^{11}$)$_2$;
with the proviso that, when any two —CH$_2$OR$^8$ groups in the compound are located 1,2- or 1,3- with respect to each other, the R$^8$ groups may be joined to form a cyclic mono- or di-substituted 1,3-dioxane or 1,3-dioxolane;
or a pharmaceutically acceptable salt thereof, and
inclusive of all enantiomers, diastereomers, and racemic mixtures thereof;

(9)
each R$^2$ is, independently, —R$^7$, —(CH$_2$)$_n$—OR$^8$, —(CH$_2$)$_n$—NR$^7$R$^{10}$, —(CH$_2$)$_n$(CHOR$^8$)(CHOR$^8$)$_n$—CH$_2$OR$^8$, —(CH$_2$CH$_2$O)$_m$—R$^8$, —(CH$_2$CH$_2$O)$_m$—CH$_2$CH$_2$NR$^7$R$^{10}$, —(CH$_2$), —C(═O)NR$^7$R$^{10}$, —(CH$_2$)$_n$—Z$_g$—R$^7$, —(CH$_2$)$_m$—NR$^{10}$—CH$_2$(CHOR$^8$)(CHOR$^8$)$_n$—CH$_2$OR$^8$, —(CH$_2$)$_n$—CO$_2$R$^7$, or

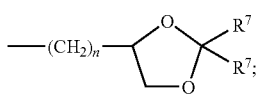

R$^3$ and R$^4$ are each, independently, hydrogen, a group represented by formula (A), lower alkyl, hydroxy lower alkyl, phenyl, phenyl-lower alkyl, (halophenyl)-lower alkyl, lower-(alkylphenylalkyl), lower (alkoxyphenyl)-lower alkyl, naphthyl-lower alkyl, or pyridyl-lower alkyl, with the proviso that at least one of R$^3$ and R$^4$ is a group represented by formula (A):

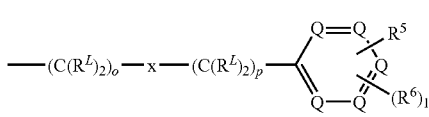

(A)

wherein
each R$^L$ is, independently, —R$^7$, —(CH$_2$)$_n$—OR$^8$, —O—(CH$_2$)$_m$—OR$^8$, —(CH$_2$)$_n$—NR$^7$R$^{10}$, —O—(CH$_2$)$_m$—NR$^7$R$^{10}$, —(CH$_2$)$_n$(CHOR$^8$)(CHOR$^8$)$_n$—CH$_2$OR$^8$, —O—(CH$_2$)$_m$(CHOR$^8$)(CHOR$^8$)$_n$—CH$_2$OR$^8$, —(CH$_2$CH$_2$O)$_m$—R$^8$, —O—(CH$_2$CH$_2$O)$_m$—R$^8$, —(CH$_2$CH$_2$O)$_m$—CH$_2$CH$_2$NR$^7$R$^{10}$, —O—(CH$_2$CH$_2$O)$_m$—CH$_2$CH$_2$NR$^7$R$^{10}$, —(CH$_2$), —C(═O)NR$^7$R$^{10}$, —O—(CH$_2$)$_m$—C(═O)NR$^7$R$^{10}$, —(CH$_2$)$_n$—(Z)$_g$—R$^7$, —O—(CH$_2$)$_m$—(Z)$_g$—R$^7$, —(CH$_2$)$_m$—NR$^{10}$—CH$_2$(CHOR$^8$)(CHOR$^8$)$_n$—CH$_2$OR$^8$, —O—(CH$_2$)$_m$—NR$^{10}$—CH$_2$(CHOR$^8$)(CHOR$^8$)$_n$—CH$_2$OR$^8$, —(CH$_2$)$_n$—CO$_2$R$^7$, —O—(CH$_2$)$_m$—CO$_2$R$^7$, —OSO$_3$H, —O-glucuronide, —O-glucose,

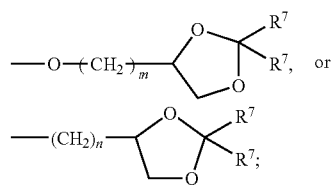

each o is, independently, an integer from 0 to 10;
each p is an integer from 0 to 10;
with the proviso that the sum of o and p in each contiguous chain is from 1 to 10;
each x is, independently, —O—, —NR$^{10}$—, —C(═O)—, —CHOH—, —C(═N—R$^{10}$)—, —CHNR$^7$R$^{10}$—, or represents a single bond;
each R$^5$ is, independently, -Link-(CH$_2$)$_m$-CAP, -Link-(CH$_2$)$_n$(CHOR$^8$)(CHOR$^8$)$_n$— CAP, -Link-(CH$_2$CH$_2$O)$_m$ —CH$_2$-CAP, -Link-(CH$_2$CH$_2$O)$_m$, —CH$_2$CH$_2$-CAP, -Link-(CH$_2$)$_m$—(Z)$_g$-CAP, -Link-(CH$_2$)$_n$(Z)$_g$—(CH$_2$)$_m$- CAP, -Link-(CH$_2$)$_n$—NR$^{13}$—CH$_2$(CHOR$^8$)(CHOR$^8$)$_n$-CAP, -Link-(CH$_2$)$_n$—(CHOR$^8$)$_m$CH$_2$—NR$^{13}$-(Z)$_g$—CAP, -Link-(CH$_2$)$_n$—NR$^{13}$—(CH$_2$)$_n$(CHOR$^8$)$_n$CH$_2$NR$^{13}$—(Z)$_g$—CAP, -Link-(CH$_2$)$_n$—(Z)$_g$ —(CH$_2$)$_m$-CAP, -Link-NH—C(═O)—NH—(CH$_2$)$_m$-CAP, -Link-(CH$_2$)$_m$—C(═O)NR$^{13}$—(CH$_2$)$_m$-CAP, -Link-(CH$_2$)$_n$—(Z)$_g$—(CH$_2$)$_m$—(Z)$_g$—CAP, or -Link-Z$_g$—(CH$_2$)$_m$-Het-(CH$_2$)$_m$-CAP;
each Link is, independently, —O—, —(CH$_2$)$_m$—, —O(CH$_2$)$_m$—, —NR$^{13}$—C(═O)—NR$^{13}$—, —NR$^{13}$—C(═O)—(CH$_2$)$_m$—, —C(═O)NR$^{13}$—(CH$_2$)$_m$—, —(CH$_2$)$_n$—Z$_g$—(CH$_2$)$_n$, —S—, —SO—, —SO$_2$—, —SO$_2$NR$^7$—, —SO$_2$NR$^{10}$—, or -Het-;
each CAP is, independently, —CR$^{10}$(—(CH$_2$)$_m$—R$^9$)(—(CH$_2$)$_m$—R$^9$), —N(—(CH$_2$)$_m$—R$^9$)(—(CH$_2$)$_m$—R$^9$), or —NR$^{13}$(—(CH$_2$)$_m$—CO$_2$R$^{13}$);
each Ar is, independently, phenyl, substituted phenyl, wherein said substituent is 1-3 groups selected, independently, from the group consisting of —OH, —OCH$_3$, —NR$^{13}$R$^{13}$, —Cl, —F, and —CH$_3$, or heteroaryl;
wherein heteroaryl is selected from the group consisting of pyridine, pyrazine, tinazine, furyl, furfuryl-, thienyl, tetrazole, thiazolidinedione and imidazoyl

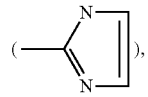

pyrrole, furan, thiophene, pyridine, quinoline, indole, adenine, pyrazole, imidazole, thiazole, isoxazole, indole, benzimidazole, purine, quinoline, isoquinoline, pyridazine, pyrimidine, pyrazine, 1,2,3-triazine, 1,2,4-triazine, 1,3,5-triazine, cinnoline, phthalazine, quinazoline, quinoxaline, and pterdine;

each $R^6$ is, independently, $-R^7$, $-OR^7$, $-OR^{11}$, $-N(R^7)_2$, $-(CH_2)_m-OR^8$, $-O-(CH_2)_m-OR^8$, $-(CH_2)_n-NR^7R^{10}$, $-O-(CH_2)_n-NR^7R^{10}$, $-(CH_2)_n(CHOR^8)(CHOR^8)_n-CH_2OR^8$, $-O-(CH_2)_m(CHOR^8)(CHOR^8)_n-CH_2OR^8$, $-(CH_2CH_2O)_m-R^8$, $-O-(CH_2CH_2O)_m-R^8$, $-(CH_2CH_2O)_m-CH_2CH_2NR^7R^{10}$, $-O-(CH_2CH_2O)_m-CH_2CH_2NR^7R^{10}$, $-(CH_2)_\cdot-C(=O)NR^7R^{10}$, $-O-(CH_2)_\cdot-C(=O)NR^7R^{10}$, $-(CH_2)_n-(Z)_g-R^7$, $-O-(CH_2)_m-(Z)_g-R^7$, $-(CH_2)_n-NR^{10}-CH_2(CHOR^8)(CHOR^8)_n-CH_2OR^8$, $-O-(CH_2)_m-NR^{10}-CH_2(CHOR^8)(CHOR^8)_n-CH_2OR^8$, $-(CH_2)_n-CO_2R^7$, $-O-(CH_2)_m-CO_2R^7$, $-OSO_3H$, $-O$-glucuronide, $-O$-glucose,

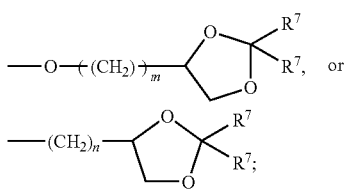

wherein when two $R^6$ are $-OR^{11}$ and are located adjacent to each other on a phenyl ring, the alkyl moieties of the two $R^6$ may be bonded together to form a methylenedioxy group;

with the proviso that when at least two $-CH_2OR^8$ are located adjacent to each other, the $R^8$ groups may be joined to form a cyclic mono- or di-substituted 1,3-dioxane or 1,3-dioxolane;

each $R^7$ is, independently, hydrogen lower alkyl, phenyl, or substituted phenyl;

each $R^8$ is, independently, hydrogen, lower alkyl, $-C(=O)-R^{11}$, glucuronide, 2-tetrahydropyranyl, or

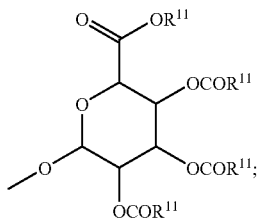

each $R^9$ is, independently, $-CO_2R^{13}$, $-CON(R^{13})_2$, $-SO_2CH_2R^{13}$, $-C(=O)R^{13}$, thiazolidinedione, oxazolidinedione, heteroaryl-$C(=O)NR^{13}R^{13}$, heteroaryl-CAP, $-CN$, $-O-C(=S)NR^{13}R^{13}$, $-Z_gR^{13}$, $-C(=O)OAr$, $-C(=O)NR^{10}Ar$, imidazoline, tetrazole, tetrazole amide, $-SO_2NHR^{13}$, $-SO_2NH-C(R^{13}R^{13})-(Z)_g-R^{31}$, $-C(=O)NR^{10}Ar$, $-SO_2NR^7R^7$, cylic sugars and oligosaccharides, including cyclic amino sugars and oligosaccharides,

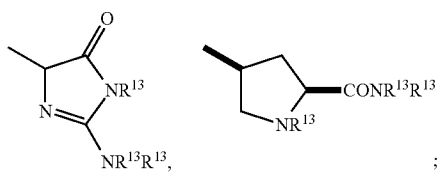

each $R^{10}$ is, independently, $-H$, $-SO_2CH_3$, $-CO_2R^7$, $-C(=O)NR^7R^9$, $-C(=O)R^7$, or $-CH_2-(CHOH)_n-CH_2OH$;

each Z is, independently, $-CHOH-$, $-C(=O)-$, $-CHNR^{13}R^{13}-$, $-C=NR^{13}R^{13}-$, or $-NR^{13}-$;

each $R^{11}$ is, independently, lower alkyl;

each $R^{12}$ is independently, $-SO_2CH_3$, $-CO_2R^{13}$, $-C(=O)NR^{13}R^{13}$, $-C(=O)R^{13}$, or $-CH_2-(CHOH)_n-CH_2OH$;

each $R^{13}$ is, independently, $-R^7$ or $-R^{10}$;

each Het is independently, $-NR^{13}-$, $-S-$, $-SO-$, $-SO_2-$, $-O-$, $-SO_2NR^{13}-$, $-NHSO_2-$, $-NR^{13}CO-$, or $-CONR^{13}-$;

each g is, independently, an integer from 1 to 6;

each m is, independently, an integer from 1 to 7;

each n is, independently, an integer from 0 to 7;

each Q is, independently, $C-R^5$, $C-R^6$, or a nitrogen atom, wherein one Q is $C-R^5$ and at most three Q in a ring are nitrogen atoms;

each V is, independently, $-(CH_2)_m-NR^7R^{10}$, $-(CH_2)_m-NR^7R^7$, $-(CH_2)_m-$

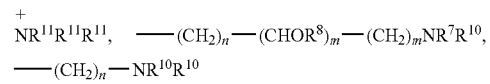

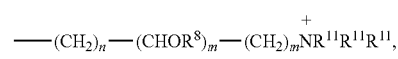

with the proviso that when V is attached directly to a nitrogen atom, then V can also be, independently, $R^7$, $R^{10}$, or $(R^{11})_2$;

wherein when two $-CH_2OR^8$ groups are located 1,2- or 1,3- with respect to each other the $R^8$ groups may be joined to form a cyclic mono- or di-substituted 1,3-dioxane or 1,3-dioxolane;

or a pharmaceutically acceptable salt thereof, and inclusive of all enantiomers, diastereomers, and racemic mixtures thereof.

2. The method of claim 1, wherein the sodium channel blocker represented by formula I is

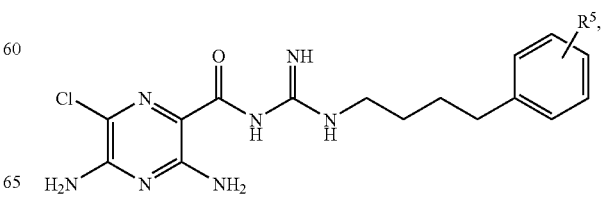

-continued

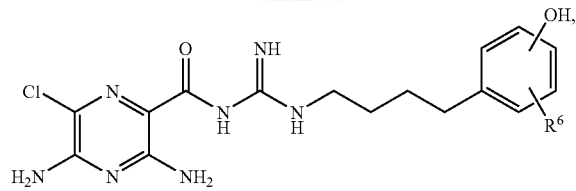

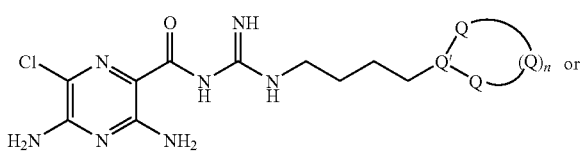

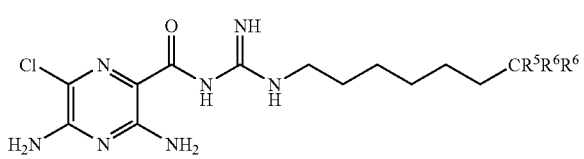

3. The method of claim 2, wherein the sodium channel blocker represented by formula I is

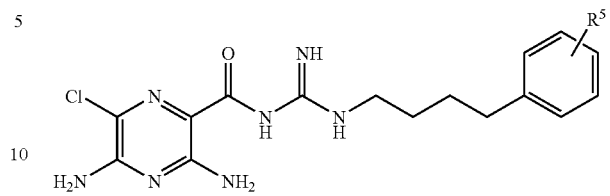

wherein $R^5$ is
—O—$(CH_2)_m Z_g R^{12}$,
-Het-$(CH_2)_m NH(C=NR^{13})NR^{13}R^{13}$,
-Het-$(CH_2)_n Z_g (CH_2)_m NH(C=NR^{13})NR^{13}R^{13}$,
-Link-$(CH_2)_m$—$(Z)_g$—$(CH_2)_m$-CAP,
-Het-$(CH_2)_m C(=O)NR^{13}R^{13}$,
—$(CH_2)_n NR^{12}R^{12}$,
—O—$(CH_2)_m NR^{11}R^{11}$,
—O—$(CH_2)_m N^+(R^{11})_3$,
—$(CH_2)_n Z_g (CH_2)_m NR^{10}R^{10}$, or
-Het-$(CH_2)_m Z_g NH(C=NR^{13})NR^{13}R^{13}$.

4. The method of claim 1, wherein the compound represented by formula (I) is:

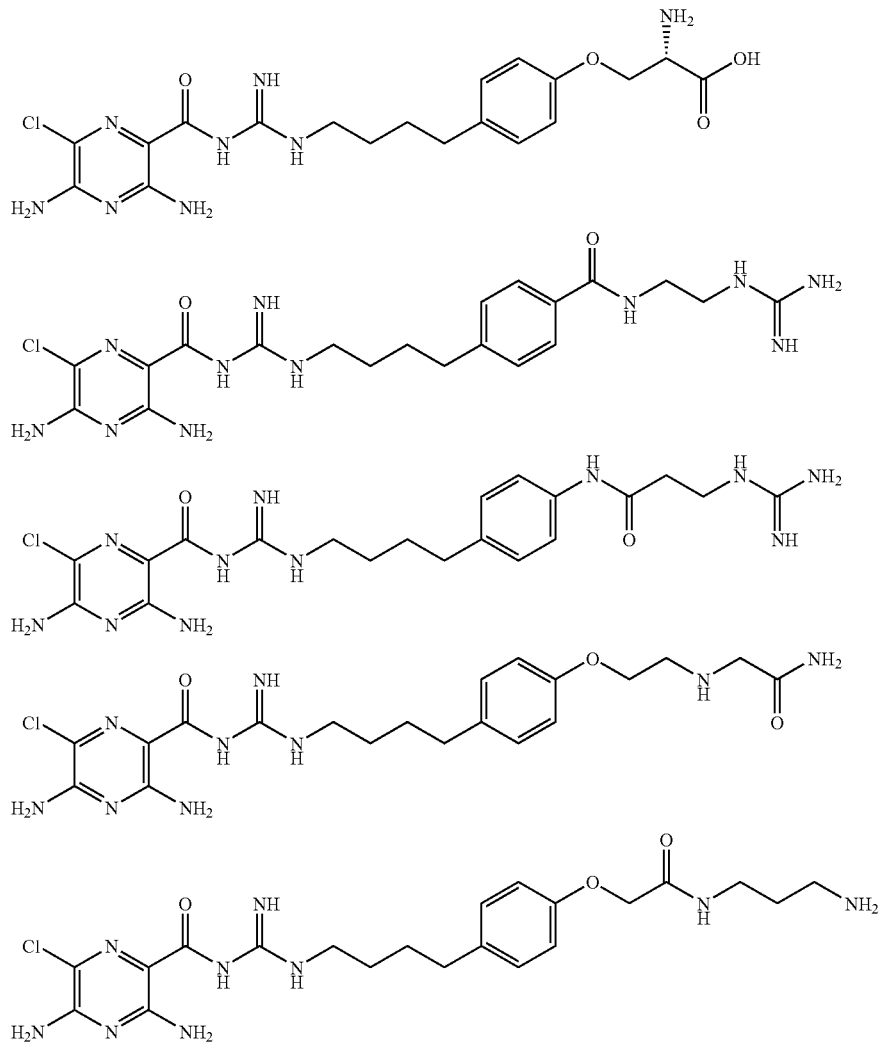

-continued
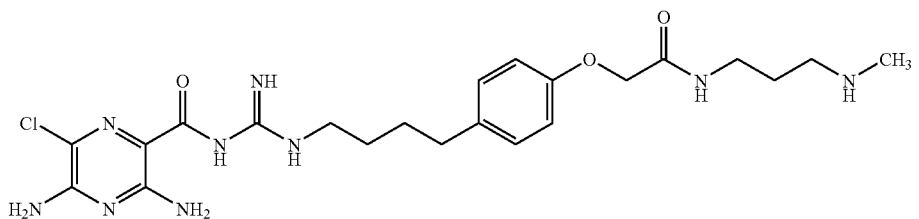
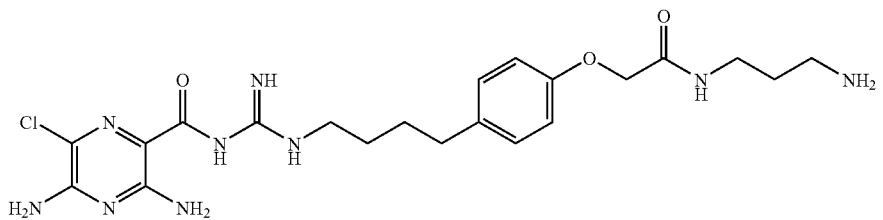
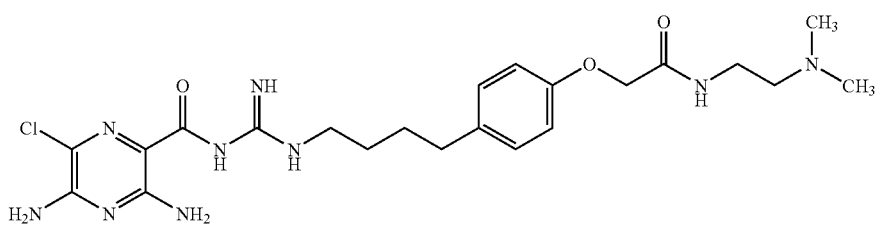
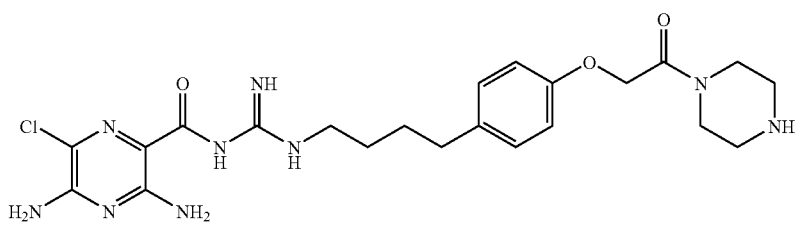
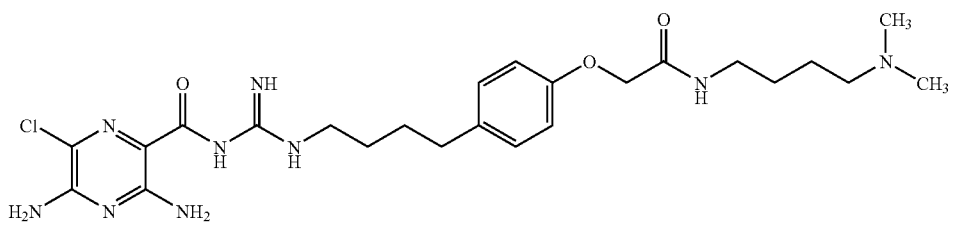
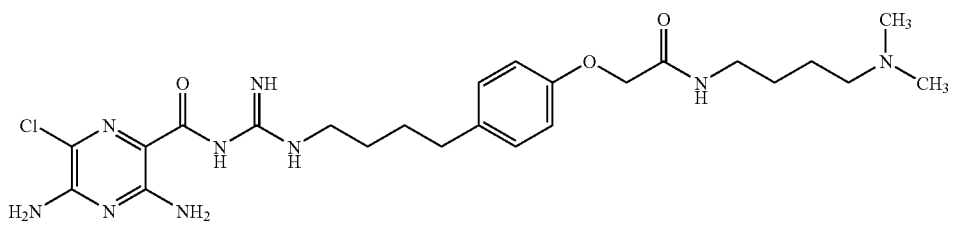
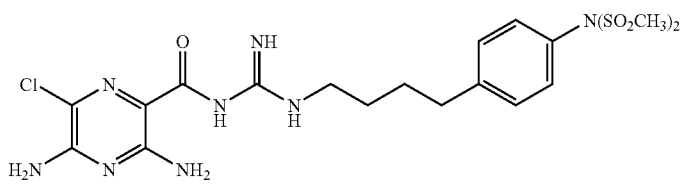

-continued
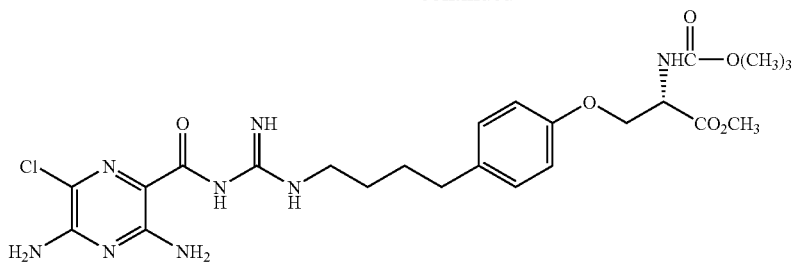
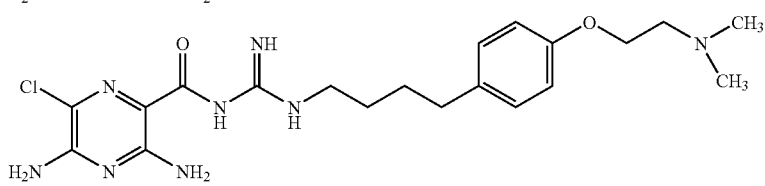
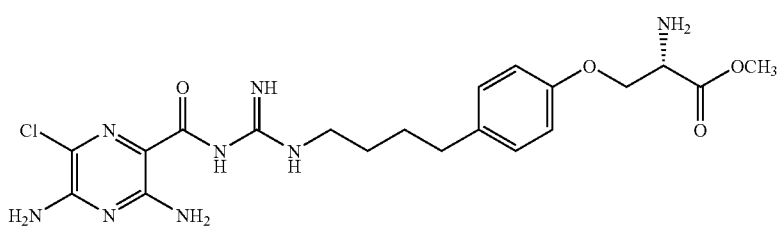
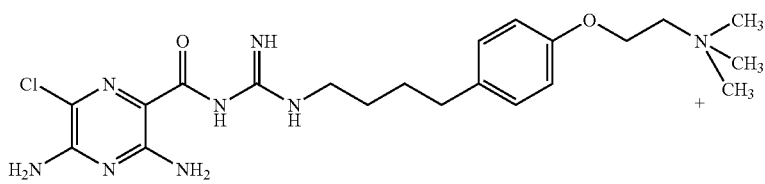
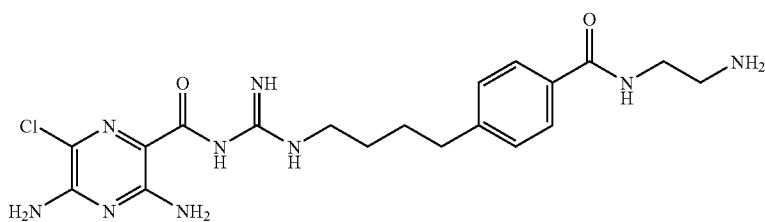
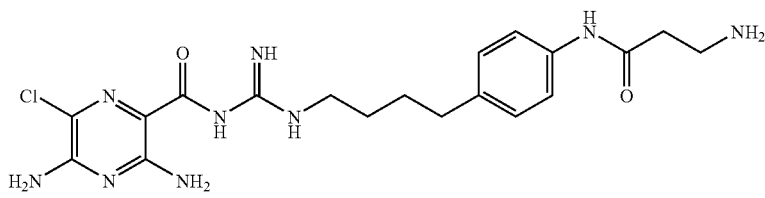
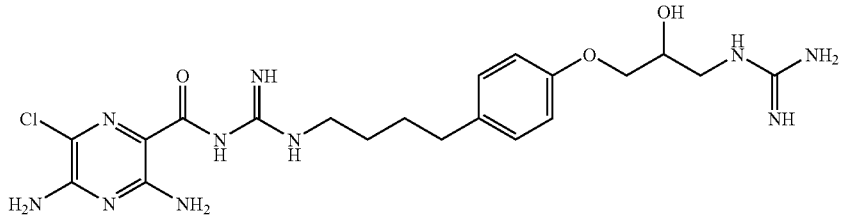
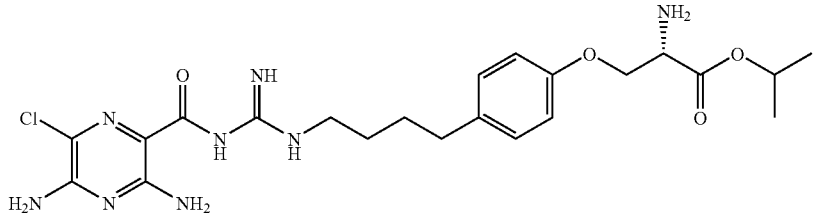

-continued

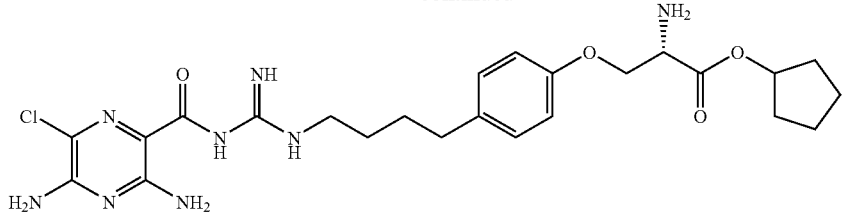

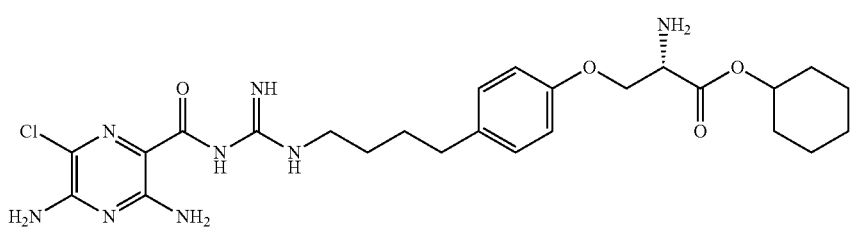

5. The method of claim 1, wherein the sodium channel blocker is administered preceding administration of the osmolyte.

6. The method of claim 1, wherein the sodium channel blocker is administered concurrent with administration of the osmolyte.

7. The method of claim 1, wherein the sodium channel blocker is administered following administration of the osmolyte.

8. The method of claim 1, wherein the osmolyte is hypertonic saline.

9. The method of claim 1, wherein the osmolyte is mannitol.

10. The method of claim 1, wherein the osmolyte is sodium chloride which is delivered as a micronized particle of respirable size.

11. The method of claim 1, wherein said effective amount of an osmolyte and a sodium channel blocker is administered by aerosolization using a device capable of delivering the formulation to the nasal passages or pulmonary airway wherein the aerosol is a respirable size.

12. The method of claim 1, which further comprises co-administering a P2Y2 receptor agonist.

13. The method of claim 1, which further comprises co-administering a bronchodilator.

14. The method of claim 1, which further comprises co-administering an antibiotic.

15. The method of claim 14, wherein the antibiotic is tobramycin, fosfomycin, or a combination thereof.

16. A method for improving the duration of action hypertonic saline in a patient in need of increased mucocilliary clearance or mucosal hydration,adi method comprising co-administering hypertonic saline with

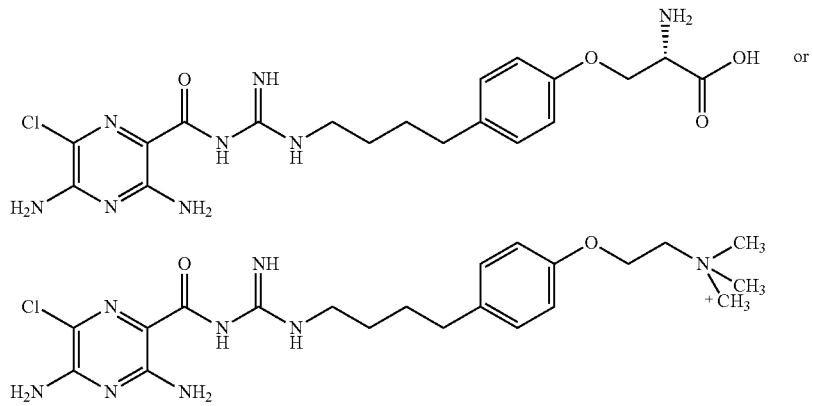

or a pharmaceutically acceptable salt thereof.

* * * * *